(12) United States Patent
Guan et al.

(10) Patent No.: US 7,378,525 B2
(45) Date of Patent: May 27, 2008

(54) CCR8 INHIBITORS

(75) Inventors: Bing Guan, Chestnut Hill, MA (US);
Charles Minor, Kingston, MA (US);
Mingshi Dai, Billerica, MA (US);
Shomir Ghosh, Brookline, MA (US);
Tracy J. Jenkins, Belmont, MA (US);
Gang Li, Framingham, MA (US);
Douglas F. Burdi, Arlington, MA (US);
Robert A. Bennett, Milford, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 271 days.

(21) Appl. No.: 10/744,585

(22) Filed: Dec. 23, 2003

(65) Prior Publication Data

US 2004/0209948 A1 Oct. 21, 2004

Related U.S. Application Data

(60) Provisional application No. 60/436,537, filed on Dec. 23, 2002.

(51) Int. Cl.
*C07D 211/06* (2006.01)
*C07D 211/68* (2006.01)

(52) U.S. Cl. .............................. 546/195; 546/192

(58) Field of Classification Search .............. 546/192, 546/195
See application file for complete search history.

(56) References Cited

U.S. PATENT DOCUMENTS

| | | | |
|---|---|---|---|
| 5,281,626 A | | 1/1994 | Oinuma et al. |
| 5,354,904 A | * | 10/1994 | Mayer et al. .................. 564/86 |
| 5,378,715 A | | 1/1995 | Stein et al. |
| 5,530,118 A | | 6/1996 | Oinuma et al. |
| 5,571,898 A | * | 11/1996 | Schloesser et al. ......... 534/604 |
| 5,663,414 A | | 9/1997 | Oinuma et al. |
| 5,994,398 A | * | 11/1999 | John et al. .................. 514/485 |
| 6,262,112 B1 | | 7/2001 | Mittendorf et al. |
| 6,417,181 B1 | | 7/2002 | Bender et al. |
| 2003/0130287 A1 | | 7/2003 | Ackermann et al. |
| 2005/0085518 A1 | | 4/2005 | Dai et al. |

FOREIGN PATENT DOCUMENTS

| | | |
|---|---|---|
| DE | 858 551 | 12/1952 |
| DE | 100 00 739 A1 | 7/2001 |
| DE | 100 53 796 A1 | 5/2002 |
| EP | 0 618 223 A2 | 10/1994 |
| EP | 1 038 868 A2 | 9/2000 |
| JP | 32002219 | 4/1957 |
| JP | 32005169 | 7/1957 |
| JP | 32008075 | 9/1957 |
| JP | 32008422 | 9/1957 |
| JP | 32009570 | 11/1957 |
| JP | 33007538 | 8/1958 |
| JP | 63017870 A2 | 1/1988 |
| JP | 63208042 A2 | 8/1988 |
| RU | 2051146 C1 | 12/1995 |
| RU | 2051147 C1 | 12/1995 |
| RU | 2053226 C1 | 1/1996 |
| TW | 402606 B | 8/2000 |
| WO | WO 99/29670 A2 | 6/1990 |
| WO | WO 91/12237 A1 | 8/1991 |
| WO | WO 95/26957 A1 | 10/1995 |
| WO | WO 96/40641 A1 | 12/1996 |
| WO | WO 97/20822 A1 | 6/1997 |
| WO | WO 99/37609 A1 | 7/1999 |
| WO | WO 99/62885 A1 | 12/1999 |
| WO | WO 01/07403 A1 | 2/2001 |
| WO | WO 01/58484 A2 | 8/2001 |
| WO | WO 02/072549 A1 | 9/2002 |
| WO | WO 2006/107252 A1 | 10/2006 |
| WO | WO 2006/107253 A1 | 10/2006 |
| WO | WO 2006/107254 A1 | 10/2006 |
| WO | WO 2007/030061 A1 | 3/2007 |

OTHER PUBLICATIONS

Campos et al., J. Org. Chem., 2005, 70, 268-274.*
Trushkin, et al., "ANSA-analysis. II. Aminonaphthalenesulfonamides as detectable groups for polysubstrate analysis of proteases," *Biokhimiya* (Moscow) 59(10): 1521-1534 (1994).
Nedospasov, A. A., et al., "The Synthesis of N(S)-alkoxyethyl-substituted aminoaphthalenesulfonamides by opening an aziridene ring," *Synlett* (8): 661-662 (1992).
Horstmann, H., et al., "Compounds With Schistosomicide Activity. 1. N4-(N-acyl-N-alkylglycyl)sulfanilamide," *European J. Of Medicinal Chem.*, 12(4): 387-392 (1977).

(Continued)

*Primary Examiner*—D. Margaret Seaman

(57) ABSTRACT

Disclosed are CCR8 inhibitors represented by Structural Formulas (I):

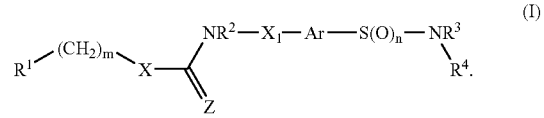

The variables in Structural Formula (I) are described herein. Also disclosed are methods of treating a subject with a CCR8 mediated condition, especially asthma, by administering one of the disclosed CCR8 inhibitors to the subject.

9 Claims, No Drawings

OTHER PUBLICATIONS

Database Chemcats 'Online!, Chemical Abstracts Service, Columbus, Ohio, US; XP002280062, Order No. 5242677, 5242739, 5242752 & "Chembridge Product List" Jan. 17, 2002, Chembridge Corporation, 16981 Via Tazon, Suite G, San Diego, CA 92127, USA.

Database Chemcats 'Online!, Chemical Abstracts Service, Columbus, Ohio, US; XP002280063, Order No. BAS 0371287 & Interchim Intermediates, Jul. 9, 2002, Interchim, 213 Avenue Kennedy, BP 1140, Montlucon, Cedex, 03103, France.

Jenkins, Tracy J., et al., "Design, synthesis, and evaluation of naphthalene-sulfonamide antagonists of human CCR8," *Journal of Medicinal Chemistry*, vol. 50, No. 3 (2007) pp. 566-584.

Jin, Jian, et al., "Oxazolidinones as novel human CCR8 antagonists," *Bioorganic & Medicinal Chemistry Letters*, vol. 17 (2007) pp. 1722-1725.

* cited by examiner

SEQUENCE LISTING

<160> NUMBER OF SEQ ID NOS: 2

<210> SEQ ID NO 1
<211> LENGTH: 36
<212> TYPE: DNA
<213> ORGANISM: Human

<400> SEQUENCE: 1
tttggatcca tggattatac acttgacctc agtgtg           36

<210> SEQ ID NO 2
<211> LENGTH: 37
<212> TYPE: DNA
<213> ORGANISM: Human

<400> SEQUENCE: 2
tttgcggccg ctcacaaaat gtagtctacg ctggagg      37

CCR8 INHIBITORS

RELATED APPLICATION

This application claims the benefit of U.S. Provisional Application No. 60/436,537, filed on Dec. 23, 2002. The entire teachings of the above application is incorporated herein by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation (Baggiolini, et. al., *Nature* 15:365 (1994)). Indeed, chemokines have been implicated in a wide range of human acute and chronic inflammatory diseases including, but not limited to, respiratory diseases such as asthma, inflammatory bowel disease, allergic disorders and certain autoimmune diseases such as rheumatoid arthritis.

Chemokines exert their biological activity by binding to specific G-protein receptors, which then transduce signals important for the development and trafficking of specific leukocyte subsets (Baggiolini, et. al., *Nature* 15:365 (1994)). A number or chemokine receptors have been characterized and each are differentially expresssed among leukocyte populations. Significantly, each chemokine binds specifically to a single receptor or to a small group of receptors. Thus, the recruitment and activation of specific classes of leukocytes or lymphocytes can be modulated by agents which selectively act at one chemokine receptor and/or block the activity of a specific chemokine. Agents which selectively block the activity of a specific chemokine or chemokine receptor are therefore useful in treating inflammatory diseases caused by aberrant activation of leukocytes or lymphocytes which express those chemokine receptors (or are activated by the chemokine) and minimally affect immune system cells which express other chemokine receptors.

CCR8 is a chemokine receptor (see WO 99/065561) whose expression is primarily restricted to Th2 cells (Zingoni et al., *J. Immunol.* 161:547 (1998) and D'Ambrosio et al., *J. Immunol.* 161:5111 (1998)). I-309 is a ligand for CCR8 and has shown to be chemotactic for Th2 cells in vitro (D'Ambrosio et al., *J. Immunol.* 161.5111 (1998). CCR8 is also involved in eosinophil recruitment (see WO 99/065561). Thus, antagonists for CCR8 are expected to be useful in treating disorders mediated by Th2 and eosinophil cells, e.g., asthma.

SUMMARY OF THE INVENTION

Disclosed herein are naphthylsulfonamides, also referred to herein as "naphthylene sulfonamides", which are effective inhibitors of CCR8 activity. For example, most of the naphthylsulfonamides shown in the Tables in the Exemplification Section inhibit CCR8 activity with a $K_i$ less than 30 μM and many with a $K_i$ less than 1.0 μM. Based on this discovery, novel CCR8 inhibitors, pharmaceutical compositions comprising these inhibitors and methods of treating inflammatory disorders with these inhibitors are disclosed herein.

One embodiment of the present invention is a compound (a CCR8 inhibitor) represented by Structural Formula (I):

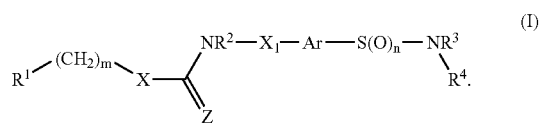

X is a covalent bond, O or $NR^5$.

$X_1$ is a covalent bond, C=O or $CR^aR^b$. In one preferred embodiment, $X_1$ is a covalent bond; and in another preferred embodiment, $X_1$ is $CH_2$.

C=Z is C=O, $CH_2$, C=NH, C=S or absent, provided that when $X_1$ is a covalent bond then C=Z is not $CH_2$. Preferably, when C=Z is absent then X is a covalent bond, and when X is $NR^5$ and C=Z is C=O then $R^4$ is not an aliphatic or substituted aliphatic group. More preferably, C=Z is C=O, $CH_2$, C=NH or C=S, provided that when $X_1$ is a covalent bond then C=Z is not $CH_2$. Even more preferably C=Z is C=O or C=S.

$R^a$ and $R^b$ are independently —H or a C1-C3 alkyl.

$R^1$ is a substituted or unsubstituted aromatic group or a substituted or unsubstituted non-aromatic ring or —$NR^5$ $(CH_2)_mR^1$, taken together, is a substituted or unsubstituted non-aromatic heterocyclic group.

$R^2$ is —H or a C1-C3 alkyl group.

$R^3$ is —H; and $R^4$ is a substituted or unsubstituted aliphatic group, a substituted or unsubstituted phenyl group, a substituted or unsubstituted benzyl group, a substituted or unsubstituted phenethyl group, a substituted or unsubstituted non-aromatic ring, a substituted or unsubstituted non-aromatic bridged bicyclic group, or, $R^3$ and $R^4$ taken together with the nitrogen atom to which they are bonded are a substituted or unsubstituted nitrogen-containing non-aromatic heterocyclic group. Preferably $R^3$ is —H and $R^4$ is a substituted or unsubstituted aromatic group or a substituted or unsubstituted non-aromatic ring.

$R^5$ is —H, or a C1-C3 alkyl group.

Ar is a substituted or unsubstituted bicyclic aromatic group comprising a substituted or unsubstituted first six membered aromatic group fused to a second substituted or unsubstituted six membered aromatic group or to a substituted or unsubstituted five or six membered non-aromatic ring. Exemplary substituents for Ar include alkyl, haloalkyl, halogen, cyano, nitro, hydroxy, haloalkoxy and alkoxy.

m is 0, 1, 2 or 3.

n is 1 or 2.

Another embodiment of the present invention method is a method of treating a subject with a CCR8 mediated condition or disease, e.g., a subject with asthma. The method comprises the step of administering to the subject an effective amount of a CCR8 inhibitor disclosed herein.

Yet another embodiment of the present invention is a pharmaceutical composition. The pharmaceutical composition comprises a pharmaceutically acceptable carrier or diluent and a CCR8 inhibitor disclosed herein. The pharmaceutical compositions can be used in therapy, for example, to treat a subject with a CCR8 mediated condition or disease, for example, a subject with asthma.

Yet another embodiment of the present invention is the use of one of the disclosed CCR8 inhibitors for the manufacture of a medicament for treating a subject with a CCR8 mediated condition or disease. The medicament comprises an effective amount of the CCR8 inhibitor.

The disclosed compounds are effective inhibitors of CCR8 and, as such, are expected to be useful in the treatment and prevention of diseases mediated by CCR8, particularly asthma. Other diseases for which the disclosed CCR8 inhibitors are expected to be effective include, but not limited to, inflammatory diseases such as atopic dermatitis, allergic rhinitis, systemic anaphylaxis or hypersensitivity responses, drug allergies (e.g., to penicillin, cephalosporins), insect sting allergies and inflammatory dermatoses such as dermatitis, eczema, allergic contact dermatitis, urticaria, atherosclerosis, restenosis, myositis or (including polymyositis, dermatomyositis).

DETAILED DESCRIPTION OF THE INVENTION

The present invention is directed to inhibitors of the chemokine receptor commonly referred to as "CCR8". CCR8 is expressed on monocytes and Th2 lymphocytes and in the brain, spleen and thymus. It is the receptor for the chemokine I-309, which is chemotactic for Th2 cells. I-309 has also shown to be involved in esinophil recruitment. Thus, the disclosed compounds can be used to inhibit CCR8 activity; to inhibit I-309 activity and to inhibit or treat (therapeutically or prophylactically) conditions mediated by CCR8 and/or I-309, including inflammatory disorders and allergic conditions. The disclosed compounds can also be advantageously used to inhibit conditions mediated by esinophils and by monocytes, T lymphocytes and other immune system cells which express CCR8, including inflammatory disorders and allergic conditions mediated by these cells.

Ar in Structural Formula (I) is preferably a naphthyl or tetrahydronaphthyl group. The invention is not limited to any particular substitution pattern of the amide and sulfonamide on the naphthyl or tetrahydronaphthyl group represented by Ar. Thus, compounds with 1,3-, 1,4-, 1,5-, 1,6- and 1,7-substitution patterns are more specific embodiments of the invention.

The compound represented by Structural Formula (I) is preferably characterized by one, two, three or more of the following features: (1) C=Z is C=O and $X_1$ is a bond or C=Z is $CH_2$ and $X_1$ is $CR^aR^b$; (2) X is a bond; (3) $R^1$ is a substituted or unsubstituted cycloalkyl group or an aromatic group optionally substituted with one or more substituent groups, e.g., the substituent groups represented by $R^{10}$; (4) R is —H; (5) $R^3$ is —H or $R^3$ and $R^4$ taken together with the nitrogen atom to which they are bonded are a substituted or unsubstituted nitrogen-containing non-aromatic heterocyclic group; (6) $R^4$ is a substituted or unsubstituted non-aromatic ring or a phenyl or benzyl group optionally substituted with one or more substituent groups, e.g., the substituent groups represented by $R^{12}$; (7) m is 0 or 1; and (8) n is 2. Exemplary values for $R^{10}$ and $R^{12}$ are provided below in the section describing suitable aromatic and aliphatic group substituents. Commonly, the compound is characterized by features (1); (2); (3); (4); (5); (6); (7); (8); (1) and (4); (1), (2) and (4); (1), (3) and (4); (1), (4) and (5); (1), (4), and (6); (1), (4) and (7); (1), (4) and (8); (1), (4), (7) and (8); (1), (2), (4), (7) and (8); (1), (3), (4), (7) and (8); (1), (4), (5), (7) and (8); (1), (4), (6), (7) and (8); (1), (2), (3), (4), (5), (7) and (8); (1), (2), (4), (5), (6), (7) and (8); and (1), (3), (4), (5), (6), (7) and (8). Preferably, the compound represented by Structural Formula (I) is characterized by all of Features (1)-(8).

Alternatively, the compound represented by Structural Formula (I) is characterized as described in the previous paragraph, except that for feature (1), $X_1$ is C=O and C=Z is absent.

In one preferred embodiment, the CCR8 inhibitor is represented by any one of Structural Formulas (II)-(VI):

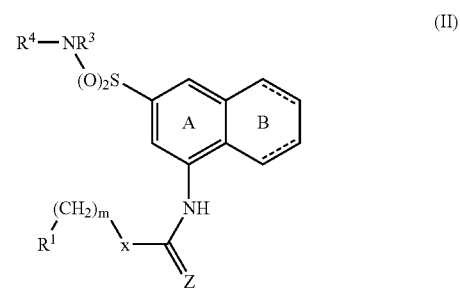

(II)

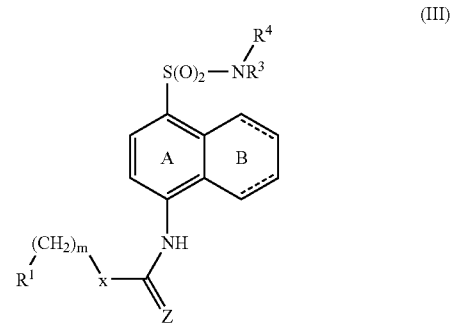

(III)

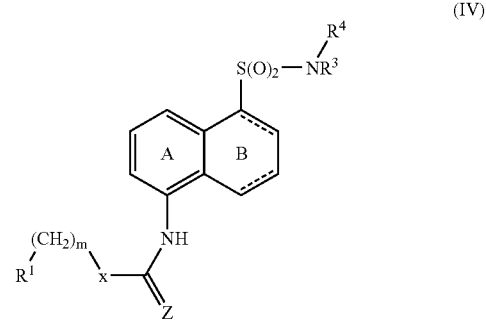

(IV)

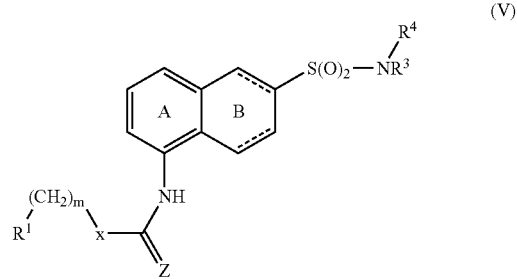

(V)

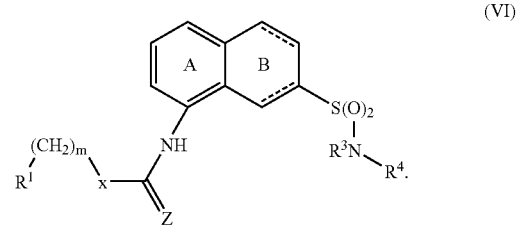

(VI)

In another preferred embodiment, the CCR8 inhibitor is represented by any one of Structural Formulas (VII)-(XI):

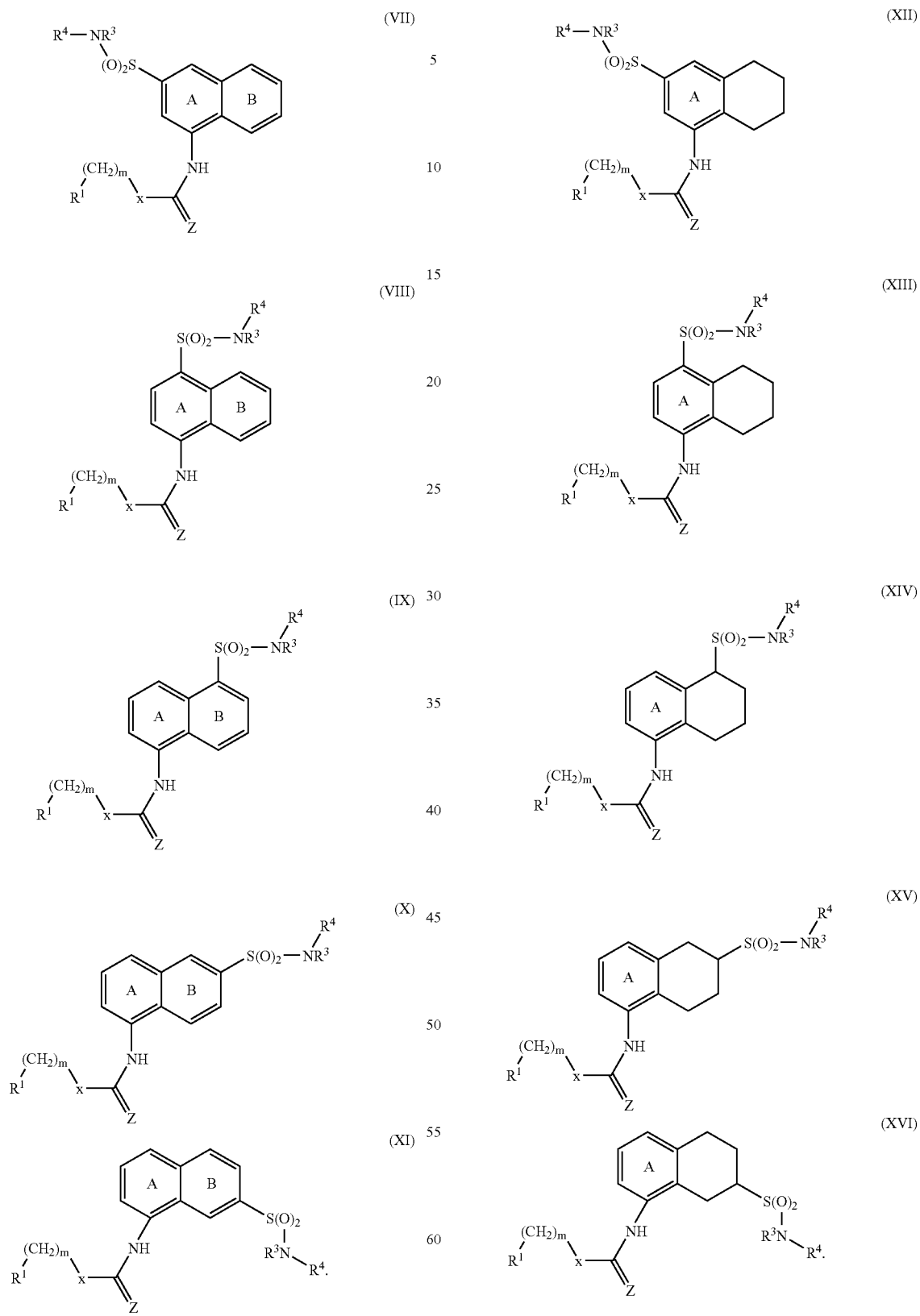
In another preferred embodiment, the CCR8 inhibitor is represented by any one of structural Formulas (XII)-(XVI):
In yet another preferred embodiment, the CCR8 inhibitor is represented by any one of structural Formulas (XVII)-(XXI):

In yet another preferred embodiment, the CCR8 inhibitor is represented by any one of structural Formulas (XXII)-(XXVI):
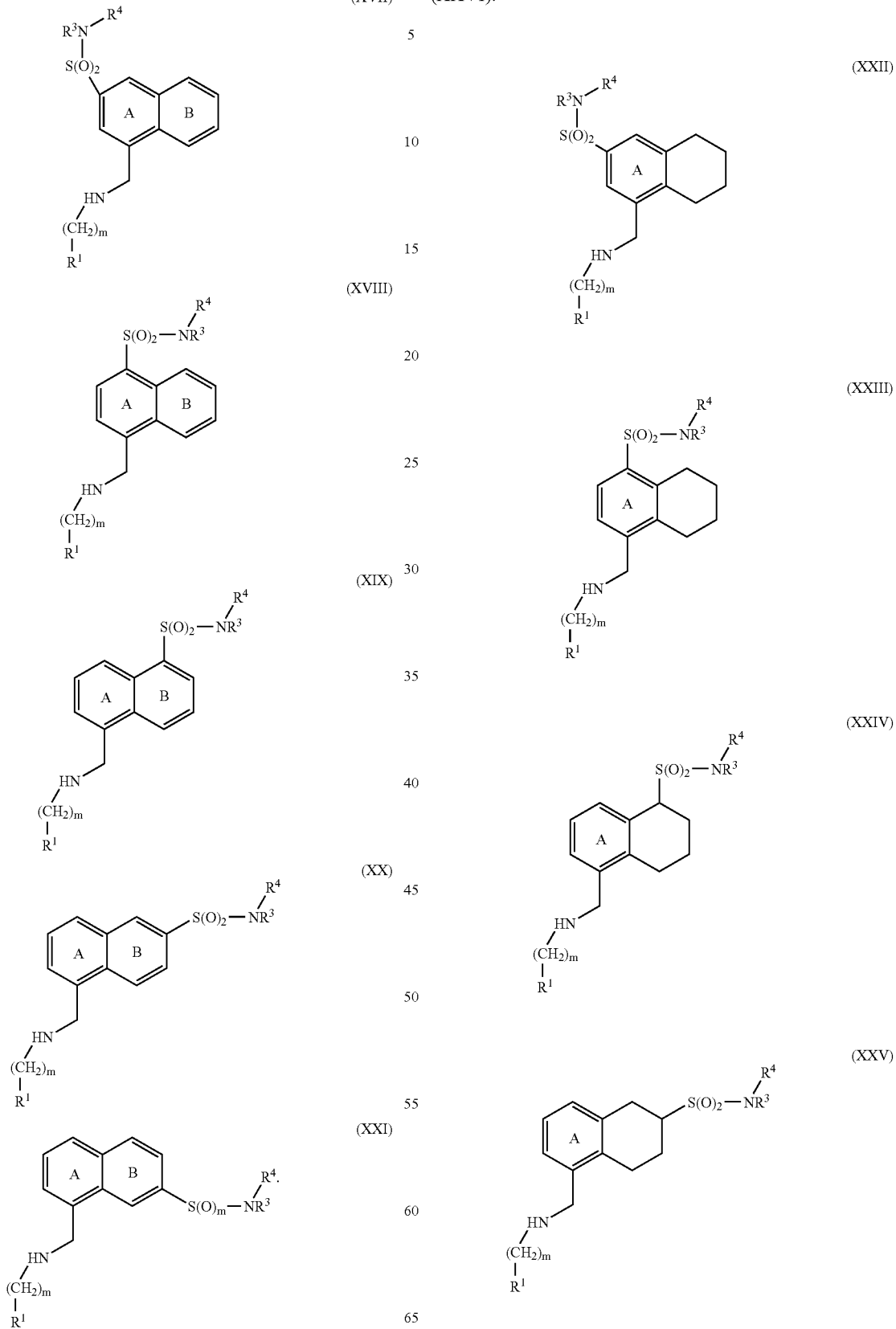

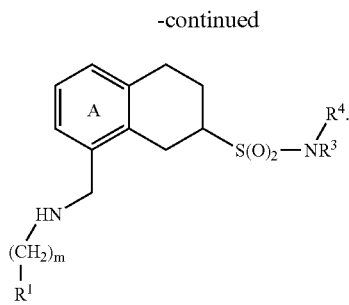

(XXVI)

In yet another preferred embodiment, the CCR8 inhibitor is represented by any one of structural Formulas (XXVII)-(XXXI):

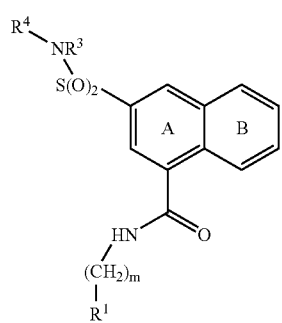

(XXVII)

(XXVIII)

(XXIX)

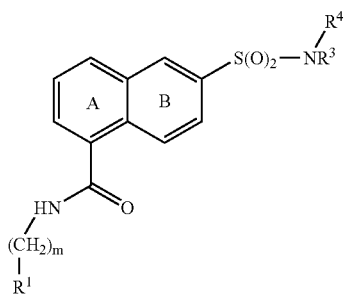

(XXX)

(XXXI)

In yet another preferred embodiment, the CCR8 inhibitor is represented by Structural Formulas (XXXII) or (XXXIII):

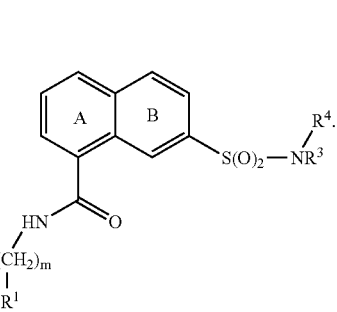

(XXXII)

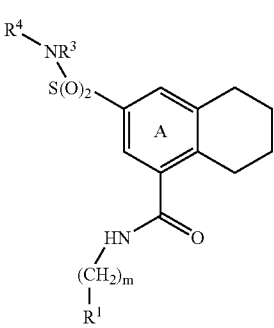

(XXXIII)

In yet another preferred embodiment, the CCR8 inhibitor is represented by structural Formulas (XXXIV) or (XXXV):

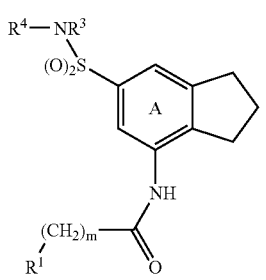

(XXXIV)

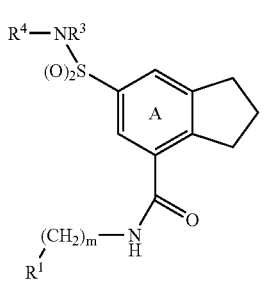

(XXXVIII)

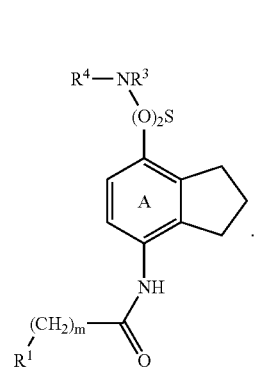

(XXXV)

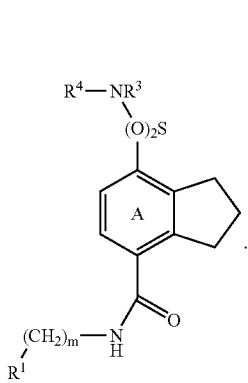

(XXXIX)

In yet another preferred embodiment, the CCR8 inhibitor is represented Structural Formulas (XXXVI) or (XXXVII):

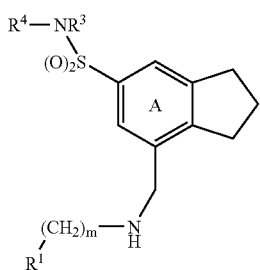

(XXXVI)

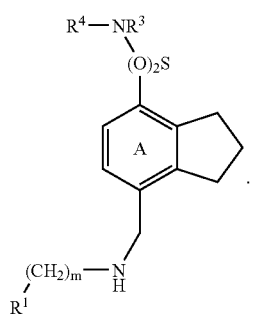

(XXXVII)

In yet another preferred embodiment, the CCR8 inhibitor is represented by Structural Formulas (XXXVIII) or (XXXIX):

The 1,4- and 1,5-substitution patterns (e.g., Structural Formulas (III), (IV), (VIII), (IX), (XIII), (XIV), (XVIII) (XXIX), (XXIII), (XXIV), (XXVIII), (XXIX) and (XXXII)-(XXXIX)) are preferred. 1,4-Naphthylsulfonamides and 1,4-tetrahydronaphthylsulfonamides are disclosed in the co-pending U.S. Provisional Patent Application No. 60/436,508 entitled CCR8 INHIBITORS, filed on Dec. 23, 2002, and U.S. Utility Application, Attorney Docket No. 1855.2047-001, entitled CCR8 INHIBITORS, filed on Dec. 22, 2003. The entire teachings of both applications are incorporated herein by reference.

Rings A and B in Structural Formulas (II)-(XI) and (XVII)-(XXXI) and Ring A in Structural Formulas (XII)-(XVI), (XXII)-XXVI) and (XXXII)-(XXXIX) are optionally and independently substituted at any one or more substitutable ring carbons. Exemplary substituents for Rings A and B are provided hereinbelow in the section describing aromatic group substituents. Preferred substituents for Rings A and B include alkyl, haloalkyl, halogen, cyano, nitro, hydroxy, haloalkoxy and alkoxy. Preferably, Rings A and B are unsubstituted.

The values of the other variables in Structural Formulas (II)-(LXXXIX) are as defined for Structural Formula (I). In Structural Formulas (II)-(XXXIX), X is preferably a covalent bond.

One preferred value for $R^4$ in Structural Formulas (I)-(XXXIX) is a substituted or unsubstituted non-aromatic ring. Suitable substituents for a non-aromatic ring represented by $R^4$ are provided hereinbelow in the section describing substituents for a non-aromatic group and in the section below describing substituents for the nitrogen atom of a non-aromatic heterocyclic group. When $R^4$ in Structural Formulas (I)-(XXXIX) is a non-aromatic ring, preferred values include a piperidinyl group, an N-substituted piperidinyl group, or a cyclohexyl group. Suitable substituents for the nitrogen atom in a piperidinyl group represented by $R^4$ are provided hereinbelow in the section describing substituents on the nitrogen atom of a non-aromatic heterocyclic group. Preferred substituents for the nitrogen atom in a piperidinyl group represented by $R^4$ include $R^{15}$, —C(O)$R^{15}$, —C(O)O$R^{15}$ and —C(O)—NH$R^{15}$. Other preferred substituents for the nitrogen atom in a piperidinyl group represented by $R^4$ include —C(O)—N($R^5$)$_2$ or —C(O)CH[N($R^{16}$)$_2$]$R^{17}$. $R^{15}$ is —H, a non-aromatic ring or a substituted or unsubstituted aliphatic group or a substituted or unsubstituted C7-C9 aralkyl group. Typically, however, —C(O)O$R^{15}$ is not —COOH. $R^{15}$ can also be a substituted non-aromatic ring. In addition, N($R^{15}$)$_2$ taken together can be a substituted or unsubstituted five or six membered non-aromatic nitrogen-containing heterocyclic group. Preferred substituents for a substitutable carbon of the non-aromatic ring represented by $R^{15}$ or the non-aromatic heterocyclic group represented by N($R^{15}$)$_2$ included methyl, ethyl hydroxyethyl and iso-propyl; suitable substituents for a substitutable nitrogen of these groups include alkyl, alkylcarbonyl, alkoxycarbonyl, aminocarbonyl, alkylaminocarbonyl and dialkylaminocarbonyl. $R^{16}$ is —H or an alkyl group. $R^{17}$ is —H; a C1-C6 alkyl group optionally substituted with —OH, —NH$_2$, phenyl or phenyl substituted with —OH; indolyl; imidazolyl; or phenyl optionally substituted with —OH.

Another preferred value for $R^4$ in Structural Formulas (I)-(XXXIX is a phenyl group, a substituted phenyl group, a benzyl group or a substituted benzyl group. Suitable substituents for phenyl and benzyl groups represented by $R^4$ are provided hereinbelow in the section describing suitable aromatic group substituents. Preferred substituents are electron donating groups such as methoxy, ethoxy, iso-propoxy, methyl, ethyl, propyl, NH$_2$, NHCH$_3$, N(CH$_3$)$_2$, NHCH$_2$CH$_3$, N(CH$_2$CH$_3$)$_2$, N(CH$_3$)(CH$_2$CH$_3$), NH(CH$_2$CH$_2$CH$_3$), N(CH$_2$CH$_2$CH$_3$)$_2$, N(CH$_3$)(CH$_2$CH$_2$CH$_3$) or N(CH$_2$CH$_3$)(CH$_2$CH$_2$CH$_3$).

In another preferred embodiment, —NR$^3$R$^4$ in Structural Formulas (I)-(XXXIX), taken together, is a substituted or unsubstituted non-aromatic heterocyclic group. Suitable substituents for a non-aromatic heterocyclic group represented by —NR$^3$R$^4$ are provided hereinbelow in the section describing suitable substituents for a non-aromatic group and in the section describing suitable substituents for the nitrogen atom of a non-aromatic heterocyclic group.

In Structural Formulas (I)-(XXXIX), $R^1$ is preferably a substituted or unsubstituted cyclohexyl group, a substituted or substituted phenyl group, a substituted or substituted benzyl group, a substituted or substituted pyridyl group or a substituted or a substituted —CH$_2$-(pyridyl) group, and more preferably is an unsubstituted phenyl group, an unsubstituted benzyl group or a phenyl or benzyl group substituted with an electron donating group. When $R^1$ has these values, then $R^4$ preferably is a piperidinyl group, an N-substituted piperidinyl group, a cyclohexyl group, a substituted cyclohexyl group, an unsubstituted phenyl group, an unsubstituted benzyl group or a phenyl or benzyl group substituted with an electron donating group or —NR$^3$R$^4$ taken together is a nitrogen-containing non-aromatic heterocyclic ring, as described in the previous three paragraphs. Preferred substituents for the nitrogen atom in the piperidinyl group represented by $R^4$ and recited in this paragraph include $R^{15}$, —C(O)$R^{15}$, —C(O)O$R^{15}$, —C(O)—NHR$^{15}$, —C(O)—N (R$^{15}$)$_2$ and —C(O)CH[N(R$^{16}$)$_2$]R$^{17}$.

Also disclosed is a compound represented by Structural Formulas (II)-(XVI) wherein the X—(C=Z)-NH group is replaced with a carbamate (—O—C(O)NH—), a thiocarbamate (—O—C(S)NH—), a urethane (NH—C(O)—NH—) or a thiourethane group (NH—C(S)—NH—).

Yet another preferred embodiment of the present invention is a compound represented by Structural Formulas (XL) or (XLI):

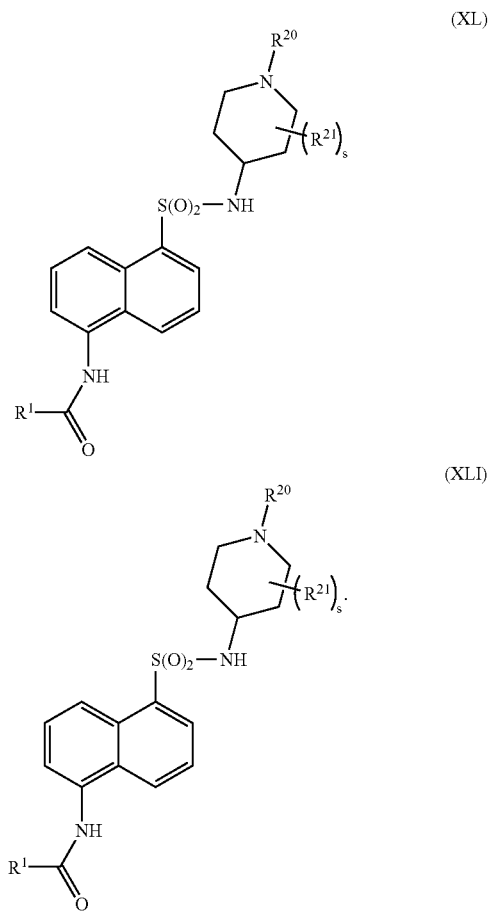

The variables in Structural Formulas (XL) and (XLI) are defined below.

$R^1$ is cyclohexyl or phenyl, furanyl, thienyl or pyridyl optionally substituted with C1-C4 alkyl, C1-C4 alkoxy, C1-C4 haloalkyl, C1-C4 haloalkoxy, methylenedioxy, ethylenedioxy, halogen, cyano, or nitro.

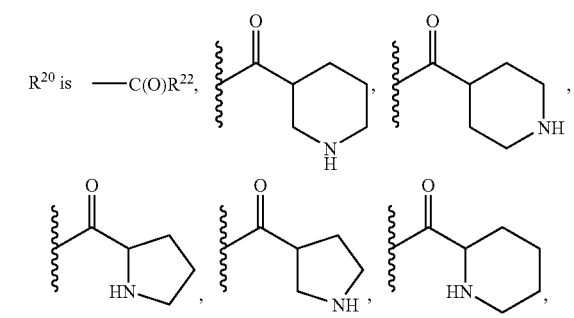

—C(O)—NHR$^{22}$, —C(O)—N(R$^{22}$)$_2$ or —C(O)CH[N(R$^{23}$)$_2$]R$^{24}$.

R$^{21}$ is methyl, ethyl 2-hydroxyethyl or iso-propyl. R$^{21}$ indicates that the piperidinyl groups in Structural Formulas (XI) and (XII) are optionally substituted at up to four substitutable carbon atoms with R$^{21}$. A substitutable methylene group in the piperidinyl rings can optionally be substituted with up to two independently selected R$^{21}$'s.

R$^{22}$ is —H or C1-C4 alkyl or —N(R$^{22}$)$_2$ taken together is N-pyrollidinyl or N-piperidinyl, provided that R$^2$ is not —H when R$^2$ is —COOR$^{22}$.

R$^{23}$ is —H, methyl or ethyl.

R$^{24}$ is —H, methyl, ethyl, phenyl, benzyl, 4-hydroxyphenyl or 4-hydroxybenzyl.

s is 0, 1, 2, 3, or 4.

Also disclosed herein is a compound represented by any one of Structural Formulas (I)-(XLI) and methods of use thereof for treating a subject with a CCR8 mediated condition or disease and pharmaceutical compositions comprising the same, wherein R$^1$ has the value corresponding to any one of the compounds in the Tables and Examples in the Exemplification Section and the remainder of the variables are as defined above.

Also disclosed herein is a compound represented by any one of structural Formulas (I)-(XLI) and methods of use thereof for treating a subject with a CCR8 mediated condition or disease and pharmaceutical compositions comprising the same, wherein NR$^3$R$^4$ has the value corresponding to any one of the compounds in the Tables or Example in the Exemplification Section and the remainder of the variables are as defined above.

The term "aliphatic" as used herein means straight-chain or branched hydrocarbons which are completely saturated or which contain one or more units of unsaturation, but which are not aromatic. An aliphatic group is typically C$_{1-8}$, more typically C$_{1-6}$. For example, suitable aliphatic groups include substituted or unsubstituted linear or branched alkyl, alkenyl, alkynyl groups and hybrids thereof. The terms "alkyl", "alkoxy", "hydroxyalkyl", "alkoxyalkylene", and "alkoxycarbonyl", used alone or as part of a larger moiety includes both straight and branched saturated chains containing one to eight carbon atoms. The terms "alkenyl" and "alkynyl" used alone or as part of a larger moiety shall include both straight and branched chains containing two to eight carbon atoms and one or more double and/or triple bonds, respectively.

The term "non-aromatic ring", used alone or as part of a larger moiety, includes non-aromatic heterocyclic groups and cycloaliphatic groups.

The term "haloalkyl" means an alkyl group substituted with one or more halogens.

The term "cycloaliphatic" used alone or as part of a larger moiety, shall include cyclic C$_3$-C$_{10}$ hydrocarbons which are completely saturated or which contain one or more units of unsaturation, but which are not aromatic. Cycloaliphatic groups are typically C$_{3-10}$, more typically C$_{3-7}$. A "cycloalkyl" is a cyclic aliphatic group that is completely saturated.

The term "non-aromatic bridged bicyclic group", used alone or as part of a larger moiety, shall include bicyclic ring systems comprising from seven to fifteen ring atoms in which at least three adjacent ring atoms in the bicyclic ring system are shared by both rings. The ring systems can be carbocyclic, in which all ring atoms are carbon, or heterocyclic ("bridged bicyclic non-aromatic heterocyclic groups"), in which one or more ring carbons are replaced with nitrogen, oxygen, sulfur and the like. Examples are shown below:

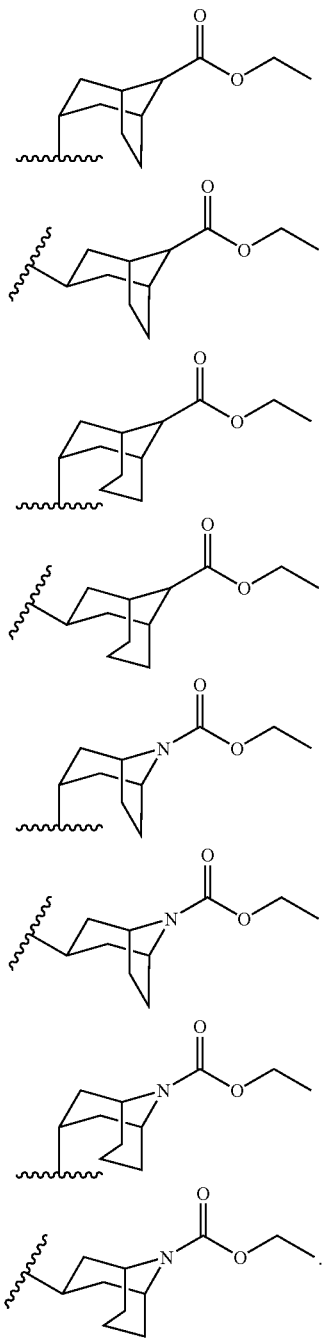

Suitable substituents for substitutable carbon atoms of a non-aromatic bridged bicyclic group are as provided below for non-aromatic heterocyclic groups. Suitable substituents for substitutable nitrogen atoms of a non-aromatic bridged bicyclic group are as provided below for non-aromatic heterocyclic groups.

"Alkoxy" means (alkyl)-O—; "alkoxyalkylene" means (alkyl)-O-(alkylene) such as methoxymethylene (CH$_3$OCH$_2$); "hydroxyalkyl" means hydroxy substituted alkyl group; "alkoxy carbonyl means a carbonyl substituted with a carbonyl as in (alkyl)-O—C(O)—; and "aralkyl" mean alkyl substituted with an aromatic group. A "C1-C4 aralkyl group", for example, has a C1-C4 alkyl group substituted with an aromatic group.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+ (as in N-substituted pyrrolidinyl).

The term "aromatic group" used alone or as part of a larger moiety as in "aralkyl", "aralkoxy", or "aryloxyalkyl", includes carbocyclic aromatic ring groups and heteroaryl rings groups. The term "aromatic group" may be used interchangeably with the terms "aryl", "aryl ring" or "aromatic ring".

Carbocyclic aromatic ring groups have only carbon ring atoms and include monocyclic aromatic rings such as phenyl and fused polycyclic aromatic ring systems in which two or more carbocyclic aromatic rings are fused to one another. Examples of carbocyclic aromatic ring groups (including carbocyclic aromatic ring groups for $R^0$, $R^1$ and $R^*$) include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (aliphatic or heterocyclic), such as in an indanyl, phthalimidyl, naphthimidyl, phenantriidinyl, or tetrahydronaphthyl, where the radical or point of attachment is on the aromatic ring.

The term "heteroaryl", "heteroaromatic" or "heteroaryl ring", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other carbocyclic or heteroaromatic aromatic rings. Examples of heteroaryl groups, including heteroaryl groups represented by $R^0$, $R^1$ and $R^*$, include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroaryl ring is fused to one or more cycloaliphatic or non-aromatic heterocyclic groups where the radical or point of attachment is on the heteroaromatic ring. Examples include tetrahydroquinolinyl, tetrahydroisoquinolinyl, and pyrido [3, 4-d] pyrimidinyl.

The term "non-aromatic heterocyclic ring", used alone or as part of a larger moiety as in "hetercyclylalkyl", refers to non-aromatic ring systems typically having five to fourteen members, preferably five to ten, in which one or more ring carbons, preferably one to four, are each replaced by a heteroatom such as N, O, or S. Examples of non-aromatic heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl.

As noted above, the CCR8 inhibitors of the present invention comprise aromatic groups, aliphatic groups and non-aromatic rings (including cycloaliphatic groups and non-aromatic heterocyclic groups) which are optionally substituted, i.e., which comprise one or more substituents. Substituents can be found at one or more substitutable carbon atoms in aromatic groups, aliphatic groups and non-aromatic rings and substitutable nitrogen atoms in heteroaromatic groups and non-aromatic heterocyclic rings. For ease of reference, exemplary substituents at the carbon atoms of an aromatic group represented by $R^1$ are represented by $R^{10}$; exemplary substituents at the carbon atoms of an aliphatic group represented by $R^4$ are represented by $R^{11}$; and exemplary substituents at the carbon atoms of an aromatic group represented by $R^4$ are represented by $R^{12}$.

Suitable values for the substituents represented by $R^{10}$-$R^{12}$ and suitable substituents for the substitutable carbon atoms of Rings A and B and for other aromatic groups, aliphatic groups and non-aromatic rings (including cycloaliphatic rings and non-aromatic heterocyclic rings) that form part(s) of the disclosed CCR8 inhibitors are those which do not significantly reduce the compounds ability to antagonize the activity of CCR8 and/or which do not significantly increase toxicity to the subject. Examples include —$R^0$, —OH, —$OR^0$, —O(haloalkyl), —SH, —$SR^0$, 1,2-methylene-dioxy, 1,2-ethylenedioxy, phenyl (Ph), substituted Ph, —O(Ph), substituted —O(Ph), —$CH_2$(Ph), substituted —$CH_2$(Ph), —$CH_2CH_2$(Ph), substituted —$CH_2CH_2$(Ph), —CN, —$NR'CO_2R^0$, —NR'NR'C(O)$R^0$, —N(R')C(O)N(R')$_2$, —NR'NR'C(O)N(R')$_2$, —NR'NR'CO$_2R^0$, —C(O)C(O)$R^0$, —C(O)CH$_2$C(O)$R^0$, —C(O)$R^0$, —OC(O)$R^0$, —OC(O)N($R^0$)$_2$, —S(O)$_2R^0$, —SO$_2$N(R')$_2$, —S(O)$R^0$, —NR'SO$_2$N(R')$_2$, —NR'SO$_2R^0$, —C(=S)N(R')$_2$, —(CH$_2$)$_y$N(R')$_2$, —C(=NH)—N(R')$_2$, haloalkyl, —V—$R^0$, —V—OH, —V—$OR^0$, —V—SH, —V—$SR^0$, —NR'C(O)$R^0$, —V—CN, —V—NR'CO$_2R^0$, —V—NR'NR'C(O)$R^0$, —V—N(R')C(O)N(R')$_2$, —V—NR'NR'C(O)N(R')$_2$, —V—NR'NR'CO$_2R^0$, —V—C(O)C(O)$R^0$, —V—C(O)CH$_2$C(O)$R^0$, —V—CO$_2R^0$, —V—C(O)$R^0$, —V—OC(O)$R^0$, —V—OC(O)N($R^0$)$_2$, —V—S(O)$_2R^0$, —V—SO$_2$N(R')$_2$, —V—S(O)$R^0$, —V—NR'SO$_2$N(R')$_2$, —V—NR'SO$_2R^0$, —V—C(=S)N(R')$_2$, —V—(CH$_2$)$_y$N(R')$_2$, or —V—C(=NH)—N(R')$_2$. Additionally, —NO$_2$, —N(R')$_2$, —C(O)N($R^0$)$_2$, —NR'C(O)$R^0$, —NR'C(O)$R^0$, —V—N(R')$_2$, —V—NR'C(O)R' and —V—C(O)N($R^0$)$_2$ are permissible values for $R^{10}$ and $R^{11}$ and are permissible substituents for the substitutable carbon atoms of Rings A and B and for other aromatic groups, aliphatic groups and non-aromatic rings that form part(s) of the disclosed CCR8 inhibitors; and —$COOR^0$ is a permissible value for $R^{10}$ and $R^{12}$ and is a permissible substituent for the substitutable carbon atoms of Rings A and B and for other aromatic groups, aliphatic groups and non-aromatic rings that form part(s) of the disclosed CCR8 inhibitors. Other examples of suitable substituents on the saturated carbon of an aliphatic group (including aliphatic groups represented by $R^4$) and a non-aromatic heterocycle include: =O, =S, =NNHR*, =NN(R*)$_2$, =NNHC(O)R*, =NNHCO$_2$(alkyl), =NNHSO$_2$(alkyl), or =NR*. Except as otherwise provided, preferred substituents for aromatic groups, aliphatic groups and non-aromatic rings (including cycloaliphatic rings and non-aromatic heterocyclic rings) that form part(s) of the disclosed CCR8 inhibitors are alkyl, haloalkyl, halogen, cyano, nitro, hydroxy, haloalkoxy and alkoxy. Amine, alkylamine and dialkyamine are also a preferred substituents for substitutable carbon atoms of an aliphatic group or a non-aromatic ring of the disclosed CCR8 inhibitors. A substitutable methylene group in an aliphatic or non-aromatic ring permissably has up to two substituents. Most commonly, however, the carbon atoms of aliphatic groups and non-aromatic rings (e.g., a non-aromatic ring represented by $R^1$, a non-aromatic heterocyclic group formed from $NR^5(CH_m)R^1$, a non-aromatic ring formed from $NR^3R^4$ or a non-aromatic ring represented by $R^4$) of the disclosed CCR8 inhibitors are unsubstituted or substituted with an alkyl group, hydroxyalkyl group or halogen.

Each R* is independently selected from hydrogen, an unsubstituted aliphatic group or a substituted aliphatic group, preferably from hydrogen or an alkyl group.

Each $R^o$ is independently hydrogen or substituted or unsubstituted aliphatic group, a substituted or unsubstituted cycloaliphatic group, a substituted or unsubstituted non-aromatic heterocyclic group or a substituted or unsubstituted aromatic group, preferably phenyl group. Preferably, each $R^o$ is independently hydrogen, an alkyl group, a cycloalkyl group, a non-aromatic heterocyclic group or an aromatic group (preferably phenyl).

Each R' is independently $R^o$, —CO$_2R^o$, —SO$_2R^o$ or —C(O)$R^o$.

V is a C1-C6 alkylene group.

Suitable substituents on the nitrogen of a non-aromatic heterocyclic group include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR$^+$SO$_2$R$^+$. Other examples include —C(O)—NHR$^+$, —C(O)—N(R$^+$)$_2$, —C(O)—CH[N(R$^+$)$_2$]R$^+$ and —C(O)—CH[OR$^+$]R$^+$.

R$^+$ is hydrogen, an aliphatic group, a substituted aliphatic group, phenyl, substituted phenyl, benzyl, substituted benzyl or an unsubstituted heteroaryl or non-aromatic heterocyclic ring. R$^+$ can also be a substituted non-aromatic heterocyclic group and a substituted or unsubstituted cycloaliphatic group; or N(R$^+$)$_2$ is a non-aromatic heterocyclic group.

Examples of substituents on the aliphatic group represented by R*, examples of substituents on the aliphatic, aromatic, cycloaliphatic or non-aromatic heterocyclic group represented by R$^o$ and examples of substituents on the aliphatic group, phenyl group, phenoxy group or benzyl group represented by R$^+$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An "electron donating group" is a substituent which results in a phenyl ring that has more electron density when the group is present than when it is absent. Electron donating groups have a Hammet sigma value greater than one (see, for example, C. Hansch, A. Leo and D. Hoeckman, "Exploring QSAR Hydrophobic, Electronic and Steric Constants", American Chemical Society (1995), pages 217-32). Examples of electron donating groups include alkoxy groups, alkyl groups, amine, alkylamine and dialkylamine.

Additionally, pharmaceutically acceptable salts of the compounds disclosed herein are also included in the present invention and can be used in the compositions and methods disclosed herein. For example, an acid salt of a compound containing an amine or other basic group can be obtained, by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fiumarates, tartrates [e.g. (+)-tartrates, (–)-tartrates or mixtures thereof including racemic mixtures], succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

Some of the disclosed CCR8 inhibitors contain one or more chiral centers. The presence of chiral centers in a molecule gives rise to stereoisomers. For example, a pair of optical isomers, referred to as "enantiomers", exist for every chiral center in a molecule; and a pair of diastereomers exist for every chiral center in a compound having two or more chiral centers.

It is to be understood that, when a disclosed CCR8 inhibitor has at least one chiral center, the present invention encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed CCR8 inhibitor has at least two chiral centers, the present invention encompasses a diastereomer free of other diastereomers, a pair of diastereomers free from other diasteromeric pairs, mixtures of diasteromers, mistures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diasteromneric pair(s), the mixture is enriched with the depicted or referenced diastereomer or diastereomeric pair(s) relative to other diastereomers or diastereomeric pair(s) for the compound, for example, by a molar excess of at least 50%, 75%, 90%, 95% 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided in Example 1.

In certain instances compounds of the present invention may associated in isolated form with solvent or water, as in a "solvate" or "hydrate". References to the disclosed compounds or structural formulas depicting the disclosed compounds are meant to include such solvates and hydrates.

The disclosed compounds, pharmaceutical compositions and methods can be used to inhibit CCR8 activity, to inhibit I-309 activity and to inhibit or treat (therapeutically or prophylactically) conditions mediated by CCR8 and/or I-309, including inflammatory disorders and allergic conditions. The disclosed compounds can also be advantageously used to inhibit conditions mediated by esinophils and monocytes, T lymphocytes and other immune system cells which express CCR8, including inflammatory disorders and allergic mediated by these cells.

Examples of allergic conditions for which the disclosed compounds, pharmaceutical compositions and methods are particularly effective include asthma. Other allergic conditions which are expected to be treatable by inhibiting CCR8 activity include, atopic dermatitis, allergic rhinitis, systemic anaphylaxis or hypersensitivity responses, drug allergies (e.g., to penicillin, cephalosporins), insect sting allergies and dermatoses such as dermatitis, eczema, atopic dermatitis, allergic contact dermatitis and urticaria.

Examples of diseases with an inflammatory component for which the disclosed compounds, pharmaceutical composition and methods are effective include rheumatoid arthritis, osteoarthritis, inflammatory bowel disease [e.g., such as ulcerative colitis, Crohn's disease, ileitis, Celiac disease, nontropical Sprue, enteritis, enteropathy associated with seronegative arthropathies, microscopic or collagenous colitis, eosinophilic gastroenteritis, or pouchitis resulting after proctocolectomy, and ileoanal anastomosis] and disorders of the skin [e.g., psoriasis, erythema, pruritis, and acne].

Many autoimmune diseases also have an inflammatory component. Examples include multiple sclerosis, systemic lupus erythematosus, myasthenia gravis, juvenile onset diabetes, glomerulonephritis and other nephritides, autoimmune thyroiditis, Behcet's disease and graft rejection (including allograft rejection or graft-versus-host disease). The inflammatory component of these disorders is believed to be mediated, at least in part, by CCR8.

Diseases characterized by repurfusion have an inflammatory component that is believed to be mediated, at least in part by CCR8. Examples include stroke, cardiac ischemia, and the like. The disclosed compounds and compositions also can be used to treat these disorders.

Other diseases and conditions with an inflammatory component believed to be mediated by CCR8 include mastitis (mammary gland), vaginitis, cholecystitis, cholangitis or pericholangitis (bile duct and surrounding tissue of the liver), chronic bronchitis, chronic sinusitis, chronic inflammatory diseases of the lung which result in interstitial fibrosis, such as interstitial lung diseases (ILD) (e.g., idiopathic pulmonary fibrosis, or ILD associated with rheumatoid arthritis, or other autoimmune conditions), hypersensitivity pneumonitis, collagen diseases and sarcoidosis. Yet other diseases or conditions with inflammatory components which are amendable to treatment according to methods disclosed herein include vasculitis (e.g., necrotizing, cutaneous, and hypersensitivity vasculitis), spondyloarthropathies, scleroderma, atherosclerosis, restenosis and myositis (including polymyositis, dermatomyositis), pancreatitis and insulin-dependent diabetes mellitus.

A subject with a condition having one or more symptoms mediated by CCR8, including one of the aforementioned diseases or conditions, is said "to be in need of CCR8 inhibition". The subject with a disease or condition of this type is "treated" when at least one of the symptoms associated with the disease or condition is alleviated (therapeutic treatment) or inhibited or prevented (prophylactic treatment), in whole or in part.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like). As noted above, a "subject in need of CCR8 inhibition" is a subject in whom a beneficial therapeutic or prophylactic effect can be achieved by inhibiting CCR8 function or activity.

An "effective amount" of the disclosed CCR8 inhibitors is the quantity which inhibits CCR8 activity in a subject in need of such inhibition, or which, when administered to a subject with a CCR8 mediated disease, ameliorates the symptoms of the disease or condition, delays the onset of the symptoms and/or increases longevity. The precise amount of CCR8 inhibitor administered to the subject will depend on the type and severity of the disease or condition and on the characteristics of the subject, such as general health, age, sex, body weight and tolerance to drugs. The dosage may also vary according to the route of administration, which includes oral, aerosol, rectal, transdermal, subcutaneous, intravenous, intramuscular, intraperitoneal and intranasal. The skilled artisan will be able to determine appropriate dosages depending on these and other factors. An "effective amount" typically ranges between about 0.01 mg/kg/day to about 100 mg/kg/day, preferably between about 0.5 mg/kg/day to about 50 mg/kg/day.

The CCR8 inhibitors described herein, and the pharmaceutically acceptable salts thereof can be used in pharmaceutical preparations in combination with a pharmaceutically acceptable carrier or diluent. Suitable pharmaceutically acceptable carriers include inert solid fillers or diluents and sterile aqueous or organic solutions. The CRTH2 inhibitor will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

For oral administration, the CCR8 inhibitor or salts thereof can be combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parental administration, the disclosed CCR8 inhibitor, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

In accordance with conventional methods for showing structural formulas of compounds, a terminal methyl group in a compound described herein can be shown as a straight line with or without "CH3" on its terminus:

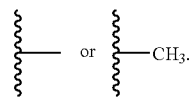

In certain aspects, the present invention is directed to a compound represented by any one of Structural Formulas (I)-(XVI) (and methods of use thereof), provided that when $R^1$ is a substituted aromatic group, then the aromatic group represented by $R^1$ is substituted with a group other than pyrazole; provided that when X is O and $R^4$ is an aliphatic group, then the aliphatic group represented by $R^4$ is substituted with a group other than —COOR$^X$; and provided that when $R^4$ is a substituted phenyl, substituted benzyl or substituted phenethyl group, then the phenyl, benzyl or phenethyl group represented by $R^4$ is substituted with a group other than —NO$_2$, —NR$^X$R$^X$, —CONR$^X$R$^X$, —NR$^X$COR$^X$, or an aliphatic group substituted with —NO$_2$, —NR$^X$R$^X$, —CONR$^X$R$^X$, —NR$^X$COR$^X$. Each R$^X$ is independently H, an aliphatic group, a substituted aliphatic group, an aryl group, a substituted aryl group, a non-aromatic ring or a substituted non-aromatic ring. Alternatively, or in addition, the subject matter encompassed by Structural Formulas (I)-(III) excludes N-[4-[[(4-methoxyphenyl)amino]sulfonyl]-1-naphthalenyl]-benzamide, N-[4-[(2-propenylamino)sulfonyl]-1-naphthalenyl]-benzamide, N-[4-(4-morpholinylsulfonyl)-1-naphthalenyl]-benzamide or N-[4-(1-piperidinylsulfonyl)-1-naphthalenyl]-benzamide.

The invention is illustrated by the following examples which are not intended to be limiting in any way.

Experimental Procedure for Naphthalene Sulfonamides

General

All reactions involving air-sensitive reagents were performed under a nitrogen atmosphere. Reagents were used as received from commercial suppliers unless otherwise noted. Anhydrous solvents such as dimethylformamide (DMF), tetrahydrofuran (THF), dichloromethane (CH$_2$Cl$_2$), and dioxane were obtained from Aldrich Chemical Company in Sure/Seal bottles. $^1$H NMR data were recorded using the Bruker UltraShield 300 MHz/54 mm instrument equipped with Bruker B-ACS60 Auto Sampler or the Varian 300 MHz instrument. Chemical shifts are expressed in ppm downfield from internal tetramethylsilane. Significant $^1$H NMR data are reported in the following order: ppm, multiplicity (s, singlet; d, doublet; t, triplet; q, quartet; m, multiplet; quin, quintet), and number of protons. Intermediates and final compounds were purified by flash chromatography using one of the following instruments: 1. Biotage 4-channel Quad UV Flash Collector equipped with a Quad 1 Pump Module and the Quad 12/25 Cartridge module. 2. Biotage 12-channel Quad UV Flash Collector equipped with a Quad 3 Pump Module and a Quad 3 Cartridge module. 3. Flash column combi-flash chromatography instrument. LC/MS spectra were obtained using a MicroMass Platform LC (Phenomenx C18 column, 5 micron, 50×4.6 mm) equipped with a Gilson 215 Liquid Handler. Standard LC/MS conditions are as follows: Formic acid-Standard conditions:

| | |
|---|---|
| % C (Water) | 95.0 |
| % D (Acetonitrile) | 5.0 |
| % Formic Acid | 0.1 |
| Flow (mL/min) | 3.500 |
| Stop Time (mins) | 4.4 |
| Min Pressure (bar) | 0 |
| Max Pressure (bar) | 400 |
| Oven Temperature Left(° C.) | 25.0 |
| Oven Temperature Right(° C.) | 25.0 |

HP1100 LC Pump Gradient Timetable
The gradient Timetable contains 5 entries which are:

| Time | A % | B % | C % | D % | Flow | Pressure |
|---|---|---|---|---|---|---|
| 0.00 | 0.0 | 0.0 | 95.0 | 5.0 | 3.500 | 400 |
| 3.50 | 0.0 | 0.0 | 0.0 | 100.0 | 3.500 | 400 |
| 4.30 | 0.0 | 0.0 | 0.0 | 100.0 | 3.500 | 400 |
| 4.40 | 0.0 | 0.0 | 95.0 | 5.0 | 4.000 | 400 |
| 5.00 | 0.0 | 0.0 | 95.0 | 5.0 | 4.000 | 400 |

LC-MS data were acquired using the "Formic acid-Standard" method unless otherwise noted.

Scheme 1: Preparation of amine intermediates
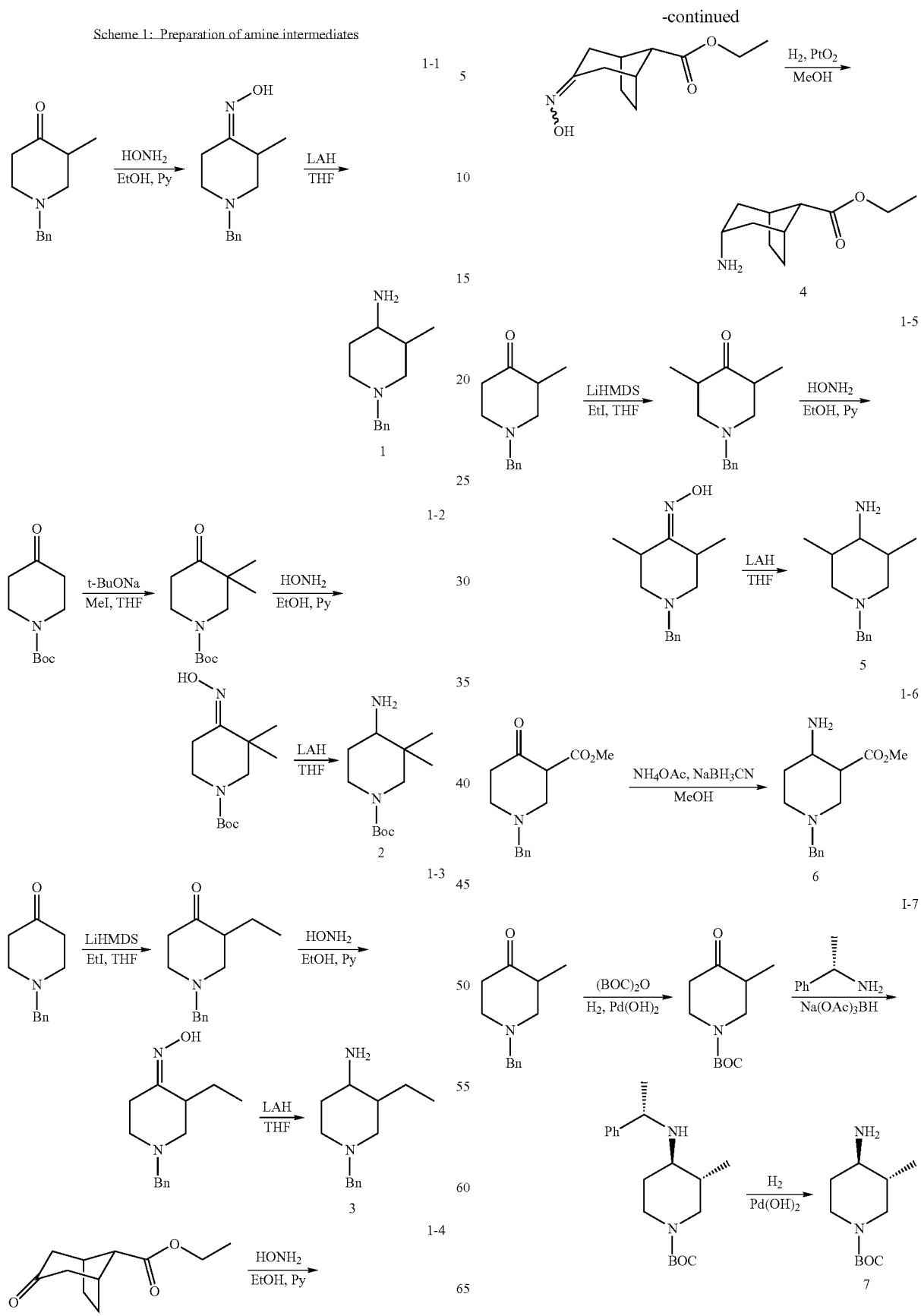

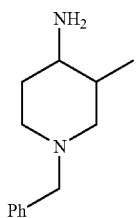

1-Benzyl-3-methyl-piperidin-4-ylamine (1)

To a solution of 1-benzyl-3-methyl-piperidin-4-one (2.04 g, 10 mmol) in EtOH (20 mL), was added pyridine (20 mL, 0.25 mol) and hydroxylamine hydrochloride (0.70 g, 10 mmol). After being stirred at 90° C. overnight, the resultant solution was concentrated in vacuo to give the crude product 1-benzyl-3-methyl-piperidin-4-one oxime. LCMS m/z: 219 (M+H)$^+$. This material was used without further purification.

To a 25° C. solution of 1-benzyl-3-methyl-piperidin-4-one oxime in anhydrous THF (20 mL) was added LAH (1.0 M solution THF), (15 mL, 15 mmol). After being stirred at 50° C. overnight, the resultant mixture was quenched with 20% KOH solution. The aqueous layer was extracted with CH$_2$Cl$_2$. The organic extracts were combined, washed with brine and dried over MgSO$_4$. The solution was filtered and concentrated in vacuo to give the crude mixture ((±)-cis:(±)-trans=1:1) 1-benzyl-3-methyl-piperidin-4-ylamine (1). LCMS m/z: 205 (M+H)$^+$. This material was used without further purification.

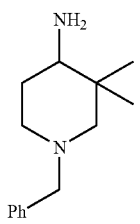

(±)-1-Benzyl-3,3-dimethyl-piperidin-4-one (2)

To a solution of 1-benzyl-3-methyl-piperidin-4-one (7.0 g, 34 mmol) and MeI (2.4 mL) in THF (100 mL) was added NaOt-Bu (4.2 g, 44 mmol) at 0° C. The reaction was slowly allowed to warm to room temperature and stirred overnight. The aqueous layer was extracted with CH$_2$Cl$_2$. The organic extracts were combined, washed with brine and dried over MgSO$_4$. The solution was filtered and concentrated in vacuo to give the crude product. Flash column chromatography (Hexane/EtOAc, gradient) of the residue gave 1-benzyl-3,3-dimethyl-piperidin-4-one, which was converted into 1-benzyl-3,3-dimethyl-piperidin-4-ylamine (2) using the same procedure as in Scheme 1-1. LCMS m/z: 220 (M+H)$^+$. This material was used without further purification.

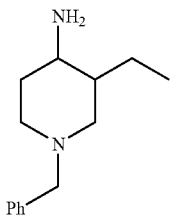

1-Benzyl-3-ethyl-piperidin-4-one (3)

To a −78° C. solution of 1-benzyl-piperidin-4-one (3.79 g, 20 mmol) in anhydrous THF (20 mL) was added lithium hexamethyldisilazide (21 mL, 21 mmol of a 1.0 M solution in THF). After being stirred at −78° C. for 30 min, a solution of iodoethane (1.7 mL, 21 mmol) in THF (5 mL) was added to the reaction mixture. The resultant solution was stirred at 25° C. for 2 h and quenched with water. The aqueous layer was extracted with CH$_2$Cl$_2$. The organic extracts were combined, washed with brine and dried over MgSO$_4$. The solution was filtered and concentrated in vacuo to give the crude product. The crude material was purified by flash column chromatography (hexane/EtOAc) to provide 0.51 g (11.5% yield) of 1-benzyl-3-ethyl-piperidin-4-one, which was converted into 1-benzyl-3-ethyl-piperidin-4-ylamine (3) using the same procedure as in Scheme 1-1. ((±)-cis:(±)-trans=1:1) LCMS m/z: 219 (M+H)$^+$. This material was used without further purification.

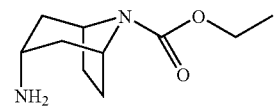

cis-3-Amino-8-aza-bicyclo[3.2.1]octane-8-carboxylic acid ethyl ester (4)

The titled compound was made following the procedure in Scheme 1-1. The oxime (prepared as detailed in Scheme 1-1) (2.5 g) was dissolved in MeOH (10 mL) and AcOH (2 mL) and PtO$_2$ (100 mg) were added at the resultant mixture stirred at room temperature. The reaction mixture was shaken for 2 days at 60 psi under an atmosphere of H$_2$. The resultant solution was filtered and concentrated to give the crude product of racemic 3-amino-8-aza-bicyclo[3.2.1]octane-8-carboxylic acid ethyl ester. It was used without further purification.

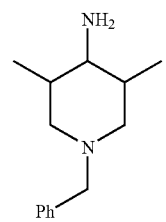

1-Benzyl-3,5-dimethyl-piperidin-4-ylamine (5)

To a −78° C. solution of 1-benzyl-3-methyl-piperidin-4-one (4.06 g, 20 mmol) in anhydrous THF (20 mL) was added lithium hexamethyldisilazide (21 mL, 21 mmol of a 1.0 M solution THF). After being stirred at −78° C. for 30 min, a solution of iodomethane (1.31 mL, 21 mmol) in THF (5 mL) was added into the reaction mixture. The resultant solution was stirred at 25° C. for 2 h and quenched with water. The aqueous layer was extracted with $CH_2Cl_2$. The organic extracts were combined, washed with brine and dried over $MgSO_4$. The solution was filtered and concentrated in vacuo to give the crude product. The crude material was purified by flash column chromatography (hexane/EtOAc) to provide 1.37 g (31.5% yield) of 1-benzyl-3,5-dimethyl-piperidin-4-one.

Following the same procedure as in Scheme 1-1, the crude product 1-benzyl-3,5-dimethyl-piperidin-4-ylamine (5) was prepared as a mixture of diastereomers. LCMS m/z: 219 (M+H)$^+$. This material was used without further purification.

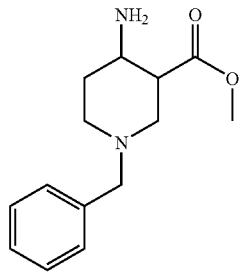

4-Amino-1-benzyl-piperidine-3-carboxylic acid methyl ester (6)

To a 25° C. solution of 1-benzyl-4-oxo-piperidine-3-carboxylic acid methyl ester hydrochloride (2.97 g, 10 mmol) in MeOH (10 mL) was added MP-Carbonate (12 g, 30 mmol, 2.54 mmol/g). After shaking at 25° C. for 1 h, the solution was filtered. To the resultant solution was added ammonium acetate (7.71 g, 100 mmol). After stirring at 65° C. overnight, sodium cyanoborohydride (610 mg, 10 mmol) was added into the resultant mixture and the mixture further stirred for 2 h at 50° C. The solution was then concentrated in vacuo to give a solid. The resultant solid was dissolved in water (100 mL) and the aqueous layer was extracted with $CH_2Cl_2$. The organic extracts were combined, washed with brine and dried over $MgSO_4$. The solution was filtered and concentrated in vacuo to give the crude product 4-amino-1-benzyl-piperidine-3-carboxylic acid methyl ester (6) as a mixture of diastereomers. LCMS showed m/z: 249 (M+H)$^+$. This material was used without further purification.

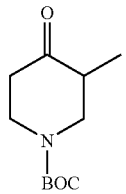

(±)-3-Methyl-4-oxo-piperidine-1-carboxylic acid tert-butyl ester

1-Benzyl-3-methyl-piperidin-4-one (6.5 g, 32.0 mmol) was dissolved in methanol (30 mL). Di-tert-butyl dicarbonate (10.46 g, 48.0 mmol) was added followed by palladium hydroxide (20%, 100 mg) and the reaction shaken overnight at 55 psi under a hydrogen atmosphere. The reaction was filtered and concentrated in vacuo to give a clear oil. Flash column chromatography (75:25 hexanes/ethyl acetate) afforded the title compound as a white solid. Wt.: 5.5 g (81%). $^1$H NMR (300 MHz, CDCl$_3$) δ 4.18 (m, 2H), 3.25 (m, 1H), 2.84 (m, 1H), 2.53 (m, 1H), 2.43 (m, 2H), 1.50 (s, 9H), 1.05 (d, 3H).

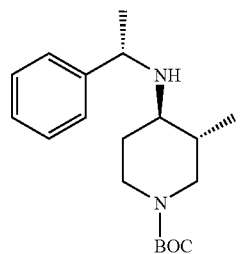

(3R, 4R)-3-methyl-4-(1-(S)-phenyl-ethylamino)-piperidine-1-carboxylic acid tert-butyl ester (±)-3-Methyl-4-oxo-piperidine-1-carboxylic acid tert-butyl ester (5.4 g, 25.3 mmol) was dissolved in dichloromethane (75 mL). S-(−)-α-Methylbenzylamine (3.1 g, 3.2 mL, 25.3 mmol) was added followed by sodium triacetoxyborohydride (10.7 g, 50.6 mmol). The reaction was stirred at room temperature overnight. LC/MS analysis revealed four components, with only one component clearly separated. The reaction was diluted with dichloromethane (150 mL) and extracted water (2×), brine and dried over MgSO$_4$. The solution was filtered and concentrated in vacuo to afford a white foam that was purified by flash column chromatography (84.5:15:0.5 dichloromethane:acetonitrile:NH$_4$OH) to afford a clear oil. This material was rechromatographed (89.5:10:0.5 dichloromethane:acetonitrile:NH$_4$OH) to afford the title compound as a clear oil. Wt.: 820 mg (10%). $^1$H NMR (300 MHz, CDCl$_3$) δ7.31 (m, 3H), 7.22 (m, 2H), 3.85 (m, 3H), 2.68 (m, 1H), 2.46 (m. 1H), 2.17 (m, 1H), 1.67 (m, 1H), 1.40 (s, 9H), 1.30 (d, 3H), 1.08 (m, 2H), 0.97 (d, 3H); LC/MS m/z 319 (M+H)$^+$.

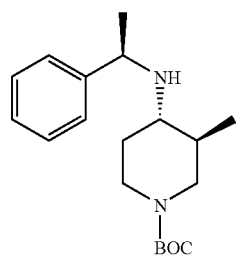

(3S, 4S)-3-methyl-4-(1-(R)-phenyl-ethylamino)-piperidine-1-carboxylic acid tert-butyl ester (±)-3-Methyl-4-oxo-piperidine-1-carboxylic acid tert-butyl ester (5.4 g, 25.3 mmol) was dissolved in dichloromethane (75 mL). R-(+)-α-Methylbenzylamine (3.1 g, 3.2 mL, 25.3 mmol) was added followed by sodium triacetoxyborohydride (10.7 g, 50.6 mmol). The reaction was stirred overnight at room temperature. LC/MS analysis revealed four components, with only one component clearly separated. The reaction was diluted with dichloromethane (150 mL) and extracted twice with water, once with brine and dried over MgSO$_4$. Filtration and concentration in vacuo afforded a white foam that was purified by flash column chromatography (84.5:15:0.5 CH$_2$Cl$_2$:acetonitrile:NH$_4$OH) to afford a clear oil. The material was rechromatographed (89.5:10:0.5 CH$_2$Cl$_2$:acetonitrile:NH$_4$OH) to afford the title compound as a clear oil. Wt.: 547 mg (7%). $^1$H NMR (300 MHz, CDCl$_3$) δ7.31 (m, 3H), 7.22 (m, 2H), 3.85 (m, 3H), 2.68 (m, 1H), 2.46 (m. 1H), 2.17 (m, 1H), 1.67 (m, 1H), 1.40 (s, 9H), 1.30 (d, 3H), 1.08 (m, 2H), 0.97 (d, 3H); LC/MS m/z 319 (M+H)$^+$.

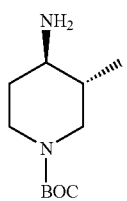

(3R, 4R)-4-amino-3-methyl-piperidine-1-carboxylic acid tert-butyl ester (7)

(3R, 4R)-3-Methyl-4-(1-(S)-phenyl-ethylamino)-piperidine-1-carboxylic acid tert-butyl ester (810 mg, 2.55 mmol) was dissolved in methanol (15 mL). Palladium hydroxide (20%, 100 mg) was added and the mixture was shaken under a hydrogen atmosphere overnight at 55 psi. The reaction was filtered and concentrated in vacuo to give the title compound as a clear oil. Wt.: 500 mg (92%). NMR (300 MHz, CDCl$_3$) δ4.06 (m, 1H), 3.96 (m, 1H), 2.73 (m, 1H), 2.34 (m, 2H), 1.77 (m, 1H), 1.43 (s, 9H), 1.27 (m, 2H), 0.94 (d, 3H); LC/MS m/z 215 (M+H)$^+$.

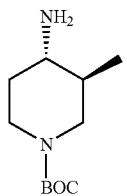

(3S, 4S)-4-amino-3-methyl-piperidine-1-carboxylic acid tert-butyl ester (single enantiomer, absolute configuration undetermined)

(3S, 4S)-3-Methyl-4-(1-(R)-phenyl-ethylamino)-piperidine-1-carboxylic acid tert-butyl ester (510 mg, 1.60 mmol) was dissolved in methanol (15 mL). Palladium hydroxide (20%, 100 mg) was added and the mixture was shaken under a hydrogen atmosphere overnight at 55 psi. The reaction was filtered and concentrated in vacuo to provide the title compound as a clear oil. Wt.: 320 mg (88%). NMR (300 MHz, CDCl$_3$) δ4.06 (m, 1H), 3.96 (m, 1H), 2.73 (m, 1H), 2.34 (m, 2H), 1.77 (m, 1H), 1.43 (s, 9H), 1.27 (m, 2H), 0.94 (d, 3H); LC/MS m/z 215 (M+H)$^+$.

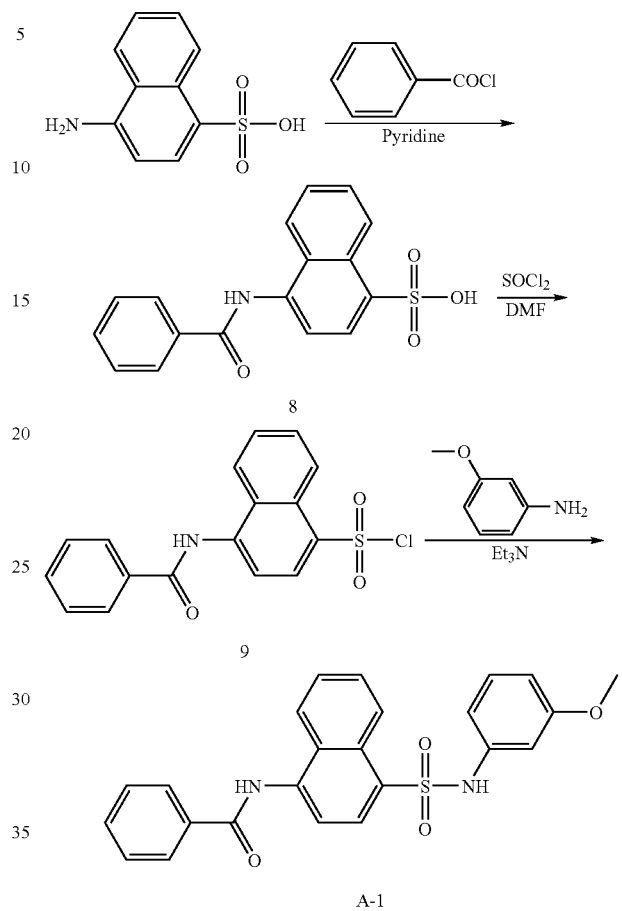

4-Benzoylamino-naphthalene-1-sulfonic acid (8)

To a solution of 4-amino-naphthalene-1-sulfonic acid (2.3 g, 10.0 mmol) in pyridine (15 mL), was added benzoyl chloride (1.4 mL, 12.0 mmol) and the resultant solution was heated at 100° C. and stirred overnight. The solvent was removed in vacuo and the crude material was recrystallized from MeOH (2×) to give the pyridinium salt of 4-benzoylamino-naphthalene-1-sulfonic acid (2.0 g) as a gray colored solid. $^1$H NMR (300 MHz, DMSO) δ8.92 (m, 3H), 8.60 (t, 1H), 8.00 (m, 6H), 7.55 (m, 6H); LC/MS m/z 327 (M−H)$^−$.

4-Benzoylamino-naphthalene-1-sulfonyl chloride (9)

To a solution of the pyridinium salt of 4-benzoylamino-napthalene-1-sulfonic acid (2.4 g, 5.9 mmol) in DMF (10 mL), was added thionyl chloride (0.6 mL, 8.8 mmol). The resultant solution was stirred at 25° C. for 3 hours. The reaction mixture was quenched by pouring into ice water and filtered to give the title compound (1.8 g) a pale white solid. This material was used without further purification.$^1$H NMR (300 MHz, DMSO) δ 8.88 (d, 1H), 8.09 (d, 2H), 7.97 (d, 2H), 7.55 (m, 6H).

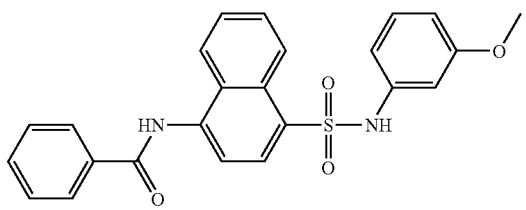

N-[4-(3-Methoxy-phenylsulfamoyl)-naphthalen-1-yl]-benzamide (A-1)

To a solution of 4-benzoylamino-naphthalene-1-sulfonyl chloride (320 mg, 0.93 mmol) in $CH_2Cl_2$ (20 mL) was added triethylamine (0.26 mL, 1.85 mmol) and m-anisidine (137 mg, 1.11 mmol). The resultant solution was stirred at 25° C. overnight. The reaction mixture was quenched with water and extracted with $CH_2Cl_2$. The organic extracts were combined, washed with brine, dried over $Na_2SO_4$, filtered and concentrated to provide the crude product as yellow viscous oil. HPLC purification of the residue gave the title compound (190 mg) as a pale white solid. $^1$H NMR (300MHz, DMSO) δ8.72 (d, 1H), 8.26 (d, 1H), 8.15 (d, 1H), 8.02 (d, 2H), 7.78 (d, 1H), 7.60 (m, 5H), 7.00 (t, 1H), 6.55 (m, 2H), 6.46 (d, 1H), 3.56 (s, 3H); LC/MS m/z 433 (M+H)$^+$.

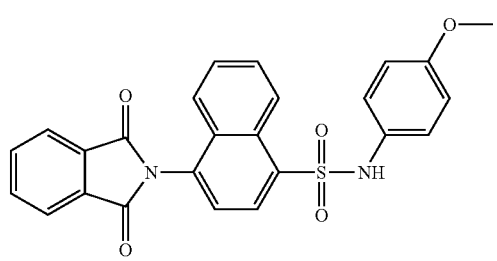

4-(1,3-Dioxo-1,3-dihydro-isoindol-2-yl)-naphthalene-1-sulfonic acid (4-methoxyphenyl)-amide (A-2)

The title compound was made following the general procedure detailed in Scheme 2, substituting phthalic anhydride for benzoyl chloride and benzylamine for m-anisidine. $^1$H NMR (300 MHz, CDCl$_3$) δ8.75 (d, 1H), 8.20 (d, 1H), 8.02 (m, 2H), 7.87 (m, 2H), 7.66 (m, 3H), 7.42 (d, 1H), 6.86 (d, 2H), 6.69 (d, 2H), 3.72 (s, 3H); LC/MS m/z 459 (M+H)$^+$.

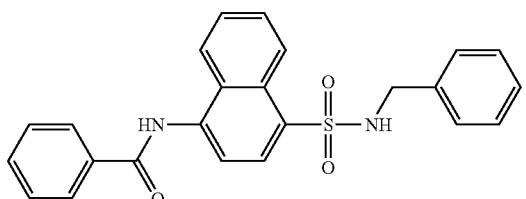

N-(4-Benzylsulfamoyl-naphthalen-1-yl)-benzamide (A-3)

The title compound was made following the general procedure in Scheme 2, substituting benzylamine for m-anisidine. $^1$H NMR (300 MHz, DMSO) δ8.71 (d, 1H), 8.18 (m, 2H), 8.11 (d, 2H), 7.90 (d, 1H), 7.60 (m, 5H), 7.40 (m, 5H), 4.05 (s, 2H); LC/MS m/z 417 (M+H)$^+$.

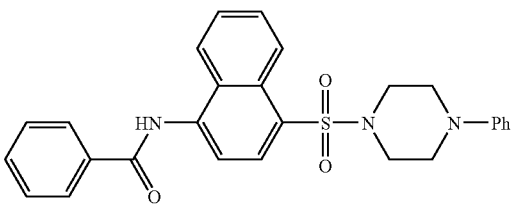

N-[4-(4-Phenyl-piperazine-1-sulfonyl)-naphthalen-1-yl]-benzamide (A-5)

The title compound was made following general procedure in Scheme 2, substituting 1-phenyl-pyrazine for m-anisidine. $^1$H NMR (300 MHz, DMSO) δ8.68 (d, 1H), 8.22 (d, 1H), 8.05 (d, 1H), 7.87 (d, 1H), 7.60 (m, 5H), 7.15 (m, 2H), 6.85 (d, 2H), 6.72 (t, 1H), 3.17 (m, 4H), 3.11 (m, 4H); LC/MS m/z 472 (M+H)$^+$.

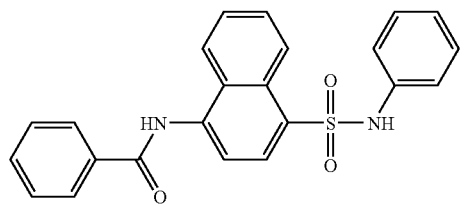

N-(4-Phenylsulfamoyl-naphthalen-1-yl)-benzamide (A-7)

The title compound was made following the general procedure in Scheme 2, substituting aniline for m-anisidine. $^1$H NMR (300 MHz, MeOD) δ8.76 (d, 1H), 8.16 (d, 1H), 8.05 (d, 1H), 7.96 (d, 2H), 7.60 (m, 6H), 7.00 (m, 5H), LC/MS m/z 403 (M+H)$^+$.

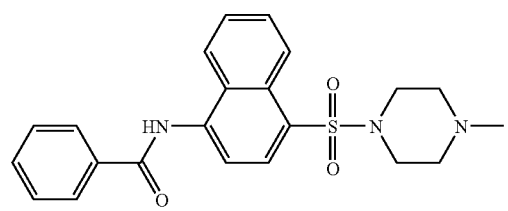

N-[4-(4-Methyl-piperazine-1-sulfonyl)-naphthalen-1-yl]-benzamide (A-8)

The title compound was made following general procedure in Scheme 2, substituting 1-methyl-pyrazine for p-anisidine. $^1$H NMR (300 MHz, MeOD) δ8.74 (d, 1 H), 8.37 (d, 1H), 8.15 (m, 2H), 8.08 (d, 2H), 7.86 (d, 1H), 7.55 (m, 5H), 3.36 (m, 4H), 2.86 (m, 4H), 2.50 (s, 3H); LC/MS m/z 410 (M+H)$^+$.

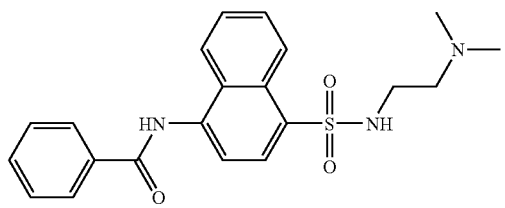

N-[4-(2-Dimethylamino-ethylsulfamoyl)-naphthalen-1-yl]-benzamide (A-9)

The title compound was made following general procedure in Scheme 2, substituting 2-dimethylamino-ethylamine for m-anisidine. $^1$H NMR (300 MHz, MeOD) δ8.74 (d, 1H), 8.45 (s, 1H), 8.30 (d, 1H), 8.22 (d, 1H), 8.08 (d, 2H), 7.85 (d, 1H), 7.65 (m, 5H), 3.10 (m, 4H), 2.74 (s, 6H); LC/MS m/z 398 (M+H)$^+$.

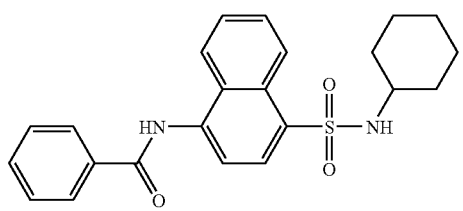

N-(4-Cyclohexylsulfamoyl-naphthalen-1-yl)-benzamide (A-10)

The title compound was made following general procedure in Scheme 2, substituting cyclohexylamine for m-anisidine. $^1$H NMR (300 MHz, MeOD) δ8.80 (d, 1H), 8.33 (d, 1H), 8.20 (d, 1H), 8.08 (d, 2H), 7.85 (d, 1H), 7.66 (m, 5H), 3.05 (br s, 1H), 1.60 (m, 3H), 1.48 (m, 1H), 1.35 (m, 1H), 1.25 (m, 5H); LC/MS m/z 409 (M+H)$^+$.

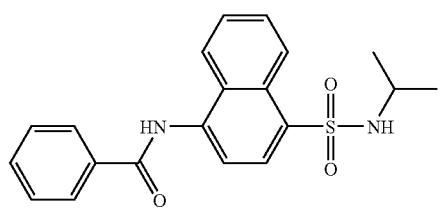

N-(4-Isopropylsulfamoyl-naphthalen-1-yl)-benzamide (A-11)

The title compound was made following general procedure in Scheme 2, substituting isopropylamine for m-anisidine. $^1$H NMR (300 MHz, DMSO) δ8.69 (d, 1H), 8.19 (d, 2H), 8.09 (d, 2H), 8.02 (d, 2H), 7.81 (d, 1H), 7.60 (m, 5H), 3.07 (m, 1H), 0.88 (m, 6H); LC/MS m/z 369 (M+H)$^+$.

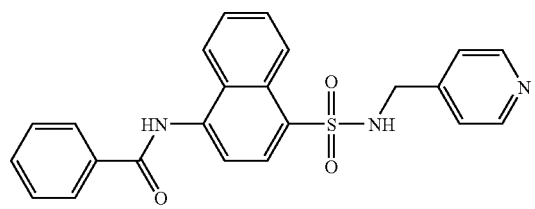

N-{4-[(Pyridin-4-ylmethyl)-sulfamoyl]-naphthalen-1-yl}-benzamide (A-13)

The title compound was made following general procedure in Scheme 2, substituting 4-aminomethyl pyridine for m-anisidine. $^1$H NMR (300 MHz, MeOD) δ8.76 (d, 1H), 8.22 (d, 2H), 8.14 (d, 1H), 8.09 (d, 2H), 7.74 (d, 1H), 7.60 (m, 5H), 7.08 (d, 2H), 4.10 (s, 2H); LC/MS m/z 418 (M+H)$^+$.

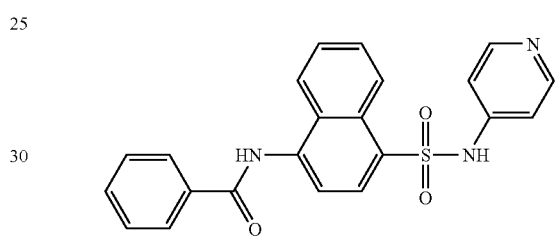

N-[4-(Pyridin-4-ylsulfamoyl)-naphthalen-1-yl]-benzamide (A-14)

The title compound was made following general procedure in Scheme 2, substituting 4-aminopyridine for m-anisidine. $^1$H NMR (300 MHz, DMSO) δ8.83 (d, 1H), 8.26 (d, 1H), 8.08 (m, 3H), 7.93 (d, 2H), 7.75 (d, 1H), 7.60 (m, 5H), 6.91 (d, 2H); LC/MS m/z 404 (M+H)$^+$.

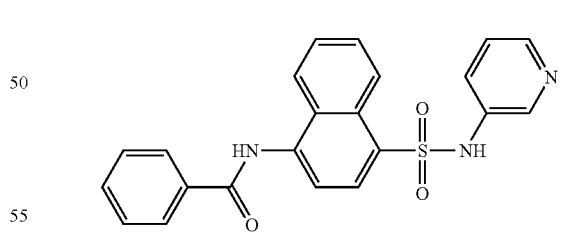

N-[4-(Pyridin-3-ylsulfamoyl)-naphthalen-1-yl]-benzamide (A-16)

The title compound was made following general procedure in Scheme 2, substituting 3-aminopyridine for m-anisidine. $^1$H NMR (300 MHz, DMSO) δ8.85 (d, 1H), 8.34 (d, 1H), 8.10 (m, 3H), 7.82 (m, 1H), 7.76 (d, 1H), 7.58 (m, 6H), 7.18 (d, 1H), 6.71 (d, 1H), LC/MS m/z 404 (M+H)$^+$.

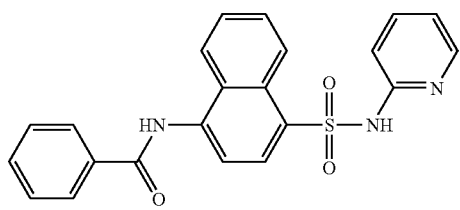

N-[4-(Pyridin-3-ylsulfamoyl)-naphthalen-1-yl]-benzamide (A-17)

The title compound was made following the general procedure in Scheme 2, substituting 2-aminopyridine for m-anisidine. $^1$H NMR (300 MHz, DMSO) δ8.76 (d, 1H), 8.28 (d, 1H), 8.20 (d, 1H), 8.10 (d, 2H), 8.06 (d, 2H), 7.65 (m, 6H), 7.41 (d, 1H), 7.10 (dd, 1H); LC/MS m/z 404 (M+H)$^+$.

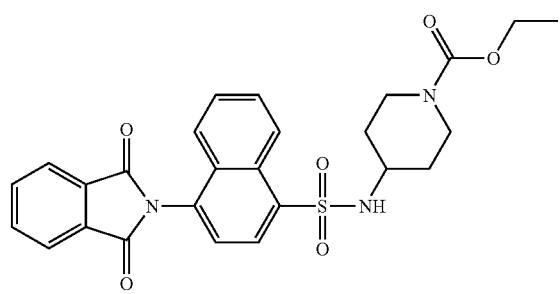

4-[4-(1,3-Dioxo-1,3-dihydro-isoindol-2-yl)-naphthalene-1-sulfonylamino]-piperidine-1-carboxylic acid ethyl ester (A-18)

The title compound was made following the general procedure in Scheme 2, substituting phthalic anhydride for benzoyl chloride, and 4-amino-piperidine-1-carboxylic acid ethyl ester for m-anisidine. $^1$H NMR (300 MHz, MeOD) δ8.71 (d, 1H), 8.39 (d, 1H), 8.03 (m, 2H), 7.89 (m, 2H), 7.58 (m, 4H), 5.10 (br s, 1H), 4.07 (q, 2H), 3.94 (m, 2H), 3.36 (br s, 1H), 3.08 (m, 1H), 2.78 (m, 2H), 1.75 (m, 2H), 1.33 (m, 2H), 1.21 (t, 3H); LC/MS m/z 508 (M+H)$^+$.

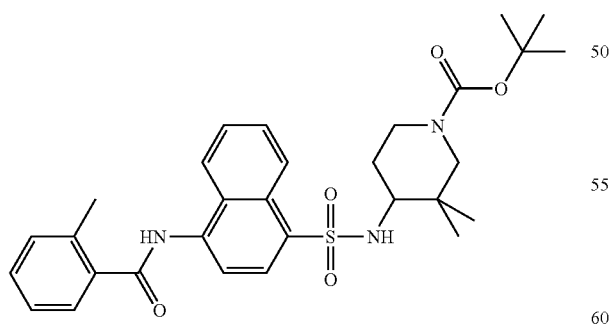

(±)-3,3-Dimethyl-4-[4-(2-methyl-benzoylamino)-naphthalene-1-sulfonylamino]-piperidine-1-carboxylic acid tert-butyl ester (A-19)

The title compound was made following general procedure in Scheme 2, substituting 2-methyl-benzoyl chloride for benzoyl chloride and 4-amino-3,3-dimethyl-piperidine-1-carboxylic acid tert-butyl ester for m-anisidine. $^1$H NMR (300 MHz, MeOD) δ8.83 (d, 1H), 8.30 (d, 1H), 8.23 (d, 1H), 7.93 (d, 1H), 7.40 (m, 3H), 3.76 (d, 1H), 3.55 (d, 1H), 2.97 (m, 1H), 2.54 (s, 6H); 1.38 (s, 3H), 1.14 (m, 1H), 0.77 (s, 3H), 0.61 (s, 3H); LC/MS m/z 552 (M+H)$^+$.

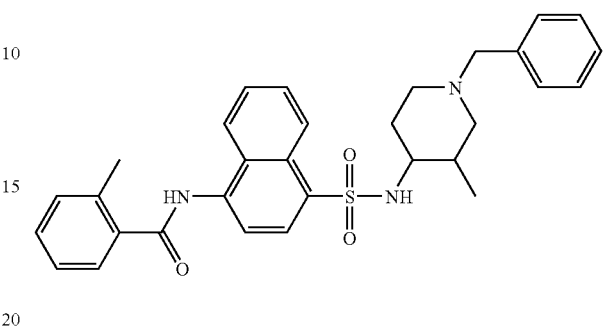

N-[4-(1-Benzyl-3-methyl-piperidin-4-ylsulfamoyl)-naphthalen-1-yl]-2-methyl-benzamide (A-20)

The title compounds (~1:1 mixture) were made following general procedure in Scheme 2, substituting 2-methyl-benzoyl chloride for benzoyl chloride and 4-amino-1-benzyl-3-methyl-piperidine for m-anisidine. LC/MS m/z 528 (M+H)$^+$.

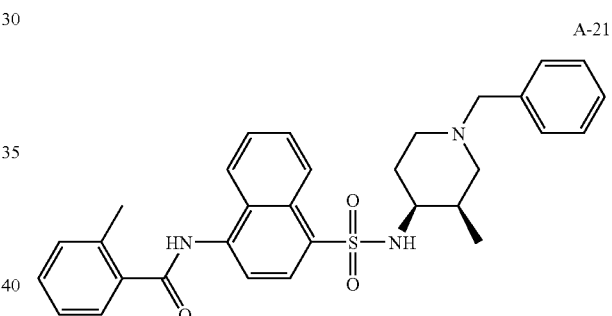

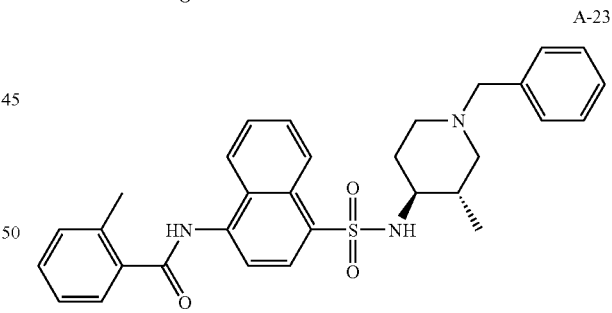

(±)-cis-N-[4-(1-Benzyl-3-methyl-piperidin-4-ylsulfamoyl)-naphthalen-1-yl]-2-methyl-benzamide (A-21) and (±)-trans-N-[4-(1-Benzyl-3-methyl-piperidin-4-ylsulfamoyl)-naphthalen-1-yl]-2-methyl-benzamide (A-23)

The title compounds were made following general procedure in Scheme 2, substituting 2-methyl-benzoyl chloride for benzoyl chloride and 4-amino-1-benzyl-3-methyl-piperidine for m-anisidine. Flash column chromatography of the mixture gave both title compounds respectively. A-21: $^1$H NMR (300 MHz, CDCl$_3$) δ 8.73 (d, 1H), 8.35 (m, 2H), 8.11

(s, 1H), 7.93 (d, 1H), 7.65 (m, 3H), 7.44 (m, 1H), 7.33 (d, 2H), 7.23(m, 5H), 4.70 (d, 1H), 3.38 (q, 2H), 3.29 (m, 1H), 2.58 (s, 3H), 2.25 (br s, 2H), 1.75 (m, 1H), 1.48 (m, 2H), 0.97 (d, 1H); 0.65 (d, 3H); LC/MS m/z 528 (M+H)+. A-23: $^1$H NMR (300 MHz, CDCl$_3$) δ8.70 (d, 1H), 8.32 (s, 1H), 8.25 (s, 2H), 7.93 (d, 1H), 7.60 (m, 3H), 7.40 (m, 1H), 7.25 (m, 6H), 4.78 (d, 1H), 3.38 (q, 2H), 2.72 (m, 2H), 2.55 (s, 3H), 2.24 (m, 1H), 1.86 (m, 1H), 1.63 (m, 3H), 1.35 (m, 2H); 0.57 (d, 3H); LC/MS m/z 528 (M+H)+.

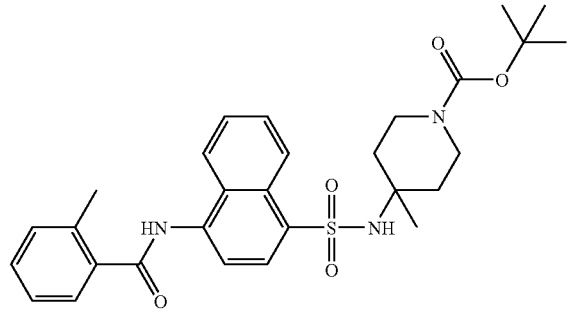

4-Methyl-4-[4-(2-methyl-benzoylamino)-naphthalene-1-sulfonylamino]-piperidine-1-carboxylic acid isopropyl ester (A-22)

The title compound was made following general procedure in Scheme 2, substituting 2-methyl-benzoyl chloride for benzoyl chloride and 4-amino-4-methyl-piperidine-1-carboxylic acid tert-butyl ester for m-anisidine. $^1$H NMR (300 MHz, MeOD) δ8.78 (d, 1H), 8.380 (m, 2H), 8.19 (d, 1H), 7.95 (d, 2H), 7.68 (m, 3H), 7.44 (m, 1H), 7.35 (m, 2H), 4.78 (s, 1H), 3.40 (m, 2H), 3.03 (m, 2H), 2.68 (s, 3H), 1.72 (m, 2H), 1.470 (m, 2H), 1.38 (s, 9H), 1.18 (s, 3H); LC/MS m/z 524 (M+H)+.

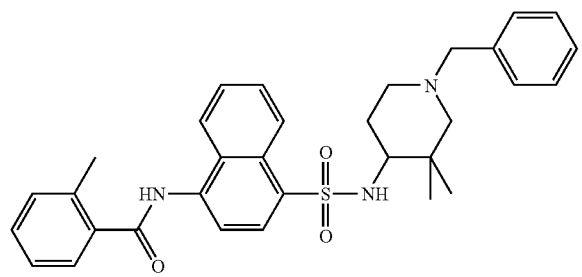

(±)-N-[4-(1-Benzyl-3,3-dimethyl-piperidin-4-ylsulfamoyl)-naphthalen-1-yl]-2-methyl-benzamide (A-24)

The title compound was made following general procedure in Scheme 2, substituting 2-methyl-benzoyl chloride for benzoyl chloride and 4-amino-1-benzyl-3,3-dimethyl-piperidine-1-carboxylic acid tert-butyl ester for m-anisidine. $^1$H NMR (300 MHz, DMSO) δ8.77 (d, 1H), 8.22 (dd, 2H), 7.91 (d, 1H), 7.70 (m, 4H), 7.35 (m, 3H), 7.22 (m, 5H), 3.30 (q, 2H), 2.67 (m, 1H), 2.57 (m, 1H), 2.47 (s, 3H), 2.25 (d, 1H), 1.68 (t, 1H), 1.56 (d, 1H), 1.47 (m, 1H), 1.04 (m, 1H); 0.85 (s, 3H), 0.45(s, 3H); LC/MS m/z 542 (M+H)+.

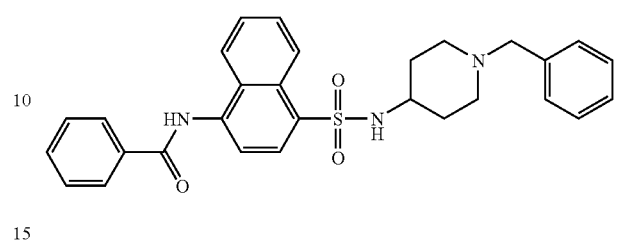

N-[4-(1-Benzyl-piperidin-4-ylsulfamoyl)-naphthalen-1-yl]-benzamide (A-25)

The title compound was prepared following the general procedure in Scheme 2, substituting 4-amino-1-benzyl-piperidine for m-anisidine.

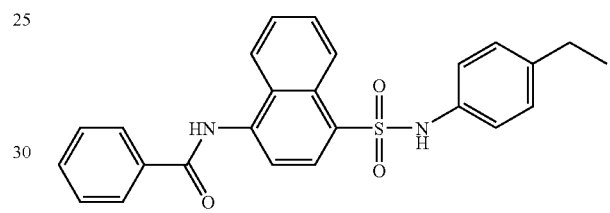

N-[4-(4-Ethyl-phenylsulfamoyl)-naphthalen-1-yl]-benzamide (A-26)

The title compound was prepared following the general procedure in Scheme 2, substituting 4-ethyl-phenylamine for m-anisidine. $^1$H NMR (300 MHz, DMSO) δ8.76 (d, 1H), 8.21 (d, 1H), 8.16 (d, 1H), 8.07 (s, 1H), 8.04 (m, 1H), 7.78 (d, 1H), 7.76 (m, 5H), 6.94 (m, 4H), 2.4 (m, 2H), 1.03 (t, 3H); LC/MS (M+H)+ m/z 431.

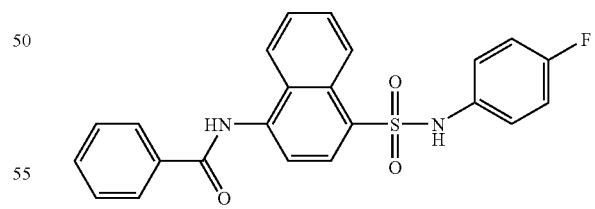

2-Methyl-penta-2,4-dienoic acid [4-(4-fluoro-phenylsulfamoyl)-naphthalen-1-yl]-amide (A-27)

The title compound was prepared following the general procedure in Scheme 2, substituting 4-fluoro-phenyl-amine for m-anisidine. $^1$H NMR (300 MHz, DMSO) δ8.74 (d, 1H), 8.18 (m, 3H), 8.06 (d, 2H), 7.67 (m, 7H), 7.0 (m, 4H); LC/MS (M+H)+ m/z 421.

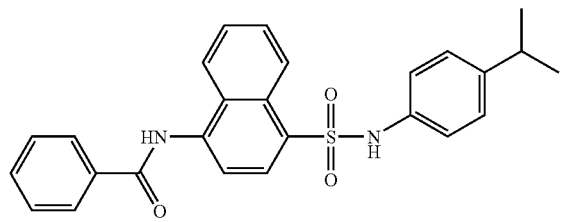

N-[4-(4-Isopropyl-phenylsulfamoyl)-naphthalene-1-yl]-benzamide (A-28)

The title compound was prepared following the general procedure in Scheme 2, substituting 4-isopropyl-phenylamine for m-anisidine. $^1$H NMR (300 MHz, DMSO) δ8.76 (d, 1H), 8.25 (d, 1H), 8.18 (d, 1H), 8.05 (m, 2H), 7.8 (d, 1H), 7.65 (m, 5H), 6.95 (m, 4H), 2.7 (m, 1H), 1.05 (d, 6H); LC/MS (M+H)$^+$ m/z 445.

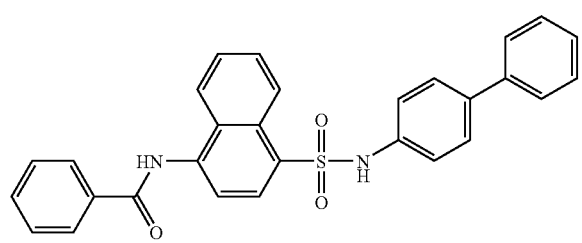

N-[Biphenyl-4-yl sulfamoyl)-naphthalen-1-yl]-benzamide (A-29)

The title compound was prepared following the general procedure in Scheme 2, substituting biphenyl-4-yl amine for m-anisidine. $^1$H NMR (300 MHz, DMSO) δ8.79 (d, 1H), 8.31 (d, 1H), 8.18 (d, 1H), 8.05 (s, 1H), 8.03 (s, 1H), 7.82 (d, 1H), 7.76 (m, 1H), 7.6 (m, 8H), 7.36 (t, 2H), 7.26 (m, 1H), 7.13 (s, 1H), 7.11 (s, 1H); LC/MS (M+H)$^+$ m/z 479.

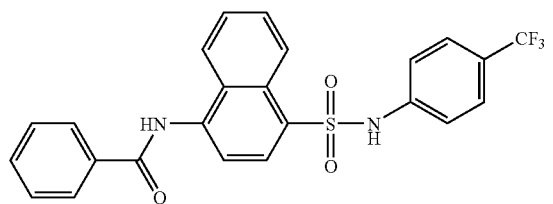

N-[4-(4-Trifluoromethyl-phenylsulfamoyl)-naphthalen-1-yl]-benzamide (A-30)

The title compound was prepared following the general procedure in Scheme 2, substituting 4-trifluoromethyl-phenylamine for m-anisidine. $^1$H NMR (300 MHz, DMSO) δ8.27 (d, 1H), 8.11 (d, 1H), 8.08 (s, 1H), 8.05 (d, 2H), 7.77 (d, 1H), 7.58 (m, 5H), 7.42 (d, 2H), 7.12 (d, 2H); LC/MS (M+H)$^+$ m/z 469.

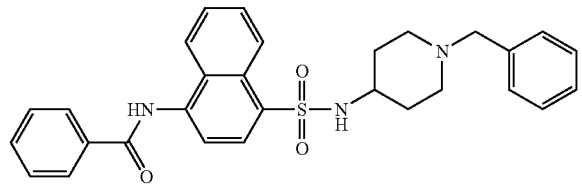

N-[4-(1-Benzyl-piperidin-4-ylsulfamoyl)-naphthalen-1-yl]-benzamide (A-31)

The title compound was prepared following the general procedure in Scheme 2, substituting 1-benzyl-piperidin-4-yl amine for m-anisidine. $^1$H NMR (300 MHz, MeOD) δ8.73 (d, 1H), 8.30 (d, 1H), 8.18 (d, 1H), 8.09 (s, 1H), 8.07 (m, 1H), 7.80 (d, 1H), 7.65 (m, 5H), 7.42 (m, 5H), 4.17 (s, 2H), 3.34 (m, 2H), 2.92 (m, 2H), 1.86 (d, 3H), 1.64 (m, 2H); LC/MS (M+H)$^+$ m/z 500.

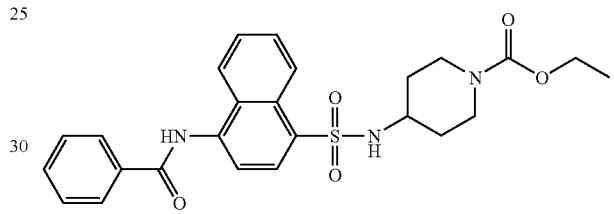

4-(4-Benzoylamino-naphthalene-1-sulfonylamino)-piperidine-1-carboxylic acid ethyl ester (A-34)

The title compound was prepared following the general procedure in Scheme 2, substituting 4-amino-piperidine-1-carboxylic acid ethyl ester for m-anisidine. $^1$H NMR (300 MHz, MeOD) δ8.75 (d, 1H), 8.31 (d, 1H), 8.11 (m, 1H), 8.09 (m, 1H), 8.07 (m, 1H), 7.82 (d, 1H), 7.65 (m, 5H), 4.03 (m, 2H), 3.82 (m, 2H), 2.78 (m, 2H), 1.56 (m, 2H), 1.28 (m, 2H), 1.19 (t, 3H); LC/MS (M+H)$^+$ m/z 480.

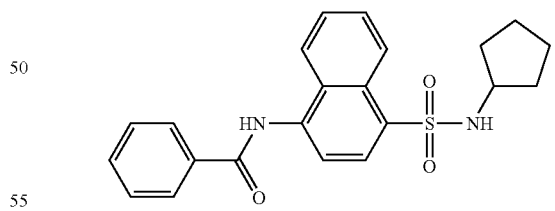

N-(4-Cyclopentysulfamoyl-naphthalen-1-yl)-benzamide (A-35)

The title compound was prepared following the general procedure in Scheme 2, substituting cyclopentylamine for m-anisidine. $^1$H NMR (300 MHz, MeOD) δ8.29 (d, 1H), 8.19 (d, 1H), 8.10 (m, 1H), 8.07 (m, 1H), 7.82 (d, 1H), 7.65 (m, 5H), 3.51 (m, 1H), 1.56 (m, 4H), 1.34 (m, 5H); LC/MS (M+H)$^+$ m/z 395.

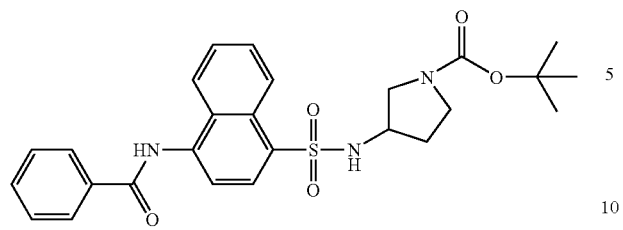

3-(4-Benzoylamino-naphthalene-1-sulfonylamino)-pyrrolidine-1-carboxylic acid tert-butyl ester (A-37)

The title compound was prepared following the general procedure in Scheme 2, substituting 3-amino-pyrrolidine-1-carboxylic acid tert-butyl ester for m-anisidine. $^1$H NMR (300 MHz, MeOD) δ8.79 (d, 1H), 8.35 (d, 1H), 8.25 (d, 1H), 8.11 (d, 2H), 7.89 (m, 1H), 7.69 (m, 5H), 3.78 (m, 1H), 3.03 (m, 1H), 1.88 (m, 1H), 1.71 (m, 1H), 1.41 (d, 9H); LC/MS (M+H)$^+$ m/z 496.

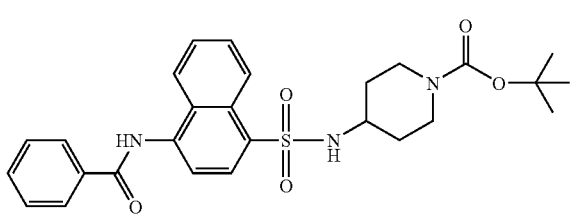

4-(4-Benzoylamino-naphthalene-1-sulfonylamino)-piperidine-1-carboxylic acid tert-butyl ester (A-38)

The title compound was prepared following the general procedure in Scheme 2, substituting 4-amino-piperidine-1-carboxylic acid tert-butyl ester for m-anisidine. $^1$H NMR (300 MHz, MeOD) δ8.75 (d, 1H), 8.31 (d, 1H), 8.19 (d, 1H), 8.09 (m, 1H), 8.07 (m, 1H), 7.82 (d, 1H), 7.65 (m, 5H), 3.78 (m, 2H), 2.73 (m, 2H), 1.52 (m, 3H), 1.39 (s, 9H), 1.28 (m, 2H); LC/MS (M+H)$^+$ m/z 510.

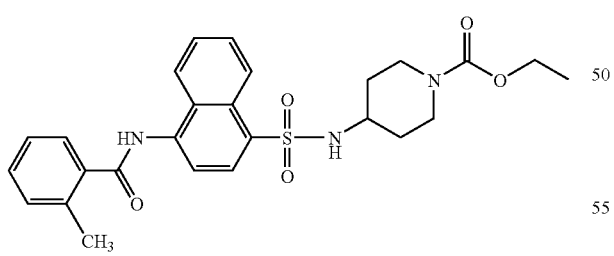

4-[4-(2-Methyl-benzoylamino)-naphthalene-1-sulfonylamino]-piperidine-1-carboxylic acid ethyl ester (A-40)

The title compound was prepared following the general procedure in Scheme 2, substituting 4-amino-piperidine-1-carboxylic acid ethyl ester for m-anisidine and 2-methyl benzoyl chloride for benzoyl chloride. $^1$H NMR (300 MHz, MeOD) δ8.74 (d, 1.H), 8.31 (d, 1H), 8.23 (d, 1H), 7.92 (d, 1H), 7.72 (m, 3H), 7.39 (m, 3H), 4.04 (q, 2H), 3.83 (m, 2H), 3.25 (m, 1H), 2.78 (m, 2H), 2.55 (s, 3H), 1.56 (m, 2H), 1.28 (m, 2H), 1.18 (t, 3H); LC/MS (M+H)$^+$ m/z 496.

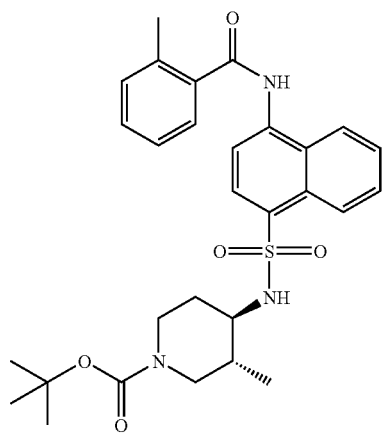

(3R, 4R)-3-Methyl-4-[4-(2-methyl-benzoylamino)-naphthalene-1-sulfonylamino]-piperidine-1-carboxylic acid tert-butyl ester (A-41)

The title compound was prepared according to the general procedure in Scheme 2, substituting (3R, 4R)-4-amino-3-methyl-piperidine-1-carboxylic acid tert-butyl ester for m-anisidine, and 2-methylbenzoyl chloride for benzoyl chloride. $^1$H NMR (300 MHz, CDCl$_3$) δ8.69 (d, 1H), 8.40 (m, 1H), 8.32 (d, 1H), 8.12 (s, 1H), 7.69 (m, 1H), 7.63 (m, 2H), 7.43 (m, 1H), 7.32 (m, 2H), 4.48 (d, 1H), 3.87 (m, 2H), 2.82 (m, 1H), 2.57 (s, 3H), 2.28 (m, 1H), 1.64 (m, 1H), 1.17 (m, 2H), 0.58 (m, 3H); LC/MS m/z 538 (M+H)$^+$.

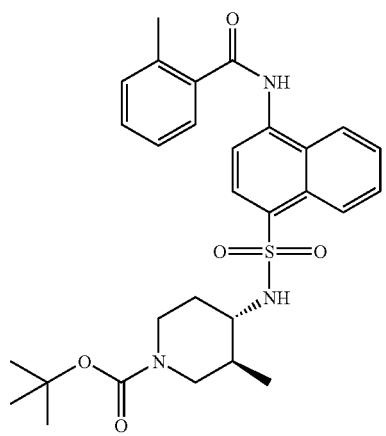

(3S, 4S)-3-Methyl-4-[4-(2-methyl-benzoylamino)-naphthalene-1-sulfonylamino]-piperidine-1-carboxylic acid tert-butyl ester (A-42)

The title compound was prepared according to the general procedure in Scheme 2, substituting (3S, 4S)-4-amino-3-methyl-piperidine-1-carboxylic acid tert-butyl ester for m-anisidine, and 2-methylbenzoyl chloride for benzoyl chloride. $^1$H NMR (300 MHz, CDCl$_3$) δ8.69 (d, 1H), 8.40

(m, 1H), 8.32 (m, 1H), 8.12 (s, 1H), 7.69 (m, 1H), 7.63 (m, 2H), 7.43 (m, 1H), 7.32 (m, 2H), 4.48 (d, 1H), 3.87 (m, 2H), 2.82 (m, 1H), 2.57 (s, 3H), 2.28 (m, 1H), 1.64 (m, 1H), 1.17 (m, 2H), 0.58 (m, 3H); LC/MS m/z 538 (M+H)+.

thalene-1-sulfonyl chloride benzylamine and substituting 4-amino-piperidine-1-carboxylic acid tert-butyl ester for m-anisidine. ¹H NMR (300 MHz, CDCl₃) δ8.70 (m, 2H), 8.36 (m, 2H), 8.08 (d, 1H), 7.90 (m, 1H), 7.67 (m, 2H), 7.48 (m, 3H), 4.80 (d, 1H), 3.82 (m, 2H), 3.25 (m, 1H), 2.70 (t, 2H), 1.65 (m, 3H), 1.35 (s, 9H), 1.20 (m, 2H); LC/MS m/z 544 (M+H)+

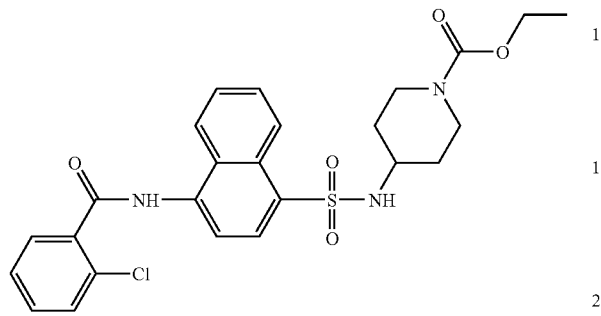

4-[4-(2-Chloro-benzoylamino)-naphthalene-1-sulfonylamino]-piperidine-1-carboxylic acid ethyl ester (A-43)

The title compound was made following general procedure in Scheme 2, substituting 4-(2-chloro-benzoylamino)-naphthalene-1-sulfonyl chloride for 4-benzoylamino-naphthalene-1-sulfonyl chloride benzylamine and substituting 4-amino-piperidine-1-carboxylic acid ethyl ester for m-anisidine. ¹H NMR (300 MHz, MeOD) δ8.75 (d, 1H), 8.31 (d, 2H), 7.98 (d, 2H), 7.73 (m, 3H), 7.53 (m, 3H), 4.02 (q, 2H), 3.72 (d, 2H), 3.42 (m, 1H), 2.75 (m, 2H), 1.55 (m, 2H), 1.25 (m, 2H), 1.15 (t, 3H); LC/MS m/z 516 (M+H)+.

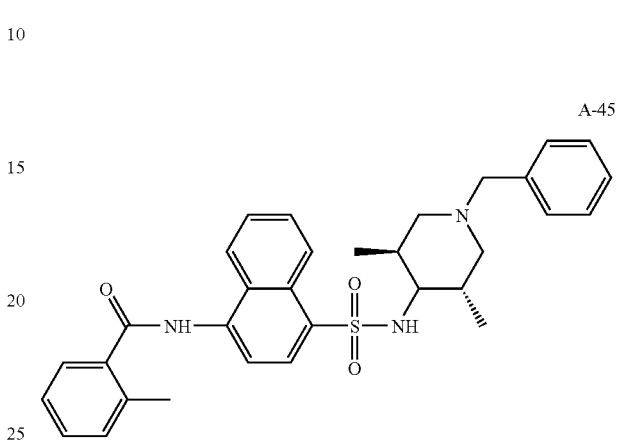

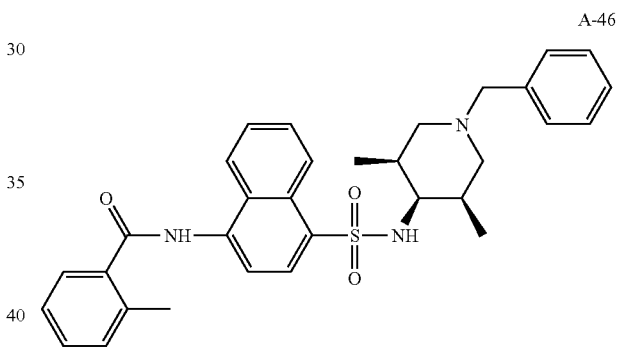

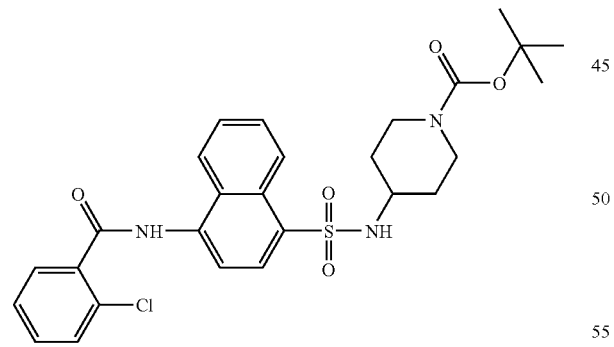

4-[4-(2-Chloro-benzoylamino)-naphthalene-1-sulfonylamino1-piperidine-1-carboxylic acid tert-butyl ester (A-44)

The title compound was made following general procedure in Scheme 2, substituting 4-(2-chloro-benzoylamino)-naphthalene-1-sulfonyl chloride for 4-benzoylamino-naph- (±)-(cis,trans)-N-[4-(1-Benzyl-3,5-dimethyl-piperidin-4-ylsulfamoyl)-naphthalen-1-yl]-2-methyl-benzamide (A-45) and (±)-(cis, cis)-N-[4-(1-Benzyl-3,5-dimethyl-piperidin-4-ylsulfamoyl)-naphthalen-1-yl]-2-methyl-benzamide (A-46)

The title compounds were made following general procedure in Scheme 2, substituting 4-(2-methyl-benzoylamino)-naphthalene-1-sulfonyl chloride for 4-benzoylamino-naphthalene-1-sulfonyl chloride benzylamine and substituting 1-benzyl-3,5-dimethyl-piperidin-4-ylamine 6 for m-anisidine. After flash column separation, A-45 and A-46 were obtained. A-45: ¹H NMR (300 MHz, CDCl₃) δ8.77(d, 1H), 8.36 (m, 2H), 8.10 (s, 1H), 7.92 (d, 1H), 7.66 (m, 3H), 7.44 (m, 1H), 7.34 (m, 1H), 7.22 (m, 6H), 4.65 (d, 1H), 3.34 (dd, 2H), 2.90 (m, 1H), 2.59 (s, 3H), 2.35 (m, 1H), 2.05 (d, 1H), 1.70 (s, br, 3H), 1.57 (s, 1H), 0.75 (d, 3H), 0.60 (d, 3H); LC/MS m/z 543 (M+H)+; A-46: ¹H NMR (300 MHz, CDCl₃) δ8.25(d, 1H), 8.34 (m, 4H), 7.98 (d, 1H), 7.64 (m, 3H), 7.43 (m, 1H), 7.31 (m, 6H), 6.15 (d, 1H), 3.84 (s, 2H), 3.40 (d, 1H), 2.80 (d, 3H), 2.56 (s, 3H), 2.30 (t, 2H), 2.10 (s, br, 2H), 0.42 (d, 6H); LC/MS m/z 543 (M+H)+

1H), 2.70 (m, 2H), 2.51 (s, 3H), 2.20 (t, 1H), 2.02 (t, 1H), 1.88 (m, 3H), 1.48 (m, 1H), 1.00 (t, 3H); LC/MS m/z 586 (M+H)+

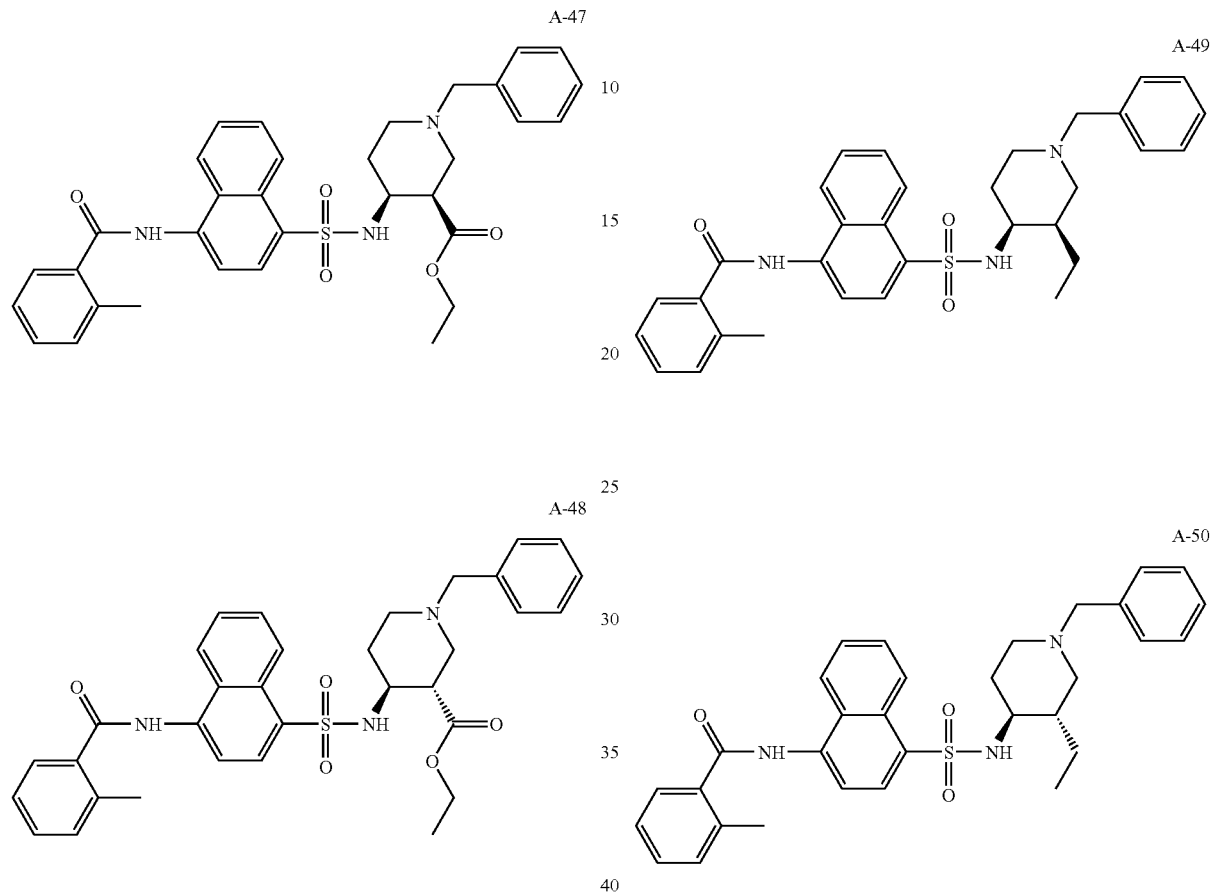

(±)-(cis)-1-Benzyl-4-[4-(2-methyl-benzoylamino)-naphthalene-1-sulfonylamino]-piperidine-3-carboxylic acid ethyl ester (A-47) and (±)-(trans)-1-Benzyl-4-[4-(2-methyl-benzoylamino)-naphthalene-1-sulfonylamino]-piperidine-3-carboxylic acid ethyl ester (A-48)

The title compounds were made following general procedure in Scheme 2, substituting 4-(2-methyl-benzoylamino)-naphthalene-1-sulfonyl chloride for 4-benzoylamino-naphthalene-1-sulfonyl chloride benzylamine and substituting 4-amino-1-benzyl-piperidine-3-carboxylic acid ethyl ester 5 for m-anisidine. After flash column separation, A-47 and A-48 were obtained. A-47: $^1$H NMR (300 MHz, CDCl$_3$) δ8.65 (d, 1H), 8.32 (m, 2H), 8.30 (s, 1H), 7.88 (d, 1H), 7.64 (m, 3H), 7.42 (t, 1H), 7.32 (m, 2H), 7.20 (m, 5H), 6.18 (d, 1H), 3.85 (m, 2H), 3.45 (m, 1H), 3.25 (m, 2H), 3.00 (d, 1H), 2.65 (s, 1H), 2.55 (s, 3H), 2.35 (s, 1H), 1.80 (m, 3H), 1.42 (m, 1H), 1.00 (t, 3H); LC/MS m/z 586 (M+H)+; A-48: $^1$H NMR (300 MHz, CDCl$_3$) δ8.64 (d, 1H), 8.36 (m, 2H), 8.10 (s, 1H), 7.90 (d, 1H), 7.65 (m, 3H), 7.42 (t, 1H), 7.32 (m, 2H), 7.24 (m, 5H), 4.95 (d, 1H), 3.50 (m, 4H), 2.86 (d, (±)-(cis)-N-[4-(1-Benzyl-3-ethyl-piperidin-4-ylsulfamoyl)-naphthalen-1-yl]-2-methyl-benzamide (A-49) and (±)-(trans)-N-[4-(1-Benzyl-3-ethyl-piperidin-4-ylsulfamoyl)-naphthalen-1-yl]-2-methyl-benzamide (A-50)

The title compounds were made following general procedure in Scheme 2, substituting 4-(2-methyl-benzoylamino)-naphthalene-1-sulfonyl chloride for 4-benzoylamino-naphthalene-1-sulfonyl chloride benzylamine and substituting 1-benzyl-3-ethyl-piperidin-4-ylamine 3 for m-anisidine. After flash column separation and further HPLC purification, A-49 and A-50 formic acid salts were obtained. A-49: $^1$H NMR (300 MHz, CDCl$_3$) δ8.42 (d, 1H), 8.18 (s, 1H), 8.00 (d, 2H), 7.65 (d, 1H), 7.30 (m, 3H), 7.05 (t, 1H), 6.95 (m, 8H), 5.30 (s, br, 1H), 3.50 (s, br, 1H), 3.20 (q, 2H), 3.08 (s, 1H), 2.21 (s, 3H), 2.05 (m, 3H), 1.20 (m, 3H), 0.60 (m, 2H), 0.05 (t, 3H); LC/MS m/z 542 (M+H)+; A-50: $^1$H NMR (300 MHz, CDCl$_3$) δ8.70 (d, 1H), 8.30 (m, 2H), 8.20 (s, 1H), 7.90 (d, 1H), 7.60 (m, 3H), 7.42 (t, 1H), 7.25 (m, 8H), 4.75 (d, 1H), 3.45 (dd, 2H), 2.85 (m, 2H), 2.60

(m, 1H), 2.55 (s, 3H), 1.85 (t, 1H), 1.75 (t, 1H), 1.40 (m, 4H), 0.85 (m, 1H), 0.55 (t, 3H); LC/MS m/z 542 (M+H)⁺

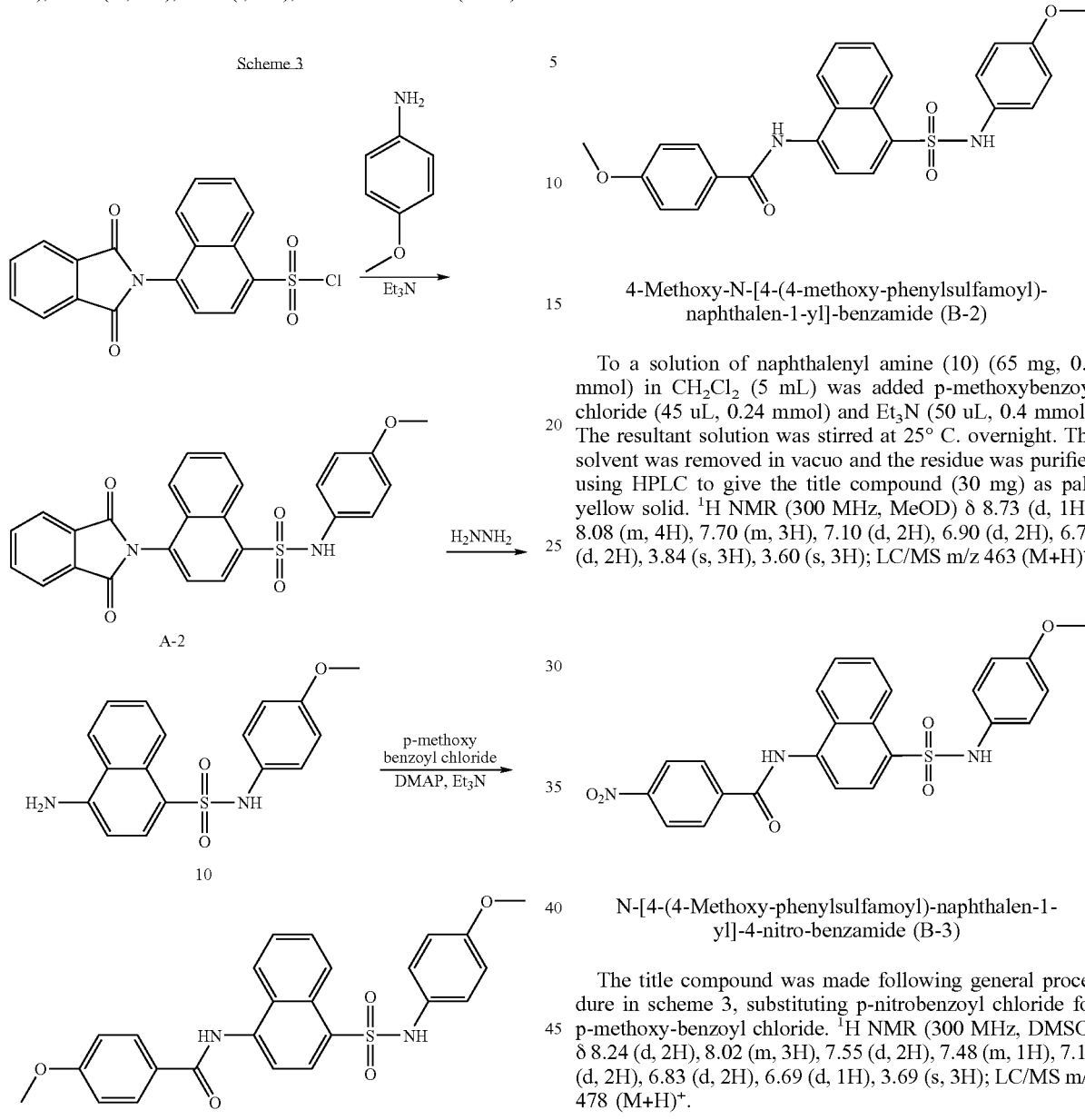

4-Amino-naphthalene-1-sulfonic acid (4-methoxy-phenyl)-amide (10)

To a solution of sulfonamide (A-2) (0.75 g, 1.64 mmol) in methanol (10 mL) was added hydrazine (1 mL). The resultant solution was stirred at 55° C. for 2 hr. A precipitate formed which was filtered and washed with a small amount of methanol. The filtrate was collected and solvent was removed in vacuo to give the title compound as white solid (0.7 g). ¹H NMR (300 MHz, DMSO) δ 9.84 (br s, 1H), 8.55 (d, 1H), 8.16 (d, 1H), 7.80 (d, 1H), 7.60 (t, 1H), 7.47 (t, 1H), 6.82 (d, 2H), 6.71 (m, 3H), 6.53 (d, 1H), 3.58 (s, 3H); LC/MS m/z 329 (M+H)⁺.

4-Methoxy-N-[4-(4-methoxy-phenylsulfamoyl)-naphthalen-1-yl]-benzamide (B-2)

To a solution of naphthalenyl amine (10) (65 mg, 0.2 mmol) in CH₂Cl₂ (5 mL) was added p-methoxybenzoyl chloride (45 uL, 0.24 mmol) and Et₃N (50 uL, 0.4 mmol). The resultant solution was stirred at 25° C. overnight. The solvent was removed in vacuo and the residue was purified using HPLC to give the title compound (30 mg) as pale yellow solid. ¹H NMR (300 MHz, MeOD) δ 8.73 (d, 1H), 8.08 (m, 4H), 7.70 (m, 3H), 7.10 (d, 2H), 6.90 (d, 2H), 6.70 (d, 2H), 3.84 (s, 3H), 3.60 (s, 3H); LC/MS m/z 463 (M+H)⁺.

N-[4-(4-Methoxy-phenylsulfamoyl)-naphthalen-1-yl]-4-nitro-benzamide (B-3)

The title compound was made following general procedure in scheme 3, substituting p-nitrobenzoyl chloride for p-methoxy-benzoyl chloride. ¹H NMR (300 MHz, DMSO) δ 8.24 (d, 2H), 8.02 (m, 3H), 7.55 (d, 2H), 7.48 (m, 1H), 7.18 (d, 2H), 6.83 (d, 2H), 6.69 (d, 1H), 3.69 (s, 3H); LC/MS m/z 478 (M+H)⁺.

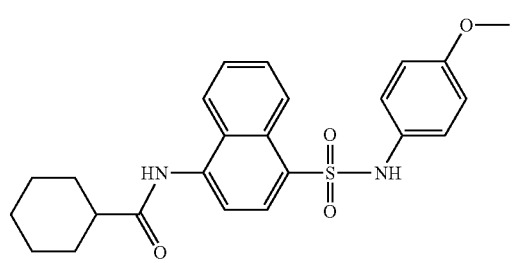

Cyclohexanecarboxylic acid [4-(4-methoxy-phenyl-sulfamoyl)-naphthalen-1-yl]-amide (B-4)

The title compound was made following general procedure in Scheme 3, substituting cyclohexyl carboxyl chloride for p-methoxy-benzoyl chloride. ¹H NMR (300 MHz, DMSO) δ 10.28 (s, 1H), 10.05 (s, 1H), 8.74 (d, 1H), 8.25 (d, 1H), 8.08 (d, 1H), 7.85 (d, 1H), 7.70 (m, 2H), 6.86 (d, 2H), 6.67 (d, 2H), 3.60 (s, 3H), 2.60 (m, 1H), 1.50 (m, 10H); LC/MS m/z 439 (M+H)⁺.

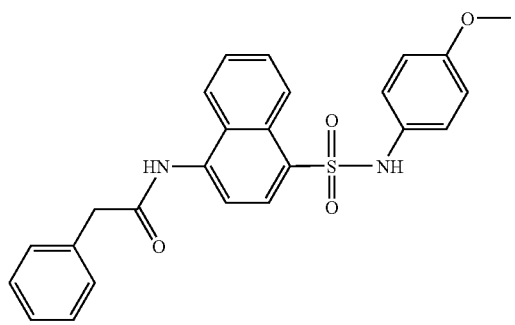

N-[4-(4-Methoxy-phenylsulfamoyl)-naphthalen-1-yl]-2-phenyl-acetamide (B-7)

The title compound was made following general procedure in Scheme 3, substituting phenylacetyl chloride for p-methoxy-benzoyl chloride. ¹H NMR (300 MHz, DMSO) δ 10.30 (s, 1H), 10.18 (s, 1H), 8.67 (d, 1H), 8.24 (d, 1H), 8.05 (s, 1H), 7.84 (d, 1H), 7.66 (m, 2H), 7.30 (m, 5H), 6.82 (d, 2H), 6.67 (d, 2H), 3.81 (s, 2H), 3.55 (s, 3H), 3.29 (s, 3H); LC/MS m/z 447 (M+H)⁺.

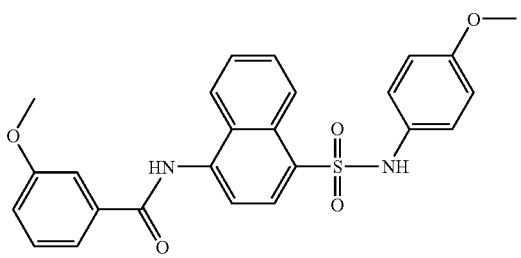

3-Methoxy-N-[4-(4-methoxy-phenylsulfamoyl)-naphthalen-1-yl]-benzamide (B-5)

The title compound was made following general procedure in Scheme 3, substituting 3-methoxy-benzoyl chloride for p-methoxy-benzoyl chloride. ¹H NMR (300 MHz, DMSO) δ 10.67 (s, 1H), 10.32 (br s, 1H), 8.79 (d, 1H), 8.22 (d, 1H), 8.19 (s, 2H), 7.90 (d, 1H), 7.79 (d, 2H), 7.62 (t, 1H), 7.31 (m, 1H), 7.18 (t, 1H), 6.92 (d, 2H), 6.76 (d, 2H); 3.63 (s, 3H), 3.37 (s, 3H); LC/MS m/z 463 (M+H)⁺.

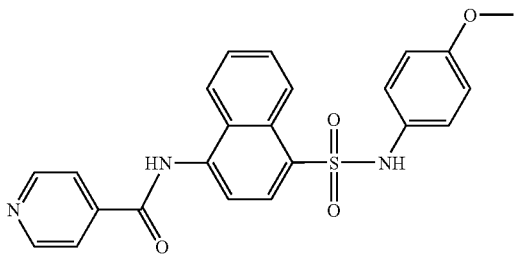

N-[4-(4-Methoxy-phenylsulfamoyl)-naphthalen-1-yl]-isonicotinamide (B-8)

The title compound was made following general procedure in Scheme 3, substituting isonicotinoyl chloride for p-methoxy-benzoyl chloride. ¹H NMR (300 MHz, DMSO) δ 8.82 (d, 2H), 8.78 (d, 1H), 8.22 (d, 1H), 8.17 (d, 1H), 7.98 (d, 2H), 7.80 (d, 2H), 7.72 (m, 1H), 6.92 (d, 2H), 6.74 (d, 2H), 3.62 (s, 3H); LC/MS m/z 434 (M+H)⁺.

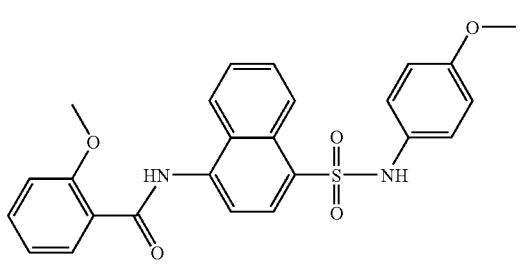

2-Methoxy-N-[4-(4-methoxy-phenylsulfamoyl)-naphthalen-1-yl]-benzamide (B-6)

The title compound was made following general procedure in Scheme 3, substituting 2-methoxy benzoyl chloride for p-methoxy-benzoyl chloride. ¹H NMR (300 MHz, DMSO) δ 10.60 (s, 1H), 10.2 (br s, 1H), 8.87 (d, 1H), 8.40 (d, 1H), 8.11 (s, 2H), 7.84 (d, 1H), 7.76 (d, 2H), 7.55 (t, 1H), 7.45 (d, 1H), 7.12 (t, 1H), 6.88 (d, 2H), 6.70 (d, 2H), 3.60 (s, 3H), 3.34 (s, 3H); LC/MS m/z 463 (M+H)⁺.

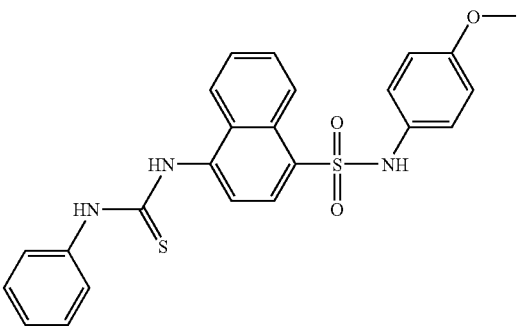

4-(3-Phenyl-thioureido)-naphthalene-1-sulfonic acid (4-methoxy-phenyl)-amide (B-9)

The title compound was made following general procedure in Scheme 3, substituting phenyl isothionitrile for p-methoxy-benzoyl chloride. $^1$H NMR (300 MHz, DMSO) δ 8.73 (d, 1H), 8.10 (d, 1H), 8.08 (d, 1H), 7.70 (m, 3H), 7.50 (d, 2H), 7.32 (t, 2H), 7.13 (t, 1H), 6.90 (d, 2H), 6.70 (d, 2H), 3.60 (s, 3H); LC/MS m/z 464 (M+H)$^+$.

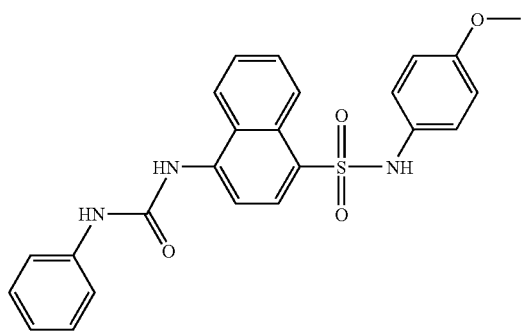

4-(3-Phenyl-ureido)-naphthalene-1-sulfonic acid (4-methoxy-phenyl)-amide (B-10)

The title compound was made following general procedure in Scheme 3, substituting phenyl isocyanate for p-methoxy-benzoyl chloride. $^1$H NMR (300 MHz, DMSO) δ 8.58 (d, 1H), 8.05 (m, 3H), 7.48 (m, 2H), 7.40 (d, 2H), 7.22 (m, 2H), 6.96 (t, 1H), 6.75 (d, 2H), 6.65 (d, 2H), 3.58 (s, 3H); LC/MS m/z 448 (M+H)$^+$.

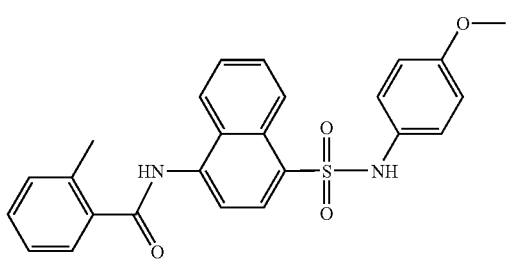

N-[4-(4-Methoxy-phenylsulfamoyl)-naphthalen-1-yl]-2-methyl-benzamide (B-11)

The title compound was made following general procedure in Scheme 3, substituting o-tolyl chloride for p-methoxy-benzoyl chloride. $^1$H NMR (300 MHz, DMSO) δ 8.75 (d, 1H), 8.24 (d, 1H), 8.14 (d, 1H), 7.86 (d, 1H), 7.71 (m, 3H), 7.42 (m, 1H), 7.36 (m, 2H), 6.90 (d, 2H), 6.70 (d, 2H); 3.60 (s, 3H), 2.45 (s, 3H); LC/MS m/z 447 (M+H)$^+$.

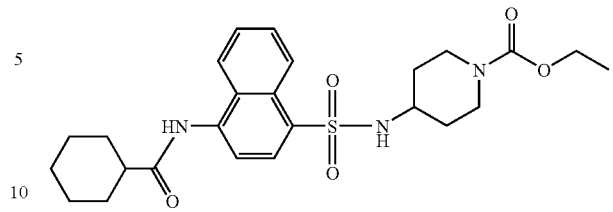

4-[4-(Cyclohexanecarbonyl-amino)-naphthalene-1-sulfonylamino]-piperidine-1-carboxylic acid ethyl ester (B-12)

The title compound was prepared following the general procedure in Scheme 3, substituting 4-amino-piperidine-1-carboxylic acid ethyl ester for p-anisidine and cyclohexane carbonyl chloride for p-methoxy-benzoyl chloride. $^1$H NMR (300 MHz, DMSO) δ 10.05 (s, 1H), 8.65 (d, 1H), 8.26 (d, 1H), 8.14 (d, 1H), 8.04 (d, 1H), 7.92 (d, 1H), 7.71 (m, 2H), 3.95 (m, 3H), 3.68 (m, 2H), 1.93 (m, 2H), 1.80 (m, 2H), 1.31 (m, 13H), 1.13 (t, 3H); LC/MS (M+H)$^+$ m/z 488.

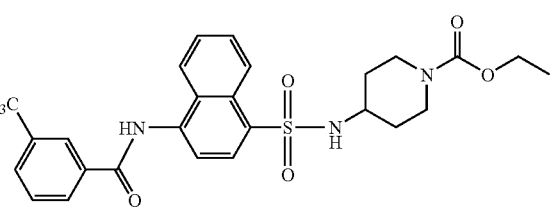

4-[4-(3-Methyl-benzoylamino)-naphthalene-1-sulfonylamino]-piperidine-1-carboxylic acid ethyl ester (B-13)

The title compound was prepared following the general procedure in Scheme 3, substituting 4-amino-piperidine-1-carboxylic acid ethyl ester for p-anisidine and 3-methyl benzoyl chloride for p-methoxy-benzoyl chloride. $^1$H NMR (300 MHz, MeOD) δ 8.75 (d, 1H), 8.30 (d, 1H), 8.18 (d, 1H), 7.80 (m, 5H), 7.46 (m, 2H), 4.03 (q, 2H), 3.83 (d, 2H), 3.23 (m, 1H), 2.78 (m, 2H), 2.47 (s, 3H), 1.56 (m, 2H), 1.28 (m, 2H), 1.19 (t, 3H); LC/MS (M+H)$^+$ m/z 496.

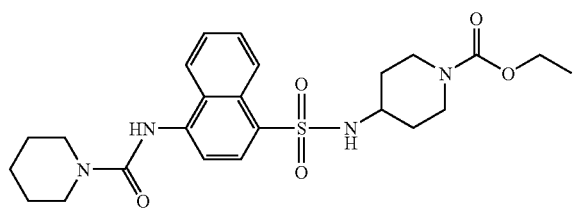

4-{4-[(Piperidine-1-carbonyl)-amino]-naphthalene-1-sulfonylamino}-piperidine-1-carboxylic acid ethyl ester (B-14)

The title compound was prepared following the general procedure in Scheme 3, substituting 4-amino-piperidine-1-carboxylic acid ethyl ester for p-anisidine and 1-piperidine carbonyl chloride for p-methoxy-benzoyl chloride.

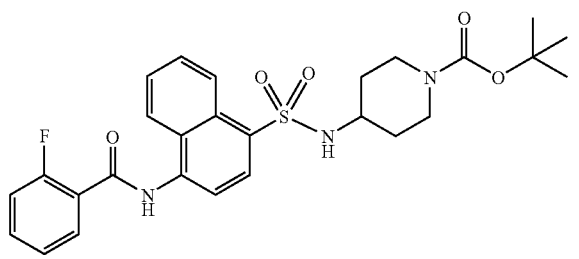

4-[4-(2-Fluoro-benzoylamino)-naphthalene-1-sulfonylamino]-piperidine-1-carboxylic acid tert-butyl ester (B-15)

The title compound was made following the general procedure in Scheme 3, substituting 4-amino-piperidine-1-carboxylic acid tert-butyl ester for p-anisidine and 2-fluorobenzoyl chloride for p-methoxy-benzoyl chloride. $^1$H NMR (300 MHz, DMSO) δ 10.72(s, 1H), 8.67(d, 1H), 8.30(d, 1H), 8.20(d, 1H), 8.10(d, 1H), 8.01(d, 1H), 7.83(t, 1H), 7.74(t, 2H), 7.65(m, 1H), 7.41(q, 2H), 3.67(d, 2H), 3.18(m, 1H), 2.70(m, 2H), 1.43(m, 2H), 1.33(s, 9H), δ 1.18(m, 2H). LC/MS m/z 527 (M−H)⁻, 529 (M+H)⁺

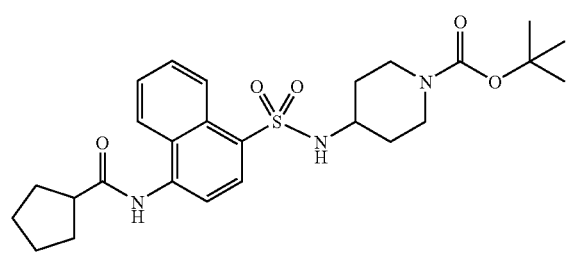

4-[4-(Cyclopentanecarbonyl-amino)-naphthalene-1-sulfonylamino]-piperidine-1-carboxylic acid tert-butyl ester (B-16)

The title compound was made following the general procedure in Scheme 3, substituting 4-amino-piperidine-1-carboxylic acid tert-butyl ester for p-anisidine, and cyclopentanecarbonyl chloride for p-methoxy-benzoyl chloride. $^1$H NMR (300 MHz, DMSO) δ 10.11(s, 1H), 8.64(d, 1H), 8.25(d, 1H), 8.13(d, 1H), 8.01(d, 1H), 7.92(d, 1H), 7.89(m, 1H), 7.70(m, 2H), 3.61(d, 2H), 3.11(m, 2H), 1.94(m, 2H), 1.84-1.60 (m, 7H), 1.38(d, 2H), 1.33(s, 9H), 1.12(m, 2H). LC/MS m/z 500 (M−H)⁻, 502 (M+H)⁺

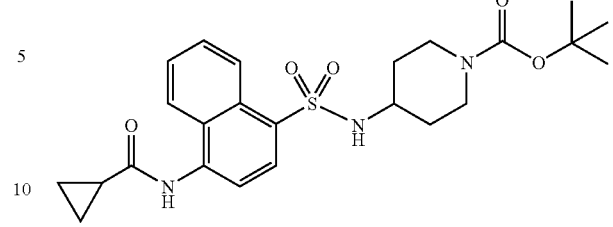

4-[4-(Cyclopropanecarbonyl-amino)-naphthalene-1-sulfonylamino]-piperidine-1-carboxylic acid tert-butyl ester (B-17)

The title compound was made following the general procedure in Scheme 3, substituting 4-amino-piperidine-1-carboxylic acid tert-butyl ester for p-anisidine, and cyclopropanecarbonyl chloride for p-methoxy-benzoyl chloride. $^1$H NMR (300 MHz, DMSO) δ 10.43 (s, 1H), 8.65 (d, 1H), 8.34 (d, 1H), 8.12 (d, 1H), 7.99(t, 2H), 7.73 (m, 2H), 3.61 (d, 2H), 3.13 (m, 1H), 2.68 (m, 2H), 2.16 (m, 2H), 2.16 (m, 1H), 1.39 (d, 2H), 1.33 (s, 9H), 1.12 (m, 2H), 0.88 (d, 4H); LC/MS m/z 472 (M−H)⁻, 474 (M+H)⁺

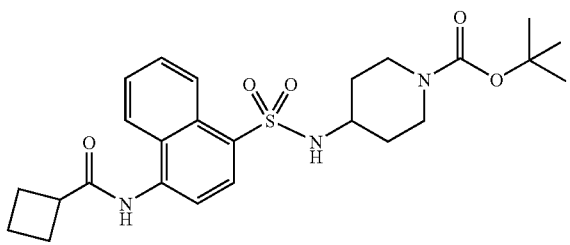

4-[4-(Cyclobutanecarbonyl-amino)-naphthalene-1-sulfonylamino]-piperidine-1-carboxylic acid tert-butyl ester (B-18)

The title compound was made following the general procedure in Scheme 3, substituting 4-amino-piperidine-1-carboxylic acid tert-butyl ester for p-anisidine, and cyclobutanecarbonyl chloride for p-methoxy-benzoyl chloride. $^1$H NMR (300 MHz, DMSO) δ 9.98 (s, 1H), 8.62 (d, 1H), 8.21 (d, 1H), 8.12 (d, 1H), 7.99 (d, 1H), 7.95 (d, 1H), 7.70 (m, 2H), 3.59 (d, 2H), 3.51 (t, 1H), 3.13 (m, 1H), 2.67 (m, 2H), 2.32-2.16 (m, 4H), 1.99 (m, 1H), 1.84 (m, 1H), 1.37 (d, 2H), 1.31 (s, 9H), 1.10(m, 2H); LC/MS m/z 486 (M−H)⁻, 488 (M+H)⁺

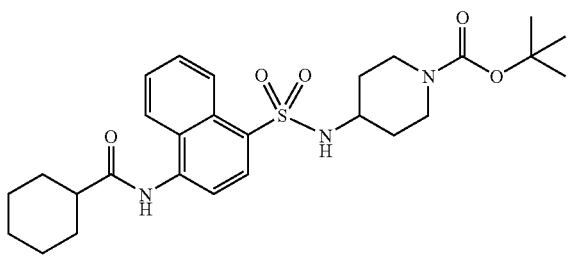

4-[4-(Cyclohexanecarbonyl-amino)-naphthalene-1-sulfonylamino]-piperidine-1-carboxylic acid tert-butyl ester (B-19)

The title compound was made following the general procedure in Scheme 3, substituting 4-amino-piperidine-1-carboxylic acid tert-butyl ester for p-anisidine and cyclohexanecarbonyl chloride for p-methoxy-benzoyl chloride. $^1$H NMR (300 MHz, DMSO) δ 10.05 (s, 1H), 8.64 (d, 1H), 8.25 (d, 1H), 8.12 (d, 1H), 8.00 (d, 1H), 7.91 (d, 1H), 7.71 (m, 2H), 3.61 (d, 2H), 3.43 (m, 1H), 3.15 (m, 1H), 2.65 (m, 2H), 1.90 (d, 2H), 1.77 (d, 2H), 1.69 (m, 1H), 1.54-1.33 (m, 5H), 1.32 (s, 9H), 1.30-1.12 (m, 4H); LC/MS m/z 486 (M−H)$^-$, 488 (M+H)$^+$

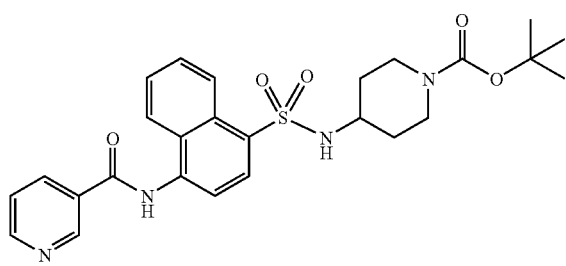

4-{4-[(Pyridine-3-carbonyl)-amino]-naphthalene-1-sulfonylamino}-piperidine-1-carboxylic acid tert-butyl ester (B-20)

The title compound was made following the general procedure in Scheme 3, substituting 4-amino-piperidine-1-carboxylic acid tert-butyl ester for p-anisidine, and nicotinoyl chloride hydrochloride for p-methoxy-benzoyl chloride. $^1$H NMR (300 MHz, DMSO) δ 10.83 (s, 1H), 9.23 (d, 1H), 8.81 (d, 1H), 8.67 (dd, 1H), 8.11 (dt, 1H), 8.27 (dd, 1H), 8.27 (dd, 1H), 8.20 (d, 1H), 8.09 (d, 1H), 7.85 (d, 1H), 7.75 (m, 2H), 7.6 (m, 1H), 3.62 (d, 2H), 3.18 (m, 1H), 2.69 (m, 2H), 1.45-1.37 (m, 2H), 1.30 (s, 9H), 1.14 (m, 2H); LC/MS m/z 509 (M−H)$^-$, 511 (M+H)$^+$

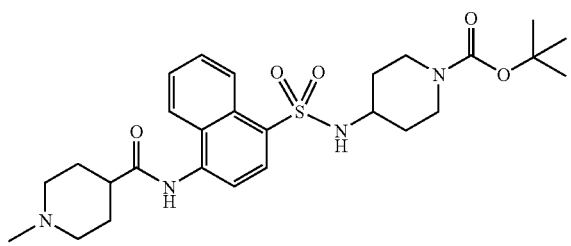

4-{4-[(1-Methyl-piperidine-4-carbonyl)-amino]-naphthalene-1-sulfonylamino}-piperidine-1-carboxylic acid tert-butyl ester (B-21)

The title compound was made following the general procedure in Scheme 3, substituting 4-amino-piperidine-1-carboxylic acid tert-butyl ester for p-anisidine, N-methyl-piperdine-4-carboxylic acid hydrochloride for p-methoxy-benzoyl chloride and reagents 1-(3-dimethylaminopropyl)-3-ethylcarbodiimide hydrochloride (EDCI), 1-hydroxybenzotriazole hydrate (HOBt) and pyridine for dimethylamino pyridine (DMAP) and triethylamine. $^1$H NMR (300 MHz, DMSO) δ 10.39 (s, 1H), 8.64 (dd, 1H), 8.29 (dd, 1H), 8.14 (d, 1H), 8.05 (d, 1H), 7.89 (d, 1H), 7.72 (m, 2H), 3.62 (d, 2H), 3.40 (m, 2H), 3.15 (m, 1H), 2.95 (m, 2H), 2.78-2.67 (m, 6H), 2.09 (m, 2H), 2.0 (m, 2H), 1.84 (m, 1H), 1.39 (m, 1H), 1.32 (s, 9H), 1.18 (m, 2H); LC/MS m/z 484 (M−H)$^-$, 486 (M+H)$^+$

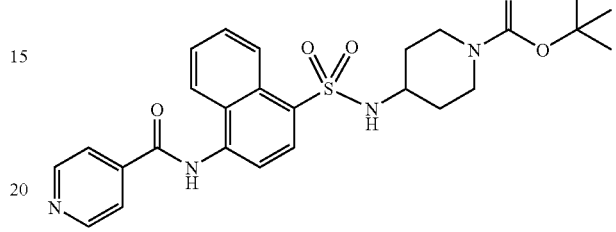

4-{4-[(Pyridine-4-carbonyl)-amino]-naphthalene-1-sulfonylamino}-piperidine-1-carboxylic acid tert-butyl ester (B-22)

The title compound was made following the general procedure in Scheme 3, substituting 4-amino-piperidine-1-carboxylic acid tert-butyl ester for p-anisidine and isonicotinoylchloride hydrochloride for p-methoxy-benzoyl chloride. LC/MS m/z 511 (M+H)$^+$

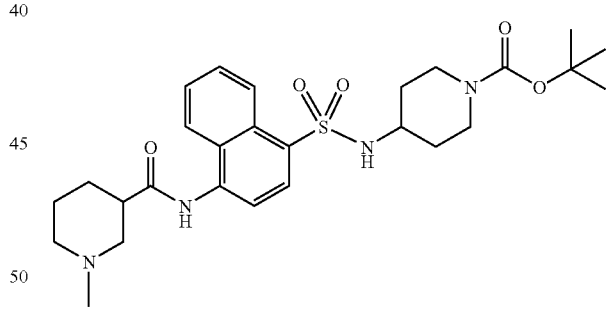

4-{4-[(1-Methyl-piperidine-3-carbonyl)-amino]-naphthalene-1-sulfonylamino}-piperidine-1-carboxylic acid tert-butyl ester (B-23)

The title compound was made following the general procedure in Scheme 3, substituting 4-amino-piperidine-1-carboxylic acid tert-butyl ester for p-anisidine, N-methyl-piperidine-3-carbonyl chloride (prepared in situ from N-methyl-piperidine-3-carboxylic acid, oxalyl chloride (1.2 eq) and triethylamine (1 eq)) for p-methoxy-benzoyl chloride. LC/MS m/z 531 (M+H)$^+$

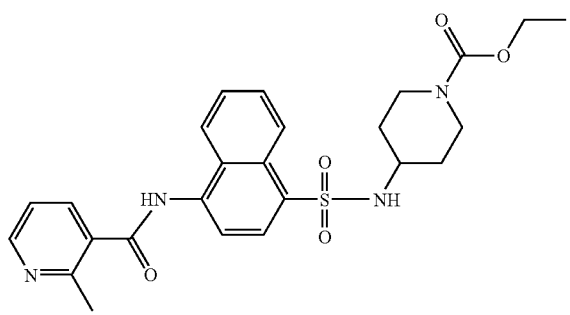

4-{4-[(2-Methyl-pyridine-3-carbonyl)-amino]-naphthalene-1-sulfonylamino}-piperidine-1-carboxylic acid ethyl ester (B-24)

To a suspension of 4-(4-Amino-naphthalene-1-sulfonylamino)-piperidine-1-carboxylic acid ethyl ester (0.26 g, 0.71 mmol) (prepared following the general procedure in Scheme 3, substituting 4-amino-piperidine-1-carboxylic acid ethyl ester for p-anisidine) in $CH_2Cl_2$ (10 mL) and aqueous saturated sodium bicarbonate solution (4 mL) was added 2-methyl nicotinic chloride (0.16 g, 1.07 mmol) and the resulting mixture was stirred at room temperature overnight. The organic layer was separated, dried over sodium sulfate and concentrated. Purification of the residue by column chromatography (2-5% $MeOH/CH_2Cl_2$) provided the B-24 (0.09g, 26%). $^1$H NMR (300 MHz, $CDCl_3$) δ 8.61-8.66 (m, 2H), 8.34 (s, 1H), 8.19-8.28 (m, 1H), 7.94 (d, 2H), 7.60-7.70 (m, 2H), 7.28-7.31(m, 1H), 4.91(d, 1H), 4.03 (q, 2H), 3.85 (d, 2H), 3.20-3.32 (m, 1H), 2.80 (s, 2H), 2.63-2.74 (m, 2H), 1.67 (br s, 4H), 1.16-1.21 (m, 5H). LC/MS m/z 497 (M+H)$^+$.

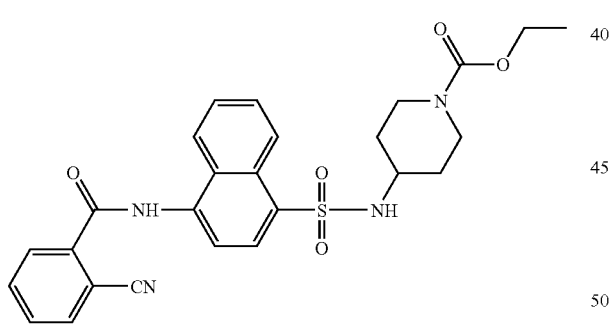

4-[4-(2-Cyano-benzoylamino)-naphthalene-1-sulfonylamino]-piperidine-1-carboxylic acid ethyl ester (B-26)

A solution of 2-cyano-benzoic acid (294 mg, 2 mmol) in thionyl chloride (5 mL) was heated to reflux where the mixture was stirred for 3 h and then concentrated in vacuo. The crude material, 2-cyano-benzoyl chloride was used without purification. The title compound was made following the general procedure in scheme 3, substituting 4-(4-amino-naphthalene-1-sulfonylamino)-piperidine-1-carboxylic acid ethyl ester for 4-amino-naphthalene-1-sulfonic acid (4-methoxy-phenyl)-amide and substituting 2-cyano-benzoyl chloride for p-methoxy-benzoyl chloride. $^1$H NMR (300 MHz, MeOD) δ 8.05 (dd, 1H), 8.36 (d, 1H), 8.05 (m, 2H), 7.92 (m, 2H), 7.83 (m, 1H), 7.75 (m, 1H), 7.64 (d, 2H), 6.89 (td, 1H), 4.05 (q, 2H), 3.85 (d, 2H), 3.30 (m, 1H), 2.80 (m, 2H), 1.60 (m, 2H), 1.30 (m, 2H), 1.20 (t, 3H); LC/MS m/z 508 (M+H)$^+$

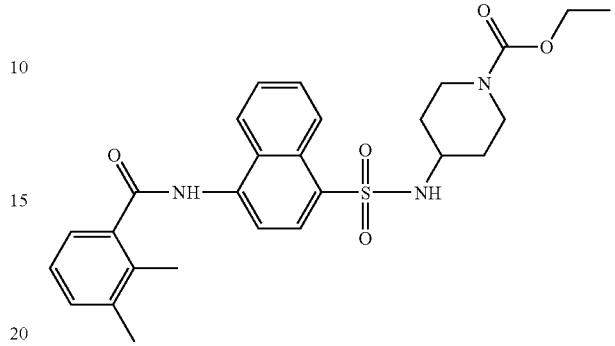

4-[4-[4-(2,3-Dimethyl-benzoylamino)-naphthalene-1-sulfonylamino]-piperidine-1-carboxylic acid ethyl ester (B-27)

The title compound was made following general procedure in Scheme 3, substituting 4-(4-amino-naphthalene-1-sulfonylamino)-piperidine-1-carboxylic acid ethyl ester for 4-amino-naphthalene-1-sulfonic acid (4-methoxy-phenyl)-amide and substituting 2,3-dimethyl-benzoyl chloride for p-methoxy-benzoyl chloride. $^1$H NMR (300 MHz, MeOD/ $CDCl_3$) δ 8.63 (d, 1H), 8.24 (m, 2H), 7.97 (d, 1H), 7.60 (m, 2H), 7.38 (m, 1H), 7.30 (m, 2H), 4.00 (q, 2H), 3.81 (d, 2H), 3.20 (m, 1H), 2.75 (m, 2H), 2.40 (s, 3H), 2.30 (s, 3H), 1.58 (m, 2H), 1.20 (m, 2H), 1.12 (t, 3H); LC/MS m/z 510 (M+H)$^+$

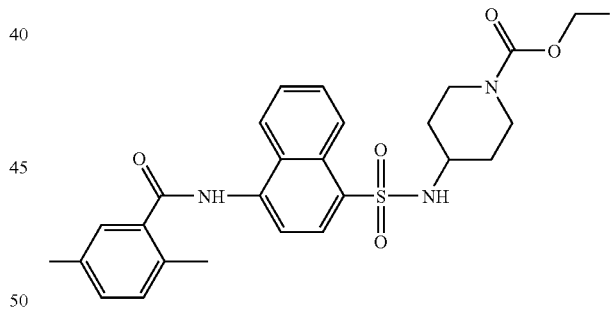

4-[4-(2,5-Dimethyl-benzoylamino)-naphthalene-1-sulfonylamino]-piperidine-1-carboxylic acid ethyl ester (B-28)

A solution of 2,5-dimethyl-benzoic acid (300 mg, 2 mmol) in thionyl chloride (5 mL) was refluxed for 3 h and then concentrated in vacuo. The crude material was used without purification as 2,5-dimethyl-benzoyl chloride. The title compound was made following general procedure in Scheme 3, substituting 4-(4-amino-naphthalene-1-sulfonylamino)-piperidine-1-carboxylic acid ethyl ester for 4-amino-naphthalene-1-sulfonic acid (4-methoxy-phenyl)-amide and substituting 2,5-dimethyl-benzoyl chloride for p-methoxy-benzoyl chloride. $^1$H NMR (300 MHz, MeOD/ $CDCl_3$) δ 8.60 (dd, 1H), 8.22 (d, 1H), 8.10 (m, 1H), 7.98 (m, 1H), 7.58 (m, 2H), 7.35 (s, 1H), 7.14 (m, 2H), 3.98 (q, 2H), 3.78 (d, 2H), 3.15 (m, 1H), 2.68 (m, 2H), 2.42 (s, 3H), 2.32 (s, 3H), 1.55 (m, 2H), 1.20 (m, 2H), 1.12 (t, 3H); LC/MS m/z 510 (M+H)$^+$

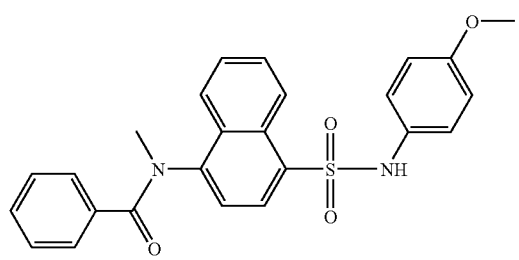

N-[4-(4-Methoxy-phenylsulfamoyl)-naphthalen-1-yl]-N-methyl-benzamide (B-33)

The title compound was made from B-30 following the general procedure in Scheme 3. $^1$H NMR (300 MHz, DMSO) δ 8.23 (t, 2H), 8.10 (d, 3H), 7.87 (d, 1H), 7.60 (m, 5H), 7.03 (d, 2H), 6.82 (d, 2H), 3.72 (s, 3H), 3.18 (s, 3H); LC/MS m/z 445 (M−H)$^-$.

Scheme 4: General procedures for amine deprotections

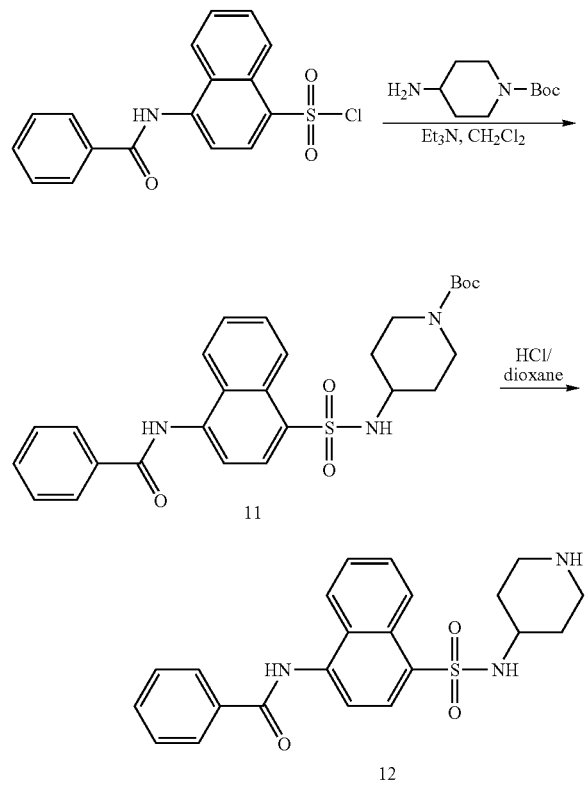

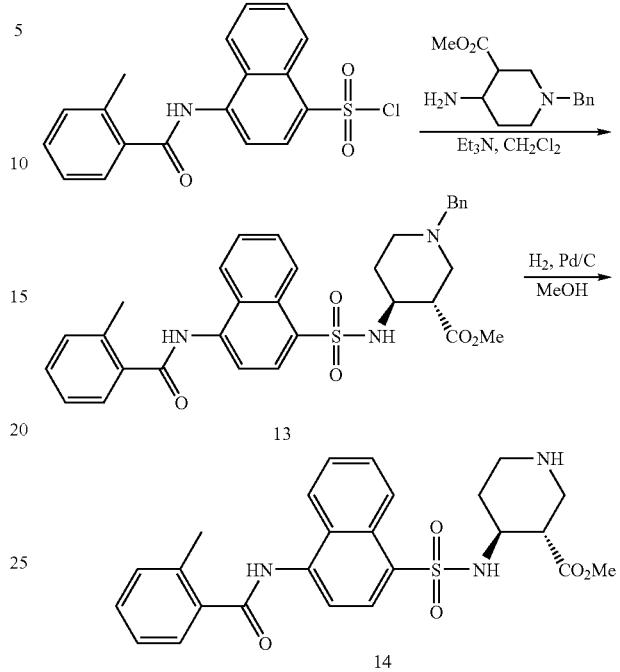

N-[4-(Piperidin-4-ylsulfamoyl)-naphthalen-1-yl]-benzamide (12)

4-(4-Benzoylamino-naphthalene-1-sulfonylamino)-piperidine-1-carboxylic acid tert-butyl ester (11) was prepared following the general procedure in Scheme 2. To a solution of 4-(4-benzoylamino-naphthalene-1-sulfonylamino)-piperidine-1-carboxylic acid tert-butyl ester (11) in MeOH was added a solution of 4 N HCl in dioxane. The reaction mixture was stirred at 25° C. for 5 h and then concentrated in vacuo. The crude material was purified by reverse phase HPLC to provide the title compound. $^1$H NMR (300 MHz, MeOH) δ 8.75 (d, 1H), 8.46 (s, 1H), 8.33 (d, 1H), 8.21 (d, 1H), 8.10 (m, 1H), 8.07 (m, 1H), 7.83 (d, 1H), 7.69 (m, 5H), 3.21 (m, 3H), 2.92 (m, 2H), 1.82 (m, 2H), 1.60 (m, 2H); LC/MS (M+H)$^+$ m/z 410.

(±)-(trans)-4-[4-(2-Methyl-benzoylamino)-naphthalene-1-sulfonylamino]-piperidine-3-carboxylic acid ethyl ester (14)

(±)-(trans)-1-Benzyl-4-[4-(2-methyl-benzoylamino)-naphthalene-1-sulfonylamino]-piperidine-3-carboxylic acid methyl ester 13 was made following general procedure in Scheme 2, substituting (±)-4-amino-1-benzyl-piperidine-3-carboxylic acid ethyl ester (5) for m-anisidine and 4-(2-methyl-benzoylamino)-naphthalene-1-sulfonyl chloride for 4-benzoylamino-naphthalene-1-sulfonyl chloride benzylamine.

To a solution of 1-benzyl-4-[4-(2-methyl-benzoylamino)-naphthalene-1-sulfonylamino]-piperidine-3-carboxylic acid methyl ester 13 (170 mg, 0.29 mmol) in MeOH was added Pd(OH)$_2$/C 20% wet (80 mg). The reaction mixture was stirred at 25° C. under an hydrogen atmosphere overnight. The resultant mixture was filtered and the solvent was concentrated in vacuo to provide the title compound 14. This material was not further purified and used directly in the next reaction.

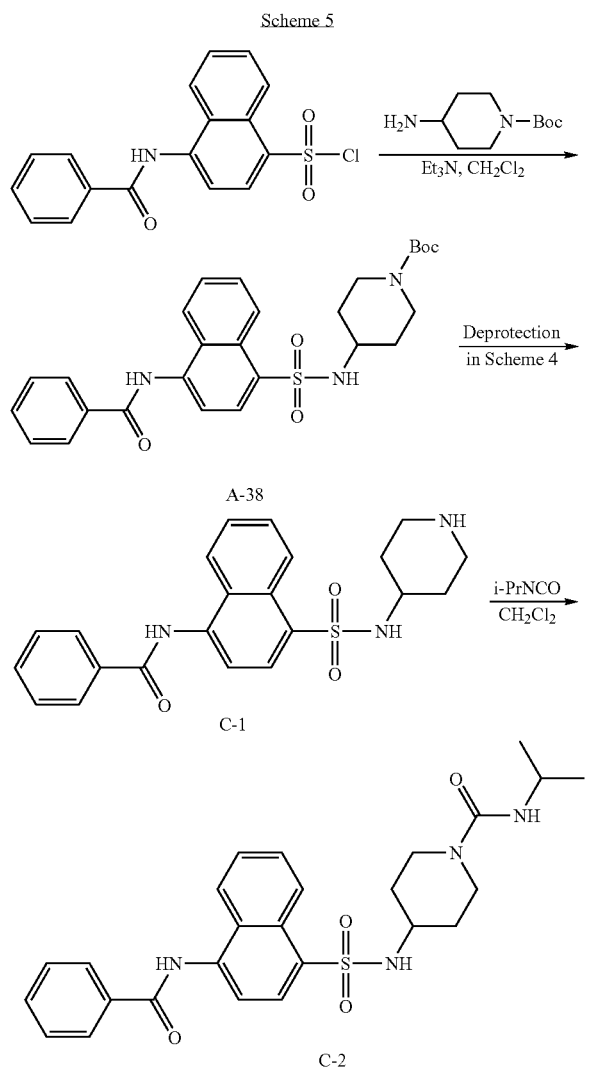

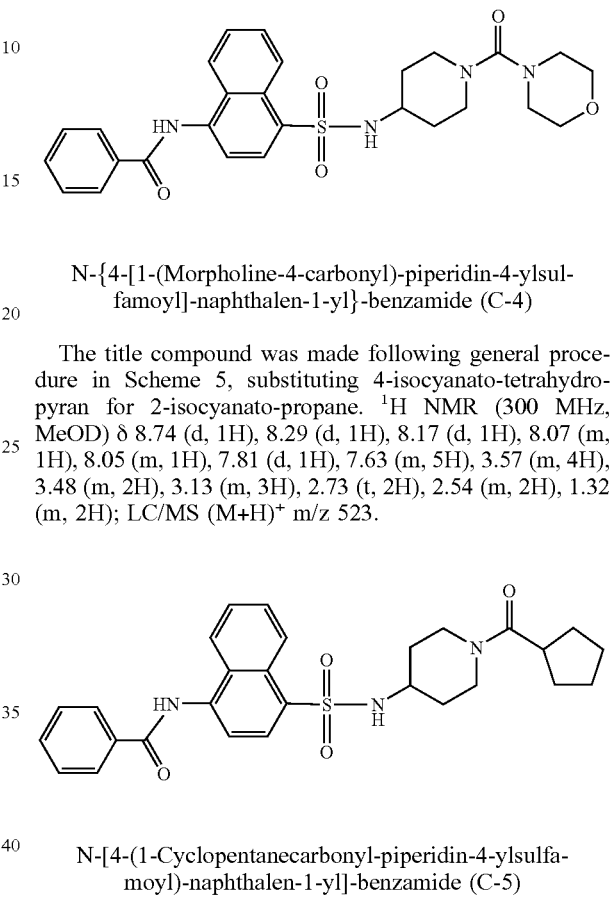

N-[4-(Piperidin-4-ylsulfamoyl)-naphthalen-1-yl]-benzamide (C-1)

4-(4-Benzoylamino-naphthalene-1-sulfonylamino)-piperidine-1-carboxylic acid tert-butyl ester (A-38) was prepared following the general procedure in Scheme 2. Deprotection was achieved following the procedure in Scheme 4-1. The reaction mixture was stirred at 25° C. for 5 h and then concentrated in vacuo. The crude material was purified by reverse phase HPLC to provide the title compound. $^1$H NMR (300 MHz, MeOH) δ 8.75 (d, 1H), 8.46 (s, 1H), 8.33 (d, 1H), 8.21 (d, 1H), 8.10 (m, 1H), 8.07 (m, 1H), 7.83 (d, 1H), 7.69 (m, 5H), 3.21 (m, 3H), 2.92 (m, 2H), 1.82 (m, 2H), 1.60 (m, 2H); LC/MS (M+H)$^+$ m/z 410.

4-(4-Benzoylamino-naphthalene-1-sulfonylamino)-piperidine-1-carboxylic acid isopropyl amide (C-2)

To a 25° C. solution of N-[4-(piperidin-4-yl sulfamoyl)-naphthalen-1-yl]-benzamide (C-1) in CH$_2$Cl$_2$ was added Et$_3$N followed by 2-isocyanato-propane. The reaction mixture was stirred at 25° C. overnight. Aqueous work-up followed by purification using reverse phase HPLC provided the title compound. $^1$H NMR (300 MHz, MeOD) δ 8.74 (d, 1H), 8.29 (d, 1H), 8.17 (d, 1H), 8.07 (s, 1H), 8.05 (s, 1H), 7.81 (d, 1H), 7.63 (m, 5H), 3.75 (m, 3H), 3.21 (m, 1H), 2.68 (t, 2H), 1.51 (m, 2H), 1.26 (m, 2H), 1.05 (d, 6H); LC/MS (M+H)$^+$ m/z 495.

N-{4-[1-(Morpholine-4-carbonyl)-piperidin-4-ylsulfamoyl]-naphthalen-1-yl}-benzamide (C-4)

The title compound was made following general procedure in Scheme 5, substituting 4-isocyanato-tetrahydropyran for 2-isocyanato-propane. $^1$H NMR (300 MHz, MeOD) δ 8.74 (d, 1H), 8.29 (d, 1H), 8.17 (d, 1H), 8.07 (m, 1H), 8.05 (m, 1H), 7.81 (d, 1H), 7.63 (m, 5H), 3.57 (m, 4H), 3.48 (m, 2H), 3.13 (m, 3H), 2.73 (t, 2H), 2.54 (m, 2H), 1.32 (m, 2H); LC/MS (M+H)$^+$ m/z 523.

N-[4-(1-Cyclopentanecarbonyl-piperidin-4-ylsulfamoyl)-naphthalen-1-yl]-benzamide (C-5)

The title compound was prepared following general procedure in Scheme 5, substituting cyclopentanecarbonyl chloride for 2-isocyanato-propane to afford the title compound as a cream colored solid. $^1$H NMR (300 MHz, MeOD) δ 8.75 (d, 1H), 8.31 (d, 1H), 8.19 (d, 1H), 8.09 (m, 1H), 8.07 (d, 1H), 7.82 (d, 1H), 7.65 (m, 6H), 4.17 (d, 1H), 3.83 (d, 1H), 2.97 (m, 2H), 2.65 (m, 1H), 1.65 (m, 11H), 1.29 (m, 2H); LC/MS (M+H)$^+$ m/z 506.

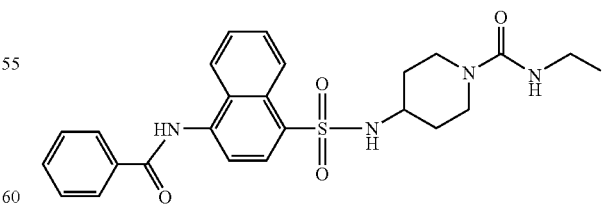

4-(4-Benzoylamino-naphthalene-1-sulfonylamino)-piperidine-1-carboxylic acid ethylamide (C-7)

The title compound was prepared following general procedure in Scheme 5, substituting isocyanato-ethane for 2-isocyanato-propane. ¹H NMR (300 MHz, MeOD) δ 8.75 (d, 1H), 8.30 (d, 1H), 8.19 (d, 1H 8.08 (d, 2H), 7.82 (d, 1H), 7.65 (m, 5H), 3.74 (d, 2H), 3.23 (m, 1H), 3.10 (m, 2H), 2.70 (t, 2H), 1.53 (m, 2H), 1.28 (m, 2H), 1.04 (t, 3H); LC/MS (M+H)⁺ m/z 481.

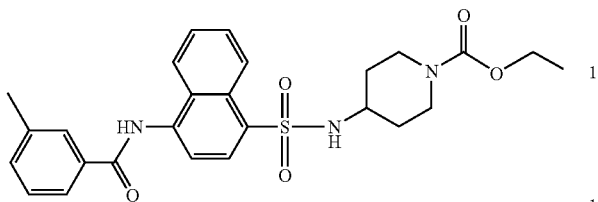

4-[4-(3-Methyl-benzoylamino)-naphthalene-1-sulfonylamino]-piperidine-1-carboxylic acid ethyl ester (C-9)

The title compound was made following general procedure in Scheme 5, substituting 4-aminopiperidine-1-carboxylic acid ethyl ester for 4-aminopiperidine-1-carboxylic acid tert-butyl ester and m-tolyl chloride for benzoyl chloride.

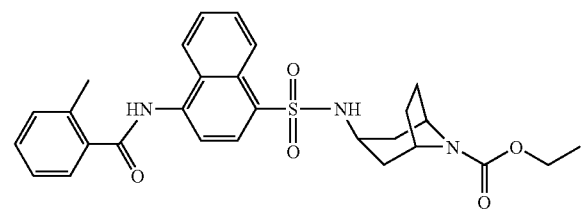

cis-3-[4-(2-Methyl-benzoylamino)-naphthalene-1-sulfonylamino]-8-aza-bicyclo[3.2.1]octane-8-carboxylic acid ethyl ester (C-10)

The title compound was made following general procedure in Scheme 5, substituting cis-3-amino-8-aza-bicyclo[3.2.1]octane-8-carboxylic acid ethyl ester for 4-aminopiperidine-1-carboxylic acid tert-butyl ester. ¹H NMR (300 MHz, DMSO) δ 8.75 (d, 1H), 8.27 (d, 1H), 8.14 (d, 1H), 7.75 (d, 1H), 7.65 (m, 4H), 7.41 (m, 1H), 7.35 (m, 2H), 3.94 (m, 4H), 3.25 (br s, 1H); 2.50 (s, 3H), 1.92 (d, 2H), 1.67 (m, 4H), 1.07 (t, 3H); LC/MS m/z 523 (M+H)⁺.

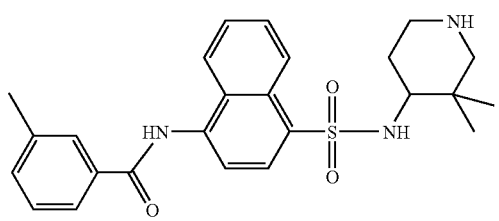

(±)-N-[4-(3,3-Dimethyl-piperidin-4-ylsulfamoyl)-naphthalen-1-yl]-2-methyl-benzamide (C-11)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride and 4-amino-3,3-dimethyl-piperidine-1-carboxylic acid tert-butyl ester for 4-amino-piperidine-1-carboxylic acid tert-butyl ester. ¹H NMR (300 MHz, MeOD) δ 8.82 (d, 1H), 8.33 (d, 1H), 8.23 (d, 1H), 7.93 (d, 1H), 7.68 (m, 3H), 7.40 (m, 3H), 3.18 (m, 3H), 3.00 (d, 1H), 2.85 (m, 2H); 2.54 (s, 3H), 1.60 (m, 3H), 0.95 (s, 3H), 0.70 (s, 3H); LC/MS m/z 452 (M+H)⁺.

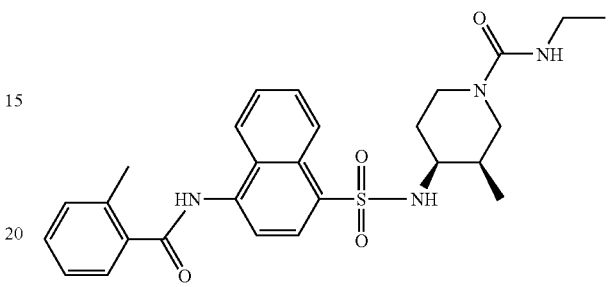

(±)-cis-3-Methyl-4-[4-(2-methyl-benzoylamino)-naphthalene-1-sulfonylamino]-piperidine-1-carboxylic acid ethylamide (C-12)

The title compounds were made following general procedure in Scheme 5 and deprotection in scheme 4-1, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and ethyl isocyanate for 2-isocyanato-propane. ¹H NMR (300 MHz, CDCl₃) δ 8.71 (d, 1H), 8.40 (s, 1H), 8.28 (s, 2H), 7.98 (d, 1H), 7.68 (m, 3H), 7.41 (m, 1H), 7.30 (m, 2H), 5.21(d, 1H), 4.36 (m, 1H), 3.35 (m, 2H), 3.15 (m, 4H), 2.98 (m, 2H), 2.57 (s, 3H), 1.71 (m, 2H), 1.40 (m, 2H), 1.10 (m, 1H), 1.03 (t, 3H) 0.63 (d, 3H); LC/MS m/z 509 (M+H)⁺.

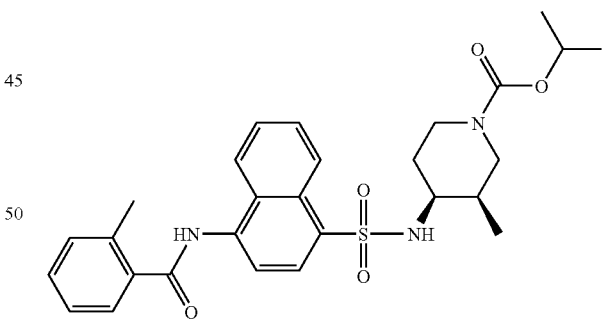

(±)-cis-3-Methyl-4-[4-(2-methyl-benzoylamino)-naphthalene-1-sulfonylamino]-piperidine-1-carboxylic acid isopropyl ester (C-13)

The title compounds were made following the general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3-methyl-piperidine for 4-amino-piperidine-1-carboxylic acid tert-butyl ester and isopropyl chloroformate for 2-isocyanato-propane. ¹H NMR (300 MHz, CDCl$_3$) δ 8.72 (d, 1H), 8.43 (d, 1H), 8.35 (d, 1H), 8.12 (d, 1H), 7.95 (d, 2H), 7.72 (m, 3H), 7.46 (m, 1H), 7.35(d, 2H), 4.85 (m, 1H), 4.66 (d, 1H), 3.55 (m, 1H), 3.37 (m, 1H), 3.17 (m, 2H), 2.59 (s, 3H), 1.74 (m, 1H), 1.58 (m, 1H), 1.40 (m, 2H) 1.18 (dd, 6H), 0.67 (m, 3H); LC/MS m/z 524 (M+H)$^+$.

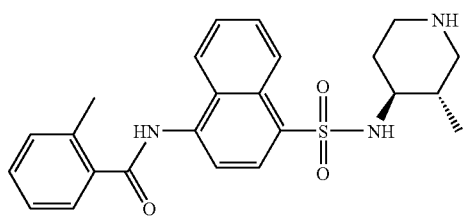

(±)-trans-2-Methyl-N-[4-(3-methyl-piperidin-4-yl-sulfamoyl)-naphthalen-1-yl]-benzamide (C-14)

The title compound was made following general procedure in Scheme 5 and flash column chromatography (Hexane/EtOAc, gradient) followed by deprotection in Scheme 4-1, substituting 4-(2-methyl-benzoylamino)-naphthalene-1-sulfonyl chloride for 4-benzoylamino-naphthalene-1-sulfonyl chloride and (±)-4-amino-1-benzyl-3-methyl-piperidine for 4-amino-piperidine-1-carboxylic acid tert-butyl ester. $^1$H NMR (300 MHz, MeOD) δ 8.77 (d, 1H), 8.48 (s, 1H), 8.32 (d, 1H), 8.24 (d, 1H), 7.94 (d, 1H), 7.75 (m, 3H), 7.40 (m, 3H), 3.25 (m, 1H), 2.90 (m, 2H), 2.55 (s, 3H), 1.60 (m, 3H), 0.65 (d, 3H); LC/MS m/z 438 (M+H)$^+$.

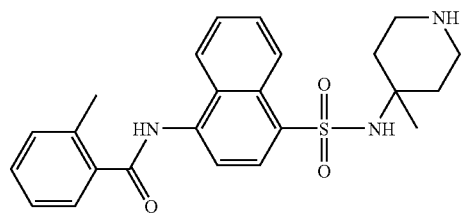

2-Methyl-N-[4-(4-methyl-piperidin-4-ylsulfamoyl)-naphthalen-1-yl]-benzamide (C-15)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride and 4-amino-4-methyl-piperidine-1-carboxylic acid tert-butyl ester for 4-amino-piperidine-1-carboxylic acid tert-butyl ester. $^1$H NMR (300 MHz, DMSO) δ 8.73 (d, 1H), 8.68 (br s, 1H), 8.28 (d, 1H), 8.23 (d, 1H), 7.95 (d, 1H), 7.70 (m, 3H), 7.40 (m, 3H), 2.90 (m, 4H), 2.48 (s, 3H), 2.00 (m, 2H), 1.58 (m, 2H), 0.95 (s, 3H); LC/MS m/z 438 (M+H)$^+$.

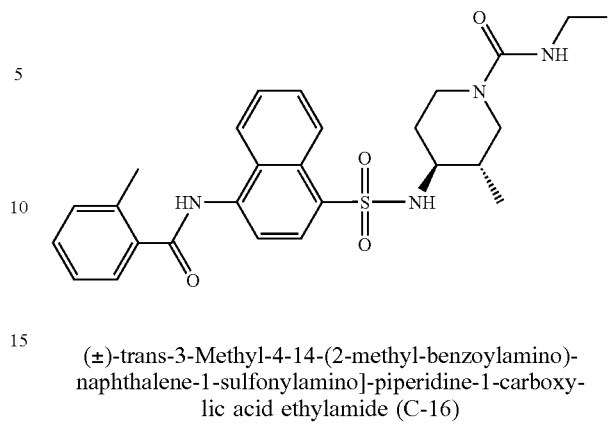

(±)-trans-3-Methyl-4-14-(2-methyl-benzoylamino)-naphthalene-1-sulfonylamino]-piperidine-1-carboxylic acid ethylamide (C-16)

The title compounds were made following general procedure in Scheme 5 and deprotection in scheme 4-1, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and ethyl isocyanate for 2-isocyanato-propane. $^1$H NMR (300 MHz, DMSO) δ 8.77 (d, 1H), 8.29 (d, 1H), 8.23 (d, 1H), 7.91 (d, 1H), 7.70 (m, 3H), 7.36 (m, 3H), 3.82 (m, 2H), 3.12 (q, 2H), 2.82 (m, 1H), 2.58 (m, 1H), 2.55 (s, 3H), 2.31 (t, 1H), 1.40 (m, 2H), 1.20 (m, 1H), 1.03 (t, 3H), 0.59 (d, 3H); LC/MS m/z 509 (M+H)$^+$.

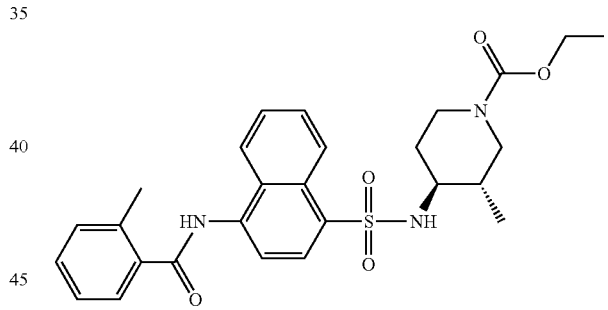

(±)-trans-3-Methyl-4-[4-(2-methyl-benzoylamino)-naphthalene-1-sulfonylamino]-piperidine-1-carboxylic acid ethyl ester (C-17)

The title compound was made following general procedure in scheme 5 and deprotection in scheme 4, substituting 4-(2-methyl-benzoylamino)-naphthalene-1-sulfonyl chloride for 4-benzoylamino-naphthalene-1-sulfonyl chloride, (±)-4-amino-1-benzyl-3-methyl-piperidine for 4-amino-piperidine-1-carboxylic acid tert-butyl ester and ethyl chloroformate for 2-isocyanato-propane. Flash column chromatography (Hexane/EtOAc, gradient) of the mixture gave C-17. $^1$H NMR (300 MHz, CDCl$_3$) δ 8.77 (d, 1H), 8.30 (d, 1H), 8.23 (d, 1H), 7.92 (d, 1H), 7.73 (m, 3H), 7.35 (m, 3H), 4.03 (q, 2H), 3.94 (t, 2H), 2.85 (dt, 1H), 2.64 (m, 1H), 2.55 (s, 3H), 2.40 (m, 1H), 1.48 (m, 1H), 1.38 (m, 1H), 1.20 (t, 3H), 0.59 (d, 3H); LC/MS m/z 510 (M+H)$^+$.

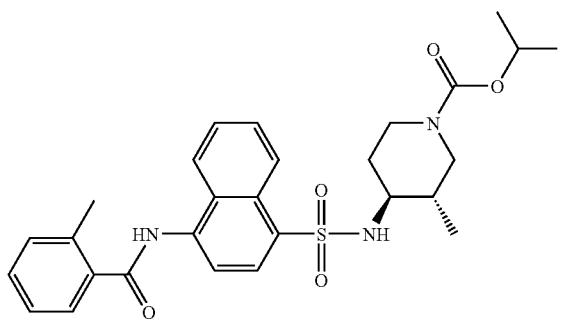

(±)-trans-3-methyl-4-[4-(2-methyl-benzoylamino)-naphthalene-1-sulfonylamino]-piperidine-1-carboxylic acid isopropyl ester (C-18)

The title compounds were made following the general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3-methyl-piperidine for 4-amino-piperidine-1-carboxylic acid tert-butyl ester and isopropyl chloroformate for 2-isocyanato-propane. C-18: $^1$H NMR (300 MHz, CDCl$_3$) δ 8.70 (d, 1H), 8.40 (m, 2H), 8.17 (s, 1H), 7.95 (d, 1H), 7.70 (m, 3H), 7.44 (m, 1H), 7.34 (m, 2H), 4.80 (m, 1H), 4.58 (d, 1H), 3.90 (d, 2H), 2.87 (m, 1H), 2.60 (m, 1H), 2.59 (s, 3H), 2.33 (m, 1H), 1.65 (m, 1H), 1.32 (m, 1H), 1.18 (d, 6H), 0.60 (br s, 3H); LC/MS m/z 524 (M+H)$^+$.

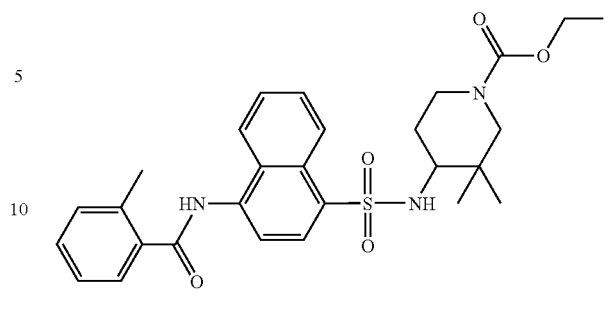

(±)-3,3-Dimethyl-4-[4-(2-methyl-benzoylamino)-naphthalene-1-sulfonylamino]-piperidine-1-carboxylic acid ethyl ester (C-20)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3,3-dimethyl-piperidine for 4-amino-piperidine-1-carboxylic acid tert-butyl ester and ethyl chloroformate for 2-isocyanato-propane. $^1$H NMR (300 MHz, DMSO) δ 8.75 (d, 1H), 8.24 (m, 2H), 7.93 (d, 1H), 7.77 (d, 1H), 7.66 (m, 3H), 7.40 (m, 3H), 3.98 (q, 2H), 3.69 (m, 1H), 3.43 (d, 1H), 2.96 (m, 1H), 2.60 (m, 1H), 2.48 (s, 3H), 1.33 (m, 1H), 1.15 (m, 1H), 1.10 (t, 3H), 0.68 (s, 3H), 0.50 (s, 3H); LC/MS m/z 524 (M+H)$^+$.

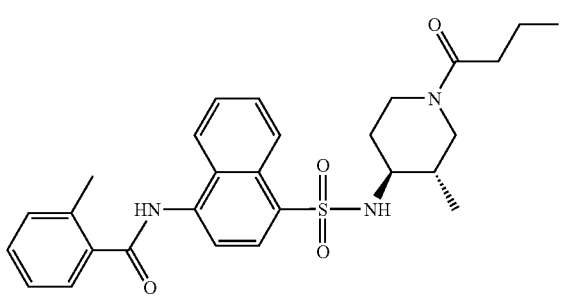

(±)-trans-N-[4-(1-Butyryl-3-methyl-piperidin-4-yl-sulfamoyl)-naphthalen-1-yl]-2-methyl-benzamide (C-19)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3-methyl-piperidine for 4-amino-piperidine-1-carboxylic acid tert-butyl ester and butyryl chloride for 2-isocyanato-propane. Flash column chromatography (Hexane/EtOAc, gradient) of the mixture gave C-19. $^1$H NMR (300 MHz, CDCl$_3$) δ 8.70 (t, 1H), 8.33 (m, 3H), 7.95 (d, 1H), 7.62 (m, 3H), 7.40 (m, 1H), 7.34 (m, 2H), 5.00 (d, 1H), 4.30 (dd, 1H), 3.63 (m, 1H), 2.85 (m, 1.5H), 2.57 (s, 3H), 2.40 (t, 0.5H), 2.15 (m, 1.5H), 2.09 (m, 0.5H), 1.83 (m, 0.5H), 1.50 (m, 1.5H); LC/MS m/z 508 (M+H)$^+$.

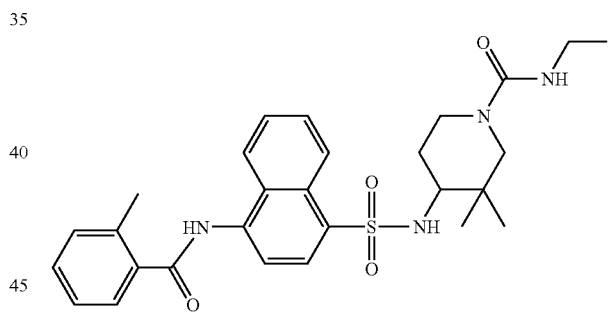

(±)-3,3-Dimethyl-4-[4-(2-methyl-benzoylamino)-naphthalene-1-sulfonylamino]-piperidine-1-carboxylic acid ethylamide (C-21)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3,3-dimethyl-piperidine for 4-amino-piperidine-1-carboxylic acid tert-butyl ester and ethyl isocyanate for 2-isocyanato-propane. $^1$H NMR (300 MHz, DMSO) δ 8.76 (d, 1H), 8.26 (m, 2H), 7.92 (d, 1H), 7.65 (m, 4H), 7.38 (m, 3H), 6.24 (m, 1H), 3.65 (d, 1H), 3.48 (d, 1H), 3.48 (d, 1H), 2.90 (m, 3H), 2.47 (s, 3H), 2.42 (m, 3H), 1.25 (m, 1H), 1.00 (m, 1H), 0.91 (t, 3H), 0.68 (s, 3H), 0.53 (s, 3H); LC/MS m/z 523 (M+H)$^+$.

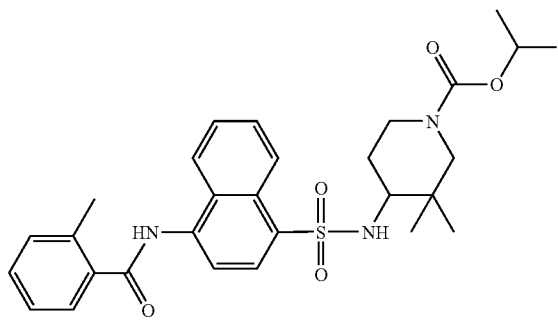

(±)-3,3-Dimethyl-4-14-(2-methyl-benzoylamino)-naphthalene-1-sulfonylamino]-piperidine-1-carboxylic acid isopropyl ester (C-22)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3,3-dimethyl-piperidine for 4-amino-piperidine-1-carboxylic acid tert-butyl ester and isopropyl chloroformate for 2-isocyanato-propane. $^1$H NMR (300 MHz, DMSO) δ 8.75 (d, 1H), 8.25 (m, 2H), 7.93 (d, 1H), 7.70 (m, 3H), 7.38 (m, 3H), 4.66 (m, 1H), 3.68 (m, 1H), 3.43 (d, 1H), 2.94 (m, 1H), 2.55 (m, 2H), 2.47 (s, 3H), 1.30 (m, 1H), 1.10 (d, 6H), 0.67 (s, 3H), 0.50 (s, 3H); LC/MS m/z 538 (M+H)$^+$.

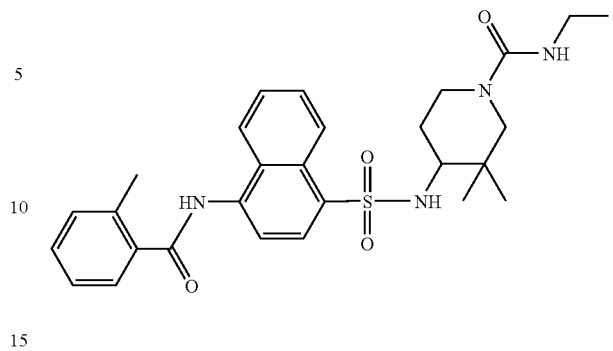

4-Methyl-4-[4-(2-methyl-benzoylamino)-naphthalene-1-sulfonylamino]-piperidine-1-carboxylic acid ethylamide (C-24)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, and 4-amino-4-methyl-piperidine-1-carboxylic acid tert-butyl ester for 4-amino-piperidine-1-carboxylic acid tert-butyl ester and ethyl isocyanate for 2-isocyanato-propane. $^1$H NMR (300 MHz, DMSO) δ 8.76 (d, 1H), 8.24 (m, 2H), 7.93 (d, 1H), 7.38 (m, 3H), 7.70 (m, 4H), 6.26 (t, 1H), 3.18 (m, 2H), 2.93 (m, 2H), 2.78 (m, 2H), 2.47 (s, 3H), 1.69 (m, 2H), 1.24 (m, 2H), 1.09 (s, 3H), 0.90 (t, 3H); LC/MS m/z 509 (M+H)$^+$.

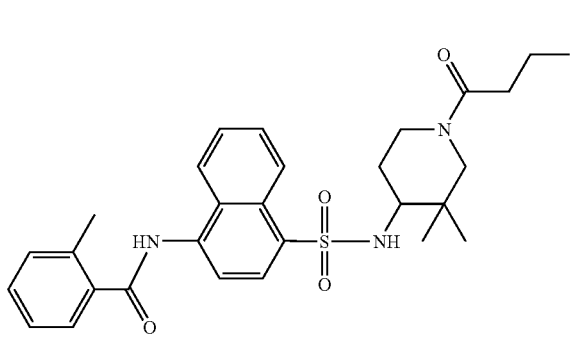

(±)-N-[4-(1-Butyryl-3,3-dimethyl-piperidin-4-ylsulfamoyl)-naphthalen-1-yl]-2-methyl-benzamide (C-23)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, (±)-4-amino-1-benzyl-3,3-dimethyl-piperidine for 4-amino-piperidine-1-carboxylic acid tert-butyl ester and butyryl chloride for 2-isocyanato-propane. $^1$H NMR (300 MHz, DMSO) δ 8.77 (dd, 1H), 8.25 (m, 2H), 7.93 (d, 1H), 7.70 (m, 4H), 7.38 (m, 3H), 4.06 (d, 0.5H), 3.85 (d, 0.5H), 3.60 (d, 0.5H), 3.37 (d, 0.5H), 2.98 (m, 1H), 2.77 (m, 1H), 2.47 (s, 3H), 2.35 (d, 0.5H), 2.16 (m, 2H), 1.40 (m, 2H), 1.24 (m, 0.5H), 1.11 (m, 0.5H), 0.80 (t, 3H), 0.70 (s, 1.5H), 0.64 (s, 1.5H), 0.55 (s, 3H); LC/MS m/z 522 (M+H)$^+$.

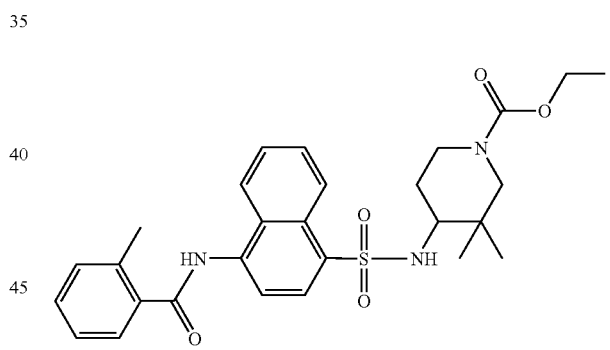

4-Methyl-4-[4-(2-methyl-benzoylamino)-naphthalene-1-sulfonylamino]-piperidine-1-carboxylic acid ethyl ester (C-25)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester and ethyl chloroformate for 2-isocyanato-propane. $^1$H NMR (300 MHz, MeOD) δ 8.80 (d, 1H), 8.29 (m, 1H), 8.23 (d, 1H), 7.93 (d, 1H), 7.65 (m, 3H), 7.38 (m, 3H), 4.02 (q, 2H), 3.43 (m, 2H), 2.90 (m, 2H), 2.54 (s, 3H), 1.87 (m, 2H), 1.15 (m, 6H); LC/MS m/z 510 (M+H)$^+$.

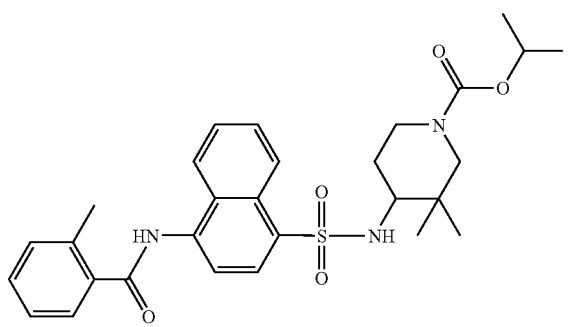

4-Methyl-4-[4-(2-methyl-benzoylamino)-naphthalene-1-sulfonylamino]-piperidine-1-carboxylic acid isopropyl ester (C-26)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester. $^1$H NMR (300 MHz, MeOD) δ 8.80 (d, 1H), 8.30 (d, 1H), 8.23 (d, 1H), 7.93 (d, 1H), 7.75 (m, 3H), 7.35 (m, 3H), 4.79 (q, 2H), 3.40 (m, 2H), 2.88 (t, 2H), 1.86 (m, 2H), 1.37 (m, 6H), 1.10 (m, 9H); LC/MS m/z 524 (M+H)$^+$.

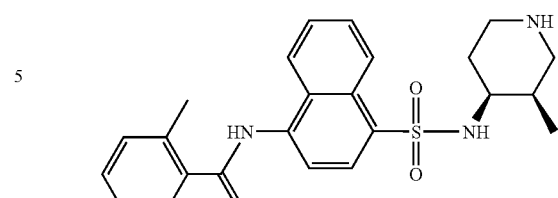

(±)-cis-2-Methyl-N-[4-(3-methyl-piperidin-4-ylsulfamoyl)-naphthalen-1-yl]-benzamide (C-28)

The title compound was made following general procedure in Scheme 5, substituting 4-(2-methyl-benzoylamino)-naphthalene-1-sulfonyl chloride for 4-benzoylamino-naphthalene-1-sulfonyl chloride and (±)-4-amino-1-benzyl-3-methyl-piperidine for 4-amino-piperidine-1-carboxylic acid tert-butyl ester. Purification of the benzyl-protected intermediate by Flash column chromatography (Hexane/EtOAc, gradient) followed by deprotection according to Scheme 4-2 gave C-28. $^1$H NMR (300 MHz, MeOD) δ 8.82 (d, 1H), 8.52 (s, 1H), 8.32 (d, 1H), 8.24 (d, 2H), 7.94 (d, 2H), 7.70 (m, 3H), 7.4 (m, 3H), 3.46 (m, 1H), 3.00 (m, 2H), 2.97 (m, 1H), 2.55 (s, 3H), 1.93 (m, 1H), 1.64 (m, 2H), 0.63 (d, 3H); LC/MS m/z 438 (M+H)$^+$.

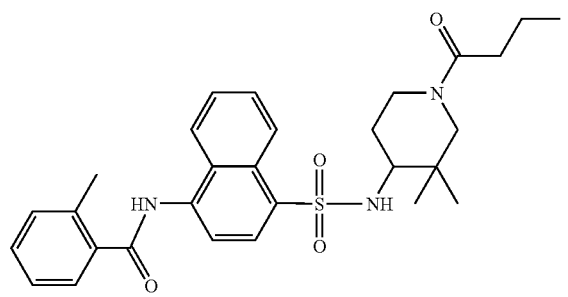

N-[4-(1-Butyryl-4-methyl-piperidin-4-ylsulfamoyl)-naphthalen-1-yl]-2-methyl-benzamide (C-27)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester and butyryl chloride for 2-isocyanato-propane. $^1$H NMR (300 MHz, DMSO) δ 8.76 (d, 1H), 8.26 (m, 2H), 7.95 (d, 1H), 7.70 (m, 3H), 7.34 (m, 3H), 3.54 (m, 1H), 3.31 (m, 1H), 3.04 (m, 1H), 2.76 (m, 1H), 2.47 (s, 3H), 2.09 (t, 3H), 1.82 (m, 2H), 1.30 (m, 6H), 1.07 (s, 3H), 0.77 (t, 3H); LC/MS m/z 508 (M+H)$^+$.

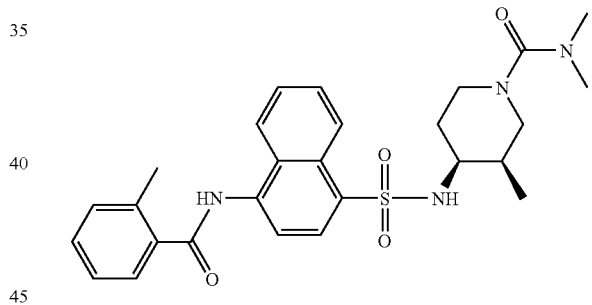

(±)-cis-3-Methyl-4-[4-(2-methyl-benzoylamino)-naphthalene-1-sulfonylamino]-piperidine-1-carboxylic acid dimethylamide (C-29)

The title compound was made following general procedure in Scheme 5 and deprotection in Scheme 4-2, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and dimethylcarbamyl chloride for 2-isocyanato-propane. $^1$H NMR (300 MHz, CDCl$_3$) δ 8.71 (d, 1H), 8.41 (s, 1H), 8.28 (s, 1H), 7.97 (d, 1H), 7.62 (m, 3H), 7.41 (m, 1H), 7.28 (m, 2H), 5.27 (d, 1H), 3.38 (m, 1H), 3.11 (m, 1H), 2.99 (dd, 1H), 2.88 (m, 2H), 2.70 (s, 6H), 2.56 (s, 3H), 1.46 (m, 1H), 1.42 (m, 2H), 0.63 (d, 3H); LC/MS m/z 509 (M+H)$^+$.

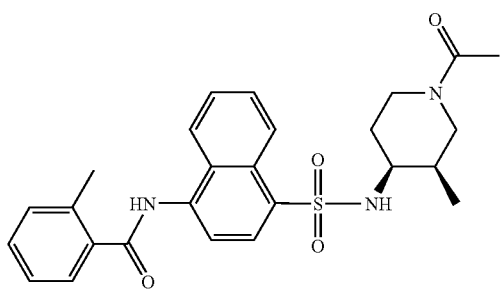

(±)-cis-N-[4-(1-Acetyl-3-methyl-piperidin-4-ylsulfamoyl)-naphthalen-1-yl]-2-methyl-benzamide (C-30)

The title compound was made following general procedure in Scheme 5 and deprotection in Scheme 4-2, substituting 4-(2-methyl-benzoylamino)-naphthalene-1-sulfonyl chloride for 4-benzoylamino-naphthalene-1-sulfonyl chloride, 4-amino-1-benzyl-3-methyl-piperidine for 4-amino-piperidine-1-carboxylic acid tert-butyl ester and acetyl chloride for 2-isocyanato-propane. $^1$H NMR (300 MHz, CDCl$_3$) δ 8.74 (m, 1H), 8.33 (br s, 3H), 7.98 (d, 1H), 7.63 (m, 3H), 7.42 (m, 1H), 7.26 (m, 2H), 5.29 (d, 1H), 3.78 (m, 0.5H), 3.38 (m, 1.5H), 3.20 (m, 1.5H), 2.97 (m, 0.5H), 2.57 (s, 3H), 2.08 (m, 1.5H), 1.96 (d, 3H), 1.83 (m, 0.5H), 1.45 (m, 2H), 0.72 (d, 1.5H), 0.56 (d, 1.5H); LC/MS m/z 480 (M+H)$^+$.

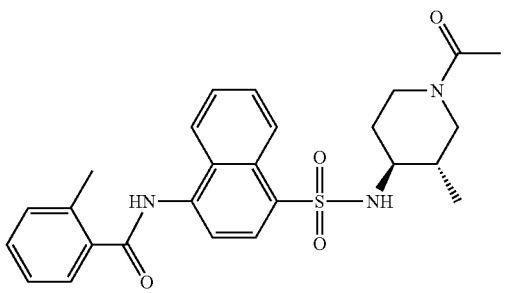

(±)-(trans)-N-[4-(1-Acetyl-3-methyl-piperidin-4-ylsulfamoyl)-naphthalen-1-yl]-2-methyl-benzamide (C-31)

The title compound was made following general procedure in Scheme 5 and deprotection in Scheme 4-1, substituting 4-(2-methyl-benzoylamino)-naphthalene-1-sulfonyl chloride for 4-benzoylamino-naphthalene-1-sulfonyl chloride, 4-amino-4-methyl-piperidine-1-carboxylic acid tert-butyl ester for 4-amino-piperidine-1-carboxylic acid tert-butyl ester and acetyl chloride for 2-isocyanato-propane. $^1$H NMR (300 MHz, CDCl$_3$) δ 8.70 (m, 1H), 8.35 (m, 3H), 7.95 (d, 1H), 7.65 (m, 3H), 7.40 (m, 1H), 7.26 (m, 2H), 5.02 (d, 1H), 4.30 (m, 1H), 3.58 (m, 1H), 2.95 (m, 2H), 2.62 (m, 0.5H), 2.58 (s, 3H), 2.45 (m, 0.5H), 1.98 (s, 3H), 1.75 (m, 1H), 1.25 (m, 2H), 0.70 (d, 1.5H), 0.51 (d, 1.5H); LC/MS m/z 480 (M+H)$^+$.

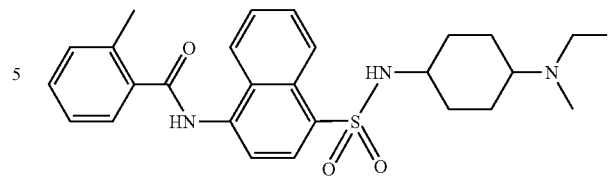

(±)-N-[4-(1-sec-Butyl-piperidin-4-ylsulfamoyl)-naphthalen-1-yl]-2-methyl-benzamide (C-32)

The title compound was made following general procedure in Scheme 5, substituting 4-(2-methyl-benzoylamino)-naphthalene-1-sulfonyl chloride for 4-benzoylamino-naphthalene-1-sulfonyl chloride, and butan-2-one/sodium triacetoxyborohydride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.39 (m, 1H), 3.15 (m, 3H), 2.98 (m, 2H), 2.55 (s, 3H), 1.88 (m, 2H), 1.72 (m, 3H), 1.43 (m, 1H), 1.19 (d, 3H), 0.95 (t, 3H); LC/MS (M+H)$^+$ m/z 480.

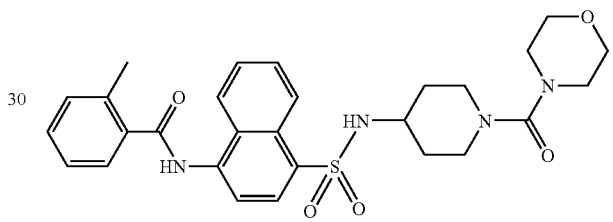

2-Methyl-N-{4-[1-(morpholine-4-carbonyl)-piperidin-4-ylsulfamoyl]-naphthalen-1-yl}-benzamide (C-33)

The title compound was made following general procedure in Scheme 5, substituting 4-(2-methyl-benzoylamino)-naphthalene-1-sulfonyl chloride for 4-benzoylamino-naphthalene-1-sulfonyl chloride, and morpholine-4-carbonyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.59 (t, 4H), 3.50 (m, 2H), 3.27 (m, 1H), 3.19 (t, 4H), 2.76 (m, 2H), 2.54 (s, 3H), 1.59 (m, 2H), 1.27 (m, 2H); LC/MS (M+H)$^+$ m/z 527.

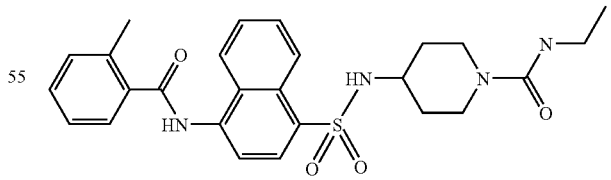

4-[4-(2-Methyl-benzoylamino)-naphthalene-1-sulfonylamino]-piperidine-1-carboxylic acid ethylamide (C-34)

The title compound was made following general procedure in Scheme 5, substituting 4-(2-methyl-benzoylamino)- naphthalene-1-sulfonyl chloride for 4-benzoylamino-naphthalene-1-sulfonyl chloride, and isocyanato-ethane for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.73 (m, 2H), 3.23 (m, 1H), 3.11 (q, 2H), 2.69 (m, 2H), 2.54 (s, 3H), 1.53 (m, 2H), 1.29 (m, 2H), 1.04 (t, 3H); LC/MS (M+H)$^+$ m/z 495.

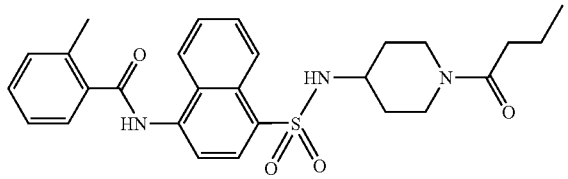

N-[4-(1-Butyryl-piperidin-4-ylsulfamoyl)-naphthalen-1-yl]-2-methyl-benzamide (C-35)

The title compound was made following general procedure in Scheme 5, substituting 4-(2-methyl-benzoylamino)-naphthalene-1-sulfonyl chloride for 4-benzoylamino-naphthalene-1-sulfonyl chloride, and butyryl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 4.19 (m, 1H), 3.74 (m, 1H), 3.33 (m, 1H), 3.01 (m, 1H), 2.64 (m, 1H), 2.54 (s, 3H), 2.74 (t, 2H), 1.62 (m, 2H), 1.55 (m, 2H), 1.29 (m, 2H), 0.89 (t, 3H); LC/MS (M+H)$^+$ m/z 496.

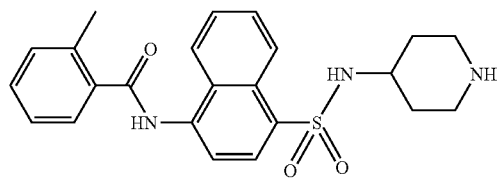

2-Methyl-N-[4-(piperidin-4-ylsulfamoyl)-naphthalen-1-yl]-benzamide (C-36)

The title compound was made following general procedure in Scheme 5, substituting 4-(2-methyl-benzoylamino)-naphthalene-1-sulfonyl chloride for 4-benzoylamino-naphthalene-1-sulfonyl chloride. $^1$H NMR (300 MHz, MeOD) δ 8.75 (d, 1H), 8.33 (d, 1H), 8.23 (d, 1H), 7.94 (d, 1H), 7.71 (m, 3H), 7.39 (m, 3H), 3.49 (m, 1H), 3.15 (m, 2H), 2.90 (m, 2H), 2.50 (s, 3H), 2.21 (m, 1H), 1.82 (m, 2H), 1.59 (m, 1H)); LC/MS (M+H)$^+$ m/z 424.

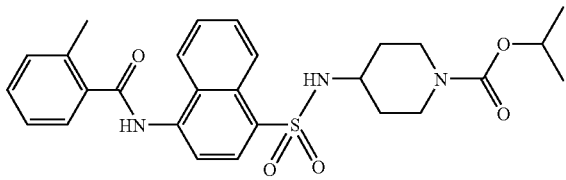

4-[4-(2-Methyl-benzoylamino)-naphthalene-1-sulfonylamino]-piperidine-1-carboxylic acid isopropyl ester (C-37)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isopropyl chloroformate for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 4.80 (m, 1H), 3.83 (m, 2H), 3.25 (m, 1H), 2.79 (m, 2H), 2.54 (s, 3H), 1.58 (m, 2H), 1.29 (m, 2H), 1.20 (t, 3H); LC/MS (M+H)$^+$ m/z 510.

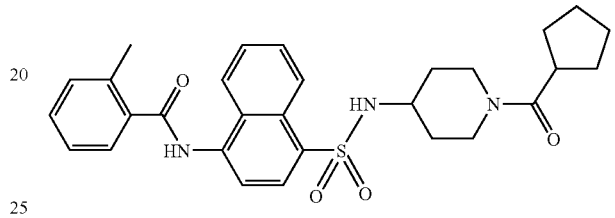

N-[4-(1-Cyclopentanecarbonyl-piperidin-4-ylsulfamoyl)-naphthalen-1-yl]-2-methyl-benzamide (C-38)

The title compound was made following general procedure in Scheme 5, substituting 4-(2-methyl-benzoylamino)-naphthalene-1-sulfonyl chloride for 4-benzoylamino-naphthalene-1-sulfonyl chloride, and cyclopentanecarbonyl chloride for 2-isocyanato-propane. $^1$H NMR (300 MHz, MeOD) δ 8.78 (d, 1H), 8.33 (d, 1H), 8.25 (d, 1H), 7.94 (d, 1H), 7.71 (m, 3H), 7.41 (m, 3H), 4.19 (m, 1H), 3.88 (m, 1H), 3.00 (m, 2H), 2.68 (m, 2H), 2.54 (s, 3H), 1.65 (m, 11H), 1.29 (m, 3H); LC/MS (M+H)$^+$ m/z 520.

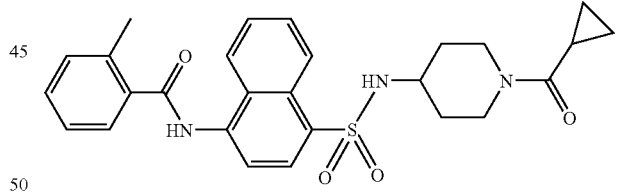

N-[4-(1-Cyclopropanecarbonyl-piperidin-4-ylsulfamoyl)-naphthalen-1-yl]-2-methyl-benzamide (C-39)

The title compound was made following general procedure in Scheme 5, substituting 4-(2-methyl-benzoylamino)-naphthalene-1-sulfonyl chloride for 4-benzoylamino-naphthalene-1-sulfonyl chloride, and cyclopropanecarbonyl chloride for 2-isocyanato-propane. $^1$H NMR (300 MHz, MeOD) δ 8.78 (d, 1H), 8.33 (d, 1H), 8.25 (d, 1H), 7.94 (d, 1H), 7.71 (m, 3H), 7.41 (m, 3H), 4.17 (m, 2H), 3.13 (m, 1H), 2.71 (m, 2H), 2.54 (s, 3H), 1.84 (m, 1H), 1.71 (m, 1H), 1.59 (m, 1H), 1.29 (m, 2H), 0.79 (m, 4H); LC/MS (M+H)$^+$ m/z 492.

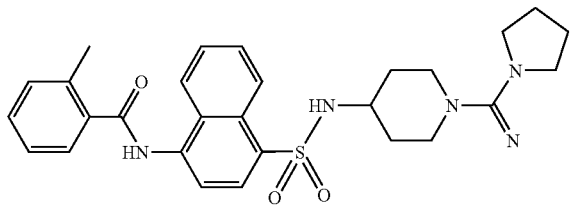

N-{4-[1-(Imino-pyrrolidin-1-yl-methyl)-piperidin-4-ylsulfamoyl]-naphthalen-1-yl}-2-methyl-benzamide (C-40)

The title compound was made following general procedure in Scheme 5, substituting 4-(2-methyl-benzoylamino)-naphthalene-1-sulfonyl chloride for 4-benzoylamino-naphthalene-1-sulfonyl chloride, and pyrrolidine-1-carbonitrile for 2-isocyanato-propane. $^1$H NMR (300 MHz, DMSO) δ 8.70 (d, 1H), 8.49 (s, 1H), 8.28 (d, 1H), 8.21 (d, 1H), 7.93 (d, 1H), 7.71 (m, 3H), 7.39 (m, 3H), 3.40 (m, 9H), 2.98 (m, 2H), 2.54 (s, 3H), 1.82 (m, 4H), 1.60 (m, 1H), 1.39 (m, 1H); LC/MS (M+H)$^+$ m/z 520.

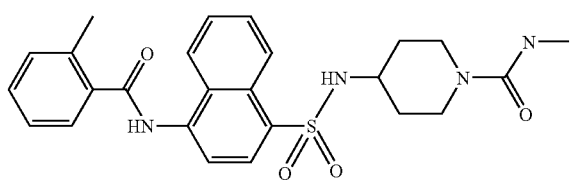

4-[4-(2-Methyl-benzoylamino)-naphthalene-1-sulfonylamino]-piperidine-1-carboxylic acid methylamide (C-41)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isocyanatomethane for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.73 (m, 2H), 3.25 (m, 1H), 2.72 (m, 2H), 2.65 (s, 3H), 2.56 (s, 3H), 1.53 (m, 2H), 1.28 (m, 2H); LC/MS (M+H)$^+$ m/z 481.

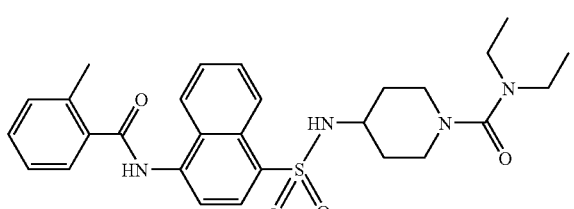

4-[4-(2-Methyl-benzoylamino)-naphthalene-1-sulfonylamino]-piperidine-1-carboxylic acid diethylamide (C-42)

The title compound was made following general procedure in Scheme 5, substituting 4-(2-methyl-benzoylamino)-naphthalene-1-sulfonyl chloride for 4-benzoylamino-naphthalene-1-sulfonyl chloride, and diethylcarbamyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.41 (m, 2H), 3.23 (m, 1H), 3.15 (q, 4H), 2.72 (m, 2H), 2.56 (s, 3H), 1.53 (m, 2H), 1.40 (m, 2H), 1.07 (t, 6H); LC/MS (M+H)$^+$ m/z 523.

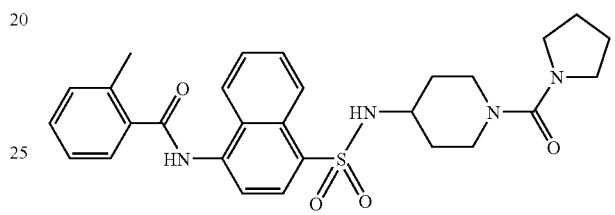

2-Methyl-N-{4-[1-(pyrrolidine-1-carbonyl)-piperidin-4-ylsulfamoyl]-naphthalen-1-yl}-benzamide (C-43)

The title compound was made following general procedure in Scheme 5, substituting 4-(2-methyl-benzoylamino)-naphthalene-1-sulfonyl chloride for 4-benzoylamino-naphthalene-1-sulfonyl chloride, and pyrrolidine-1-carbonyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.55 (m, 2H), 3.25 (m, 5H), 2.72 (m, 2H), 2.56 (s, 3H), 1.72 (m, 4H), 1.59 (m, 2H), 1.38 (m, 2H); LC/MS (M+H)$^+$ m/z 521.

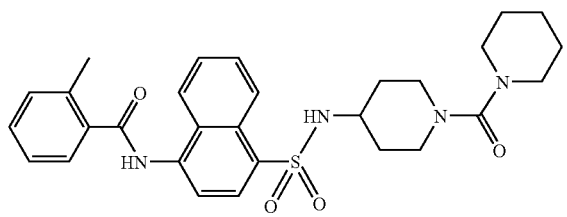

2-Methyl-N-{4-[1-(piperidine-1-carbonyl)-piperidin-4-ylsulfamoyl]-naphthalen-1-yl}-benzamide (C-44)

The title compound was made following general procedure in Scheme 5, substituting 4-(2-methyl-benzoylamino)-naphthalene-1-sulfonyl chloride for 4-benzoylamino-naphthalene-1-sulfonyl chloride, and piperidine-1-carbonyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.39 (m, 3H), 3.41 (m, 4H), 3.15 (m, 5H), 2.72 (m, 2H), 2.56 (s, 3H), 1.58 (m, 8H); LC/MS (M+H)+ m/z 535.

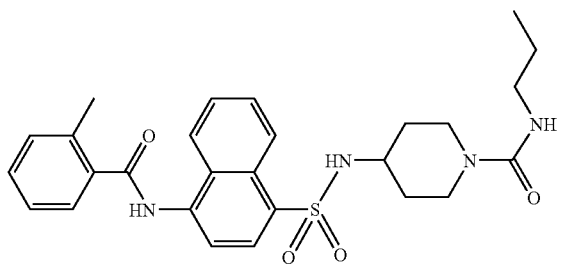

4-[4-(2-Methyl-benzoylamino)-naphthalene-1-sulfonylamino]-piperidine-1-carboxylic acid propylamide (C-45)

The title compound was made following general procedure in Scheme 5, substituting 4-(2-methyl-benzoylamino)-naphthalene-1-sulfonyl chloride for 4-benzoylamino-naphthalene-1-sulfonyl chloride, and 1-isocyanato-propane for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.75 (m, 2H), 3.25 (m, 1H), 3.06 (t, 2H), 2.74 (m, 2H), 2.59 (s, 3H), 1.59 (m, 2H), 1.49 (m, 2H), 1.30 (m, 2H), 0.89 (t, 3H); LC/MS (M+H)+ m/z 509.

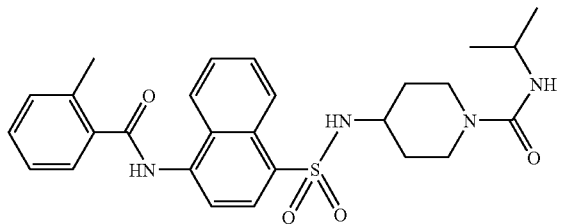

4-[4-(2-Methyl-benzoylamino)-naphthalene-1-sulfonylamino]-piperidine-1-carboxylic acid isopropylamide (C-46)

The title compound was made following general procedure in Scheme 5, substituting 4-(2-methyl-benzoylamino)-naphthalene-1-sulfonyl chloride for 4-benzoylamino-naphthalene-1-sulfonyl chloride. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.76 (m, 2H), 3.25 (m, 2H), 2.71 (m, 2H), 2.57 (s, 3H), 1.59 (m, 2H), 1.30 (m, 2H), 1.05 (d, 6H); LC/MS (M+H)+ m/z 509.

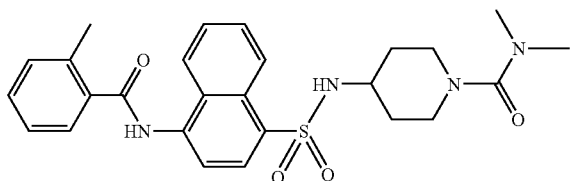

4-[4-(2-Methyl-benzoylamino)-naphthalene-1-sulfonylamino]-piperidine-1-carboxylic acid dimethylamide (C-47)

The title compound was made following general procedure in Scheme 5, substituting 4-(2-methyl-benzoylamino)-naphthalene-1-sulfonyl chloride for 4-benzoylamino-naphthalene-1-sulfonyl chloride, and dimethylcarbamyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 3.54 (m, 2H), 3.25 (m, 1H), 2.75 (s, 6H), 2.71 (m, 2H), 2.55 (s, 3H), 1.59 (m, 2H), 1.35 (m, 2H); LC/MS (M+H)+ m/z 495.

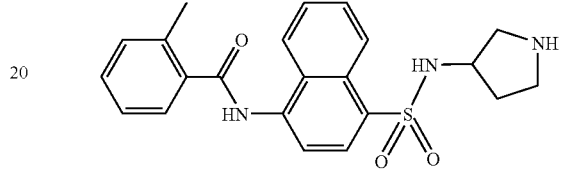

(±)-2-Methyl-N-[4-(pyrrolidin-3-ylsulfamoyl)-naphthalen-1-yl]-benzamide (C-48)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester. $^1$H NMR (300 MHz, DMSO) δ 8.78 (d, 1H), 8.33 (m, 2H), 8.23 (d, 1H), 7.94 (d, 1H), 7.71 (m, 3H), 7.43 (m, 1H), 7.38 (m, 2H), 3.69 (m, 1H), 3.88 (m, 3H), 2.61 (m, 1H), 2.48 (s, 3H), 1.74 (m, 1H), 1.49 (m, 1H); LC/MS (M+H)+ m/z 410.

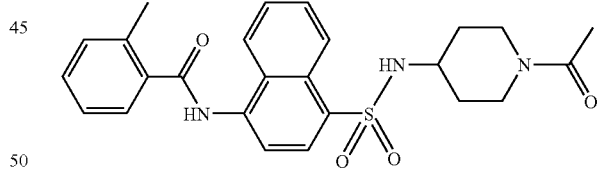

N-[4-(1-Acetyl-piperidin-4-ylsulfamoyl)-naphthalen-1-yl]-2-methyl-benzamide (C-49)

The title compound was made following general procedure in Scheme 5, substituting 4-(2-methyl-benzoylamino)-naphthalene-1-sulfonyl chloride for 4-benzoylamino-naphthalene-1-sulfonyl chloride, and acetyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 4.15 (m, 1H), 3.69 (m, 1H), 3.25 (m, 1H), 3.03 (m, 1H), 2.69 (m, 1H), 2.55 (s, 3H), 1.98 (s, 3H), 1.59 (m, 2H), 1.31 (m, 2H); LC/MS (M+H)+ m/z 466.

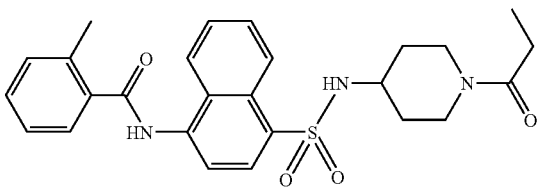

2-Methyl-N-[4-(1-propionyl-piperidin-4-ylsulfamoyl)-naphthalen-1-yl]-benzamide (C-50)

The title compound was made following general procedure in Scheme 5, substituting 4-(2-methyl-benzoylamino)-naphthalene-1-sulfonyl chloride for 4-benzoylamino-naphthalene-1-sulfonyl chloride, and propionyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 4.19 (m, 1H), 3.72 (m, 1H), 3.25 (m, 1H), 3.01 (m, 1H), 2.69 (m, 1H), 2.55 (s, 3H), 2.41 (q, 2H), 1.61 (m, 2H), 1.31 (m, 2H), 1.02 (t, 3H); LC/MS (M+H)$^+$ m/z 480.

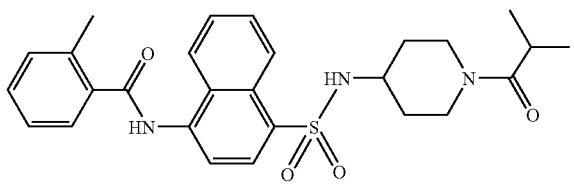

N-[4-(1-Isobutyryl-piperidin-4-ylsulfamoyl)-naphthalen-1-yl]-2-methyl-benzamide (C-51)

The title compound was made following general procedure in Scheme 5, substituting 4-(2-methyl-benzoylamino)-naphthalene-1-sulfonyl chloride for 4-benzoylamino-naphthalene-1-sulfonyl chloride, and isobutyryl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H), 7.38 (m, 2H), 4.20 (m, 1H), 3.72.

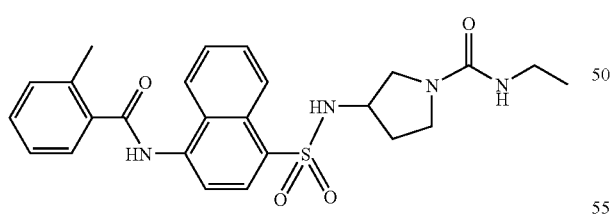

(±)-3-[4-(2-Methyl-benzoylamino)-naphthalene-1-sulfonylamino]-pyrrolidine-1-carboxylic acid ethylamide (C-52)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester and isocyanato-ethane for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H), 7.38 (m, 2H), 3.80 (m, 1H), 3.19 (m, 1H), 3.11 (q, 2H), 3.09 (m, 3H), 2.55 (s, 3H), 1.89 (m, 1H), 1.73 (m, 1H), 1.03 (t, 3H); LC/MS (M+H)$^+$ m/z 481.

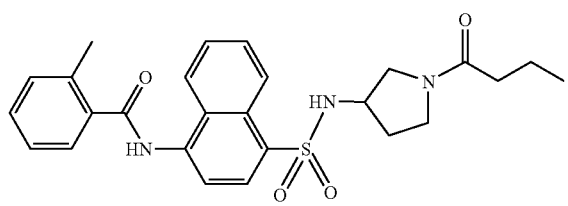

(±)-3-[4-(2-Methyl-benzoylamino)-naphthalene-1-sulfonylamino]-pyrrolidine-1-carboxylic acid ethylamide (C-53)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester and butyryl chloride for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H), 7.38 (m, 2H), 3.85 (m, 1H), 3.40 (m, 3H), 3.15 (m, 1H), 2.53 (s, 3H), 2.19 (t, 1H), 1.95 (t, 1H), 1.85 (m, 2H), 0.88 (m, 3H); LC/MS (M+H)$^+$ m/z 480.

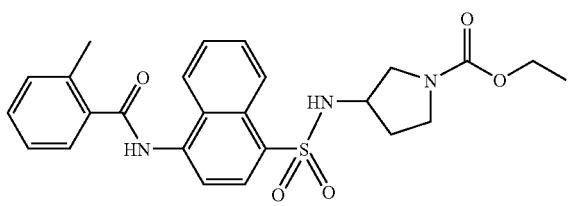

(±)-3-[4-(2-Methyl-benzoylamino)-naphthalene-1-sulfonylamino]-pyrrolidine-1-carboxylic acid ethyl ester (C-54)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-pyrrolidine-1-carboxylic acid tert-butyl ester for 4-amino-piperidine-1-carboxylic acid tert-butyl ester and ethyl chlorofomate for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H), 7.38 (m, 2H), 4.06 (m, 2H), 3.80 (m, 1H), 3.38 (m, 1H), 3.25 (m, 1H), 3.09 (m, 2H), 2.55 (s, 3H), 1.89 (m, 1H), 1.73 (m, 1H), 1.20 (m, 3H); LC/MS (M+H)$^+$ m/z 483.

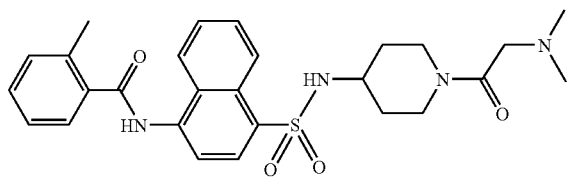

N-{4-[1-(2-Dimethylamino-acetyl)-piperidin-4-yl-sulfamoyl]-naphthalen-1-yl}-2-methyl-benzamide (C-55)

The title compound was made following general procedure in Scheme 5, substituting 4-(2-methyl-benzoylamino)-naphthalene-1-sulfonyl chloride for 4-benzoylamino-naphthalene-1-sulfonyl chloride, and dimethylamino-acetyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 4.18 (m, 1H), 3.94 (d, 2H), 3.54 (m, 1H), 3.34 (m, 1H), 3.03 (m, 1H), 2.80 (m, 1H), 2.77 (s, 6H), 2.55 (s, 3H), 1.68 (m, 2H), 1.39 (m, 2H); LC/MS (M+H)$^+$ m/z 509.

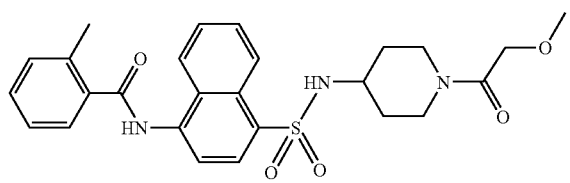

N-{4-[1-(2-Methoxy-acetyl)-piperidin-4-ylsulfamoyl]-naphthalen-1-yl}-2-methyl-benzamide (C-56)

The title compound was made following general procedure in Scheme 5, substituting 4-(2-methyl-benzoylamino)-naphthalene-1-sulfonyl chloride for 4-benzoylamino-naphthalene-1-sulfonyl chloride, and methoxy-acetyl chloride for 2-isocyanato-propane. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 4.15 (m, 1H), 4.04 (d, 2H), 3.94 (d, 2H), 3.63 (m, 1H), 3.34 (s, 3H), 3.32 (m, 1H), 3.01 (m, 1H), 2.71 (m, 1H), 2.55 (s, 3H), 1.63 (m, 2H), 1.41 (m, 2H); LC/MS (M+H)$^+$ m/z 496.

2-Methyl-N-[4-(1-pyrimidin-2-yl-piperidin-4-ylsulfamoyl)-naphthalen-1-yl]-benzamide (C-57)

The title compound was made following general procedure in Scheme 5, substituting 4-[4-(2-methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting 2-bromo-pyrimidine for 2-isocyanato-propane. $^1$H NMR (300 MHz, CDCl$_3$/MeOD) δ 8.57 (d, 1H), 8.19 (d, 2H), 8.08 (d, 2H), 7.97 (d, 2H), 7.52 (m, 3H), 7.27 (t, 1H), 7.18 (d, 2H), 6.32 (t, 1H), 4.30 (d, 2H), 3.93 (s, 3H), 3.21 (m, 1H), 2.79 (dt, 2H), 2.43 (s, 3H), 1.58 (m, 2H), 1.20 (m, 3H); LC/MS m/z 500 (M−H)$^−$

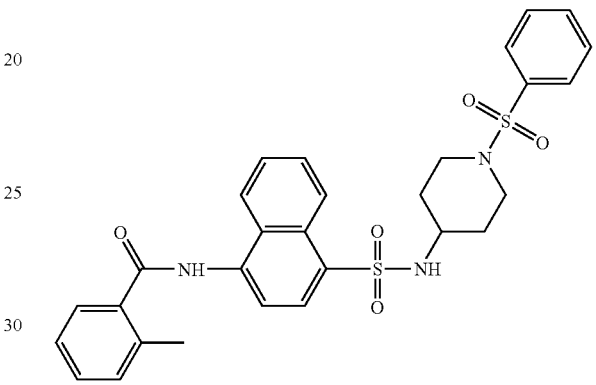

N-[4-(1-Benzenesulfonyl-piperidin-4-ylsulfamoyl)-naphthalen-1-yl]-2-methyl-benzamide (C-58)

The title compound was made following general procedure in Scheme 5, substituting 4-[4-(2-methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting benzenesulfonyl chloride for 2-isocyanato-propane. $^1$H NMR (300 MHz, CDCl$_3$) δ 8.60 (d, 1H), 8.22 (m, 3H), 7.94 (d, 1H), 7.48 (m, 11H), 4.57 (d, 1H), 3.49 (m, 2H), 3.02 (s, br, 1H), 2.55 (s, 3H), 2.28 (t, 2H), 1.60 (m, 2H), 1.40 (m, 2H); LC/MS m/z 564 (M+H)$^+$

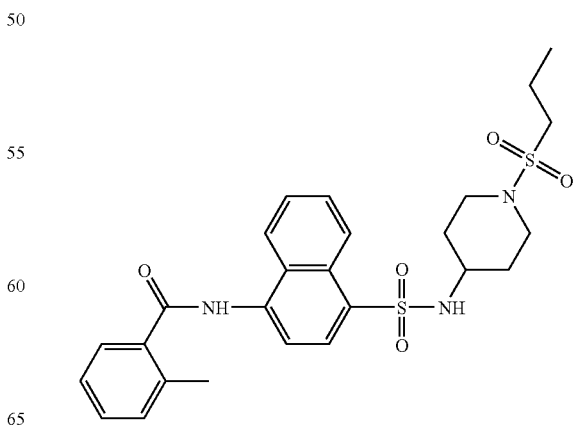

2-Methyl-N-{4-[1-(propane-1-sulfonyl)-piperidin-4-ylsulfamoyl]-naphthalen-1-yl}-benzamide (C-59)

The title compound was made following general procedure in Scheme 5, substituting 4-[4-(2-methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting propane-1-sulfonyl chloride for 2-isocyanato-propane. $^1$H NMR (300 MHz, MeOD/CDCl$_3$) δ 8.69 (d, 1H), 8.27 (d, 1H), 8.17 (d, 1H), 7.97 (m, 1H), 7.62 (m, 4H), 7.34 (m, 2H), 3.50 (d, 2H), 3.15 (m, 1H), 2.75 (m, 4H), 2.54 (s, 3H), 1.68 (m, 4H), 1.45 (m, 2H), 1.00 (s, 3H); LC/MS m/z 528 (M−H)$^−$

N-[4-(1-Butyryl-piperidin-4-ylsulfamoyl)-naphthalen-1-yl]-2,3-dimethyl-benzamide (C-61)

The title compound was made following general procedure in Scheme 5, substituting 4-[4-(2,3-dimethyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting butyl chloride for 2-isocyanato-propane. $^1$H NMR (300 MHz, MeOD) δ 8.75 (d, 1H), 8.32 (d, 1H), 8.22 (d, 1H), 7.96 (m, 1H), 7.71 (m, 2H), 7.46 (m, 1H), 7.29 (m, 2H), 4.35 (d, 1H), 3.75 (d, 1H), 3.02 (t, 1H), 2.65 (m, 1H), 2.45 (s, 3H), 2.35 (s, 3H), 2.25 (m, 1H), 1.60 (m, 4H), 1.28 (m, 2H), 2.75 (m, 2H), 0.90 (m, 5H); LC/MS m/z 508 (M+H)$^+$

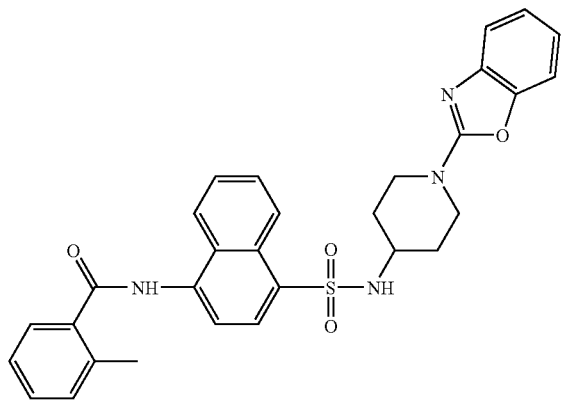

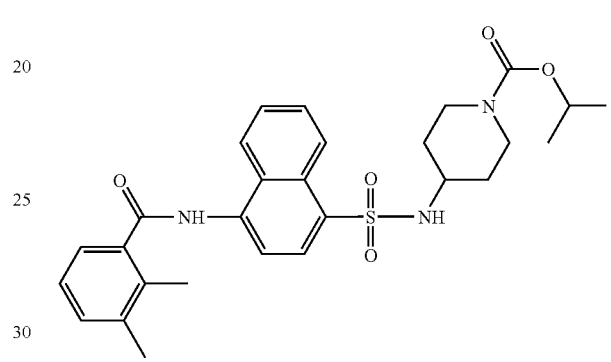

N-[4-(1-Benzooxazol-2-yl-piperidin-4-ylsulfamoyl)-naphthalen-1-yl]-2-methyl-benzamide (C-60)

The title compound was made following general procedure in Scheme 5, substituting 4-[4-(2-Methyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting 2-chloro-benzooxazole for 2-isocyanato-propane. $^1$H NMR (300 MHz, MeOD/CDCl$_3$) δ 8.47 (dd, 1H), 8.08 (d, 1H), 8.94 (m, 1H), 7.80 (m, 1H), 7.44 (m, 3H), 7.12 (m, 3H), 6.98 (t, 2H), 6.89 (td, 1H), 6.76 (td, 1H), 3.75 (d, 2H), 3.10 (m, 1H), 2.75 (td, 2H), 2.30 (s, 3H), 1.50 (m, 2H), 1.25 (m, 2H); LC/MS m/z 528 (M+H)$^+$

4-[4-(2,3-Dimethyl-benzoylamino)-naphthalene-1-sulfonylamino]-piperidine-1-carboxylic acid isopropyl ester (C-62)

The title compound was made following general procedure in Scheme 5, substituting 4-[4-(2,3-dimethyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting isopropyl chloroformate for 2-isocyanato-propane. $^1$H NMR (300 MHz, MeOD) δ 8.75 (d, 1H), 8.31 (d, 1H), 8.22 (d, 1H), 7.96 (m, 1H), 7.71 (m, 2H), 7.46 (m, 1H), 7.29 (m, 2H), 4.78 (m, 1H), 3.82 (d, 2H), 3.25 (m, 1H), 2.75 (m, 2H), 2.45 (s, 3H), 2.35 (s, 3H), 1.50 (m, 2H), 1.25 (m, 2H), 1.15 (d, 6H); LC/MS m/z 524 (M+H)$^+$

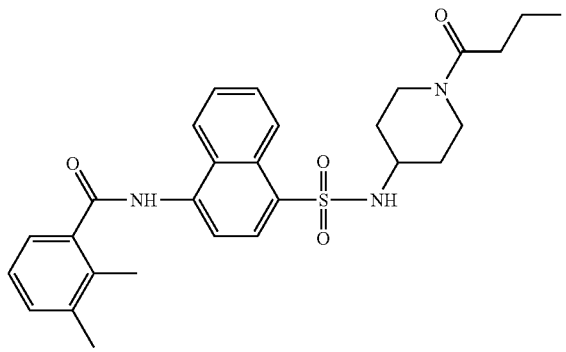

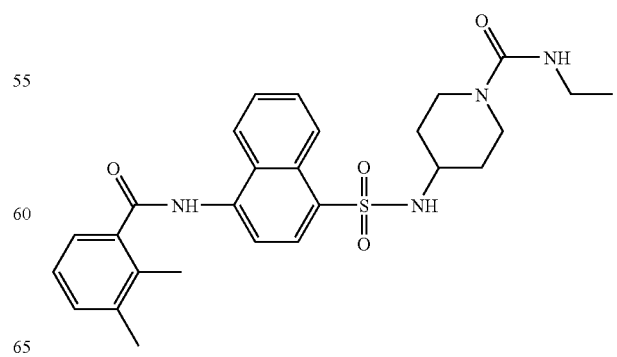

4-[4-(2,3-Dimethyl-benzoylamino)-naphthalene-1-sulfonylamino]-piperidine-1-carboxylic acid ethylamide (C-63)

The title compound was made following general procedure in Scheme 5, substituting 4-[4-(2,3-dimethyl-benzoylamino)-naphthalene-1-sulfonylamino]-piperidine-1-carboxylic acid tert-butyl ester for 4-(4-benzoylamino-naphthalene-1-sulfonylamino)-piperidine-1-carboxylic acid tert-butyl ester (A-28), and substituting isocyanato-ethane for 2-isocyanato-propane. $^1$H NMR (300 MHz, MeOD) δ 8.75 (d, 1H), 8.31 (d, 1H), 8.22 (d, 1H), 7.96 (m, 1H), 7.71 (m, 2H), 7.46 (m, 1H), 7.29 (m, 2H), 3.75 (d, 2H), 3.82 (d, 2H), 3.25 (m, 1H), 3.10 (q, 2H), 2.72 (t, 2H), 2.45 (s, 3H), 2.35 (s, 3H), 1.55 (m, 2H), 1.25 (m, 2H), 1.05 (t, 3H); LC/MS m/z 509 (M+H)$^+$

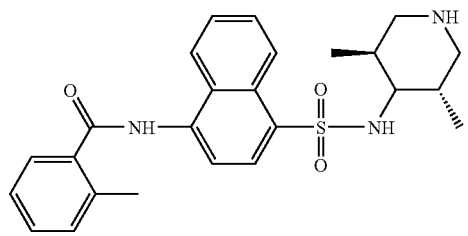

(±)-(cis,trans)-N-[4-(3,5-Dimethyl-piperidin-4-ylsulfamoyl)-naphthalen-1-yl]-2-methyl-benzamide (C-64)

The title compound was made following general procedure in scheme 4-2, substituting (±)-1-benzyl-3,5-dimethyl-piperidin-4-ylamine (5) for (±)-4-amino-1-benzyl-piperidine-3-carboxylic acid ethyl ester (6). $^1$H NMR (300 MHz, CDCl$_3$) δ 8.65 (d, 1H), 8.35 (s, 1H), 8.18 (d, 1H), 8.05 (m, 2H), 7.55 (m, 3H), 7.30 (m, 1H), 7.20 (m, 2H), 3.85 (s, br, 1H), 3.05 (m, 2H), 2.80 (m, 2H), 2.50 (s, 3H), 2.40 (m, 1H), 1.85 (m, 2H), 0.63 (dd, 6H); LC/MS m/z 453 (M+H)$^+$

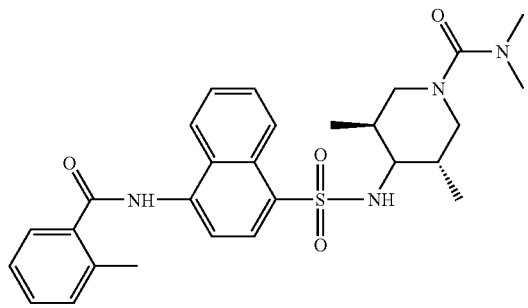

(±)-(cis,trans)-3,5-Dimethyl-4-[4-(2-methyl-benzoylamino)-naphthalene-1-sulfonylamino]-piperidine-1-carboxylic acid dimethylamide (C-65)

The title compound was made following general procedure in Scheme 5, substituting (±)-(cis,trans)-N-[4-(3,5-dimethyl-piperidin-4-ylsulfamoyl)-naphthalen-1-yl]-2-methyl-benzamide (C-64) for N-[4-(piperidin-4-ylsulfamoyl)-naphthalen-1-yl]-benzamide (C-1) and substituting dimethylcarbamyl chloride for 2-isocyanato-propane. $^1$H NMR (300 MHz, CDCl$_3$) δ 8.75 (d, 1H), 8.34 (m, 2H), 8.21 (s, 1H), 7.95 (d, 1H), 7.65 (m, 3H), 7.43 (m, 1H), 7.34 (m, 2H), 4.85 (m, 1H), 3.44 (d, 1H), 3.18 (d, 1H), 2.90 (m, 2H), 2.73 (s, 6H), 2.56 (s, 3H), 2.37 (dd, 1H), 1.74 (m, 2H), 0.71 (d, 3H), 0.59 (d, 3H); LC/MS m/z 524 (M+H)$^+$

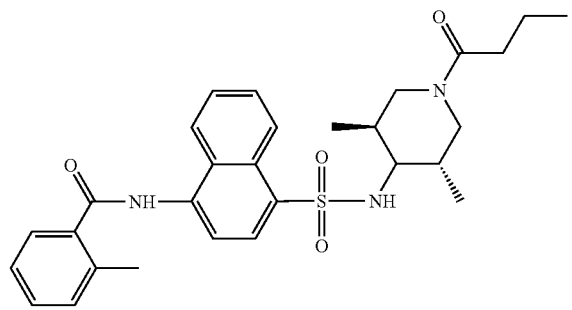

(±)-(cis,trans)-N-[4-(1-Butyryl-3,5-dimethyl-piperidin-4-ylsulfamoyl)-naphthalen-1-yl]-2-methyl-benzamide (C-66)

The title compound was made following general procedure in Scheme 5, substituting (±)-(cis,trans)-N-[4-(3,5-dimethyl-piperidin-4-ylsulfamoyl)-naphthalen-1-yl]-2-methyl-benzamide (C-64) for N-[4-(piperidin-4-ylsulfamoyl)-naphthalen-1-yl]-benzamide (C-1) and substituting butyl chloride for 2-isocyanato-propane. $^1$H NMR (300 MHz, CDCl$_3$) δ 8.74(d, 1H), 8.33 (m, 3H), 7.96 (m, 1H), 7.64 (m, 3H), 7.42 (m, 1H), 7.31 (m, 2H), 5.12 (m, 1H), 3.60 (m, 2H), 3.18 (d, 1H), 3.00 (m, 2H), 2.56 (s, 3H), 2.15 (m, 2H), 1.80 (m, 2H), 1.55 (m, 3H), 0.86 (m, 3H), 0.68 (m, 3H), 0.49 (m, 3H); LC/MS m/z 523 (M+H)$^+$

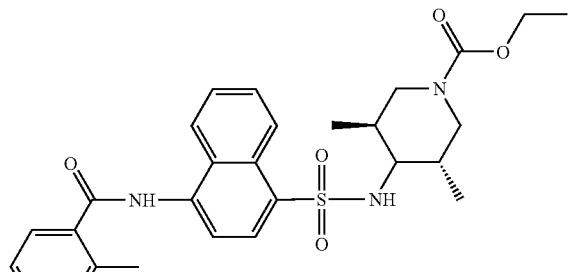

(±)-(cis,trans)-3,5-Dimethyl-4-[4-(2-methyl-benzoylamino)-naphthalene-1-sulfonylamino]-piperidine-1-carboxylic acid ethyl ester (C-67)

The title compound was made following general procedure in Scheme 5, substituting (±)-(cis,trans)-N-[4-(3,5-dimethyl-piperidin-4-ylsulfamoyl)-naphthalen-1-yl]-2-methyl-benzamide (C-64) for N-[4-(piperidin-4-ylsulfamoyl)-naphthalen-1-yl]-benzamide (C-1) and substituting ethyl chloroformate for 2-isocyanato-propane. $^1$H NMR (300 MHz, CDCl$_3$) δ 8.75 (d, 1H), 8.35 (m, 2H), 8.19 (s, 1H), 7.95 (d, 1H), 7.66 (m, 3H), 7.38 (m, 3H), 4.79 (d, 1H), 4.05 (m, 2H), 3.74 (m, 2H), 2.95 (m, 2H), 2.59 (s, 3H), 2.40 (m, 1H),1.80 (s, br, 2H), 1.18 (t, 3H), 0.62 (m, 6H); LC/MS m/z 525 (M+H)$^+$

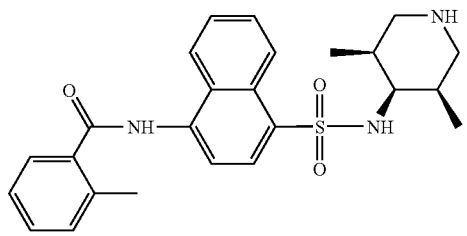

(±)-(cis,cis)-N-[4-(3,5-Dimethyl-piperidin-4-ylsulfamoyl)-naphthalen-1-yl]-2-methyl-benzamide (C-68)

The title compound was made following general procedure in Scheme 4-2, substituting (±)-1-benzyl-3,5-dimethyl-piperidin-4-ylamine (5) for (±)-4-amino-1-benzyl-piperidine-3-carboxylic acid ethyl ester (6). $^1$H NMR (300 MHz, CDCl$_3$) δ 8.75 (d, 1H), 8.39 (s, 1H), 8.16 (d, 1H), 8.05 (m, 2H), 7.58 (m, 3H), 7.32 (m, 1H), 7.20 (m, 2H), 3.75 (s, br, 1H), 3.45 (s, 1H), 2.75 (m, 2H), 2.56 (m, 2H), 2.45 (s, 3H), 1.82 (m, 2H), 0.40 (d, 6H); LC/MS m/z 453 (M+H)$^+$

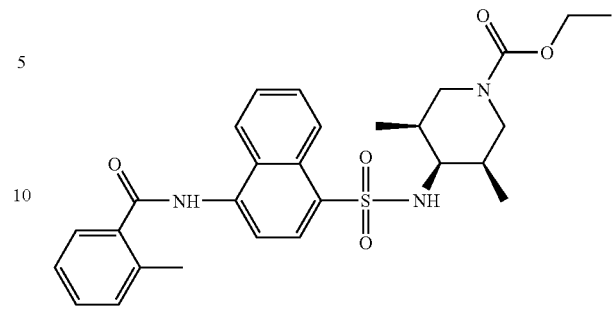

(±)-(cis,cis)-3,5-Dimethyl-4-[4-(2-methyl-benzoylamino)-naphthalene-1-sulfonylamino]-piperidine-1-carboxylic acid ethyl ester (C-70)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting ethyl chloroformate for 2-isocyanato-propane. $^1$H NMR (300 MHz, CDCl$_3$) δ 8.77 (d, 1H), 8.33 (m, 2H), 8.15 (s, 1H), 7.94 (d, 1H), 7.67 (m, 3H), 7.37 (m, 3H), 4.77 (d, 1H), 4.07 (q, 2H), 3.75 (s, br, 2H), 3.48 (m, 2H), 2.58 (s, 3H), 2.37 (m, 1H), 1.72 (m, 2H), 1.22 (t, 3H), 0.48 (s, br, 6H); LC/MS m/z 525 (M+H)$^+$

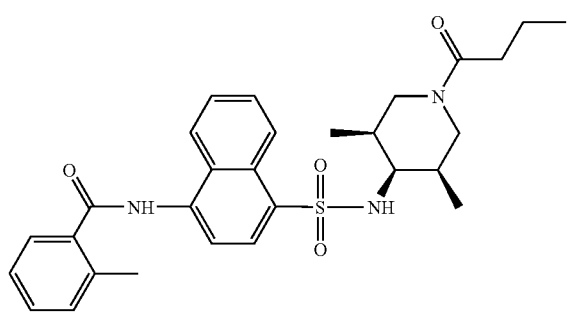

(±)-(cis,cis)-N-[4-(1-Butyryl-3,5-dimethyl-piperidin-4-ylsulfamoyl)-naphthalen-1-yl]-2-methyl-benzamide (C-69)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting butyl chloride for 2-isocyanato-propane. $^1$H NMR (300 MHz, CDCl$_3$) δ 8.80 (d, 1H), 8.28 (m, 3H), 7.96 (d, 1H), 7.64 (m, 3H), 7.42 (m, 1H), 7.32 (m, 2H), 5.16 (d, 1H), 4.18 (dd, 1H), 3.51 (d, 1H), 3.38 (d, 1H), 2.68 (t, 1H), 2.55 (s, 3H), 2.18 (m, 3H), 1.62 (m, 4H), 0.90 (t, 3H), 0.63 (d, 3H), 0.36 (d, 3H); LC/MS m/z 523 (M+H)$^+$

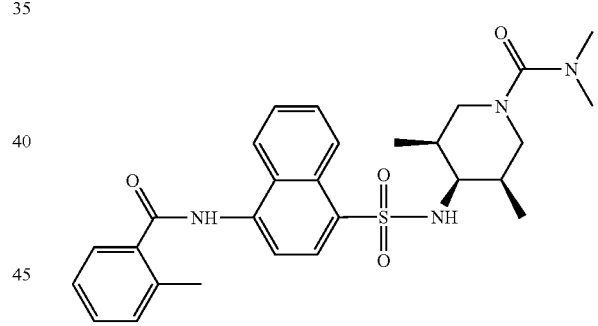

(±)-(cis,cis)-3,5-Dimethyl-4-[4-(2-methyl-benzoylamino)-naphthalene-1-sulfonylamino]-piperidine-1-carboxylic acid dimethylamide (C-71)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting dimethylcarbamyl chloride for 2-isocyanato-propane. $^1$H NMR (300 MHz, CDCl$_3$) δ 8.76 (d, 1H), 8.26 (m, 3H), 7.95 (d, 1H), 7.65 (m, 3H), 7.34 (m, 3H), 5.20 (d, 1H), 3.51 (m, 1H), 3.20 (d, 2H), 2.76 (s, 6H), 2.56 (s, 3H), 2.40 (t, 2H), 1.78 (m, 2H), 0.44 (dd, 6H); LC/MS m/z 524 (M+H)$^+$

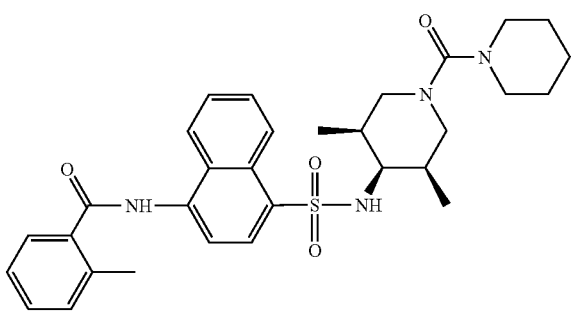

(±)-(cis,cis)-N-{4-[3,5-Dimethyl-1-(piperidine-1-carbonyl)-piperidin-4-ylsulfamoyl]-naphthalen-1-yl}-2-methyl-benzamide (C-72)

The title compound was made following general procedure in Scheme 5, substituting (±)-(cis, cis)-N -[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting piperidine-1-carbonyl chloride for $^2$-isocyanato-propane. $^1$H NMR (300 MHz, CDCl$_3$) δ 8.75 (d, 1H), 8.33 (s, 1H), 8.25 (m, 2H), 7.95 (d, 1H), 7.63 (m, 3H), 7.32 (m, 3H), 5.08 (d, 1H), 3.49 (d, 1H), 3.18 (dd, 2H), 3.07 (s, br, 4H), 2.55 (s, 3H), 2.39 (t, 2H), 1.75 (m, 2H), 1.50 (s, br, 5H), 0.43 (dd, 6H); LC/MS m/z 564 (M+H)$^+$

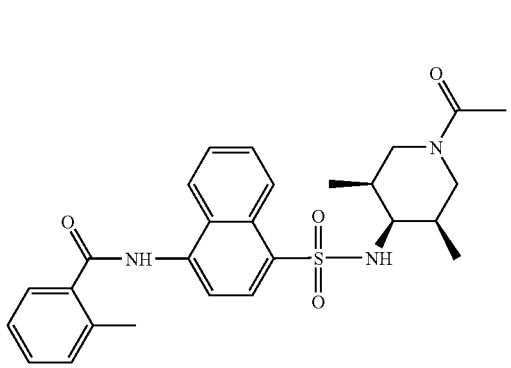

(±)-(cis,cis)-N-[4-(1-Acetyl-3,5-dimethyl-piperidin-4-ylsulfamoyl)-naphthalen-1-yl]-2-methyl-benzamide (C-73)

The title compound was made following general procedure in Scheme 5, substituting (±)-(cis, cis)-N-[4-(3,5-dimethyl-piperidin-4-ylsulfamoyl)-naphthalen-1-yl]-2-methyl-benzamide (C-68) for N-[4-(piperidin-4-ylsulfamoyl)-naphthalen-1-yl]-benzamide (C-1) and substituting acetyl chloride for 2-isocyanato-propane. $^1$H NMR (300 MHz, CDCl$_3$) δ 8.80 (d, 1H), 8.28 (m, 3H), 7.76 (d, 1H), 7.64 (m, 3H), 7.35 (m, 3H), 5.26 (d, 1H), 4.16 (dd, 1H), 3.51 (dd, 1H), 3.32 (dd, 1H), 3.32 (dd, 1H), 2.74 (t, 1H), 2.56 (s, 3H), 2.18 (t, 1H), 1.99 (s, 3H), 1.70 (m, 2H), 0.60 (d, 3H), 0.38 (d, 3H); LC/MS m/z 495 (M+H)$^+$

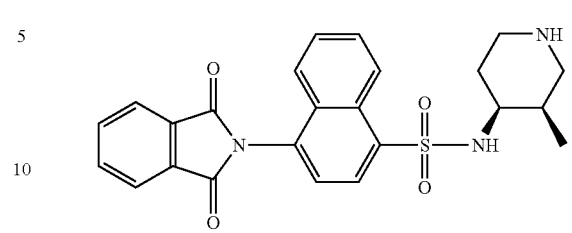

(±)-(cis)-4-(1,3-Dioxo-1,3-dihydro-isoindol-2-yl)-naphthalene-1-sulfonic acid (3-methyl-piperidin-4-yl)-amide (C-74)

The title compound was made as its formate salt following general procedure in Scheme 4-2, substituting (±)-1-benzyl-3-methyl-piperidin-4-ylamine (1) for (±)-4-amino-1-benzyl-piperidine-3-carboxylic acid ethyl ester (6) and substituting 4-(1,3-dioxo-1,3-dihydro-isoindol-2-yl)-naphthalene-1-sulfonyl chloride for 4-(2-methyl-benzoylamino)-naphthalene-1-sulfonyl chloride. $^1$H NMR (300 MHz, MeOD) δ 8.88 (d, 1H), 8.45 (s, 1H), 8.39 (d, 1H), 8.02 (m, 2H), 7.93 (m, 2H), 7.80 (m, 2H), 7.67 (d, 2H), 3.50 (m, 1H), 3.05 (m, 3H), 2.80 (t, 1H), 1.95 (m, 1H), 1.65 (m, 2H), 0.60 (d, 3H); LC/MS m/z 451 (M+H)$^+$

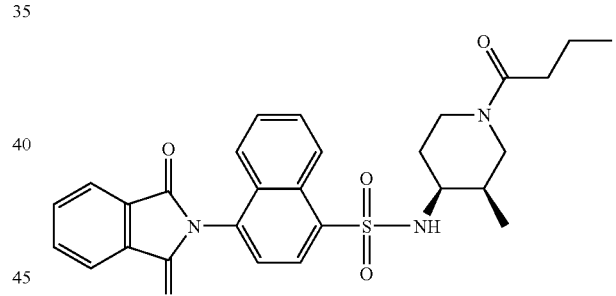

(±)-(cis)-4-(1,3-Dioxo-1,3-dihydro-isoindol-2-yl)-naphthalene-1-sulfonic acid (1-butyryl-3-methyl-piperidin-4-yl)-amide (C-75)

The title compound was made following general procedure in Scheme 5, substituting (±)-(cis)-4-(1,3-dioxo-1,3-dihydro-isoindol-2-yl)-naphthalene-1-sulfonic acid (3-methyl-piperidin-4-yl)-amide (C-74) for N -[4-(piperidin-4-ylsulfamoyl)-naphthalen-1-yl]-benzamide (C-1) and substituting butyl chloride for 2-isocyanato-propane. $^1$H NMR (300 MHz, CDCl$_3$) δ 8.76 (dd, 1H), 8.41 (dd, 1H), 8.03 (dd, 2H), 7.88 (m, 2H), 7.74 (m, 2H), 7.58 (m, 2H), 5.25 (dd, 1H), 3.30 (m, 4H), 2.22 (m, 2H), 1.65 (m, 6H), 0.90 (t, 3H), 0.70 (dd, 3H); LC/MS m/z 521 (M+H)$^+$

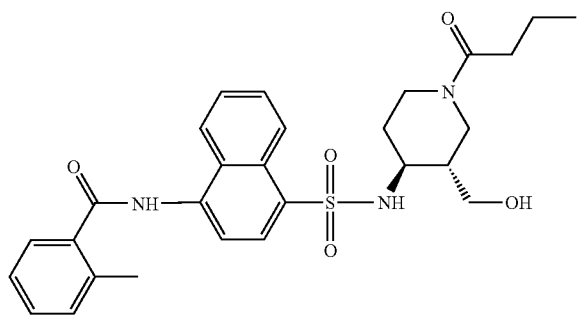

(±)-(trans)-N-[4-(1-butyryl-3-hydroxymethyl-piperidin-4-ylsulfamoyl)-naphthalen-1-yl]-2-methyl-benzamide (C-76)

(±)-(trans)-1-Butyryl-4-[4-(2-methyl-benzoylamino)-naphthalene-1-sulfonylamino]-piperidine-3-carboxylic acid ethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting butyl chloride for 2-isocyanato-propane. To the solution of (±)-(trans)-1-butyryl-4-[4-(2-methyl-benzoylamino)-naphthalene-1-sulfonylamino]-piperidine-3-carboxylic acid ethyl ester (121 mg, 0.21 mmol) in THF (5 mL), was added lithium borohydride in THF solution (1.07 mL, 2.1 mmol) and the resultant solution was stired at 0° C. for 2 h. The solvent was removed in vacuo and the crude material was purified by HPLC to give the title compound. $^1$H NMR (300 MHz, MeOD) δ 8.75 (d, 1H), 8.32 (dd, 1H), 8.24 (d, 1H), 7.93 (d, 1H), 7.70 (m, 3H), 7.38 (m, 3H), 4.00 (m, 3H), 3.20 (m, 2H), 2.88 (m, 1H), 2.55 (s, 3H), 2.46 (m, 1H), 2.28 (m, 2H), 1.50 (m, 3H), 1.24 (m, 2H), 0.90 (dd, 3H); LC/MS m/z 525 (M+H)$^+$

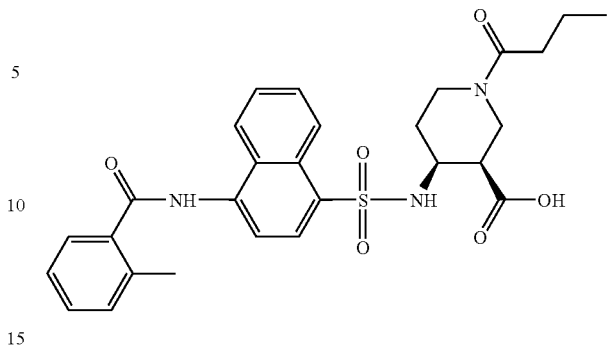

(±)-(cis)-1-Butyryl-4-[4-(2-methyl-benzoylamino)-naphthalene-1-sulfonylamino]-piperidine-3-carboxylic acid (C-78)

(±)-(cis)-1-Butyryl-4-[4-(2-methyl-benzoylamino)-naphthalene-1-sulfonylamino]-piperidine-3-carboxylic acid ethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting butyl chloride for 2-isocyanato-propane. To the solution of (±)-(cis)-1-butyryl-4-[4-(2-methyl-benzoylamino)-naphthalene-1-sulfonylamino]-piperidine-3-carboxylic acid ethyl ester (70 mg, 0.12 mmol) in THF (5 mL), was added lithium hydroxide in water solution (6 mg, 0.25 mmol) and the resultant solution was stired at 25° C. for 2 h. The reaction mixture was extracted with CH$_2$Cl$_2$. The organic extracts were washed with brine, dried over Na$_2$SO$_4$, filtered and concentrated to provide the crude product. HPLC purification of the residue gave the title compound. $^1$H NMR (300 MHz, DMSO) δ 10.62 (s, 1H), 8.77 (t, 1H), 8.24 (m, 3H), 7.95 (d, 1H), 7.70 (m, 3H), 7.38 (m, 3H), 3.72 (m, 2H), 3.35 (m, 6H), 3.12 (m, 1H), 2.60 (m, 1H), 2.15 (m, 2H), 1.32 (m, 4H), 0.80 (dd, 3H); LC/MS m/z 539 (M+H)$^+$

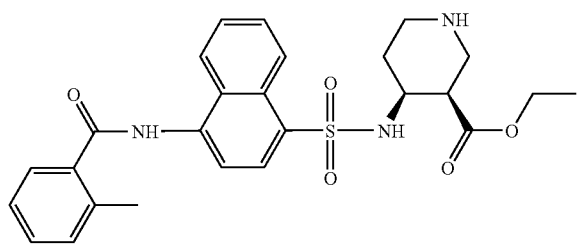

(±)-(cis)-4-[4-(2-Methyl-benzoylamino)-naphthalene-1-sulfonylamino]-piperidine-3-carboxylic acid ethyl ester (C-77)

The title compound was prepared as its formate salt following general procedure in Scheme 4-2. $^1$H NMR (300 MHz, MeOD) δ 8.75 (d, 1H), 8.52 (s, 1H), 8.34 (d, 1H), 8.25 (d, 3H), 7.97 (d, 1H), 7.71 (m, 3H), 7.40 (m, 3H), 3.93 (m, 1H), 3.70 (m, 2H), 3.28 (m, 2H), 3.07 (m, 2H), 2.90 (m, 1H), 2.56 (s, 3H), 1.82 (m, 2H), 0.98 (t, 3H); LC/MS m/z 497 (M+H)$^+$

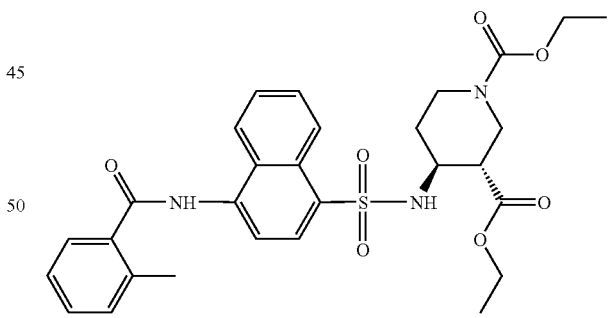

(±)-(trans)-4-[4-(2-Methyl-benzoylamino)-naphthalene-1-sulfonylamino]-piperidine-1,3-dicarboxylic acid diethyl ester (C-79)

The title compound was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting ethyl chloroformate for 2-isocyanato-propane. $^1$H NMR (300 MHz, MeOD) δ 8.68 (d, 1H), 8.30 (d, 1H), 8.23 (d, 1H), 7.93 (d, 1H), 7.70 (m, 3H), 7.38 (m, 3H), 4.00 (m, 4H), 3.48 (m, 3H), 2.85 (m, 2H), 2.55 (s, 3H), 2.36 (dt, 1H), 1.75 (d, 1H), 1.32 (d, 1H), 1.21 (t, 3H), 0.96 (t, 3H); LC/MS m/z 568 (M+H)+

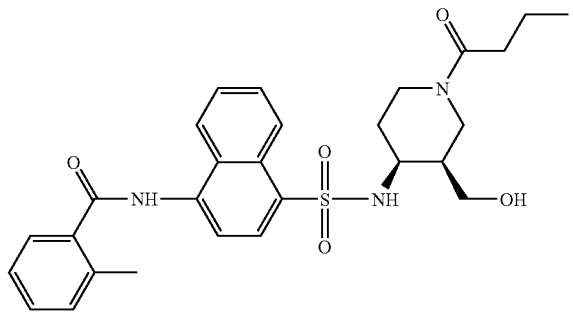

(±)-(cis)-N-[4-(1-Butyryl-3-hydroxymethyl-piperidin-4-ylsulfamoyl)-naphthalen-1-yl]-2-methyl-benzamide (C-80)

(±)-(cis)-1-Butyryl-4-[4-(2-methyl-benzoylamino)-naphthalene-1-sulfonylamino]-piperdine-3-carboxylic acid ethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting butyl chloride for 2-isocyanato-propane. To the solution of (±)-(cis)-1-butyryl-4-[4-(2-methyl-benzoylamino)-naphthalene-1-sulfonylamino]-piperidine-3-carboxylic acid ethyl ester (48 mg, 0.085 mmol) in THF (5 mL), was added lithium borohydride in THF solution (0.5 mL, 0.25 mmol) and the resultant solution was stired at 0 ° C. for 2 h. The solvent was removed in vacuo and the crude material was purified by HPLC to give the title compound. $^1$H NMR (300 MHz, MeOD) δ 8.81 (d, 1H), 8.34 (d, 1H), 8.25 (d, 1H), 7.95 (d, 1H), 7.72 (m, 3H), 7.40 (m, 3H), 3.46 (m, 7H), 2.56 (s, 3H), 2.32 (m, 2H), 2.55 (s, 3H), 1.52 (m, 5H), 0.92 (m, 3H); LC/MS m/z 525 (M+H)+

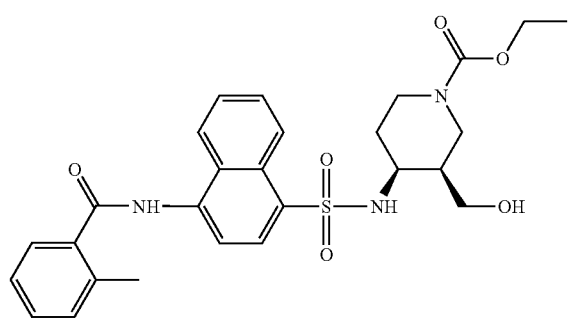

(±)-(cis)-3-Hydroxymethyl-4-[4-(2-methyl-benzoylamino)-naphthalene-1-sulfonylamino]-piperidine-1-carboxylic acid ethyl ester (C-81)

(±)-(cis)-4-[4-(2-Methyl-benzoylamino)-naphthalene-1-sulfonylamino]-piperidine-1,3-dicarboxylic acid diethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester, and substituting ethyl chloroformate for 2-isocyanato-propane. To the solution of (±)-(cis)-4-[4-(2-Methyl-benzoylamino)-naphthalene-1-sulfonylamino]-piperidine-1,3-dicarboxylic acid diethyl ester (57 mg, 0.1 mmol) in THF (5 mL), was added lithium borohydride in THF solution (0.5 mL, 0.25 mmol) and the resultant solution was stired at 0 ° C. for 2 h. The solvent was removed in vacuo and the crude material was purified by HPLC to give the title compound. $^1$H NMR (300 MHz, MeOD) δ 8.81 (d, 1H), 8.33 (d, 1H), 8.24 (d, 1H), 7.94 (d, 1H), 7.72 (m, 3H), 7.40 (m, 3H), 4.06 (q, 2H), 3.55 (m, 2H), 3.32 (m, 5H), 2.56 (s, 3H), 1.75 (m, 1H), 1.30 (m, 2H), 1.20 (t, 3H; LC/MS m/z 526 (M+H)+

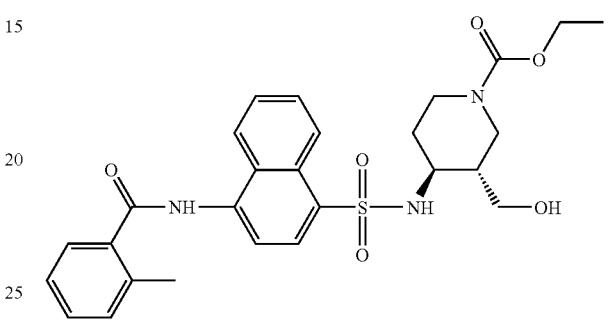

(±)-(trans)-3-Hydroxymethyl-4-[4-(2-methyl-benzoylamino)-naphthalene-1-sulfonylamino]-piperidine-1-carboxylic acid ethyl ester (C-82)

(±)-(trans)-4-[4-(2-Methyl-benzoylamino)-naphthalene-1-sulfonylamino]-piperidine-1,3-dicarboxylic acid diethyl ester was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting ethyl chloroformate for 2-isocyanato-propane. To the solution of (±)-(trans)-4-[4-(2-methyl-benzoylamino)-naphthalene-1-sulfonylamino]-piperidine-1,3-dicarboxylic acid diethyl ester (57 mg, 0.1 mmol) in THF (5 mL), was added lithium borohydride in THF solution (0.5 mL, 0.25 mmol) and the resultant solution was stired at 0 ° C. for 2 h. The solvent was removed in vacuo and the crude material was purified by HPLC to give the title compound. $^1$H NMR (300 MHz, MeOD) δ 8.73 (d, 1H), 8.30 (d, 1H), 8.22 (d, 1H), 7.93 (d, 1H), 7.68 (m, 3H), 7.36 (m, 3H), 4.15 (d, 1H), 4.05 (q, 2H), 3.85 (d, 1H), 3.55 (d, 1H), 3.25 (m, 1H), 3.10 (m, 1H), 2.60 (m, 2H), 2.56 (s, 3H), 1.40 (m, 3H), 1.20 (t, 3H); LC/MS m/z 526 (M+H)+

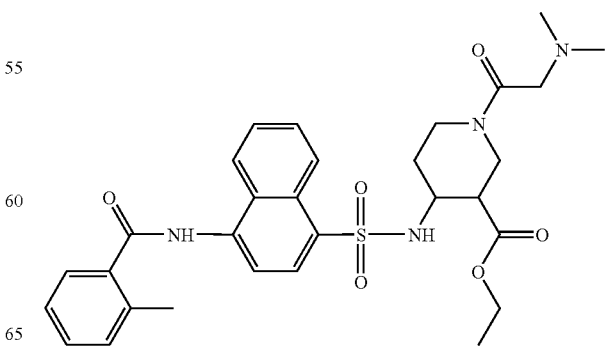

1-(2-Dimethylamino-acetyl)-4-[4-(2-methyl-benzoylamino)-naphthalene-1-sulfonylamino]-piperidine-3-carboxylic acid ethyl ester (C-83)

The title compound was made following general procedure in Scheme 5, substituting (±)-4-amino-1-benzyl-piperidine-3-carboxylic acid ethyl ester (5) for 4-amino-piperidine-1-carboxylic acid tert-butyl ester and substituting dimethylamino-acetyl chloride hydrochloride for 2-isocyanato-propane. $^1$H NMR (300 MHz, CDCl$_3$) δ 8.62 (m, 1H), 8.32 (m, 3H), 7.94 (d, 1H), 7.64 (m, 3H), 7.36 (m, 3H), 5.95 (m, 1H), 4.10 (m, 4H), 3.50 (s, br, 1H), 3.05 (m, 6H), 2.56 (m, 3H), 2.25 (dd, 6H), 1.84 (m, 1H), 1.10 (m, 3H); LC/MS m/z 581 (M+H)$^+$

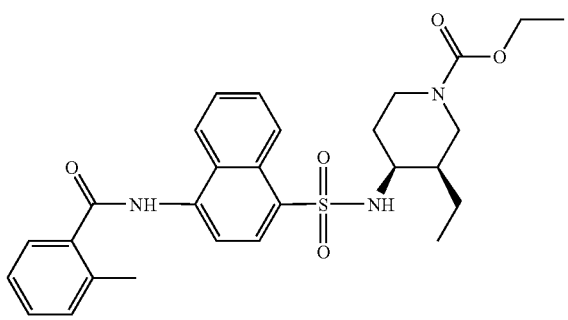

(±)-(cis)-3-Ethyl-4-[4-(2-methyl-benzoylamino)-naphthalene-1-sulfonylamino]-piperidine-1-carboxylic acid ethyl ester (C-84)

The title compound was made following general procedure in Scheme 5, substituting (±)-1-benzyl-3-ethyl-piperidin-4-ylamine (3) for 4-amino-piperidine-1-carboxylic acid tert-butyl ester and substituting ethyl chloroformate for 2-isocyanato-propane. $^1$H NMR (300 MHz, CDCl$_3$) δ 8.71 (d, 1H), 8.37 (m, 2H), 8.13 (s, 1H), 7.93 (d, 1H), 7.66 (m, 3H), 7.43 (m, 1H), 7.33 (m, 2H), 4.78 (d, 1H), 4.05 (m, 2H), 3.42 (m, 1H), 3.22 (m, 4H), 2.58 (s, 3H), 1.35 (s, br, 2H), 1.17 (t, 3H), 1.00 (s, br, 2H), 0.55 (s, br, 3H); LC/MS m/z 524(M+H)$^+$

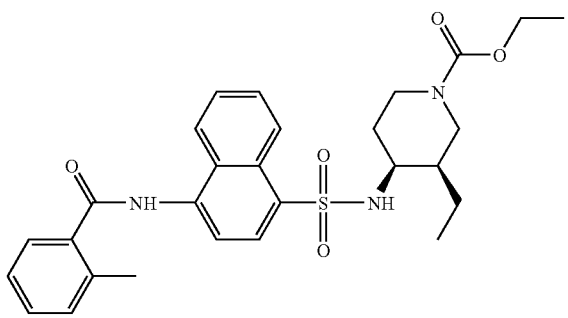

(±)-(cis)-N-[4-(1-Butyryl-3-ethyl-piperidin-4-ylsulfamoyl)-naphthalen-1-yl]-2-methyl-benzamide (C-85)

The title compound was made following general procedure in Scheme 5, substituting (±)-1-benzyl-3-ethyl-piperidin-4-ylamine (3) for 4-amino-piperidine-1-carboxylic acid tert-butyl ester, and substituting butyl chloride for 2-isocyanato-propane. $^1$H NMR (300 MHz, CDCl$_3$) δ 8.72 (d, 1H), 8.37 (m, 2H), 8.16 (s, 1H), 7.94 (d, 1H), 7.66 m, 3H), 7.43 (m, 1H), 7.33 (m, 2H), 4.90 (m, 1H), 3.32 (m, 5H), 2.58 (s, 3H), 2.18 (m, 2H), 1.45 (m, 6H), 0.87 (t, 3H), 0.50 (m, 3H); LC/MS m/z 522 (M+H)$^+$

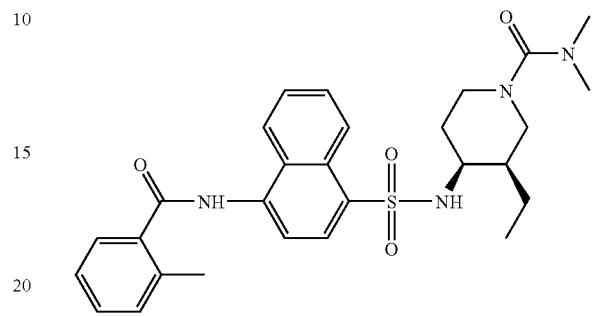

(±)-(cis)-3-Ethyl-4-[4-(2-methyl-benzoylamino)-naphthalene-1-sulfonylamino]-piperidine-1-carboxylic acid dimethylamide (C-86)

The title compound was made following general procedure in Scheme 5, substituting (±)-1-benzyl-3-ethyl-piperidin-4-ylamine (3) for 4-amino-piperidine-1-carboxylic acid tert-butyl ester, and substituting dimethylamino-acetyl chloride hydrochloride for 2-isocyanato-propane. $^1$H NMR (300 MHz, CDCl$_3$) δ 8.72 (d, 1H), 8.36 (m, 2H), 8.16 (s, 1H), 7.93 (d, 1H), 7.65 (m, 3H), 7.42 (m, 1H), 7.32 (m, 2H), 4.88 (d, 1H), 3.45 (m, 1H), 3.20 (m, 1H), 3.00 (m, 2H), 2.80 (m, 1H), 2.70 (s, 6H), 2.50 (s, 3H), 1.40 (m, 3H), 1.00 (m, 2H), 0.52 (t, 3H); LC/MS m/z 523 (M+H)$^+$

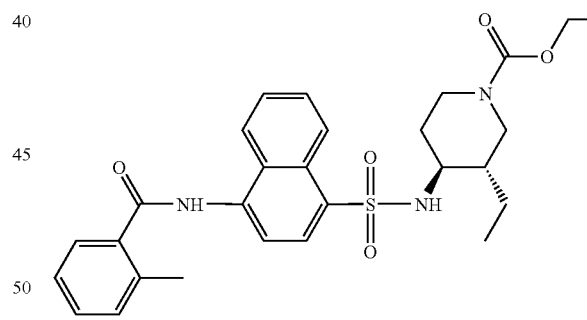

(±)-(trans)-3-Ethyl-4-[4-(2-methyl-benzoylamino)-naphthalene-1-sulfonylamino]-piperidine-1-carboxylic acid ethyl ester (C-87)

The title compound was made following general procedure in Scheme 5, substituting (±)-1-benzyl-3-ethyl-piperidin-4-ylamine (3) for 4-amino-piperidine-1-carboxylic acid tert-butyl ester, and substituting ethyl chloroformate for 2-isocyanato-propane. $^1$H NMR (300 MHz, CDCl$_3$) δ 8.69 (d, 1H), 8.36 (m, 2H), 8.12 (s, 1H), 7.93 (d, 1H), 7.66 (m, 3H), 7.43 (m, 1H), 7.33 (m, 2H), 4.50 (d, 1H), 4.05 (m, 2H), 3.55 (d, 1H), 2.95 (m, 1H), 2.70 (t, 1H), 2.57 (s, 3H), 2.49 (m, 1H), 1.50 (m, 3H), 1.17 (m, 5H), 0.85 (m, 1H), 0.65 (s, br, 3H); LC/MS m/z 524 (M+H)$^+$

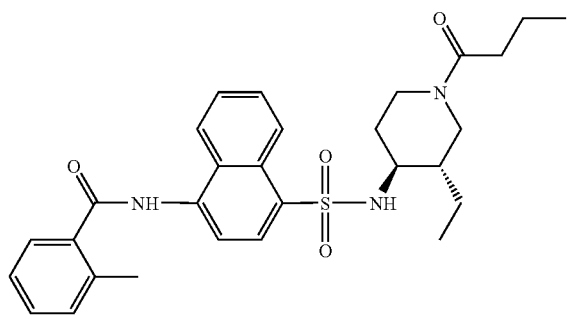

(±)-(trans)-N-[4-(1-Butyryl-3-ethyl-piperidin-4-yl-sulfamoyl)-naphthalen-1-yl]-2-methyl-benzamide (C-88)

The title compound was made following general procedure in Scheme 5, substituting (±)-1-benzyl-3-ethyl-piperidin-4-ylamine (3) for 4-amino-piperidine-1-carboxylic acid tert-butyl ester and substituting butyl chloride for 2-isocyanato-propane. $^1$H NMR (300 MHz, CDCl$_3$) δ 8.68 (m, 1H), 8.35 (m, 2H), 8.18 (s, 1H), 7.94 (d, 1H), 7.66 (m, 3H), 7.42 (m, 1H), 7.32 (m, 2H), 4.65 (d, 1H), 4.30 (m, 1H), 3.68 (m, 1H), 2.95 (m, 2H), 2.57 (s, 3H), 2.50 (m, 1H), 2.20 (m, 2H), 1.55 (m, 5H), 1.15 (m, 2H), 0.85 (t, 3H), 0.60 (m, 3H); LC/MS m/z 522 (M+H)$^+$

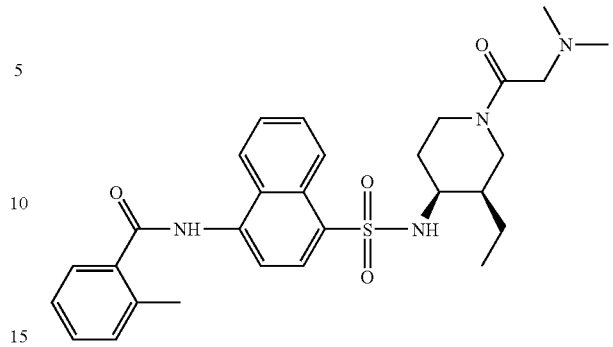

(±)-(cis)-N-{4-[1-(2-Dimethylamino-acetyl)-3-ethyl-piperidin-4-ylsulfamoyl]-naphthalen-1-yl}-2-methyl-benzamide (C-90)

The title compound (formic acid salt) was made following general procedure in Scheme 5, substituting (±)-1-benzyl-3-ethyl-piperidin-4-ylamine (3) for 4-amino-piperidine-1-carboxylic acid tert-butyl ester, and substituting dimethylamino-acetyl chloride hydrochloride for 2-isocyanato-propane. $^1$H NMR (300 MHz, MeOD) δ 8.85 (d, 1H), 8.55 (s, 1H), 8.32 (d, 1H), 8.25 (d, 1H), 7.94 (d, 1H), 7.71 (m, 3H), 7.43 (m, 1H), 7.35 (m, 2H), 3.47 (m, 4H), 3.25 (m, 2H), 2.55 (s, 3H), 2.33 (d, 6H), 1.38 (m, 3H), 1.15 (m, 3H), 0.50 (m, 3H); LC/MS m/z 537 (M+H)$^+$

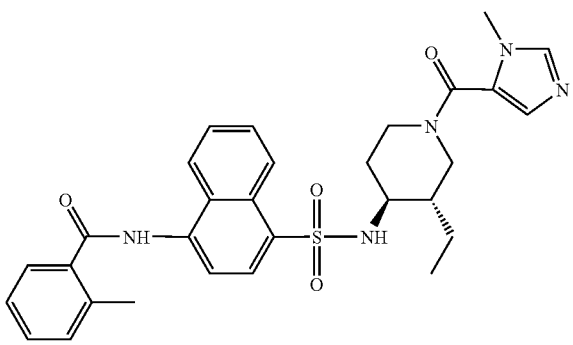

(±)-(trans)-N-{4-[3-Ethyl-1-(3-methyl-3H-imidazole-4-carbonyl)-piperidin-4-ylsulfamoyl]-naphthalene-1yl}-2-methyl-benzamide (C-89)

The title compound was made following general procedure in Scheme 5, substituting (±)-1-benzyl-3-ethyl-piperidin-4-ylamine (3) for 4-amino-piperidine-1-carboxylic acid tert-butyl ester and substituting 3-methyl-3H-imidazole-4-carbonyl chloride hydrochloride for 2-isocyanato-propane. $^1$H NMR (300 MHz, MeOD) δ 8.79 (d, 1H), 8.33 (d, 1H), 8.25 (d, 1H), 8.15 (s, 1H), 7.94 (d, 1H), 7.70 (m, 4H), 7.43 (m, 1H), 7.36 (m, 2H), 7.14 (s, 1H), 4.20 (m, 2H), 3.75 (s, 3H), 3.05 (m, 2H), 2.70 (m, 1H), 2.55 (s, 3H), 1.55 (m, 3H), 1.30 (m, 1H), 0.85 (m, 1H), 0.62 (m, 3H); LC/MS m/z 560 (M+H)$^+$

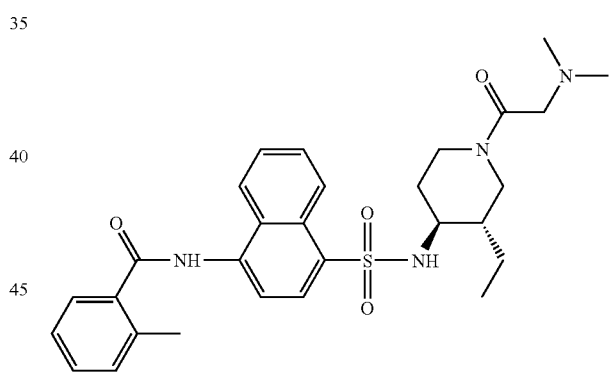

(±)-(trans)-N-{4-[1-(2-Dimethylamino-acetyl)-3-ethyl-piperidin-4-ylsulfamoyl]-naphthalen-1-yl}-2-methyl-benzamide (C-91)

The title compound (formic acid salt) was made following general procedure in Scheme 5, substituting (±)-1-benzyl-3-ethyl-piperidin-4-ylamine (3) for 4-amino-piperidine-1-carboxylic acid tert-butyl ester and substituting dimethylamino-acetyl chloride hydrochloride for 2-isocyanato-propane. $^1$H NMR (300 MHz, MeOD) δ 8.78 (d, 1H), 8.55 (s, 1H), 8.32 (d, 1H), 8.25 (d, 1H), 7.94 (d, 1H), 7.71 (m, 3H), 7.43 (m, 1H), 7.35 (m, 2H), 4.05 (m, 2H), 3.10 (m, 3H), 2.60 (m, 1H), 2.55 (s, 3H), 2.30 (s, 6H), 1.25 (m, 2H), 1.10 (m, 3H), 0.90 (m, 1H), 0.85 (m, 3H); LC/MS m/z 537 (M+H)$^+$

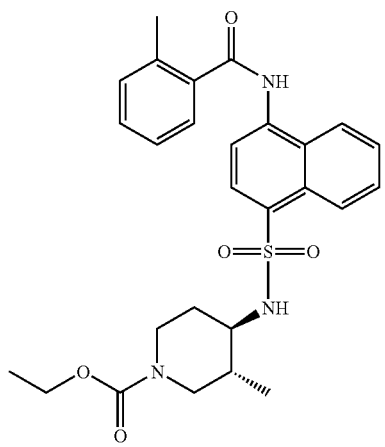

(3R, 4R)-3-Methyl-4-[4-(2-methyl-benzoylamino)-naphthalene-1-sulfonylamino]-piperidine-1-carboxylic acid ethyl ester (C-92)

The title compound was prepared according to the general procedure in Scheme 5, substituting (3R, 4R)-4-amino-3-methyl-piperidine-1-carboxylic acid tert-butyl ester for 4-amino-piperidine-1-carboxylic acid tert-butyl ester, and ethyl chloroformate for 2-isocyanato-propane. $^1$H NMR (300 MHz, CDCl$_3$) δ 8.77 (d, 1H), 8.30 (d, 1H), 8.23 (d, 1H), 7.92 (d, 1H), 7.73 (m, 3H), 7.35 (m, 3H), 4.03 (q, 2H), 3.94 (t, 2H), 2.85 (dt, 1H), 2.64 (m, 1H), 2.55 (s, 3H), 2.40 (m, 1H), 1.48 (m, 1H), 1.38 (m, 1H), 1.20 (t, 3H), 0.59 (d, 3H); LC/MS m/z 510 (M+H)$^+$.

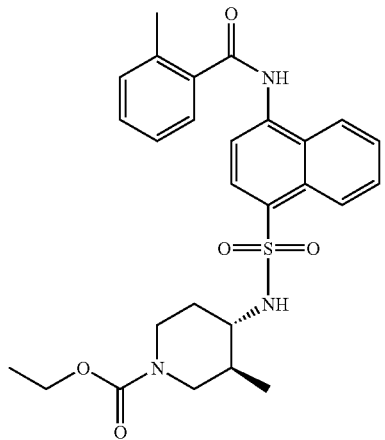

(3S, 4S)-3-Methyl-4-[4-(2-methyl-benzoylamino)-naphthalene-1-sulfonylamino]-piperidine-1-carboxylic acid ethyl ester (C-93)

The title compound was prepared according to the general procedure in Scheme 5, substituting (3S, 4S)-4-amino-3-methyl-piperidine-1-carboxylic acid tert-butyl ester for 4-amino-piperidine-1-carboxylic acid tert-butyl ester, and ethyl chloroformate for 2-isocyanato-propane. $^1$H NMR (300 MHz, CDCl$_3$) δ 8.77 (d, 1H), 8.30 (d, 1H), 8.23 (d, 1H), 7.92 (d, 1H), 7.73 (m, 3H), 7.35 (m, 3H), 4.03 (q, 2H), 3.94 (t, 2H), 2.85 (dt, 1H), 2.64 (m, 1H), 2.55 (s, 3H), 2.40 (m, 1H), 1.48 (m, 1H), 1.38 (m, 1H), 1.20 (t, 3H), 0.59 (d, 3H); LC/MS m/z 510 (M+H)$^+$.

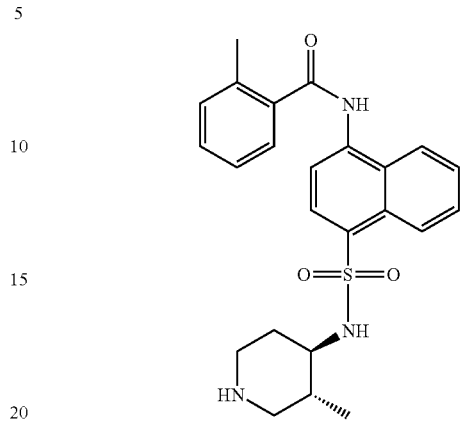

(3R, 4R)-2-Methyl-N-[4-(3-methyl-piperidin-4-yl-sulfamoyl)-naphthalen-1-yl]-benzamide (C-94)

The title compound was prepared according to the general procedure in Scheme 5, substituting (3R, 4R)-4-amino-3-methyl-piperidine-1-carboxylic acid tert-butyl ester for 4-amino-piperidine-1-carboxylic acid tert-butyl ester. $^1$H NMR (300 MHz, MeOD) δ 8.78 (dd, 1H), 8.34 (d, 1H), 8.24 (dd, 1H), 7.94 (d, 1H), 7.78 (m, 1H), 7.74 (m, 1H), 7.69 (m, 1H), 7.44 (m, 1H), 7.37 (m, 2H), 3.23 (m, 2H), 3.00 (m, 1H), 2.78 (m, 1H), 2.64 (m, 1H), 2.55 (s, 3H), 1.76 (m, 2H), 1.58 (m, 1H), 0.66 (d, 3H); LC/MS m/z 438 (M+H)$^+$.

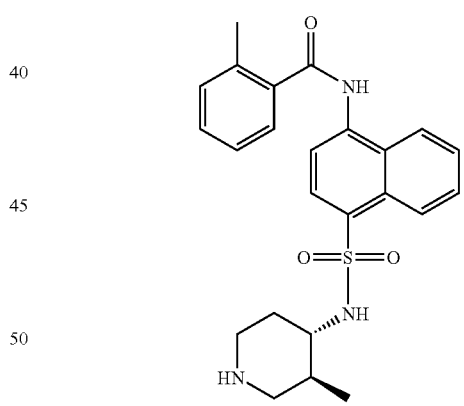

(3S, 4S)-2-Methyl-N-[4-(3-methyl-piperidin-4-ylsulfamoyl)-naphthalen-1-yl]-benzamide (C-95)

The title compound was prepared according to the general procedure in Scheme 5, substituting (3S, 4S)-4-amino-3-methyl-piperidine-1-carboxylic acid tert-butyl ester for 4-amino-piperidine-1-carboxylic acid tert-butyl ester. $^1$H NMR (300 MHz, MeOD) δ 8.78 (dd, 1H), 8.34 (d, 1H), 8.24 (dd, 1H), 7.94 (d, 1H), 7.78 (m, 1H), 7.74 (m, 1H), 7.69 (m, 1H), 7.44 (m, 1H), 7.37 (m, 2H), 3.23 (m, 2H), 3.00 (m, 1H), 2.78 (m, 1H), 2.64 (m, 1H), 2.55 (s, 3H), 1.76 (m, 2H), 1.58 (m, 1H), 0.66 (d, 3H); LC/MS m/z 438 (M+H)$^+$.

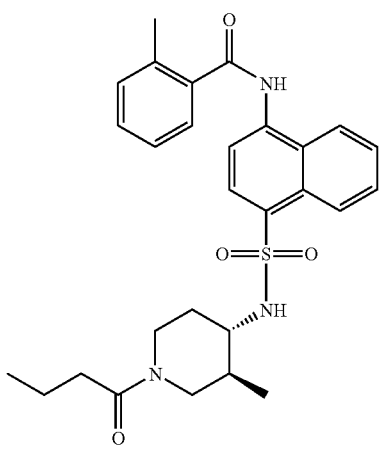

(3S, 4S)—N-[4-(1-Butyryl-3-methyl-piperidin-4-ylsulfamoyl)-naphthalen-1-yl]-2-methyl-benzamide (C-96)

The title compound was prepared according to the general procedure in Scheme 5, substituting (3S, 4S)-4-amino-3-methyl-piperidine-1-carboxylic acid tert-butyl ester for 4-amino-piperidine-1-carboxylic acid tert-butyl ester, and butyryl chloride for 2-isocyanato-propane. $^1$H NMR (300 MHz, CDCl$_3$) δ 8.70 (t, 1H), 8.33 (m, 3H), 7.95 (d, 1H), 7.62 (m, 3H), 7.40 (m, 1H), 7.34 (m, 2H), 5.00 (d, 1H), 4.30 (dd, 1H), 3.63 (m, 1H), 2.85 (m, 1.5H), 2.57 (s, 3H), 2.40 (t, 0.5H), 2.15 (m, 1.5H), 2.09 (m, 0.5H), 1.83 (m, 0.5H), 1.50 (m, 1.5H); LC/MS m/z 508 (M+H)$^+$.

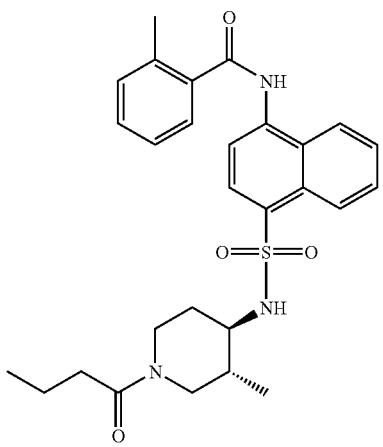

(3R, 4R)—N-[4-(1-Butyryl-3-methyl-piperidin-4-ylsulfamoyl)-naphthalen-1-yl]-2-methyl-benzamide (C-97)

The title compound was prepared according to the general procedure in Scheme 5, substituting (3R, 4R)-4-amino-3-methyl-piperidine-1-carboxylic acid tert-butyl ester for 4-amino-piperidine-1-carboxylic acid tert-butyl ester, and butyryl chloride for 2-isocyanato-propane. $^1$H NMR (300 MHz, CDCl$_3$) δ 8.70 (t, 1H), 8.33 (m, 3H), 7.95 (d, 1H), 7.62 (m, 3H), 7.40 (m, 1H), 7.34 (m, 2H), 5.00 (d, 1H), 4.30 (dd, 1H), 3.63 (m, 1H), 2.85 (m, 1.5H), 2.57 (s, 3H), 2.40 (t, 0.5H), 2.15 (m, 1.5H), 2.09 (m, 0.5H), 1.83 (m, 0.5H), 1.50 (m, 1.5H); LC/MS m/z 508 (M+H)$^+$.

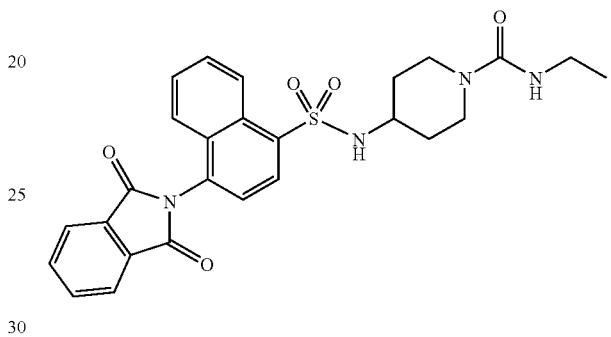

4-[4-(1,3-Dioxo-1,3-dihydro-isoindol-2-yl)-naphthalene-1-sulfonylamino]-piperidine-1-carboxylic acid ethylamide (C-98)

The title compound was prepared following the general procedure in Scheme 5, beginning with 4-(1,3-dioxo-1,3-dihydro-isoindol-2-yl)-naphthalene-1-sulfonyl chloride, and substituting ethyl isocyanate for 2-isocyanato-propane. $^1$H NMR (300 MHz, DMSO) δ 8.75 (d, 1H), 8.29 (d, 1H), 8.23 (d, 1H), 8.03 (m, 5H), 7.83 (d, 1H), 7.80 (t, 1H), 7.67 (t, 1H), 6.36 (t, 1H), 3.69 (d, 2H), 3.27 (m, 1H), 2.97 (p, 2H), 2.64 (t, 2H), 1.47 (d, 2H), 1.23 (m, 2H), 0.95 (t, 3H); LC/MS m/z 505 (M−H)$^−$.

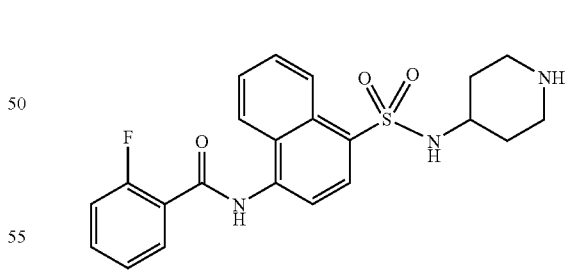

2-Fluoro-N-[4-(piperidin-4-ylsulfamoyl)-naphthalen-1-yl]-benzamide (C-99)

The title compound was prepared following the general procedure in Scheme 5, beginning with 4-(2-fluoro-benzoylamino)-naphthalene-1-sulfonyl chloride. $^1$H NMR (300 MHz, DMSO) δ 10.72 (s, 1H), 8.67 (d, 1H), 8.30 (d, 1H), 8.20 (d, 1H), 8.10 (d, 1H), 8.01 (d, 1H), 7.83 (t, 1H), 7.74

(t, 2H), 7.65 (m, 1H), 7.41 (q, 2H), 3.67 (d, 2H), 3.18 (m, 1H), 2.70 (m, 2H), 1.43 (m, 2H), 1.18(m, 2H); LC/MS m/z 426 (M−H)[31], 428 (M+H)+

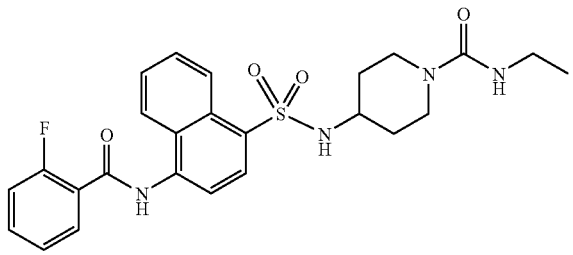

4-[4-(2-Fluoro-benzoylamino)-naphthalene-1-sulfonylamino]-piperidine-1-carboxylic acid ethylamide (C-100)

The title compound was prepared following the general procedure in Scheme 5, beginning with 4-(2-fluoro-benzoylamino)-naphthalene-1-sulfonyl chloride, and substituting ethyl isocyanate for 2-isocyanato-propane. $^1$H NMR (300 MHz, DMSO) δ 10.74 (s, 1H), 8.67 (d, 1H), 8.29 (d, 1H), 8.19 (d, 1H), 8.05 (d, 1H), 7.99 (d, 1H), 7.82 (t, 1H), 7.73 (t, 2H), 7.65 (t, 2H), 7.41 (q, 2H), 6.32 (t, 1H), 3.67 (d, 2H), 3.17 (m, 1H), 2.94 (m, 2H), 2.59 (t, 2H), 1.36 (d, 2H), 1.14 (m, 2H), 0.95 (t, 3H); /MS m/z 498 (M−H)[31], 500 (M+H)+

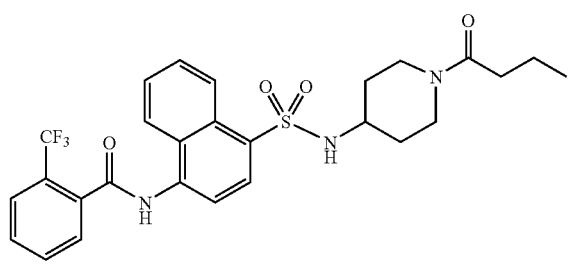

N-[4-(1-Butyryl-piperidin-4-ylsulfamoyl)-naphthalen-1-yl]-2-trifluoromethyl-benzamide (C-101)

The title compound was prepared following the general procedure in Scheme 5, beginning with 4-(2-trifluoromethyl-benzoylamino)-naphthalene-1-sulfonyl chloride and substituting butyryl chloride and triethylamine for 2-isocyanato-propane. $^1$H NMR (300 MHz, DMSO) δ 10.91(s, 1H), 8.68 (d, 1H), 8.25 (m, 2H), 8.11 (d, 1H), 7.85 (m, 4H), 7.76 (m, 3H), 4.06 (m, 1H), 4.01(m, 1H), 3.62 (d, 1H), 2.94 (t, 1H), 2.59 (t, 2H), 1.48 (m, 2H), 1.41 (m, 2H), 1.19 (m, 2H), 0.82 (t, 3H); LC/MS m/z 546 (M−H)−, 548 (M+H)+

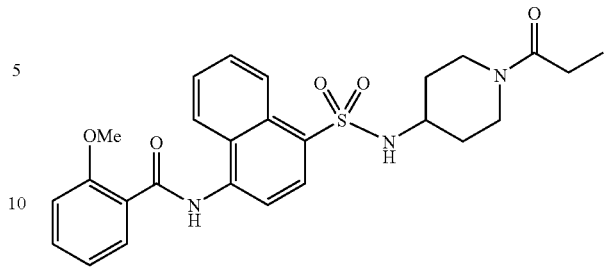

2-Methoxy-N-[4-(1-propionyl-piperidin-4-ylsulfamoyl)-naphthalen-1-yl]-benzamide (C-102)

The title compound was prepared following the general procedure in Scheme 5 beginning with 4-(2-methoxy-benzoylamino)-naphthalene-1-sulfonyl chloride, and substituting propionyl chloride and triethylamine for 2-isocyanato-propane. LC/MS m/z 495 (M−H)−, 497 (M+H)+

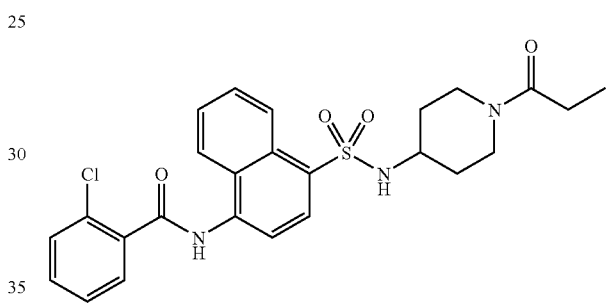

2-Chloro-N-[4-(1-propionyl-piperidin-4-ylsulfamoyl)-naphthalen-1-yl]-benzamide (C-103)

The title compound was prepared following the general procedure in Scheme 5 beginning with 4-(2-chloro-benzoylamino)-naphthalene-1-sulfonyl chloride, and substituting propionyl chloride and triethylamine for 2-isocyanato-propane. $^1$H NMR (300 MHz, DMSO) δ 10.86 (s, 1H), 8.68 (d, 1H), 8.33 (d, 1H), 8.22 (d, 1H), 8.12 (d, 1H), 7.98 (d, 1H), 7.74 (m, 3H), 7.64 (t, 1H), 7.54 (m, 2H), 4.01 (m, 1H), 3.59 (d, 1H), 3.24 (m, 1H), 3.16 (d, 1H), 2.96 (t, 1H), 2.20 (q, 2H), 1.51 (d, 2H), 1.20 (m, 2H), 0.81 (t, 3H); LC/MS m/z 498 (M−H)−, 500 (M+H)+

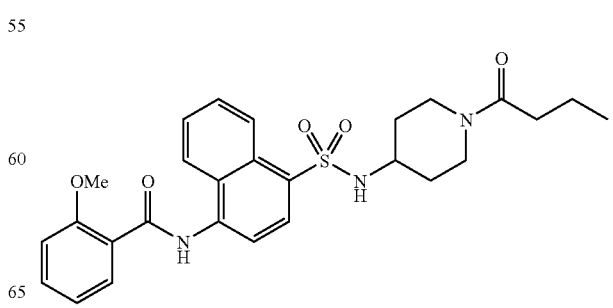

N-[4-(1-Butyryl-piperidin-4-ylsulfamoyl)-naphthalen-1-yl]-2-methoxy-benzamide (C-104)

The title compound was prepared following the general procedure in Scheme 5, beginning with 4-(2-methoxy-benzoylamino)-naphthalene-1-sulfonyl chloride, and substituting butyric chloride and triethylamine for 2-isocyanatopropane. LC/MS m/z 508 (M–H)⁻, 510 (M+H)⁺

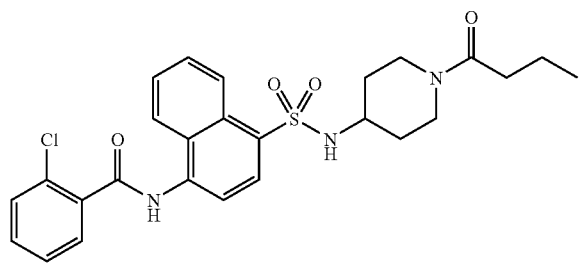

N-[4-(1-Butyryl-piperidin-4-ylsulfamoyl)-naphthalen-1-yl]-2-chloro-benzamide (C-105)

The title compound was prepared following the general procedure in Scheme 5, beginning with 4-(2-chloro-benzoylamino)-naphthalene-1-sulfonyl chloride, and substituting butyryl chloride and triethylamine for 2-isocyanato-propane. ¹H NMR (300 MHz, DMSO) δ 10.86 (s, 1H), 8.68 (d, 1H), 8.35 (d, 1H), 8.25 (d, 1H), 8.13 (d, 1H), 8.0 (m, 1H), 7.74 (m, 3H), 7.64 (m, 3H), 4.00 (d, 1H), 3.60 (d, 1H), 3.26 (m, 1H), 2.93 (t, 1H), 2.59 (m, 2H), 2.17 (t, 2H), 1.46 (m, 2H), 1.43 (q, 2H), 1.17 (m, 1H), 0.82 (t, 3H); LC/MS m/z 512 (M–H)⁻, 514 (M+H)⁺

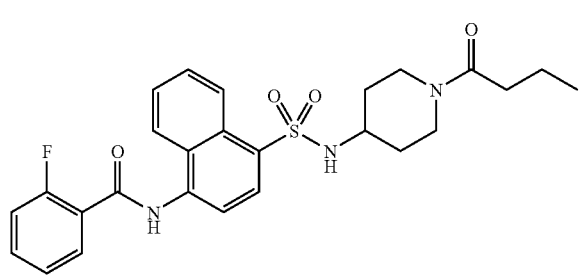

N-[4-(1-Butyryl-piperidin-4-ylsulfamoyl)-naphthalen-1-yl]-2-fluoro-benzamide (C-106)

The title compound was prepared following the general procedure in Scheme 5, beginning with ⁴-(2-fluoro-benzoylamino)-naphthalene-1-sulfonyl chloride and substituting butyryl chloride and triethylamine for 2-isocyanato-propane. ¹H NMR (300 MHz, DMSO) δ 10.73 (s, 1H), 8.69 (d, 1H), 8.28 (d, 1H), 8.21 (d, 1H), 8.11 (d, 1H), 7.99 (d, 1H), 7.83 (t, 1H), 7.76 (m, 2H), 7.64 (m, 1H), 7.40 (q, 2H), 4.00 (d, 1H), 3.60 (d, 1H), 3.26 (m, 1H), 2.93 (t, 1H), 2.59 (m, 2H), 2.17 (t, 2H), 1.46 (m, 2H), 1.43 (q, 2H), 1.17 (m, 1H), 0.82 (t, 3H); LC/MS m/z 496 (M–H)⁻, 498 (M+H)⁺

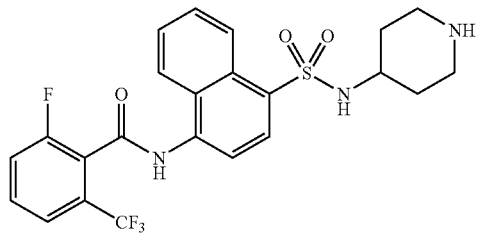

2-Fluoro-N-[4-(piperidin-4-ylsulfamoyl)-naphthalen-1-yl]-6-trifluoromethyl-benzamide (C-107)

The title compound was prepared following the general procedure in Scheme 5, beginning with ⁴-(²-fluoro-6-trifluoromethyl-benzoylamino)-naphthalene-1-sulfonyl chloride. ¹H NMR (300 MHz, DMSO) δ 11.15 (s, 1H), 8.70 (d, 1H), 8.32 (d, 1H), 8.29 (m, 1H), 8.01 (d, 1H), 7.77 (m, 1H), 7.65 (m, 1H), 7.32 (m, 1H), 6.94 (m, 1H), 3.08 (d, 1H), 2.85 (m, 1H), 2.54 (m, 5H), 1.64 (m, 1H), 1.51 (m, 1H). LC/MS m/z 494 (M–H)⁻, 496 (M+H)⁺

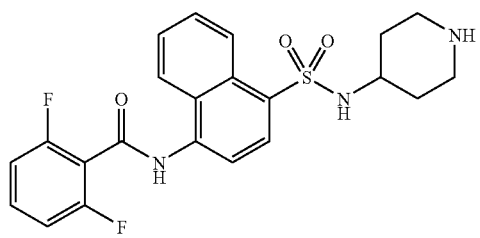

2,6-Difluoro-N-[4-(piperidin-4-ylsulfamoyl)-naphthalen-1-yl]-benzamide (C-108)

The title compound was prepared following the general procedure in Scheme 5, beginning with 4-(2,6-difluoro-benzoylamino)-naphthalene-1-sulfonyl chloride. ¹H NMR (300 MHz, DMSO) δ 11.15 (s, 1H), 8.70 (d, 1H), 8.32 (d, 1H), 8.29 (m, 1H), 8.01 (d, 1H), 7.77 (m, 1H), 7.65 (m, 1H), 7.32 (m, 1H), 6.94 (m, 1H), 3.08 (d, 1H), 2.85 (m, 1H), 2.54 (m, 5H), 1.64 (m, 1H), 1.51 (m, 1H). LC/MS m/z 444 (M–H)⁻, 446 (M+H)⁺

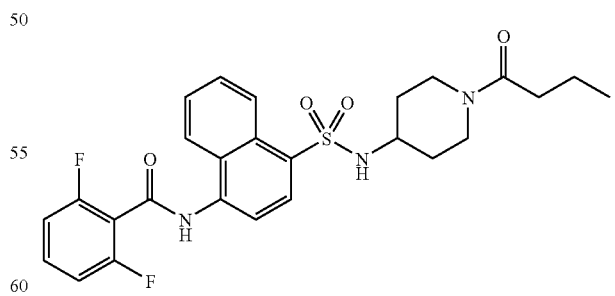

N-[4-(1-Butyryl-piperidin-4-ylsulfamoyl)-naphthalen-1-yl]-2,6-difluoro-benzamide (C-109)

The title compound was prepared following the general procedure in Scheme 5, beginning with 4-(2,6-difluorobenzoylamino)-naphthalene-1-sulfonyl chloride, and substituting butyryl chloride and triethylamine for 2-isocyanato-propane. $^1$H NMR (300 MHz, DMSO) δ 11.12(s, 1H), 8.71 (m, 1H), 8.26 (m, 2H), 8.13 (d, 1H), 7.98 (d, 1H), 7.75 (m, 2H), 7.62 (m, 1H), 7.31 (t, 2H), 4.01 (d, 1H), 3.60 (d, 1H), 2.93 (t, 1H), 2.59 (m, 2H), 2.15 (t, 2H), 1.45 (m, 2H), 1.43 (q, 2H), 1.17 (m, 2H), 0.81 (t, 3H); LC/MS m/z 514 (M–H)$^-$, 516 (M+H)$^+$

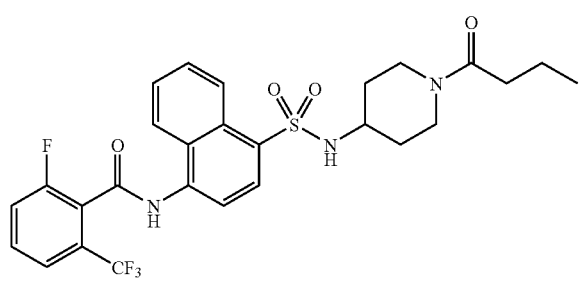

N-[4-(1-Butyryl-piperidin-4-ylsulfamoyl)-naphthalen-1-yl]-2-fluoro-6-trifluoromethyl-benzamide (C-110)

The title compound was prepared following the general procedure in Scheme 5, beginning with 4-(2-fluoro-6-trifluoromethyl-benzoylamino)-naphthalene-1-sulfonyl chloride and substituting butyric chloride and triethylamine for 2-isocyanato-propane. $^1$H NMR (300 MHz, DMSO) δ 11.12 (s, 1H), 8.71 (m, 1H), 8.26 (m, 2H), 8.13 (m, 1H), 7.98 (d, 1H), 7.79 (m, 6H), 4.01 (d, 1H), 3.60 (d, 1H), 2.93 (t, 1H), 2.59 (m, 2H), 2.15 (t, 2H), 1.45 (m, 2H), 1.43 (q, 2H), 1.17 (m, 2H), 0.81 (t, 3H). LC/MS m/z 514 (M–H)$^-$, 516 (M+H)$^+$

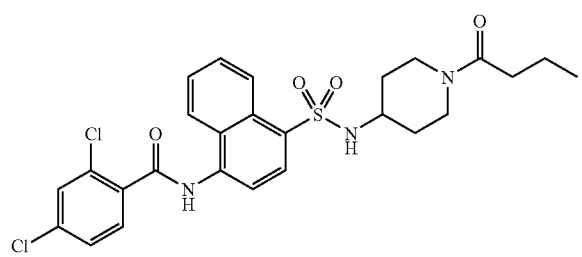

N-[4-(1-Butyryl-piperidin-4-ylsulfamoyl)-naphthalen-1-yl]-2,4-dichloro-benzamide (C-111)

The title compound was prepared following the general procedure in Scheme 5, beginning with 4-(2,4-dichloro-benzoylamino)-naphthalene-1-sulfonyl chloride and substituting butyryl chloride and triethylamine for 2-isocyanato-propane. $^1$H NMR (300 MHz, DMSO) δ 10.87 (s, 1H), 8.70 (dd, 1H), 8.34 (dd, 1H), 8.21 (d, 1H), 8.13 (d, 1H), 8.01 (d, 1H), 7.82 (m, 2H), 7.73 (m, 1H), 7.63 (d, 1H), 4.00 (d, 1H), 3.6 (d, 1H), 3.24 (m, 1H), 2.92 (t, 1H), 2.59 (m, 1H), 2.17 (t, 2H), 1.47 (m, 2H), 1.43 (m, 2H), 1.18 (m, 2H), 0.82 (t, 3H). LC/MS m/z 548 (M–H)$^-$, 560 (M+H)$^+$

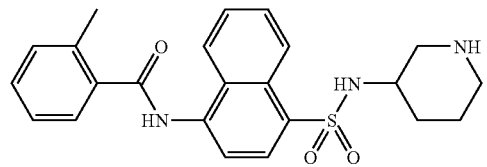

(±)-2-Methyl-N-[4-(piperidin-3-ylsulfamoyl)-naphthalen-1-yl]-benzamide (C-112)

The title compound was made following general procedure in Scheme 5, substituting 4-(2-methyl-benzoylamino)-naphthalene-1-sulfonyl chloride for 4-benzoylamino-naphthalene-1-sulfonyl chloride, and 3-amino-piperidine-1-carboxylic acid tert-butyl ester for 4-amino-piperidine-1-carboxylic acid tert-butyl ester. $^1$H NMR (300 MHz, MeOD) δ 8.78 (d, 1H), 8.33 (d, 2H), 8.25 (d, 1H), 7.96 (d, 1H), 7.71 (m, 3H), 7.45 (m, 1H), 7.38 (m, 2H), 3.33 (m, 1H), 3.19 (m, 2H), 2.70 (m, 2H), 2.57 (s, 3H), 1.83 (m, 1H), 1.55 (m, 3H); LC/MS (M+H)$^+$ m/z 424.

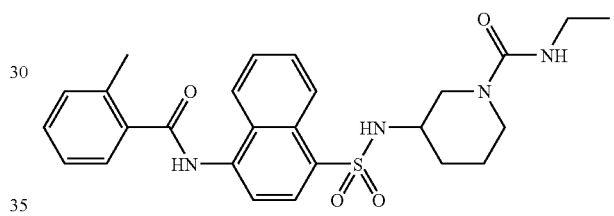

(±)-3-[4-(2-Methyl-benzoylamino)-naphthalene-1-sulfonylamino]-piperidine-1-carboxylic acid ethylamide (C-113)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-piperidine-1-carboxylic acid tert-butyl ester for 4-amino-piperidine-1-carboxylic acid tert-butyl ester and isocyanato-ethane for 2-isocyanato-propane. $^1$H NMR (300 MHz, MeOD) δ 8.78 (d, 1H), 8.33 (m, 2H), 8.23 (d, 1H), 7.94 (d, 1H), 7.71 (m, 3H), 7.43 (m, 1H ), 7.38 (m, 2H), 3.79 (m, 1H), 3.55 (m, 1H), 3.12 (q, 2H), 3.10 (m, 1H), 2.85 (m, 1H), 2.72 (m, 1H), 2.55 (s, 3H), 1.58 (m, 2H), 1.30 (m, 2H), 1.19 (m, 3H); LC/MS (M+H)$^+$ m/z 495.

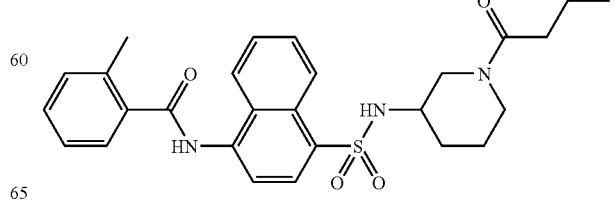

(±)-N-[4-(1-Butyryl-piperidin-3-ylsulfamoyl)-naphthalen-1-yl]-2-methyl-benzamide (C-114)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-piperidine-1-carboxylic acid tert-butyl ester for 4-amino-piperidine-1-carboxylic acid tert-butyl ester and butyryl chloride for 2-isocyanato-propane. $^{1}$H NMR (300 MHz, MeOD) δ 8.78 (m, 1H), 8.33 (m, 2H), 8.23 (m, 1H), 7.94 (m, 1H), 7.71 (m, 3H), 7.43 (m, 1H ), 7.38 (m, 2H), 3.79 (m, 1H), 3.91 (m, 1H), 3.55 (q, 1H), 3.08 (m, 1H ), 2.95 (m, 1H), 2.82 (m, 1H), 2.55 (s, 3H), 2.01 (m, 2H), 1.50 (m, 6H), 0.90 (m, 3H); LC/MS (M+H)$^{+}$ m/z 494.

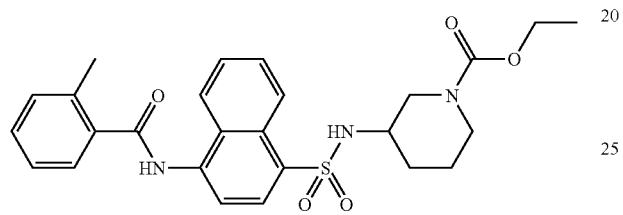

(±)-3-[4-(2-Methyl-benzoylamino)-naphthalene-1-sulfonylamino]-piperidine-1-carboxylic acid ethyl ester (C-115)

The title compound was made following general procedure in Scheme 5, substituting 4-(2-methyl-benzoylamino)-naphthalene-1-sulfonyl chloride for 4-benzoylamino-naphthalene-1-sulfonyl chloride, 3-amino-piperidine-1-carboxylic acid tert-butyl ester for 4-amino-piperidine-1-carboxylic acid tert-butyl ester and ethyl chlorofomate for 2-isocyanato-propane. $^{1}$H NMR (300 MHz, MeOD) δ 8.78 (m, 1H), 8.33 (m, 2H), 8.23 (m, 1H), 7.94 (m, 1H), 7.71 (m, 3H), 7.43 (m, 1H), 7.38 (m, 2H), 4.02 (m, 2H), 3.70 (m, 2H), 3.06 (m, 1H), 2.69 (m, 1H ), 2.38 (m, 1H), 2.55 (s, 3H), 1.71 (m, 2H), 1.30 (m, 2H), 1.18 (m, 3H); LC/MS (M+H)$^{+}$ m/z 496.

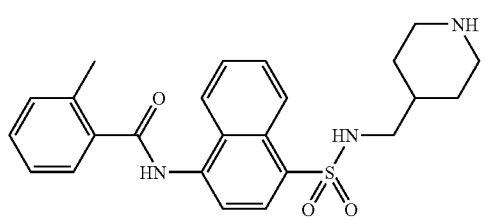

2-Methyl-N-{4-[(piperidin-4-ylmethyl)-sulfamoyl]-naphthalen-1-yl}-benzamide (C-116)

The title compound was made following general procedure in Scheme 5, substituting 4-(2-methyl-benzoylamino)-naphthalene-1-sulfonyl chloride for 4-benzoylamino-naphthalene-1-sulfonyl chloride, and 4-aminomethyl-piperidine-1-carboxylic acid tert-butyl ester for 4-amino-piperidine-1-carboxylic acid tert-butyl ester. $^{1}$H NMR (300 MHz, MeOD) δ 8.78 (d, 1H), 8.29 (m, 2H), 7.93 (m, 1H), 7.74 (m, 3H), 7.41 (m, 3H), 3.30 (m, 2H), 2.82 (m, 2H), 2.80 (d, 2H), 2.55 (s, 3H), 1.84 (m, 2H), 1.65 (m, 1H), 1.28 (m, 2H); LC/MS (M+H)$^{+}$ m/z 438.

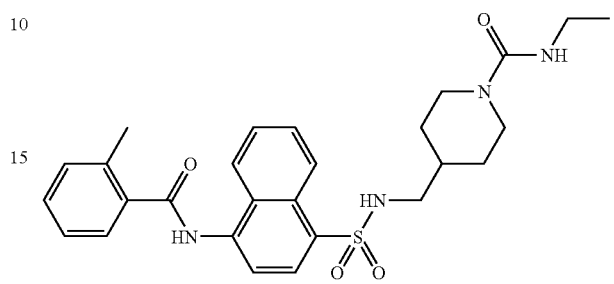

4-{[4-(2-Methyl-benzoylamino)-naphthalene-1-sulfonylamino]-methyl}-piperidine-1-carboxylic acid ethylamide (C-117)

The title compound was made following general procedure in Scheme 5, substituting 4-(2-methyl-benzoylamino)-naphthalene-1-sulfonyl chloride for 4-benzoylamino-naphthalen-1-sulfonyl chloride, 4-aminomethyl-piperidine-1-carboxylic acid tert-butyl ester for 4-amino-piperidine-1-carboxylic acid tert-butyl ester and isocyanato-ethane for 2-isocyanato-propane. $^{1}$H NMR (300 MHz, MeOD) δ 8.78 (d, 1H), 8.29 (m, 2H), 7.93 (m, 1H), 7.74 (m, 3H), 7.41 (m, 3H ), 3.79 (m, 2H), 3.25 (q, 2H), 2.78 (d, 2H), 2.61 (m, 2H), 2.57 (s, 3H), 1.56 (m, 3H), 1.09 (t, 3H), 0.92 (m, 2H); LC/MS (M+H)$^{+}$ m/z 509.

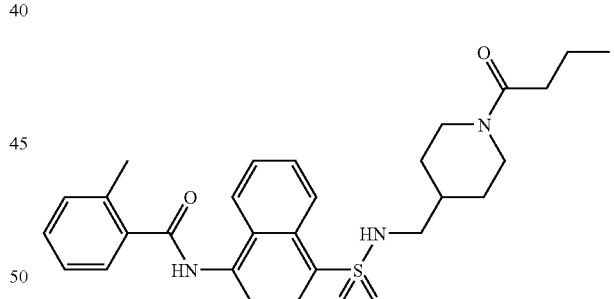

N-{4-[(1-Butyryl-piperidin-4-ylmethyl)-sulfamoyl]-naphthalen-1-yl}-2-methyl-benzamide (C-118)

The title compound was made following general procedure in Scheme 5, substituting 4-(2-methyl-benzoylamino)-naphthalene-1-sulfonyl chloride for 4-benzoylamino-naphthalene-1-sulfonyl chloride, 4-aminomethyl-piperidine-1-carboxylic acid tert-butyl ester for 4-amino-piperidine-1-carboxylic acid tert-butyl ester and butyryl chloride for 2-isocyanato-propane. $^{1}$H NMR (300 MHz, MeOD) δ 8.78 (d, 1H), 8.29 (m, 2H), 7.93 (m, 1H), 7.74 (m, 3H), 7.41 (m, 3H ), 4.49 (m, 1H), 3.85 (m, 1H), 2.89 (m, 1H), 2.78 (d, 2H), 2.57 (s, 3H), 2.41 (m, 1H), 2.30 (t, 2H), 1.61 (m, 5H), 0.96 (t, 3H), 0.93 (m, 2H); LC/MS (M+H)+ m/z 508.

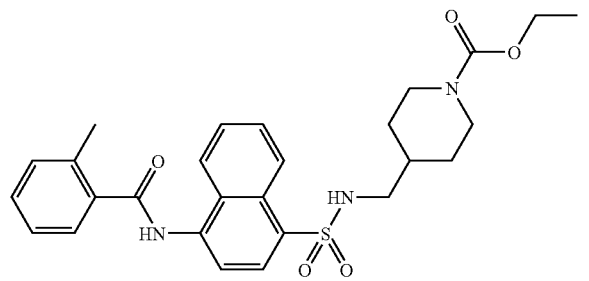

4-{[4-(2-Methyl-benzoylamino)-naphthalene-1-sulfonylamino]-methyl}-piperidine-1-carboxylic acid ethyl ester (C-119)

The title compound was made following general procedure in Scheme 5, substituting 4-(2-methyl-benzoylamino)-naphthalene-1-sulfonyl chloride for 4-benzoylamino-naphthalene-1-sulfonyl chloride, 4-aminomethyl-piperidine-1-carboxylic acid tert-butyl ester for 4-amino-piperidine-1-carboxylic acid tert-butyl ester and ethyl chlorofomate for 2-isocyanato-propane. $^1$H NMR (300 MHz, MeOD) δ 8.78 (d, 1H), 8.29 (m, 2H), 7.93 (m, 1H), 7.74 (m, 3H), 7.41 (m, 3H ), 4.09 (q, 2H), 4.00 (m, 2H), 2.78 (d, 2H), 2.59 (m, 2H), 2.57 (s, 3H), 1.59 (m, 3H), 1.22 (t, 3H), 0.90 (m, 2H); LC/MS (M+H)$^{30}$ m/z 510.

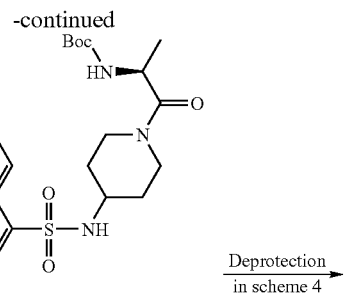

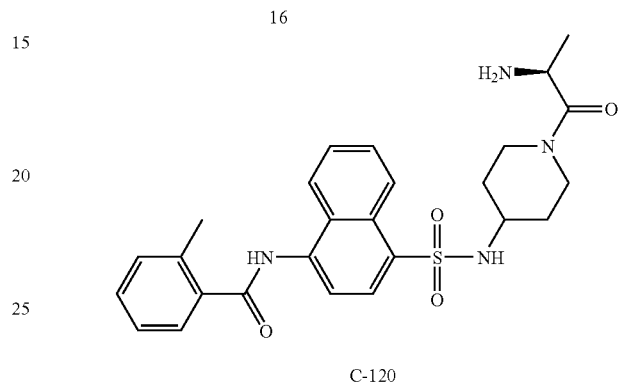

4-[4-(2-methyl-benzoylamino)-naphthalene-1-sulfonylamino]-piperidine-1-carboxylic acid tert-butyl ester (15)

The title compound was prepared following the general procedure in Scheme 2, substituting 4-amino-piperidine-1-carboxylic acid tert-butyl ester for p-anisidine and 2-methylbenzoyl chloride for benzoyl chloride. LC/MS (M+H)+ m/z 524.

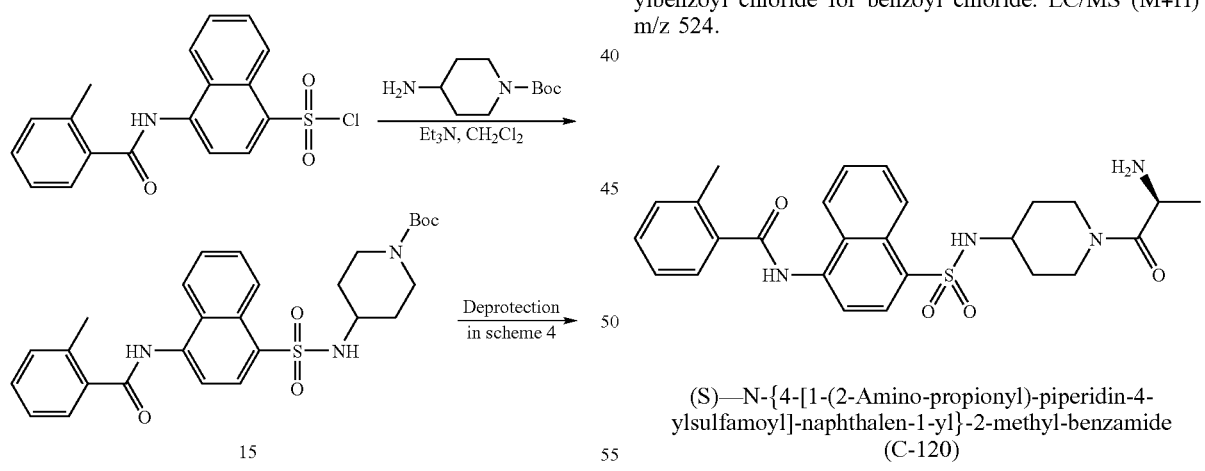

(S)—N-{4-[1-(2-Amino-propionyl)-piperidin-4-ylsulfamoyl]-naphthalen-1-yl}-2-methyl-benzamide (C-120)

2-Methyl-N-[4-(piperidin-4-ylsulfamoyl)-naphthalen-1-yl]-benzamide (C-36) was prepared from 4-[4-(2-methyl-benzoylamino)-naphthalene-1-sulfonylamino]-piperidine-1-carboxylic acid tert-butyl ester 15 via coupling and deprotection as shown in Scheme 4-1. To a 25° C. mixture of 2-methyl-N-[4-(piperidin-4-ylsulfamoyl)-naphthalen-1-yl]-benzamide (C-36) hydrochloride (368 mg, 0.8 mmol) in CH$_2$Cl$_2$ (12 mL), was added 1-hydroxybenzotriazole hydrate (108 mg, 0.8 mmol), 1-(3-dimethylaminopropyl)-3-ethylcarbodiimide hydrochloride (184 mg, 0.96 mmol), N-methylmorpholine (243 mg, 2.4 mmol) and (S)-2-tert-

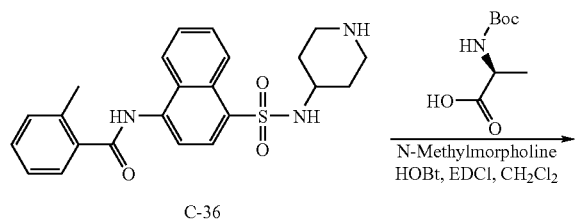
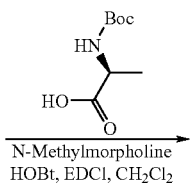

butoxycarbonylamino-propionic acid. After stirring at 25° C. for 20 hours, the reaction mixture was filtered and the filtrate was concentrated to dryness in vacuo to afford 16. A solution of 4N HCl/Dioxane (5 mL) was added and the mixture was stirred for 2 hours. After removing the solvent, the crude product was purified via chromatography. $^1$H NMR (300 MHz, MeOD) δ 8.71 (d, 1H), 8.28 (m, 3H), 7.96 (d, 1H), 7.71 (m, 3H), 7.43 (m, 1H), 7.38 (m, 2H), 4.00 (m, 2H), 3.60 (m, 2H), 3.01 (m, 1H), 2.71 (m, 1H), 2.49 (s, 3H), 1.57 (m, 2H), 1.22 (m, 2H), 1.09 (m, 3H); LC/MS (M+H)$^+$ m/z 495.

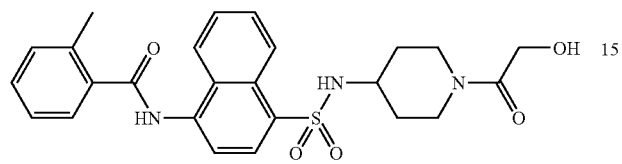

N-{4-[1-(2-Hydroxy-acetyl)-piperidin-4-ylsulfamoyl]-naphthalen-1-yl}-2-methyl-benzamide (C-121)

The title compound was made following general procedure in Scheme 6, substituting hydroxy-acetic acid for (S)-2-tert-butoxycarbonylamino-propionic acid. $^1$H NMR (300 MHz, MeOD) δ 8.78 (d, 1H), 8.33 (d, 1H), 8.23 (d, 1H), 7.94 (d, 1H), 7.71 (m, 3H), 7.43 (m, 1H ), 7.38 (m, 2H), 4.16 (m, 1H), 4.13 (s, 2H), 3.55 (m, 1H), 3.34 (m, 1H), 2.95 (m, 1H), 2.74 (m, 1H), 2.55 (s, 3H), 1.63 (m, 2H), 1.41 (m, 2H); LC/MS (M+H)$^+$ m/z 483.

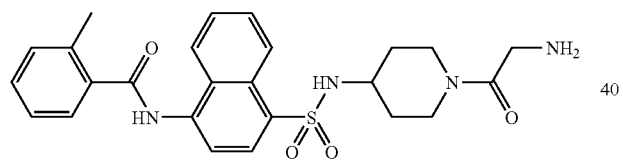

N-{4-[1-(2-Amino-acetyl)-piperidin-4-ylsulfamoyl]-naphthalen-1-yl}-2-methyl-benzamide (C-122)

The title compound was made following general procedure in Scheme 6, substituting tert-butoxycarbonylamino-acetic acid for (S)-2-tert-butoxycarbonylamino-propionic acid. $^1$H NMR (300 MHz, MeOD) δ 8.72 (d, 1H), 8.25 (m, 3H), 7.94 (d, 1H), 7.71 (m, 3H), 7.43 (m, 1H ), 7.38 (m, 2H), 4.05 (m, 1H), 3.60 (m, 4H), 2.95 (m, 1H ), 2.74 (m, 1H), 2.49 (s, 3H), 1.55 (m, 2H), 1.31 (m, 2H); LC/MS (M+H)$^+$ m/z 481.

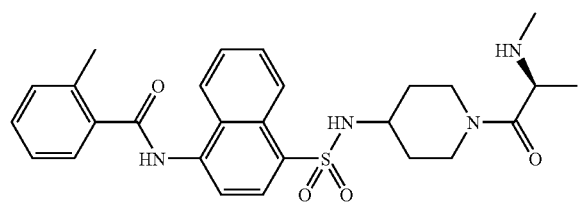

(S)-2-Methyl-N-{4-[1-(2-methylamino-propionyl)-piperidin-4-ylsulfamoyl]-naphthalen-1-yl}-benzamide (C-123)

The title compound was made following general procedure in Scheme 6, substituting (S)-2-(tert-butoxycarbonyl-methyl-amino)-propionic acid for (S)-2-tert-butoxycarbonylamino-propionic acid. $^1$H NMR (300 MHz, MeOD) δ 8.72 (d, 1H), 8.25 (m, 3H), 7.96 (d, 1H), 7.71 (m, 3H), 7.43 (m, 1H), 7.38 (m, 2H), 4.10 (m, 1H), 3.60 (m, 2H), 3.01 (m, 1H), 2.71 (m, 1H), 2.49 (s, 3H), 2.19 (d, 3H), 1.57 (m, 2H), 1.22 (m, 2H), 1.05 (m, 3H); LC/MS (M+H)$^+$ m/z 509.

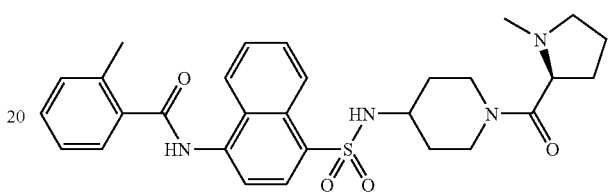

(S)-2-Methyl-N-{4-[1-(1-methyl-pyrrolidine-2-carbonyl)-piperidin-4-ylsulfamoyl]-naphthalen-1-yl}-benzamide (C-124)

The title compound was made following general procedure in Scheme 6, substituting (S)-1-methyl-pyrrolidine-2-carboxylic acid for (S)-2-tert-butoxycarbonylamino-propionic acid. $^1$H NMR (300 MHz, MeOD) δ 8.72 (d, 1H), 8.25 (m, 3H), 7.96 (d, 1H), 7.71 (m, 3H), 7.43 (m, 1H ), 7.38 (m, 2H), 4.03 (m, 2H), 3.40 (m, 5H), 2.99 (m, 1H), 2.68 (m, 1H), 2.49 (s, 3H), 2.21 (d, 3H), 2.02 (m, 1H), 1.71 (m, 2H), 1.55 (m, 2H), 1.20 (m, 2H); LC/MS (M+H)$^+$ m/z 535.

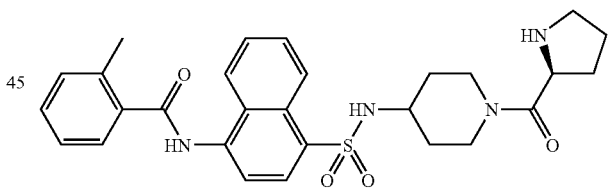

(S)-2-Methyl-N-{4-[1-(pyrrolidine-2-carbonyl)-piperidin-4-ylsulfamoyl]-naphthalen-1-yl}-benzamide (C-125)

The title compound was made following general procedure in Scheme 6, substituting (S)-pyrrolidine-1,2-dicarboxylic acid 1-tert-butyl ester for (S)-2-tert-butoxycarbonylamino-propionic acid. $^1$H NMR (300 MHz, MeOD) δ 8.72 (d, 1H), 8.25 (m, 3H), 7.96 (d, 1H), 7.71 (m, 3H), 7.43 (m, 1H ), 7.38 (m, 2H), 4.03 (m, 2H), 3.40 (m, 2H), 3.02 (m, 2H ), 2.78 (m, 2H), 2.49 (s, 3H), 2.06 (m, 1H), 1.62 (m, 5H), 1.25 (m, 2H); LC/MS (M+H)$^+$ m/z 521.

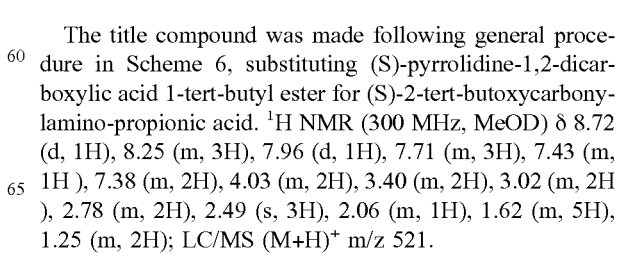

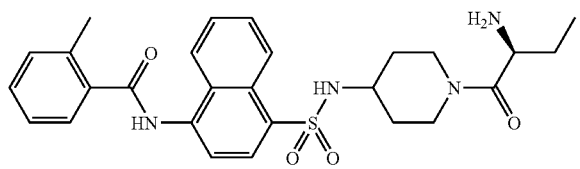

(S)—N-{4-[1-(2-Amino-butyryl)-piperidin-4-ylsulfamoyl]-naphthalen-1-yl}-2-methyl-benzamide (C-126)

The title compound was made following general procedure in Scheme 6, substituting (S)-2-tert-butoxycarbonylamino-butyric acid for (S)-2-tert-butoxycarbonylamino-propionic acid. $^1$H NMR (300 MHz, MeOD) δ 8.71 (d, 1H), 8.28 (m, 3H), 7.96 (d, 1H), 7.71 (m, 3H), 7.43 (m, 1H), 7.38 (m, 2H), 4.09 (m, 1H), 3.78 (m, 2H), 3.01 (m, 2H), 2.71 (m, 1H), 2.49 (s, 3H), 1.57 (m, 2H), 1.25 (m, 4H), 0.82 (m, 3H); LC/MS (M+H)$^+$ m/z 509.

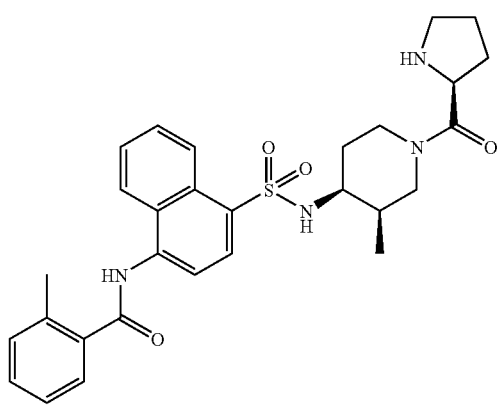

(±)-cis-2-Methyl-N-{4-[3-methyl-1-((s)-pyrrolidine-2-carbonyl)-piperidin-4-ylsulfamoyl]-naphthalen-1-yl}-benzamide (C-127) (mixture of two diastereomers)

The title compound (mixture of disatereomers) was made following general procedure in scheme 6, substituting 1-benzyl-3-methyl-piperidin-4-ylamine for 4-amino-piperidine-1-carboxylic acid tert-butyl ester, and substituting (s)-pyrrolidine-1,2-dicarboxylic acid 1-tert-butyl ester for (s)-2-tert-butoxycarbonylamino-propionic acid. LC/MS (M+H)$^+$ m/z 535.

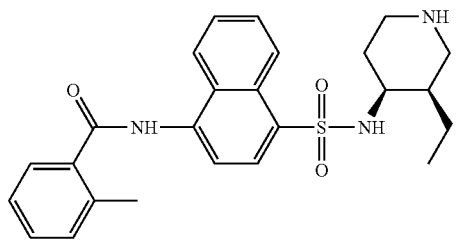

(±)-(cis-N-[4-(3-Ethyl-piperidin-4-ylsulfamoyl)-naphthalen-1-yl]-2-methyl-benzamide (C-128)

The title compound was prepared as its formate salt following general procedure in scheme 4-2, substituting (±)-1-benzyl-3-ethyl-piperidin-4-ylamine (3) for (±)-4-amino-1-benzyl-piperidine-3-carboxylic acid ethyl ester (6). $^1$H NMR (300 MHz, MeOD) δ 8.84 (d, 1H), 8.53 (s, 1H), 8.35 (d, 1H), 8.26 (d, 1H), 7.96 (d, 1H), 7.73 (m, 3H), 7.38 (m, 3H), 3.55 (m, 1H), 3.05 (m, 3H), 2.92 (m, 1H), 2.55 (s, 3H), 1.68 (m, 3H), 1.00 (m, 2H), 0.42 (t, 3H); LC/MS m/z 452 (M+H)$^+$

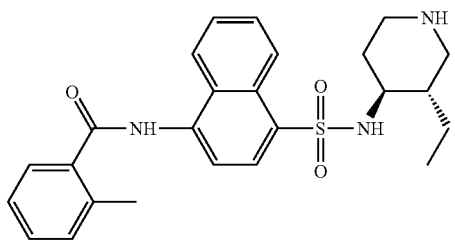

(±)-(trans)-N-[4-(3-Ethyl-piperidin-4-ylsulfamoyl)-naphthalen-1-yl]-2-methyl-benzamide (C-129)

The title compound was prepared as its formate salt following general procedure in scheme 4-2, substituting (±)-1-benzyl-3-ethyl-piperidin-4-ylamine (3) for (±)-4-amino-1-benzyl-piperidine-3-carboxylic acid ethyl ester (6). $^1$H NMR (300 MHz, MeOD) δ 8.78 (d, 1H), 8.53 (s, 1H), 8.33 (d, 1H), 8.25 (d, 1H), 7.94 (d, 1H), 7.72 (m, 3H), 7.40 (m, 3H), 3.35 (m, 1H), 3.20 (m, 2H), 2.85 (m, 1H), 2.60 (m, 1H), 2.56 (s, 3H), 1.75 (m, 1H), 1.52 (m, 3H), 0.90 (m, 1H), 0.58 (t, 3H); LC/MS m/z 452 (M+H)$^+$

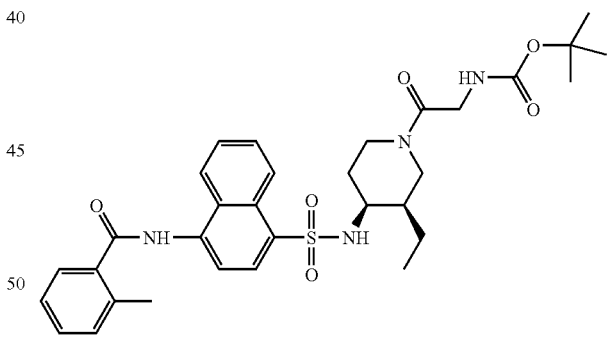

(±)-(cis)-(2-{3-Ethyl-4-[4-(2-methyl-benzoylamino)-naphthalene-1-sulfonylamino]-piperidin-1-yl}-2-oxo-ethyl)-carbamic acid tert-butyl ester (C-130)

The title compound was made following general procedure in Scheme 6, substituting (±)-(cis)-N-[4-(3-ethyl-piperidin-4-ylsulfamoyl)-naphthalen-1-yl]-2-methyl-benzamide (C-128) for N-[4-(piperidin-4-ylsulfamoyl)-naphthalen-1-yl]-benzamide (C-1) and substituting tert-butoxycarbonylamino-acetic acid for 3-tert-butoxycarbonylamino-butyric acid. $^1$H NMR (300 MHz, MeOD) δ 8.85 (d, 1H), 8.33 (d, 1H), 8.25 (d, 1H), 7.95 (d, 1H), 7.71 (m, 3H), 7.43 (m, 1H), 7.36 (m, 2H), 3.80 (s, 2H), 3.45 (m, 3H), 3.25 (m, 2H), 2.56 (s, 3H), 1.40 (m, 12H), 1.04 (m, 2H), 0.50 (m, 3H); LC/MS m/z 609 (M+H)⁺

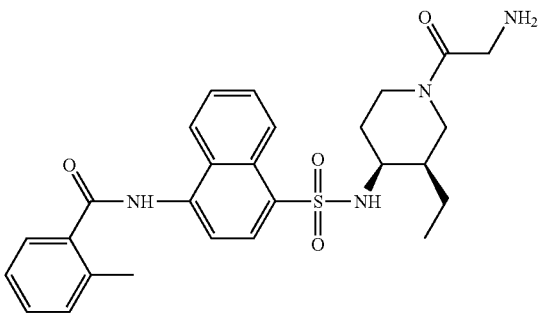

(±)-(cis)-N-{4-[1-(2-Amino-acetyl)-3-ethyl-piperidin-4-ylsulfamoyl]-naphthalen-1-yl}-2-methyl-benzamide (C-131)

The title compound was prepared as its formate salt following general procedure in Scheme 6, substituting (±)-(cis)-N-[4-(3-ethyl-piperidin-4-ylsulfamoyl)-naphthalen-1-yl]-2-methyl-benzamide (C-128) for N-[4-(piperidin-4-ylsulfamoyl)-naphthalen-1-yl]-benzamide (C-1), and substituting tert-butoxycarbonylamino-acetic acid for 3-tert-butoxycarbonylamino-butyric acid. ¹H NMR (300 MHz, MeOD) δ 8.85 (d, 1H), 8.52 (s, 1H), 8.33 (d, 1H), 8.25 (d, 1H), 7.95 (d, 1H), 7.72 (m, 3H), 7.43 (m, 1H), 7.36 (m, 2H), 3.78 (m, 2H), 3.45 (m, 3H), 3.20 (m, 2H), 2.56 (s, 3H), 1.45 (m, 3H), 1.05 (m, 2H), 0.50 (m, 3H); LC/MS m/z 509 (M+H)⁺

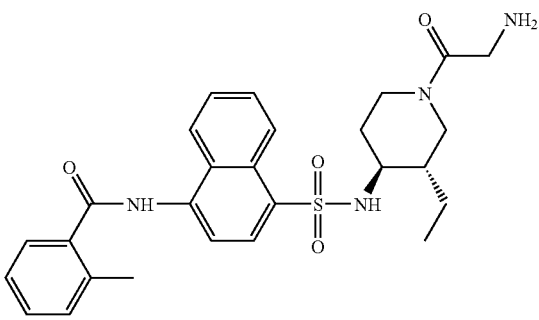

(±)-(trans)-N-{4-[1-(2-Amino-acetyl)-3-ethyl-piperidin-4-ylsulfamoyl]-naphthalen-1-yl}-2-methyl-benzamide (C-132)

The title compound was prepared as its formate salt following general procedure in Scheme 6, substituting (±)-(trans)-N-[4-(3-ethyl-piperidin-4-ylsulfamoyl)-naphthalen-1-yl]-2-methyl-benzamide (C-129) for N-[4-(piperidin-4-ylsulfamoyl)-naphthalen-1-yl]-benzamide (C-1) and substituting tert-butoxycarbonylamino-acetic acid for 3-tert-butoxycarbonylamino-butyric acid. ¹H NMR (300 MHz, MeOD) δ 8.78 (d, 1H), 8.52 (s, 1H), 8.33 (d, 1H), 8.25 (d, 1H), 7.95 (d, 1H), 7.72 (m, 3H), 7.43 (m, 1H), 7.36 (m, 2H), 4.25 (m, 1H), 3.75 (m, 2H), 3.55 (m, 1H), 3.05 (m, 2H), 2.56 (s, 3H), 2.50 (m, 1H), 1.40 (m, 4H), 0.85 (m, 1H), 0.65 (m, 3H); LC/MS m/z 509 (M+H)⁺

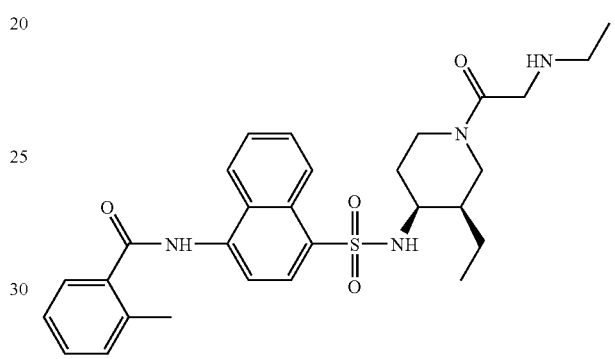

(±)-(cis)-N-{4-[3-Ethyl-1-(2-ethylamino-acetyl)-piperidin-4-ylsulfamoyl]-naphthalen-1-yl}-2-methyl-benzamide (C-133)

To a 25 °C. solution of (±)-(cis)-N-{4-[1-(2-amino-acetyl)-3-ethyl-piperidin-4-ylsulfamoyl]-naphthalen-1-yl}-2-methyl-benzamide (C-131) (65 mg, 0.128 mmol) in MeOH (4 mL) was added acetyl aldehyde (5.62 mg, 0.128 mmol) and sodium cyanoborohydride (40 mg, 0.64 mmol). After stirring for 2 h at 25° C., the solution was concentrated in vacuo to give a solid. The resultant solid was purified by reverse phase HPLC to provide the title compound. ¹H NMR (300 MHz, MeOD) δ 8.85 (d, 1H), 8.33 (d, 1H), 8.25 (d, 1H), 7.94 (d, 1H), 7.71 (m, 3H), 7.43 (m, 1H), 7.35 (m, 2H), 3.55 (m, 5H), 3.20 (m, 2H), 2.85 (m, 2H), 2.56 (s, 3H), 1.25 (m, 7H), 0.50 (m, 3H); LC/MS m/z 537 (M+H)⁺

Scheme 7

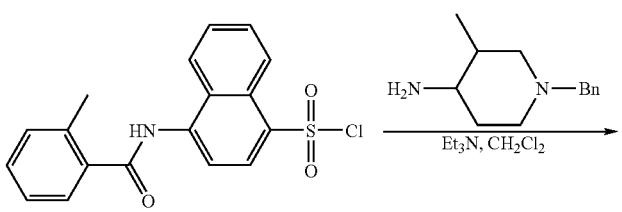

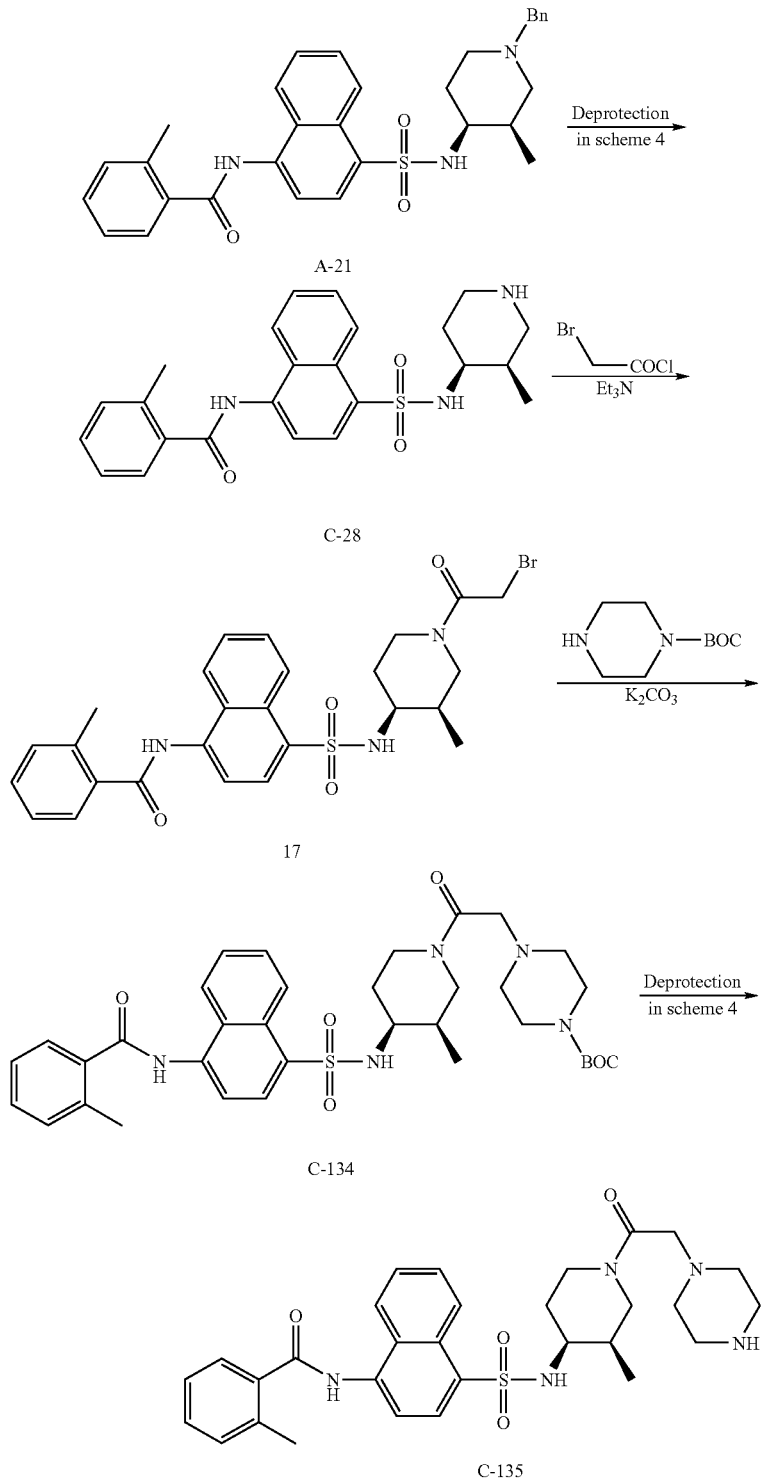

N-{4-[1-(2-bromo-acetyl)-3-cis-methyl-piperidin-4-ylsulfamoyl]-naphthalen-1-yl}-2-methyl-benzamide (17)

(±)-cis-N-[4-(1-Benzyl-3-methyl-piperidin-4-ylsulfamoyl)-naphthalen-1-yl]-2-methyl-benzamide (A-21) was prepared as described previously according to the general procedure in Scheme 2. Deprotection of A-21 to afford 2-Methyl-N-[4-(3-cis-methyl-piperidin-4-ylsulfamoyl)-naphthalen-1-yl]-benzamide (C-28) was achieved according to the general procedure described in Scheme 4-2. 2-Methyl-N-[4-(3-cis-methyl-piperidin-4-ylsulfamoyl)-naphthalen-1-yl]-benzamide (C-28) (700 mg, 1.6 mmol) was dissolved in dichloromethane (8 mL). Triethylamine (192 mg, 0.26 mL, 1.9 mmol) was added followed by bromoacetyl chloride (378 mg, 0.20 mL, 2.4 mmol). The reaction was stirred for 1 hour at room temperature and then passed through a plug of silica gel. Elution with ethyl acetate followed by evaporation in vacuo afforded the title product (644 mg, 72%) as a white solid. This material was used without further purification. LC/MS m/z 556 (M−H)⁻.

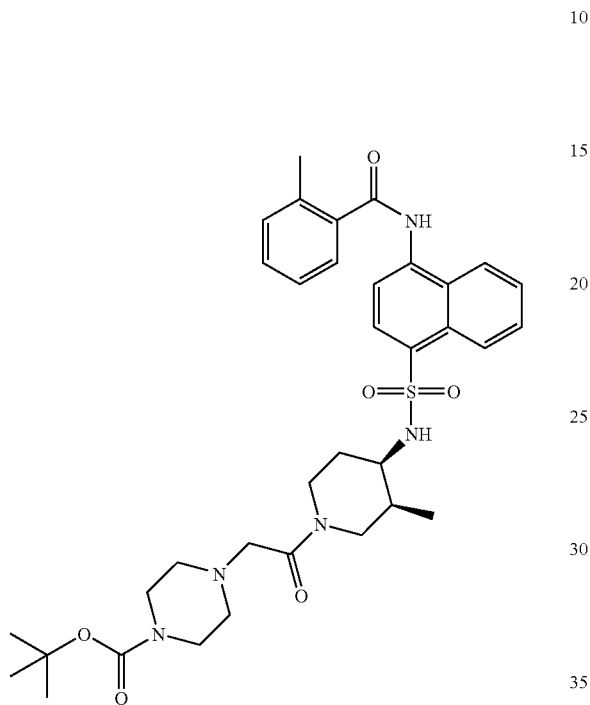

(±)-4-(2-{3-cis-methyl-4-[4-(2-methyl-benzoylamino)-naphthalene-1-sulfonylamino]-piperidin-1-yl}-2-oxo-ethyl)-piperazine-1-carboxylic acid tert-butyl ester (C-134)

N-{4-[1-(2-Bromo-acetyl)-3-cis-methyl-piperidin-4-ylsulfamoyl]-naphthalen-1-yl}-2-methyl-benzamide (100 mg, 0.18 mM) was dissolved in a mixture of acetonitrile (1 mL) and water (0.25 mL). Potassium carbonate (37 mg, 0.27 mmol) was added followed by piperazine-1-carboxylic acid tert-butyl ester (37 mg, 0.2 mM). The reaction was stirred for 1 hour at room temperature before being passed through a plug of silica gel. Elution with ethyl acetate:methanol (90:10) afforded the titled compound (43 mg, 34%) as a yellow solid. ¹H NMR (300 MHz, CD₃OD) (1:1 mixture of rotamers) δ 8.85 (d, 1H), 8.30 (d, 1H), 8.22 (d, 1H), 7.95 (d, 1H), 7.70 (m, 3H), 7.38 (m, 4H), 3.57 (m, 5H), 3.40 (m, 6H), 3.18 (m, 4H), 2.58 (s, 3H), 1.78 (m, 1H), 1.52 (m, 2H), 1.42 (s, 9H), 0.70 (d, 1.5H), 0.65 (d, 1.5H); LC/MS m/z 664 (M+H)⁺.

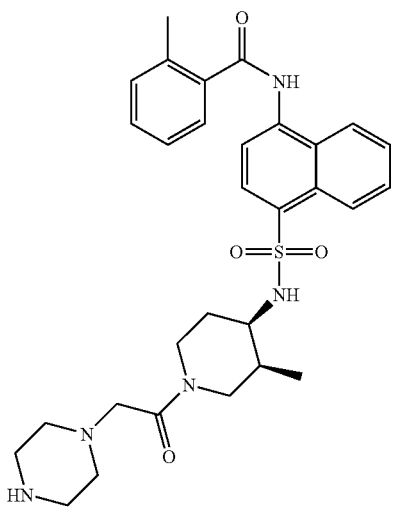

(±)-2-methyl-N-{4-[3-cis-methyl-1-(2-piperazin-1-yl-acetyl)-piperidin-4-ylsulfamoyl]-naphthalen-1-yl}-benzamide (C-135)

(±)-4-(2-{3-cis-Methyl-4-[4-(2-methyl-benzoylamino)-naphthalene-1-sulfonylamino]-piperidin-1yl}-2oxo-ethyl)-piperazine-1-carboxylic acid tert-butyl ester (43 mg, 0.07 mmol) was dissolved in a solution of 4N HCl/dioxane (3 mL). The reaction was left standing for 3 hours at room temperature; concentration in vacuo afforded the titled compound (14 mg, 40%) as its bis-hydrochloride salt. ¹H NMR (300 MHz, CD₃OD) (1:1 mixture of rotamers) δ 8.85 (d, 1H), 8.32 (d, 1H), 8.24 (d, 1H), 7.96 (d, 1H), 7.72 (m, 3H), 7.40 (m, 4H), 4.30 (m, 2H), 3.52 (m, 12H), 3.22 (m, 2H), 2.58 (s, 3H), 1.83 (m, 1H), 1.58 (m, 2H), 0.74 (d, 1.5H), 0.68 (d, 1.5H); LC/MS m/z 564 (M+H)⁺.

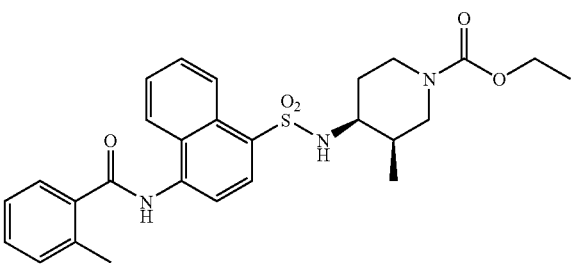

(±)-cis-3-Methyl-4-[4-(2-methyl-benzoylamino)-naphthalene-1-sulfonylamino]-piperidine-1-carboxylic acid ethyl ester (C-136)

The title compound was prepared from A-21 according to the general procedure in Scheme 7. To a solution of A-21 in ethyl acetate was added Pd(OH)$_2$ and diethyl pyrocarbonate (1.0 eq). The vessel was evacuated and pressurized to 50 psi H$_2$ and allowed to agitate on a Parr apparatus overnight. The solution was filtered through a celite plug, washed with hot ethyl acetate and concentrated at 40° C. at reduced pressure. The residue was purified using flash chromatography to provide the title compound. $^1$H NMR (300 MHz, DMSO) δ 10.63 (s, 1H), 8.77 (d, 1H), 8.28 (d, 1H), 8.21 (d, 1 H), 8.12 (d, 1H), 7.97 (d, 1H), 7.74 (m, 3H), 7.45 (d, 1H), 7.38 (m, 2H), 3.98 (q, 2H), 3.38(m, 1H), 3.29 (m, 1H), 3.21 (m, 3H), 2.52 (s, 3H), 1.67 (m, 1H), 1.30 (m, 2H), 1.13 (t, 3H), 0.57 (d, 3H); LC/MS m/z 508 (M–H)$^-$, 510 (M+H)$^+$

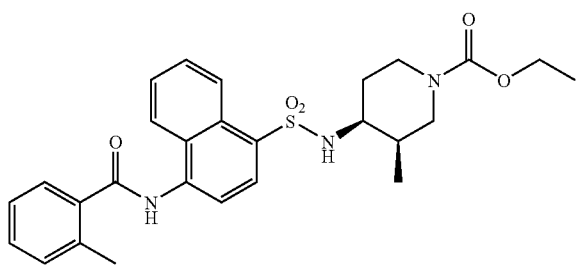

cis-3-Methyl-4-[4-(2-methyl-benzoylamino)-naphthalene-1-sulfonylamino]-piperidine-1-carboxylic acid ethyl ester (single enantiomer, absolute stereochemistry not determined) (C-137)

Compound C-136 was subjected to reverse phase chiral HPLC separation, and the title compound was the first enantiomer to elute from the column. $^1$H NMR (300 MHz, DMSO) δ 8.70 (d, 1H), 8.42 (d, 1H), 8.34 (d, 1H), 8.11 (s, 1H), 7.93 (d, 1H), 7.63 (m, 3H), 7.42 (d, 1H), 7.34 (d, 2H), 4.64 (d, 1H), 4.05 (m, 2H), 3.48 (m, 0.5H), 3.38 (m, 1H), 3.21 (m, 2.5H), 2.59 (s, 3H), 1.74 (m, 1H), 1.48 (s, 1H), 1.43 (m, 2H), 1.19 (t, 3H), 0.66 (s, 3H. LC/MS m/z 508 (M–H)$^-$, 510 (M+H)$^+$

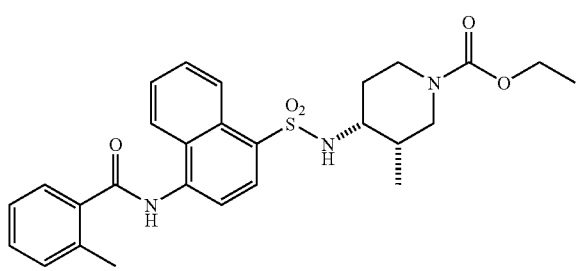

cis-3-Methyl-4-[4-(2-methyl-benzoylamino)-naphthalene-1-sulfonylamino]-piperidine-1-carboxylic acid ethyl ester (single enantiomer, absolute stereochemistry not determined) (C-138)

Compound C-136 was subjected to reverse phase chiral HPLC separation, and the title compound was the second enantiomer to elute from the column. $^1$H NMR (300 MHz, DMSO) δ 8.70 (d, 1H), 8.42 (d, 1H), 8.34 (d, 1H), 8.11 (s, 1H), 7.93 (d, 1H), 7.63 (m, 3H), 7.42 (d, 1H), 7.34 (d, 2H), 4.64 (d, 1H), 4.05 (m, 2H), 3.48 (m, 0.5H), 3.38 (m, 1H), 3.21 (m, 2.5H), 2.59 (s, 3H), 1.74 (m, 1H), 1.48 (s, 1H), 1.43(m, 2H), 1.19 (t, 3H), 0.66 (s, 3H). LC/MS m/z 508 (M–H)$^-$, 510 (M+H)$^+$

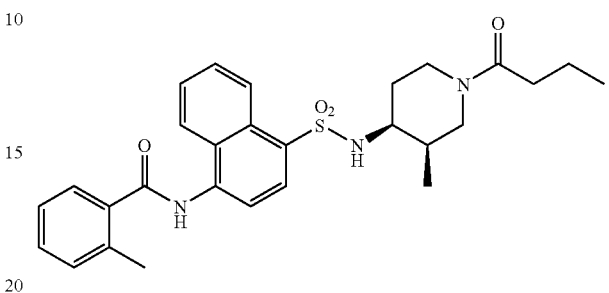

(±)-cis-N-[4-(1-Butyryl-3-methyl-piperidin-4-ylsulfamoyl)-naphthalen-1-yl]-2-methyl-benzamide (C-139)

The title compound was prepared from A-21 according to the general procedure in Scheme 7. To a solution of A-21 in ethyl acetate was added Pd(OH)$_2$ and butyric anhydride (1.0 eq). The vessel was evacuated and pressurized to 50 psi H$_2$ and allowed to agitate on a Parr apparatus overnight. The solution was filtered through a celite plug, washed with hot ethyl acetate and concentrated at 40° C. at reduced pressure. The residue was purified using flash chromatography to provide the title compound. $^1$H NMR (300 MHz, DMSO) δ 8.75 (m, 1H), 8.32 (m, 3H), 7.95 (d, 1H), 7.63 (m, 3H), 7.43 (m, 1H), 7.33 (m, 2H), 5.20 (d, 1H), 3.63 (m, 0.5H), 3.40 (m, 2H), 3.20 (m, 2H), 3.01 (m, 0.5H), 2.57 (s, 3H), 2.19 (m, 2H), 1.82 (m, 0.5H), 1.67 (m, 0.5H), 1.56 (m, 3H), 1.30 (m 1H), 0.95 (dt, 3H), 0.73 (d, 0.5H), 0.59 (d, 0.5H). LC/MS m/z 506 (M–H)$^-$, 508 (M+H)$^+$

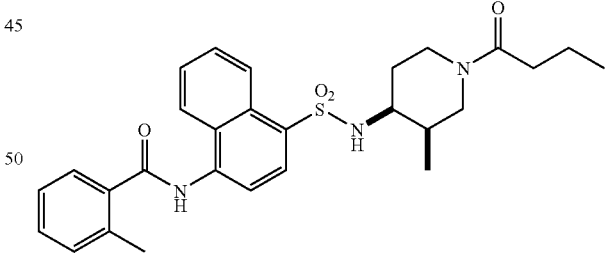

cis-N-[4-(1-butyryl-3-methyl-piperidin-4-ylsulfamoyl)-naphthalen-1-yl]-2-methyl-benzamide (C-140) (single enantiomer, absolute stereochemistry not determined)

Compound C-139 was subjected to reverse phase chiral HPLC separation, and the title compound was the first enantiomer to elute from the column. $^1$H NMR (300 MHz, CDCl$_3$) δ 8.71 (m, 1H), 8.42 (d, 1H), 8.37 (d, 1H), 8.12 (s, 1H), 7.94 (d, 1H), 7.73 (m, 1H), 7.63 (m, 2H), 7.43 (m, 1H), 7.34 (d, 2H), 4.68 (m, 1H), 3.42–3.20 (m, 3H), 2.59 (s, 3H), 2.20 (m, 2H), 1.57 (m, 4H), 1.35 (m, 1H), 1.25 (m, 2H), 0.89 (m, 3H), 0.74 (d, 1.5H), 0.55 (d, 1.5H). LC/MS m/z 506 (M−H)⁻, 508 (M+H)⁺

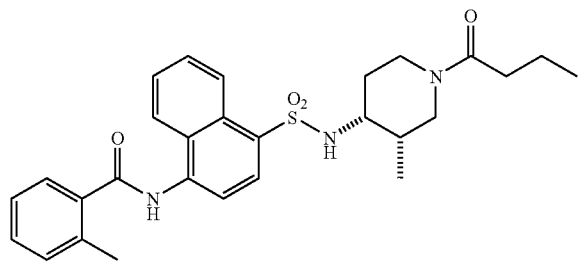

cis-N-[4-(1-butyryl-3-methyl-piperidin-4-ylsulfamoyl)-naphthalen-1-yl]-2-methyl-benzamide (C-141) (single enantiomer, absolute stereochemistry not determined)

Compound C-139 was subjected to reverse phase chiral HPLC separation, and the title compound was the second enantiomer to elute from the column. ¹H NMR (300 MHz, CDCl₃) δ 8.71 (m, 1H), 8.42 (d, 1H), 8.37 (d, 1H), 8.12 (s, 1H), 7.94 (d, 1 H), 7.73 (m, 1H), 7.63 (m, 2H), 7.43 (m, 1H), 7.34 (d, 2H), 4.68 (m, 1H), 3.42-3.20 (m, 3H), 2.59 (s, 3H), 2.20 (m, 2H), 1.57 (m, 4H), 1.35 (m, 1H), 1.25 (m, 2H), 0.89 (m, 3H), 0.74 (d, 1.5H), 0.55 (d, 1.5H). LC/MS m/z 506 (M−H)⁻, 508 (M+H)⁺

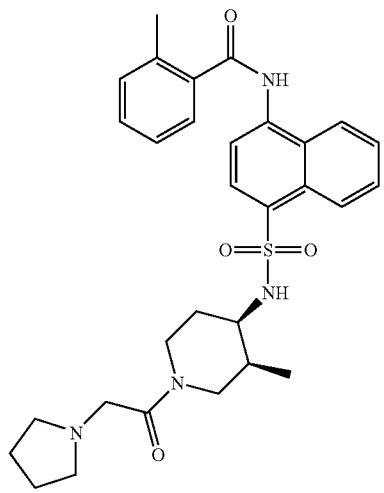

(±)-2-Methyl-N-{4-[cis-3-methyl-1-(2-pyrrolidin-1-yl-acetyl)-piperidin-4-ylsulfamoyl]-naphthalen-1yl}-benzamide (C-142)

The title compound was prepared as shown in Scheme 7 for the preparation of C-134 except substituting pyrrolidine for piperazine-1-carboxylic acid tert-butyl ester. Reverse phase HPLC purification afforded the title compound as its formate salt. Wt.: 37 mg (38%). ¹H NMR (300 MHz, CD₃OD) (1:1 mixture of rotamers) δ 8.85 (d, 1H), 8.47 (s, 1H), 8.36 (d, 1H), 8.27 (d, 1H), 8.10 (d, 1H), 7.70 (m, 3H), 7.96 (d, 1H), 7.70 (m, 3H), 7.40 (m, 3H), 4.22 (m, 2H), 3.68 (m, 1H), 3.45 (m, 4H), 3.24 (m, 4H), 2.58 (s, 3H), 2.04 (m, 4H), 1.80 (m, 1H), 1.47 (m, 2H), 0.70 (d, 1.5H), 0.65 (d, 1.5H); LC/MS m/z 549 (M+H)⁺.

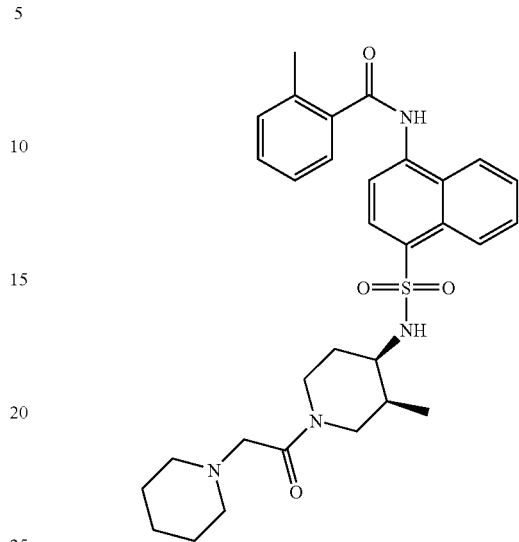

(±)-2-Methyl-N-{4-[cis-3-methyl-1-(2-piperidin-1-yl-acetyl)-piperidin-4-ylsulfamoyl]-naphthalen-1-yl}-benzamide (C-143)

The title compound was prepared as shown in Scheme 7 for the preparation of C-134 except substituting piperidine for piperazine-1-carboxylic acid tert-butyl ester. Reverse phase HPLC purification afforded the title compound as its formate salt. Wt.: 43 mg (43%). ¹H NMR (300 MHz, CD₃OD) (1:1 mixture of rotamers) δ 8.85 (d, 1H), 8.33 (d, 2H), 8.25 (d, 1H), 7.95 (d, 1H), 7.70 (m, 3H), 7.40 (m, 3H), 4.04 (m, 2H), 3.63 (m, 1H), 3.45 (m, 4H), 3.20 (m, 4H), 2.56 (s, 3H), 1.88 (m, 6H), 1.67 (m, 2H), 1.45 (m, 1H), 0.70 (d, 1.5H), 0.64 (d, 1.5H); LC/MS m/z 563 (M+H)⁺.

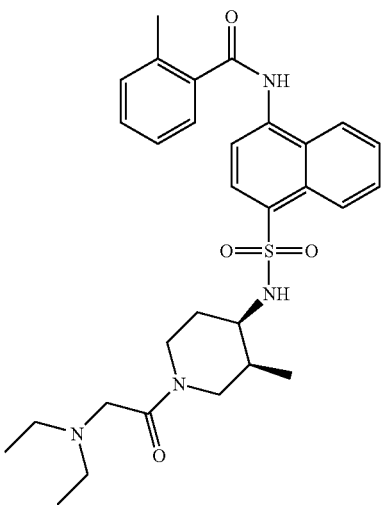

131

(±)-N-{4-[1-(2-diethylamino-acetyl)-3-cis-methyl-piperidin-4-ylsulfamoyl]-naphthalen-1-yl}-2-methyl-benzamide (C-144)

The title compound was prepared as shown in Scheme 7 for the preparation of C-134 except substituting diethylamine for piperazine-1-carboxylic acid tert-butyl ester. Reverse phase HPLC purification afforded the title compound as its formate salt. Wt.: 49 mg (50%). $^1$H NMR (300 MHz, CD$_3$OD) (1 :1 mixture of rotamers) δ 8.85 (d, 1H), 8.46 (s, 1H), 8.38 (d, 1H), 8.28 (d, 1H), 7.95 (d, 1H), 7.70 (m, 3H), 7.40 (m, 3H), 4.16 (m, 2H), 3.65 (m, 1H), 3.44 (m, 4H), 3.19 (m, 4H), 2.56 (s, 3H), 1.80 (m, 1H), 1.52 (m, 2H), 1.25 (t, 6H), 0.70 (d, 1.5H), 0.64 (d, 1.5H); LC/MS m/z 551 (M+H)$^+$.

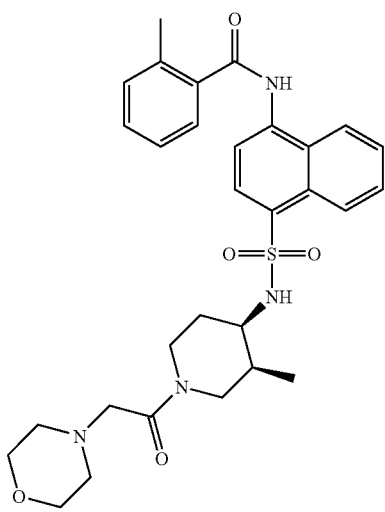

(±)-2-Methyl-N-{4-[3-cis-methyl-1-(2-morpholin-4-yl-acetyl)-piperidin-4-ylsulfamoyl]naphthalen-1-yl}-benzamide (C-145)

The title compound was prepared as shown in Scheme 7 for the preparation of C-134 except substituting morpholine for piperazine-1-carboxylic acid tert-butyl ester. Wt.: 60 mg (58%). $^1$H NMR (300 MHz, CD$_3$OD) (1:1 mixture of rotamers) δ 8.88 (d, 1H), 8.38 (d, 1H), 8.32 (d, 1H), 8.00 (d, 1H), 7.80 (m, 3H), 7.45 (m, 3H), 4.26 (m, 2H), 4.06 (m, 2H), 3.86 (m, 3H), 3.50 (m, 4H), 3.24 (m, 3H), 2.60 (s, 3H), 1.85 (m, 1H), 1.55 (m, 2H), 0.76 (d, 1.5H), 0.69 (d, 1.5H); LC/MS m/z 565 (M+H)$^+$.

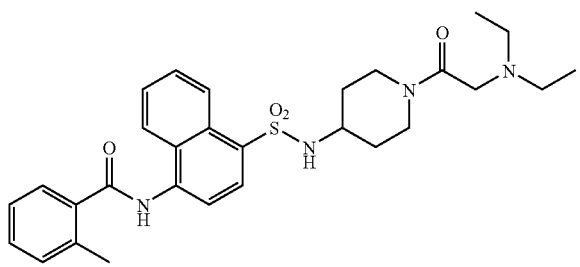

132

N-{4-[1-(2-Diethylamino-acetyl)-piperidin-4-ylsulfamoyl]-naphthalen-1-yl}-2-methyl-benzamide (C-146)

The title compound was prepared following the general procedure for preparing C-134 in Scheme 7, substituting 4-amino-piperidine-1-carboxylic acid tert-butyl ester for 1-benzyl-3-methyl-piperidin-4-ylamine, and diethyl amine for piperazine-1-carboxylic acid tert-butyl ester. $^1$H NMR (300 MHz, DMSO) δ 10.66 (s, 1H), 9.08 (m, 1H), 8.69 (d, 1H), 8.27 (d, 1H), 8.22 (t, 2H), 7.94 (d, 1H), 7.70 (m, 3H), 7.42 (m, 1H), 7.35 (m, 2H), 4.27-4.02 (m, 2H), 4.03 (d, 1H), 3.40 (m, 3H), 2.98 (m, 3H), 2.83 (m, 1H), 2.56 (s, 3H), 1.92 (m, 5 H), 1.58 (m, 2H), 1.30 (m, 2H), 1.11 (t, 2H). LC/MS m/z 536 (M–H)$^-$, 538 (M+H)$^+$

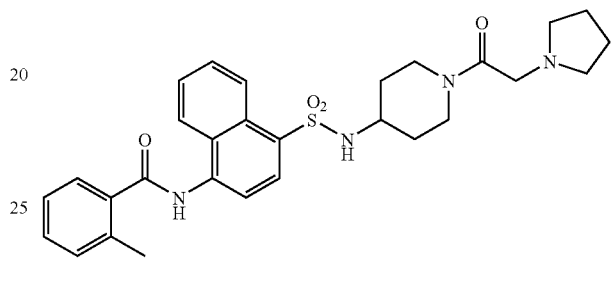

2-Methyl-N-{4-[1-(2-pyrrolidin-1-yl-acetyl)-piperidin-4-ylsulfamoyl]-naphthalen-1-yl}-benzamide (C-147)

The title compound was prepared following the general procedure for preparing C-134 in Scheme 7, substituting 4-amino-piperidine-1-carboxylic acid tert-butyl ester for 1-benzyl-3-methyl-piperidin-4-ylamine, and pyrrole for piperazine-1-carboxylic acid tert-butyl ester. $^1$H NMR (300 MHz, DMSO) δ 10.56 (s, 1H), 9.28 (m, 1H), 8.68 (d, 1H), 8.27 (d, 1H), 8.21 (m, 2H), 7.94 (d, 1H), 7.72 (m, 3H), 7.43 (d, 1H), 7.38 (m, 2H), 4.31 (m, 2H), 4.03 (d, 1H), 3.27 (m, 2H), 2.98 (m, 3H), 2.83 (m, 1H), 2.56 (s, 3H), 1.92 (m, 5H), 1.58 (m, 2H), 1.3 (m, 2H). LC/MS m/z 534 (M–H)$^-$, 535 (M+H)$^+$

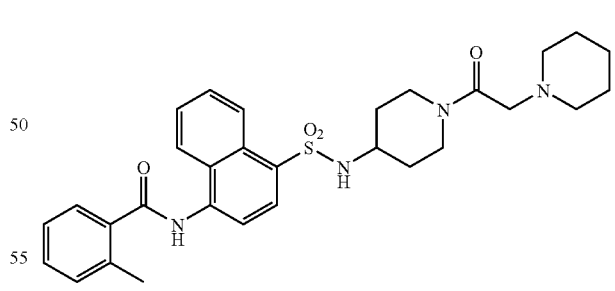

2-Methyl-N-{4-[1-(2-piperidin-1-yl-acetyl)-piperidin-4-ylsulfamoyl]-naphthalen-1-yl}-benzamide (C-148)

The title compound was prepared following the general procedure for preparing C-134 in Scheme 7, substituting 4-amino-piperidine-1-carboxylic acid tert-butyl ester for 1-benzyl-3-methyl-piperidin-4-ylamine, and substituting piperidine for piperazine-1-carboxylic acid tert-butyl ester.

¹H NMR (300 MHz, DMSO) δ 10.56 (s, 1H), 9.28 (m, 1H), 8.68 (d, 1H), 8.27 (d, 1H), 8.21 (m, 2H), 7.94 (d, 1H), 7.72 (m, 3H), 7.43 (d, 1H), 7.38 (m, 2H), 4.15 (m, 3H), 3.36 (m, 3H), 2.99 (m, 1H), 2.80 (m, 3H), 2.56 (s, 3H), 1.74 (m, 3H), 1.58 (m, 4H), 1.27 (m, 3H). LC/MS m/z 548 (M–H)⁻, 549 (M+H)⁺

-continued

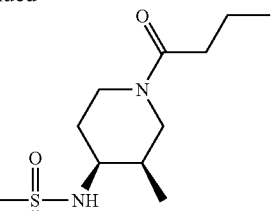

D-3

Scheme 8

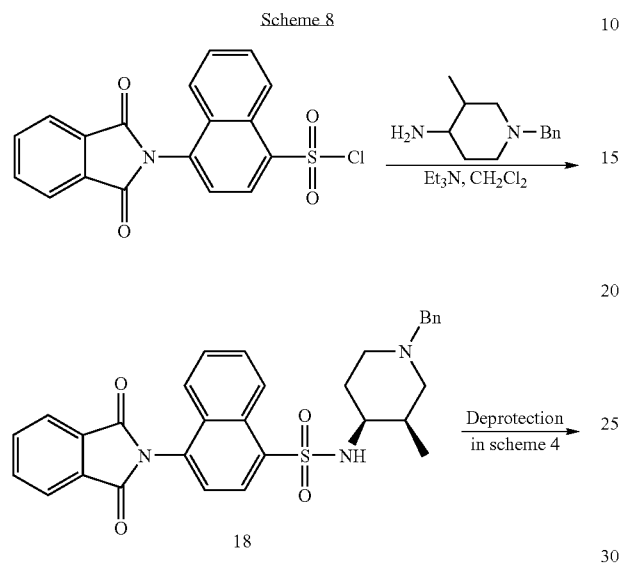

18

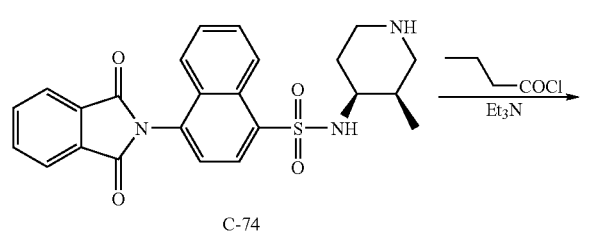

C-74

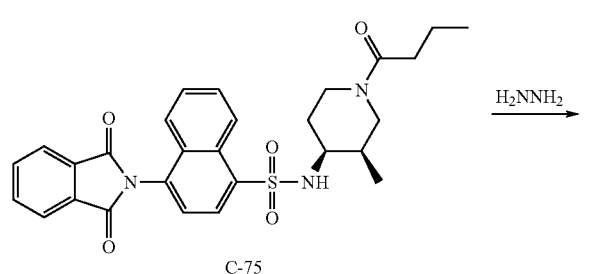

C-75

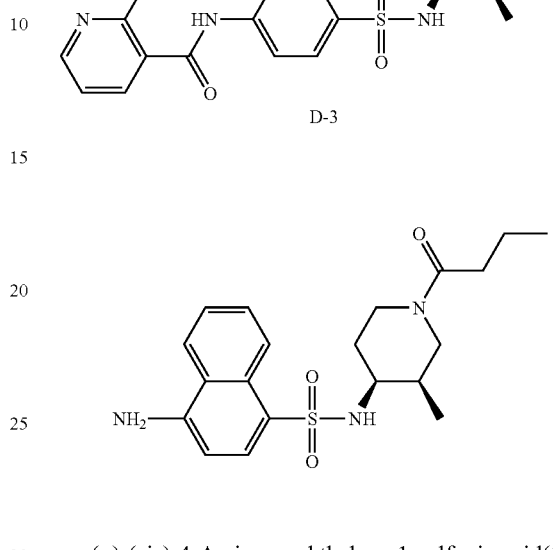

(±)-(cis)-4-Amino-naphthalene-1-sulfonic acid(1-butyryl-3-methyl-piperidin-4-yl)-amide (D-1)

(±)-cis-N-[4-(1-Benzyl-3-methyl-piperidin-4-ylsulfamoyl)-naphthalen-1-yl]-2-methyl-benzamide (18) was prepared as described previously according to the general procedure in Scheme 3, substituting 1-benzyl-3-methyl-piperidin-4-ylamine for p-anisidine. (±)-(cis)-4-(1,3-Dioxo-1,3-dihydro-isoindol-2-yl)-naphthalene-1-sulfonic acid(3-methyl-piperidin-4-yl)-amide (C-74) and (±)-(cis)-4-(1,3-dioxo-1,3-dihydro-isoindol-2-yl)-naphthalene-1-sulfonic acid(1-butyryl-3-methyl-piperidin-4-yl)-amide (C-75) were prepared as described previously according to the general procedure in Scheme 5. The title compound was made following general procedure in Scheme 3, substituting (±)-(cis)-4-(1,3-dioxo-1,3-dihydro-isoindol-2-yl)-naphthalene-1-sulfonic acid(1-butyryl-3-methyl-piperidin-4-yl)-amide (C-75) for 4-(1,3-dioxo-1,3-dihydro-isoindol-2-yl)-naphthalene-1-sulfonic acid(4-methoxy-phenyl)-amide (A-2). ¹H NMR (300 MHz, MeOD) δ 8.62 (d, 1H), 8.30 (d, 1H), 7.98 (d, 1H), 7.60 (dt, 1H), 7.48 (dt, 1H), 6.70 (d, 1H), 3.66 (m, 1H), 3.42 (m, 1H), 3.28 (m, 5H), 2.25 (m, 2H), 1.67 (m, 1H), 1.50 (m, 2H), 1.30 (m, 2H), 0.88 (t, 3H), 0.64 (m, 3H); LC/MS m/z 391 (M+H)⁺

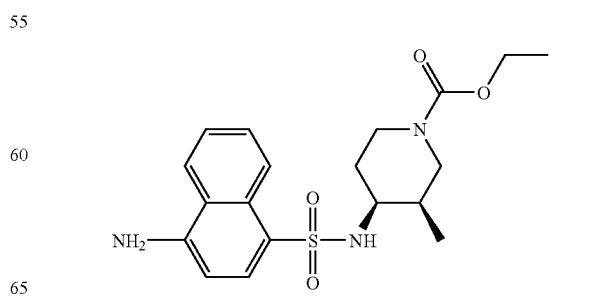

(±)-(cis)-4-(4-Amino-naphthalene-1-sulfonylamino)-
3-methyl-piperidine-1-carboxylic acid ethyl ester
(D-2)

The title compound was made following general procedure in Scheme 8, substituting ethyl chloroformate for butyryl chloride. $^1$H NMR (300 MHz, MeOD) δ 8.61 (d, 1H), 8.10 (d, 1H), 7.97 (d, 1H), 7.60 (t, 1H), 7.48 (t, 1H), 6.70 (d, 1H), 4.02 (q, 2H), 3.47 (m, 1H), 3.24 (m, 4H), 1.64 (m, 1H), 1.38 (m, 1H), 1.25 (m, 1H), 1.17 (t, 3H), 0.64 (d, 3H); LC/MS m/z 393 (M+H)$^+$

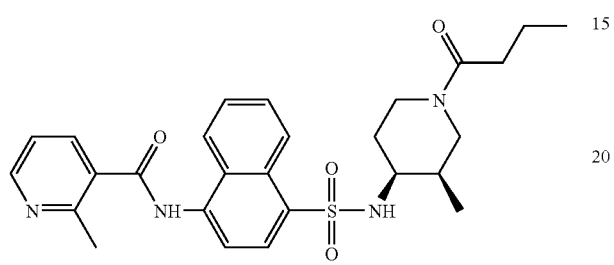

(±)-(cis)-N-[4-(1-Butyryl-3-methyl-piperidin-4-yl-
sulfamoyl)-naphthalen-1-yl]-2-methyl-nicotinamide
(D-3)

To a solution of naphthalenyl amine (D-1) (78 mg, 0.2 mmol) in CH$_2$Cl$_2$ (3 mL) was added acetyl chloride (20 uL, 0.24 mmol) and Et$_3$N (60 uL, 0.4 mmol). The resultant solution was stirred at 25 ° C. overnight. The solvent was removed in vacuo and the residue was purified using HPLC to give the title compound. $^1$H NMR (300 MHz, MeOD) δ 8.84 (d, 1H), 8.57 (dd, 1H), 8.31 (d, 1H), 8.24 (d, 1H), 8.11 (m, 1H), 7.98 (m, 1H), 7.72 (m, 2H), 7.43 (dd, 1H), 3.40 (m, 5H), 2.75 (s, 3H), 2.25 (m, 2H), 1.50 (m, 5H), 0.90 (t, 3H), 0.65 (dd, 3H); LC/MS m/z 510 (M+H)$^+$

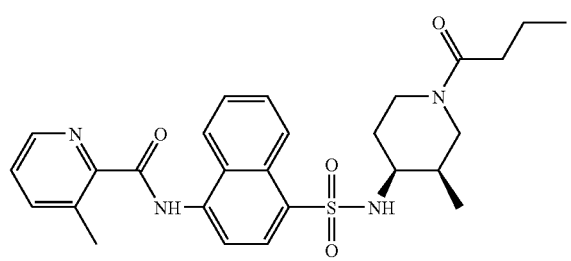

(±)-(cis)-3-Methyl-pyridine-2-carboxylic acid [4-(1-
butyryl-3-methyl-piperidin-4-ylsulfamoyl)-naphtha-
len-1yl]-amide (D-4)

The title compound was made following general procedure in Scheme 8, substituting 3-methyl-pyridine-2-carbonyl chloride for 2-methyl-nicotinoyl chloride. $^1$H NMR (300 MHz, MeOD) δ 8.83 (m, 1H), 8.59 (d, 1H), 8.28 (m, 3H), 7.74 (m, 3H), 7.53 (dd, 1H), 3.40 (m, 5H), 2.75 (s, 3H), 2.25 (m, 2H), 1.50 (m, 5H), 0.95 (t, 3H), 0.80 (dd, 3H); LC/MS m/z 510 (M+H)$^+$

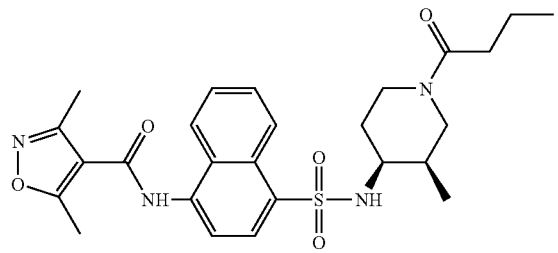

(±)-(cis)-3,5-dimethyl-isoxazole-4-carboxylic acid
[4-(1-butyryl-3-methyl-piperidin-4-ylsulfamoyl)-
naphthalen-1-yl]-amide (D-5)

The title compound was made following general procedure in Scheme 8, substituting 3,5-dimethyl-isoxazole-4-carbonyl chloride for 2-methyl-nicotinoyl chloride. $^1$H NMR (300 MHz, MeOD) δ 8.82 (d, 1H), 8.28 (d, 1H), 8.18 (d, 1H), 7.93 (d, 1H), 7.71 (m, 2H), 3.34 (m, 5H), 2.70 (s, 3H), 2.47 (s, 3H), 2.25 (m, 2H), 1.50 (m, 5H), 0.89 (t, 3H), 0.63 (dd, 3H); LC/MS m/z 514 (M+H)$^+$

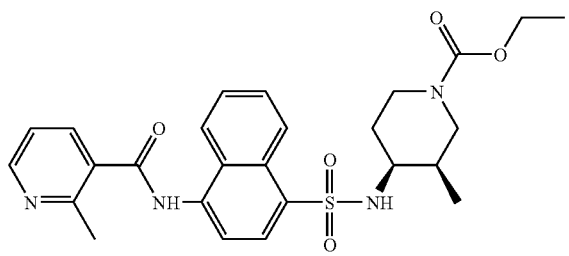

(±)-(cis)-3-Methyl-4-{4-[(2-methyl-pyridine-3-car-
bonyl)-amino]-naphthalene-1-sulfonylamino}-pip-
eridine-1-carboxylic acid ethyl ester (D-6)

The title compound was made following general procedure in Scheme 8, substituting (±)-(cis)-4-(4-amino-naphthalene-1-sulfonylamino)-3-methyl-piperidine-1-carboxylic acid ethyl ester (D-2) for (±)-(cis)-4-amino-naphthalene-1-sulfonic acid(1-butyryl-3-methyl-piperidin-4-yl)-amide (D-1). $^1$H NMR (300 MHz, MeOD) δ 8.83 (d, 1H), 8.56 (dd, 1H), 8.31 (d, 1H), 8.23 (d, 1H), 8.12 (d, 1H), 7.97 (d, 1H), 7.71 (m, 2H), 7.43 (dd, 1H), 4.03 (q, 2H), 3.48 (m, 1H), 3.28 (m, 4H), 2.75 (s, 3H), 1.68 (m, 1H), 1.40 (m, 1H), 1.29 (m, 1H), 1.18 (t, 3H), 0.64 (d, 3H); LC/MS m/z 512 (M+H)$^+$

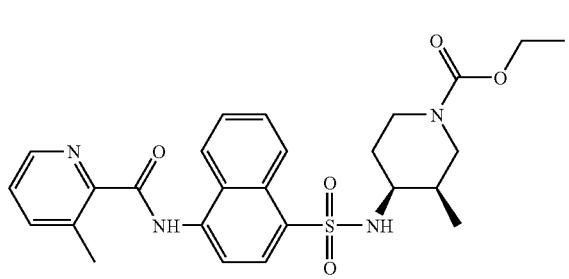

(±)-(cis)-3-Methyl-4-{4-[(3-methyl-pyridine-2-carbonyl)-amino]-naphthalene-1-sulfonylamino}-piperidine-1-carboxylic acid ethyl ester (D-7)

The title compound was made following general procedure in Scheme 8, substituting (±)-(cis)-4-(4-amino-naphthalene-1-sulfonylamino)-3-methyl-piperidine-1-carboxylic acid ethyl ester (D-2) for (±)-(cis)-4-amino-naphthalene-1-sulfonic acid(1-butyryl-3-methyl-piperidin-4-yl)-amide (D-1), and substituting 3-methyl-pyridine-2-carbonyl chloride for 2-methyl-nicotinoyl chloride. $^1$H NMR (300 MHz, MeOD) δ 8.82 (m, 1H), 8.56 (d, 1H), 8.28 (m, 1H), 8.18 (m, 1H), 7.74 (m, 3H), 7.59 (dd, 1H), 4.02 (q, 2H), 3.48 (m, 1H), 3.28 (m, 4H), 2.73 (s, 3H), 1.68 (m, 1H), 1.40 (m, 1H), 1.28 (m, 1H), 1.17 (t, 3H), 0.63 (d, 3H); LC/MS m/z 512 (M+H)$^+$

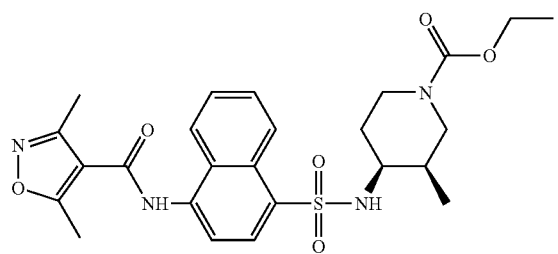

(±)-(cis)-4-{4-[(3,5-Dimethyl-isoxazole-4-carbonyl)-amino]-naphthalene-1-sulfonylamino}-3-methyl-piperidine-1-carboxylic acid ethyl ester (D-8)

The title compound was made following general procedure in Scheme 8, substituting (±)-(cis)-4-(4-amino-naphthalene-1-sulfonylamino)-3-methyl-piperidine-1-carboxylic acid ethyl ester (D-2) for (±)-(cis)-4-amino-naphthalene-1-sulfonic acid(1-butyryl-3-methyl-piperidin-4-yl)-amide (D-1) and substituting 3,5-dimethyl-isoxazole-4-carbonyl chloride for 2-methyl-nicotinoyl chloride. $^1$H NMR (300 MHz, MeOD) δ 8.82 (d, 1H), 8.27 (d, 1H), 8.18 (d, 1H), 7.93 (d, 1H), 7.71 (m, 2H), 4.03 (q, 2H), 3.30 (m, 5H), 2.70 (s, 3H), 2.47 (s, 3H), 1.68 (m, 1H), 1.40 (m, 1H), 1.28 (m, 1H), 1.18 (t, 3H), 0.64 (d, 3H); LC/MS m/z 516 (M+H)$^+$

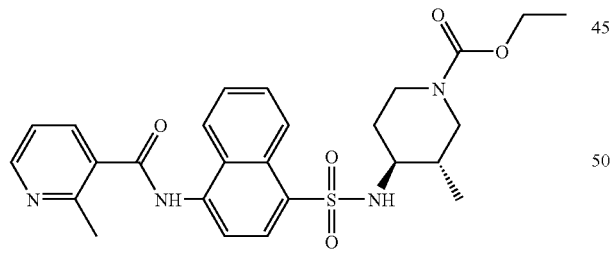

(±)-(trans)-3-Methyl-4-{4-[(2-methyl-pyridine-3-carbonyl)-amino]-naphthalene-1-sulfonylamino}-piperidine-1-carboxylic acid ethyl ester (D-9)

The title compound was made following general procedure in Scheme 8, substituting (±)-(trans)-4-(4-amino-naphthalene-1-sulfonylamino)-3-methyl-piperidine-1-carboxylic acid ethyl ester for (±)-(cis)-4-amino-naphthalene-1-sulfonic acid(1-butyryl-3-methyl-piperidin-4-yl)-amide (D-1). $^1$H NMR (300 MHz, MeOD) δ 8.78 (d, 1H), 8.58 (dd, 1H), 8.32 (d, 1H), 8.23 (d, 1H), 8.12 (d, 1H), 7.98 (d, 1H), 7.72 (m, 2H), 7.44 (dd, 1H), 4.04 (q, 2H), 3.88 (m, 2H), 3.28 (m, 1H), 2.82 (m, 1H), 2.75 (s, 3H), 2.65 (m, 1H), 2.38 (s, br, 1H), 1.40 (m, 2H), 1.18 (t, 3H), 0.57 (d, 3H); LC/MS m/z 512 (M+H)$^+$

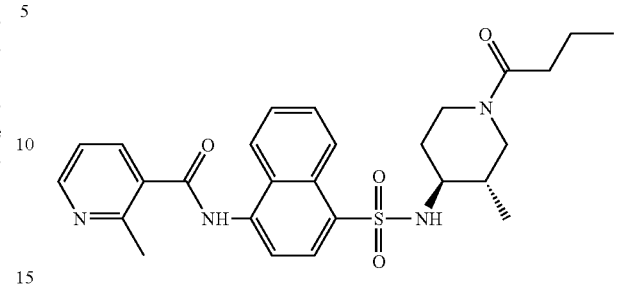

(±)-(trans)-N-[4-(1-Butyryl-3-methyl-piperidin-4-ylsulfamoyl)-naphthalen-1-yl]-2-methyl-nicotinamide (D-10)

The title compound was made following general procedure in Scheme 8, substituting (±)-(trans)-4-amino-naphthalene-1-sulfonic acid(1-butyryl-3-methyl-piperidin-4-yl)-amide for (±)-(cis)-4-amino-naphthalene-1-sulfonic acid(1-butyryl-3-methyl-piperidin-4-yl)-amide (D-1). $^1$H NMR (300 MHz, MeOD) δ 8.78 (d, 1H), 8.57 (dd, 1H), 8.31 (d, 1H), 8.23 (d, 1H), 8.12 (d, 1H), 7.98 (d, 1H), 7.72 (m, 2H), 7.42 (dd, 1H), 4.28 (t, 1H), 3.72 (m, 1H), 2.90 (m, 1H), 2.74 (s, 3H), 2.56 (m, 1H), 2.23 (m, 3H), 1.53 (m, 3H), 1.28 (m, 2H), 0.89 (m, 3H), 0.61 (dd, 3H); LC/MS m/z 510 (M+H)$^+$ Scheme 9

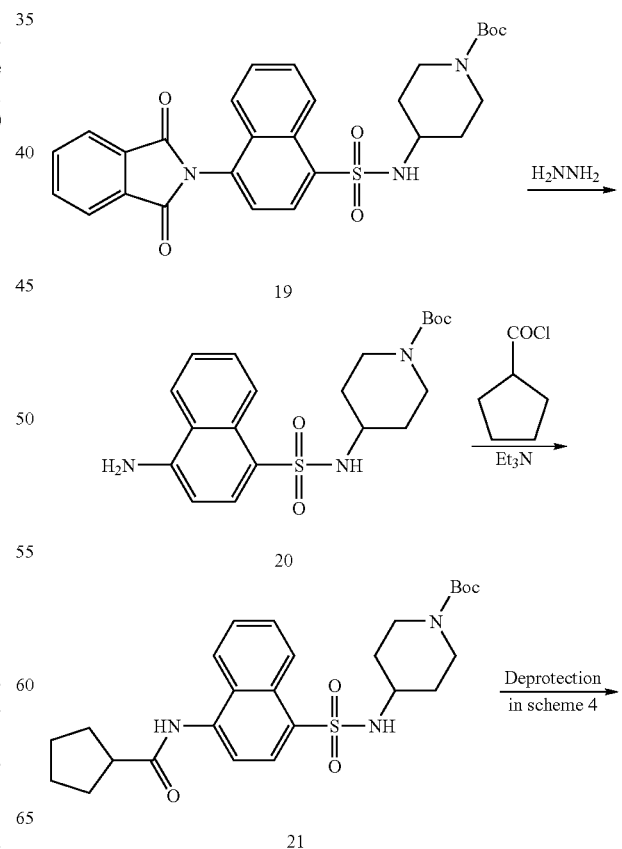

-continued

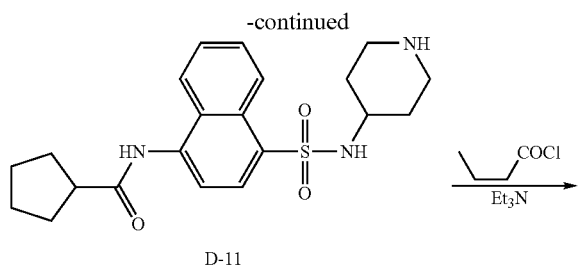

D-11

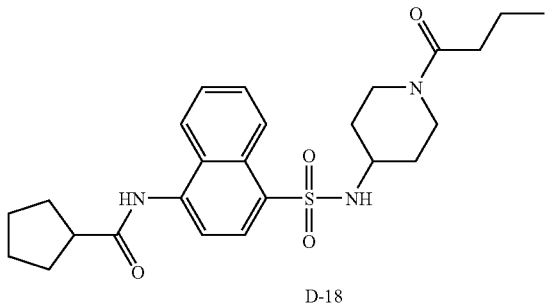

D-18

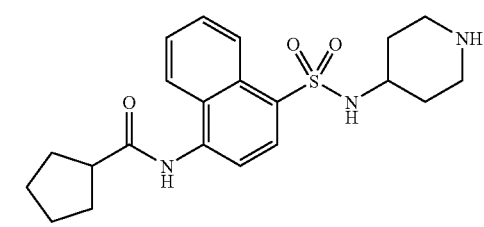

Cyclopentanecarboxylic acid [4-(piperidin-4-ylsulfamoyl)-naphthalen-1-yl]-amide (D-11)

4-[4-(1,3-Dioxo-1,3-dihydro-isoindol-2-yl)-naphthalene-1-sulfonylamino]-piperidine-1-carboxylic acid tert-butyl ester (19) was prepared according to the general procedure in Scheme 3, substituting 4-amino-piperidine-1-carboxylic acid tert-butyl ester for p-anisidine.

4-(4-Amino-naphthalene-1-sulfonylamino)-piperidine-1-carboxylic acid tert-butyl ester (20) was prepared according to the general procedure in Scheme 3 substituting 4-[4-(1,3-dioxo-1,3-dihydro-isoindol-2-yl)-naphthalene-1-sulfonylamino]-piperidine-1-carboxylic acid tert-butyl ester for 4-(1,3-dioxo-1,3-dihydro-isoindol-2-yl)-naphthalene-1-sulfonic acid(4-methoxyphenyl)-amide.

4-[4-(Cyclopentanecarbonyl-amino)-naphthalene-1-sulfonylamino]-piperidine-1-carboxylic acid tert-butyl ester (21) was prepared according to the general procedure in Scheme 3, substituting cyclopentanecarbonyl chloride for acetyl chloride.

The title compound (D-11) was prepared according to Scheme 9 by following the general deprotection strategy in Scheme 4-1. $^1$H NMR (300 MHz, DMSO) δ 10.15 (s, 1H), 8.66 (m, 1H), 8.58 (m, 1H), 8.41 (m, 1H), 8.26 (m, 2H), 8.12 (d, 1H), 7.94 (d, 1H), 7.71 (m, 2H), 3.11 (m, 3H), 2.82 (m, 2H), 1.94 (m, 2H), 1.86-1.40 (m, 10H). LC/MS m/z 400 (M–H)$^-$, 402 (M+H)$^+$

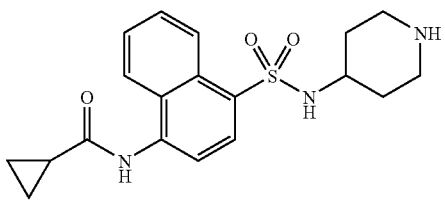

Cyclopropanecarboxylic acid [4-(piperidin-4-ylsulfamoyl)-naphthalen-1-yl]-amide (D-12)

The title compound was made following the general procedure in Scheme 9, substituting cyclopropanecarbonyl chloride for cyclopentanecarbonyl chloride. $^1$H NMR (300 MHz, DMSO) δ 10.49 (s, 1H), 8.67 (m, 1H), 8.54 (m, 1H), 8.39 (m, 1H), 8.26 (d, 1H), 8.11 (d, 1H), 8.01 (d, 1H), 7.73 (m, 2H), 3.56 (s, 1H), 3.05 (m, 2H), 2.79 (m, 2H), 2.19 (m, 1H), 1.60 (m, 2H), 1.50 (m, 2H), 0.87 (d, 4H). LC/MS m/z 372 (M–H)$^-$, 374 (M+H)$^+$

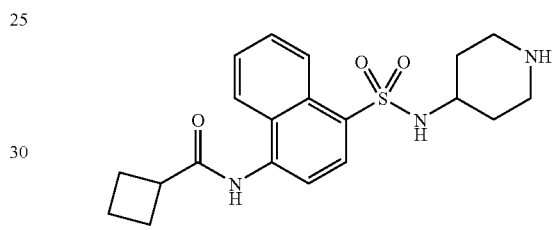

Cyclobutanecarboxylic acid [4-(piperidin-4-ylsulfamoyl)-naphthalen-1-yl]-amide (D-13)

The title compound was made following the general procedure in Scheme 9, substituting cyclobutanecarbonyl chloride for cyclopentanecarbonyl chloride. $^1$H NMR (300 MHz, DMSO) δ 9.98 (s, 1H), 8.62 (d, 1H), 8.21 (d, 1H), 8.12 (d, 1H), 7.99 (d, 1H), 7.95 (d, 1H), 7.70 (m, 2H), 3.59 (d, 2H), 3.51 (t, 1H), 3.13 (m, 1H), 2.67 (m, 2H), 2.32-2.16 (m, 4H), 1.99 (m, 1H), 1.84 (m, 1H), 1.37 (d, 2H), 1.10 (m, 2H). LC/MS m/z 386 (M–H)$^-$, 388 (M+H)$^+$

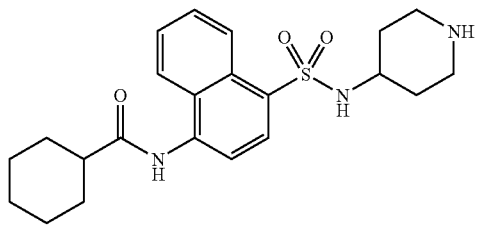

Cyclohexanecarboxylic acid [4-(piperidin-4-ylsulfamoyl)-naphthalen-1-yl]-amide (D-14)

The title compound was made following the general procedure in Scheme 9, substituting cyclohexanecarbonyl chloride for cyclopentanecarbonyl chloride. $^1$H NMR (300 MHz, DMSO) δ 10.07 (s, 1H), 8.64 (dd, 1H), 8.25 (m, 4 H), 8.12 (d, 1H), 7.96 (d, 1H), 7.72 (m, 2H), 3.06 (m, 2H), 2.81

(m, 2H), 2.66 (m, 2H), 1.91 (d, 2H), 1.78 (d, 2H), 1.61 (m, 3H), 1.49 (m, 4H), 1.31 (m, 2H). LC/MS m/z 415 (M−H)−, 417 (M+H)+

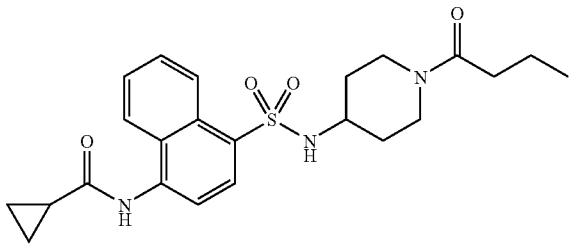

Cyclopropanecarboxylic acid [4-(1-butyryl-piperidin-4-ylsulfamoyl)-naphthalen-1-yl]-amide (D-15)

The title compound was made following the general procedure in Scheme 9, substituting cyclopropanecarbonyl chloride for cyclopentanecarbonyl chloride. $^1$H NMR (300 MHz, DMSO) δ 10.43 (s, 1H), 8.64 (m, 1H), 8.33 (m, 1H), 8.13 (m, 1H), 8.02 (d, 1H), 7.97 (m, 2H), 3.98 (d, 1H), 3.59 (m, 1H), 3.19 (m, 1H), 2.90 (t, 1H), 2.61 (m, 1H), 2.13 (m, 3H), 1.40 (m, 4H), 1.16 (m, 2H), 0.84 (d, 4H), 0.80 (t, 3H). LC/MS m/z 442 (M−H)−, 444 (M+H)+

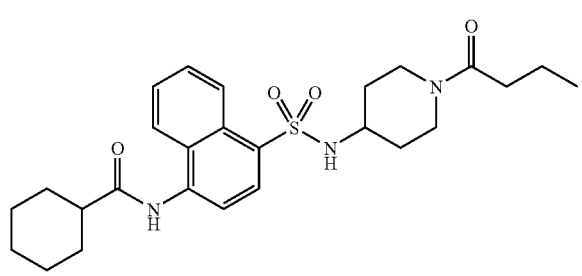

Cyclohexanecarboxylic acid [4-(1-butyryl-piperidin-4-ylsulfamoyl)-naphthalen-1-yl]-amide (D-16)

The title compound was made following the general procedure in Scheme 9, substituting cyclohexanecarbonyl chloride for cyclopentanecarbonyl chloride. $^1$H NMR (300 MHz, DMSO) δ 10.05 (s, 1H), 8.64 (dd, 1H), 8.25 (dd, 1H), 8.13 (d, 1H), 8.03 (d, 1H), 7.91 (d, 1H), 7.71 (m, 2H), 3.98 (d, 1H), 3.59 (d, 1H), 3.18 (m, 1H), 2.91 (t, 1H), 2.61 (t, 1H), 2.16 (t, 2H), 1.90 (d, 2H), 1.77 (m, 2H), 1.67 (m, 2H), 1.49-1.20 (m, 9H), 0.81 (t, 3H). LC/MS m/z 529 (M−H)−, 531 (M+H)+

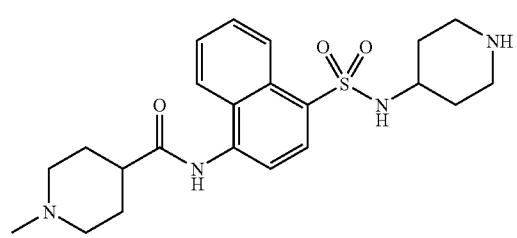

1-Methyl-piperidine-4-carboxylic acid [4-(piperidin-4-ylsulfamoyl)-naphthalen-1-yl]-amide (D-17)

The title compound was made following general procedure in Scheme 9, substituting 1-methyl-piperidine-4-carbonyl chloride (prepared in situ from the corresponding acid using oxalyl chloride) for cyclopentanecarbonyl chloride. $^1$H NMR (300 MHz, DMSO) δ 10.39 (s, 1H), 8.64 (dd, 1H), 8.29 (dd, 1H), 8.14 (d, 1H), 8.05 (d, 1H), 7.89 (d, 1H), 7.72 (m, 2H), 3.62 (d, 2H), 3.40 (m, 2H), 3.15 (m, 1H), 2.95 (m, 2H), 2.78-2.67 (m, 6H), 2.09 (m, 2H), 2.00 (m, 2H), 1.84 (m, 1H), 1.39 (m, 1H), 1.18 (m, 2H). LC/MS m/z 384 (M−H)−, 386 (M+H)+

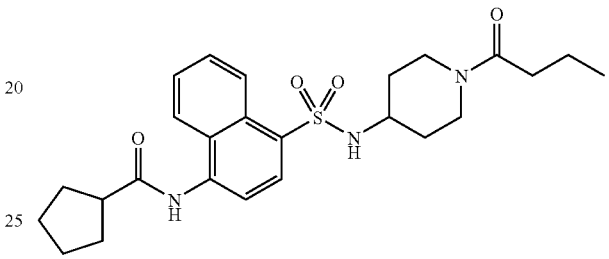

Cyclopentanecarboxylic acid [4-(1-butyryl-piperidin-4-ylsulfamoyl)-naphthalen-1-yl]-amide (D-18)

The title compound was made following the general procedure in Scheme 9. $^1$H NMR (300 MHz, DMSO) δ 10.12 (s, 1H), 8.66 (m, 1H), 8.28 (m, 1H), 8.13 (d, 1H), 7.95 (d, 1H), 7.71 (m, 2H), 3.98 (d, 1H), 3.59 (d, 1H), 3.19 (m, 1H), 3.09 (m, 1H), 2.90 (m, 1H), 2.57 (m, 1H), 2.16 (t, 2H), 1.94 (m, 2H), 1.81 (m, 2H), 1.71 (m, 2H), 1.62 (m, 2H), 1.42 (m, 4H), 1.16 (m, 2H), 0.81 (t, 3H). LC/MS m/z 471 (M−H)−, 473 (M+H)+

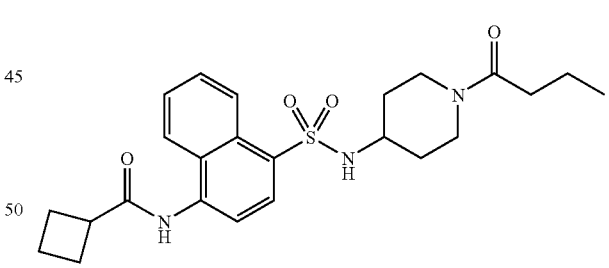

Cyclobutanecarboxylic acid [4-(1-butyryl-piperidin-4-ylsulfamoyl)-naphthalen-1-yl]-amide (D-19)

The title compound was made following the general procedure in Scheme 9, substituting cyclobutanecarbonyl chloride for cyclopentanecarbonyl chloride. $^1$H NMR (300 MHz, DMSO) δ 9.98 (s, 1H), 8.62 (d, 1H), 8.21 (d, 1H), 8.12 (d, 1H), 7.99 (d, 1H), 7.95 (d, 1H), 7.70 (m, 2H), 3.59 (d, 2H), 3.51 (t, 1H), 3.13 (m, 1H), 2.67 (m, 2H), 2.32-2.16 (m, 4H), 2.16 (t, 2H), 1.99 (m, 1H), 1.84 (m, 1H), 1.42 (m, 2H), 1.37 (d, 2H), 1.10 (m, 2H), 0.81 (t, 3H). LC/MS m/z 457 (M−H)−, 459 (M+H)+

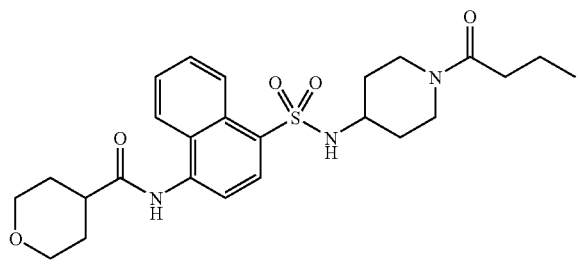

Tetrahydro-pyran-4-carboxylic acid [4-(1-butyryl-piperidin-4-ylsulfamoyl)-naphthalen-1-yl]-amide (D-20)

The title compound was made following the general procedure in Scheme 9, substituting tetrahydro-pyran-4-carbonyl chloride (prepared in situ from the corresponding acid using oxalyl chloride) for cyclopentanecarbonyl chloride. LC/MS m/z 488 (M+H)$^+$

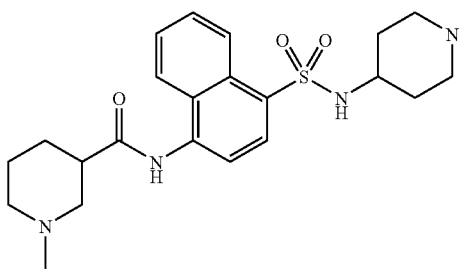

1-Methyl-piperidine-3-carboxylic acid [4-(piperidin-4-ylsulfamoyl)-naphthalen-1-yl]-amide (D-22)

The title compound was made following the general procedure in Scheme 9, substituting 1-methyl-piperidine-3-carbonyl chloride (prepared in situ from the corresponding acid using oxalyl chloride) for cyclopentanecarbonyl chloride. LC/MS m/z 431 (M+H)$^+$.

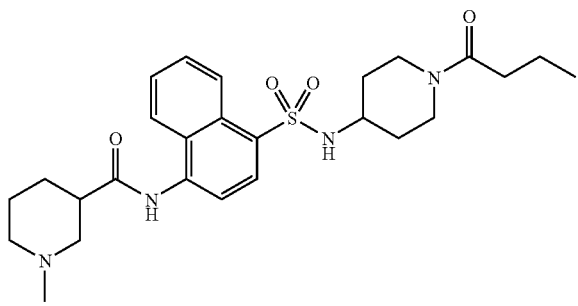

1-Methyl-piperidine-3-carboxylic acid [4-(1-butyryl-piperidin-4-ylsulfamoyl)-naphthalen-1-yl]-amide (D-23)

The title compound was made following the general procedure in Scheme 9, substituting 1-methyl-piperidine-3-carbonyl chloride (prepared in situ from the corresponding acid using oxalyl chloride) for cyclopentanecarbonyl chloride. LC/MS m/z 501 (M+H)$^+$.

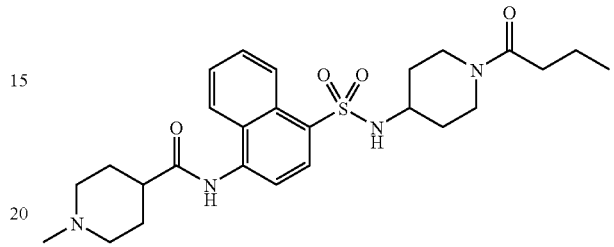

1-Methyl-piperidine-4-carboxylic acid [4-(1-butyryl-piperidin-4-ylsulfamoyl)-naphthalen-1-yl]-amide (D-24)

The title compound was made following the general procedure in Scheme 9, substituting 1-methyl-piperidine-4-carbonyl chloride (prepared in situ from the corresponding acid using oxalyl chloride) for cyclopentanecarbonyl chloride. $^1$H NMR (300 MHz, DMSO) δ 10.39 (s, 1H), 8.64 (dd, 1H), 8.29 (dd, 1H), 8.14 (d, 1H), 8.05 (d, 1H), 7.891 (d, 1H), 7.72 (m, 2H), 3.62 (d, 2H), 3.40 (m, 2H), 3.15 (m, 1H), 2.95 (m, 2H), 2.78-2.67 (m, 6H), 2.17 (t, 2H), 2.09 (m, 2H), 2.0 (m, 2H), 1.84 (m, 1H), 1.43 (m, 2H), 1.39 (m, 1H), 1.18 (m, 2H), 0.82 (t, 3H). LC/MS m/z 501 (M+H)$^+$

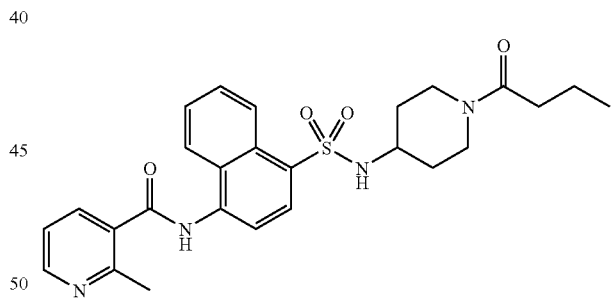

N-[4-(1-Butyryl-piperidin-4-ylsulfamoyl)-naphthalen-1-yl-2-methyl-nicotinamide (D-25)

The title compound was prepared following the general procedure in Scheme 5, beginning with 4-[(2-methyl-pyridine-3-carbonyl)-amino]-naphthalene-1-sulfonyl chloride, and substituting butyryl chloride and triethylamine for 2-isocyanato-propane. $^1$H NMR (300 MHz, DMSO) δ 10.76 (s, 1H), 8.68 (d, 1H), 8.59 (d, 1H), 8.31 (d, 1H), 8.24 (d, 1H), 8.10 (d, 1H), 8.04 (d, 1H), 7.98 (d, 1H), 7.73 (m, 2H), 7.41 (m, 1H), 4.00 (d, 1H), 3.61 (d, 1H), 3.23 (m, 1H), 2.93 (t, 1H), 2.66 (s, 3H), 2.59 (m, 1H), 2.17 (t, 2H), 1.48 (m, 2H), 1.43 (m, 2H), 1.19 (m, 2H), 0.82 (m, 2H). LC/MS m/z 494 (M−H)$^-$, 496 (M+H)$^+$

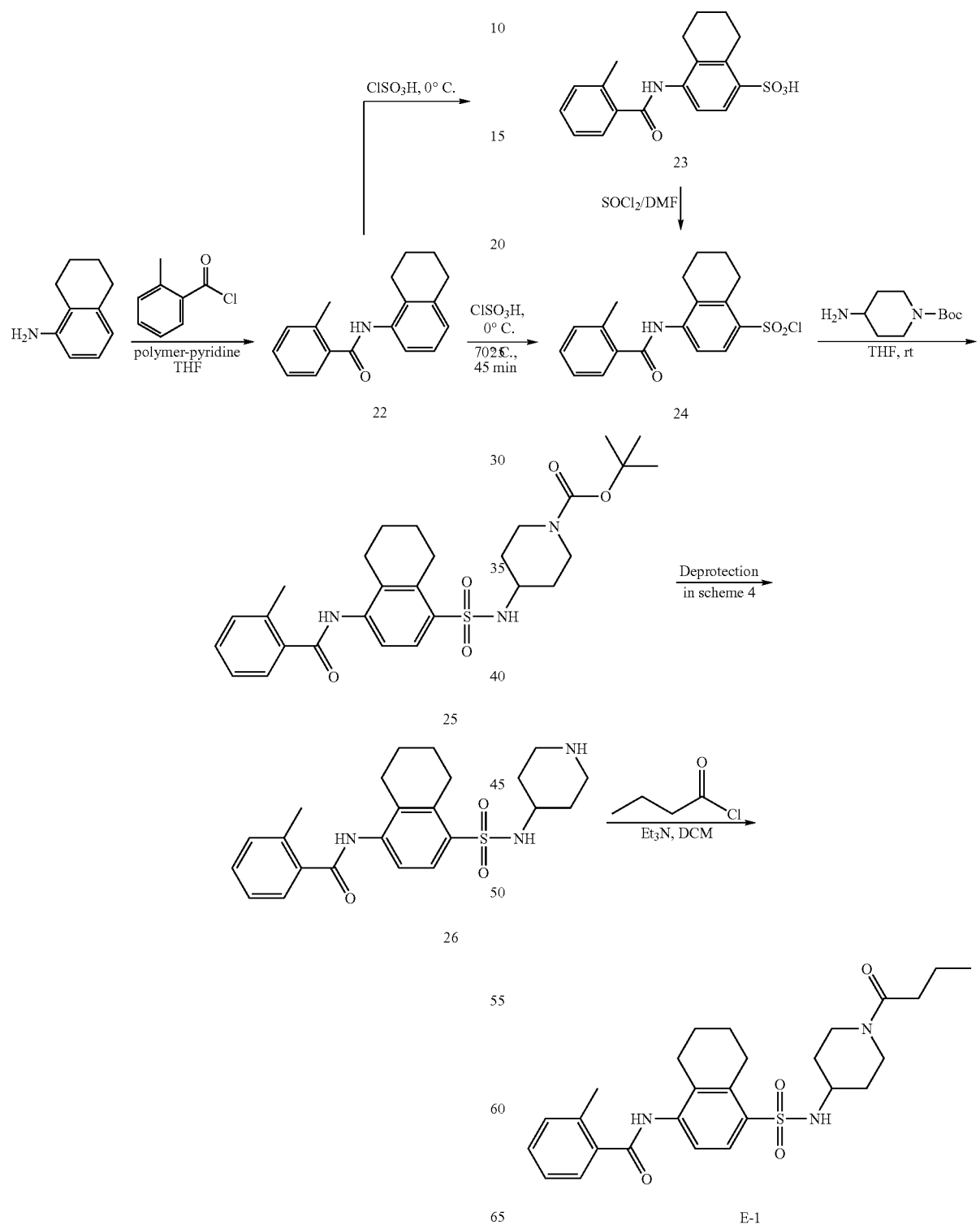

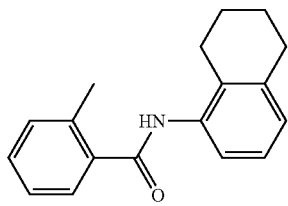

2-Methyl-N-(5,6,7,8-tetrahydro-naphthalen-1-yl)-benzamide (22)

To a 25° C. solution of aniline (1 eq) in anhydrous THF (2 mL per mmol aniline), was added polymer bound pyridine (1.5 eq) followed by acid chloride (1 eq). The mixture was stirred at 25° C. for 12-24 h. The reaction mixture was filtered and the filtrate concentrated in vacuo. Hexane or MeOH was added to the residue and the resulting precipitate was collected by filtration, resulting in a white solid (yield 65%). LC/MS (M+H)⁺ m/z 266. The crude material was used without further purification.

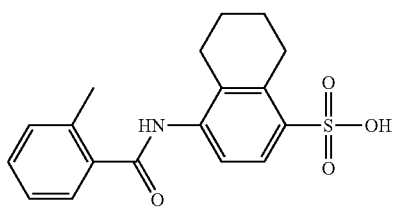

4-(2-Methyl-benzoylamino)-5,6,7,8-tetrahydro-naphthalene-1-sulfonic acid (23)

To a 0° C. solution of amide (22) in TFA (1 mL per mmol amide), was added chlorosulfonic acid (2 eq) dropwise under nitrogen atmosphere. The temperature was allowed to warm to 25° C. and stirred for 72 hours. The reaction mixture was quenched by pouring into ice water. The desired product was collected via precipitation from either water/methanol, or ethyl acetate/methanol solution, resulting in a white solid (yield 68%). LC/MS (M+H)⁺ m/z 346, (M−H)⁻ m/z 344. The crude material was used without further purification.

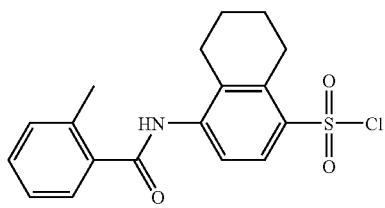

4-(2-Methyl-benzoylamino)-5,6,7,8-tetrahydro-naphthalene-1-sulfonyl chloride (24)

Method A: To a 0° C. solution of sulfonic acid (23) in DMF (1 mL per mmol acid), was added thionyl chloride (1.1 eq.) dropwise under nitrogen atmosphere. The temperature was allowed to warm to 25° C. and stirred for 18 hours. The reaction mixture was quenched by pouring into ice water and filtered to give the title compound as a white solid.

Method B: To neat amide (22), at 0° C., was added chlorosulfonic acid (5 eq) dropwise. The temperature was allowed to warm to 25° C. and then heated at 70° C. for 45 minutes. After cooling to 25° C., the reaction mixture was poured into ice water, and the resultant precipitate was collected by filtration to give the title sulfonyl chloride as a white solid. The product was used without further purification.

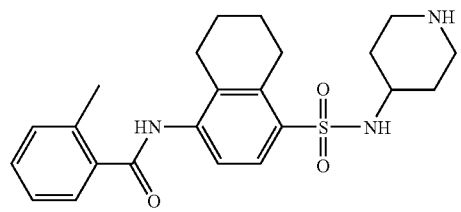

2-Methyl-N-[4-(piperidin-4-ylsulfamoyl)-5,6,7,8-tetrahydro-naphthalen-1-yl]-benzamide (26)

To a 25° C. solution of sulfonyl chloride (24) (1.61 g, 4 mmol) in THF (60 mL) was added 4-amino-piperidine-1-carboxylic acid tert-butyl ester (880 mg, 4.4 mmol), and followed by triethyl amine (668 mg, 6.6 mmol). The resultant solution was stirred at 25° C. for 18 hours. The reaction mixture was filtered and the filtrate was concentrated in vacuo to afford 25. 4 N HCl/Dioxane was added and this mixture was stirred for 2 hours, followed by filtration to collect a light gray solid (1.7 g, yield 75%) as the HCl salt of the title compound. LC/MS (M+H)⁺ m/z 527.

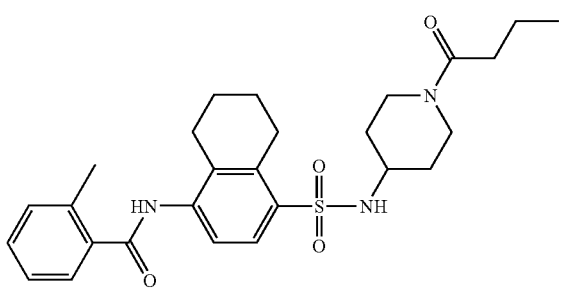

N-[4-(1-Butyryl-piperidin-4-ylsulfamoyl)-5,6,7,8-tetrahydro-naphthalen-1-yl]-2-methyl-benzamide (E-1)

To a 25° C. mixture of sulfonamide (26) (134 mg, 0.29 mmol) in THF (10 mL) was added butyryl chloride (77 mg, 0.725 mmol) and triethylamine (367 mg, 3.625 mmol). The mixture was stirred for 18 hours, followed by filtration to remove the precipitate. The filtrate was concentrated in vacuo and purified via chromatography, resulting in the title compound as white solid (50 mg). ¹H NMR (300 MHz, MeOD) δ 7.91 (d, 1H), 7.55 (m, 2H), 7.41 (m, 1H), 7.31 (m, 2H), 4.30 (m, 1H), 3.89 (m, 1H), 3.21 (m, 2H), 3.09 (m, 1H), 2.85 (m, 2H), 2.61 (m, 1H), 2.55 (s, 3H), 2.34 (t, 2H), 1.88 (m, 7H), 1.62 (m, 2H), 1.39 (m, 2H), 0.95 (t, 3H) ); LC/MS (M +H)⁺ m/z 498.

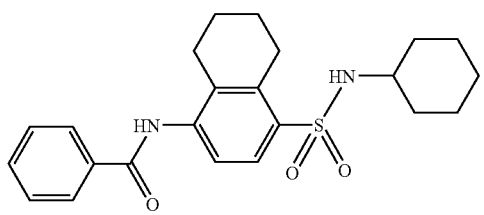

N-(4-Cyclohexylsulfamoyl-5,6,7,8-tetrahydro-naph-thalen-1-yl)-benzamide (E-2)

The title compound was made following general procedure in Scheme 10, substituting benzoyl chloride for 2-methyl-benzoyl chloride, and cyclohexylamine for 4-amino-piperidine-1-carboxylic acid tert-butyl ester. $^1$H NMR (300 MHz, CDCl$_3$) δ 8.19 (d, 1H), 7.95 (d, 1H), 7.89 (m, 2H), 7.82 (br s, 1H, NH), 7.53 (m, 3H), 3.90 (m, 1H), 3.20 (t, 2H), 2.72 (t, 2H), 1.52 (m, 14H); LC/MS (M+H)$^+$ m/z 413.

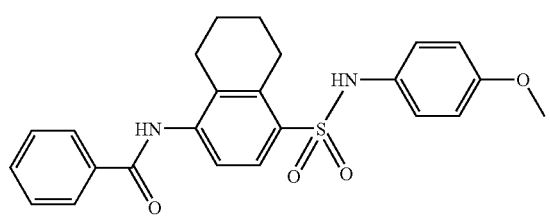

N-[4-(4-Methoxy-phenylsulfamoyl)-5,6,7,8-tetrahydro-naphthalen-1-yl]-benzamide (E-3)

The title compound was made following general procedure in Scheme 10, substituting benzoyl chloride for 2-methyl-benzoyl chloride, and 4-methoxy-phenylamine for 4-amino-piperidine-1-carboxylic acid tert-butyl ester. $^1$H NMR (300 MHz, CDCl$_3$) δ 8.10 (d, 1H), 7.84 (m, 4H), 7.55 (m, 3H), 6.96 (dd, 2H), 6.74 (dd, 2H), 6.64 (br s, 1H, N—H), 3.73 (s, 3H), 3.19 (t, 2H), 2.70 (t, 2H), 1.82 (m, 4H); LC/MS (M+H)$^+$ m/z 437.

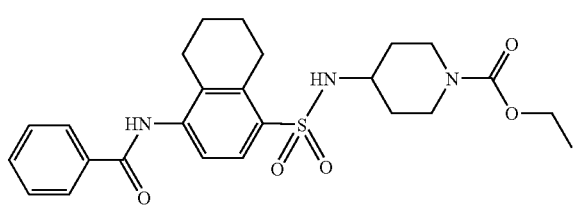

4-(4-Benzoylamino-5,6,7,8-tetrahydro-naphthalene-1-sulfonylamino)-piperidine-1-carboxylic acid ethyl ester (E-4)

The title compound was made following general procedure in Scheme 10, substituting benzoyl chloride for 2-methyl-benzoyl chloride, and ethyl chloroformate for butyryl chloride. $^1$H NMR (300 MHz, CDCl$_3$) δ 8.15 (d, 1H), 7.94 (d, 1H), 7.89 (m, 2H), 7.53 (m, 3H), 4.70 (m, 1H), 4.08 (q, 2H), 3.92 (m, 2H), 3.32 (m, 1H), 3.15 (m, 2H), 2.76 (m, 4H), 1.80 (m, 4H), 1.36 (m, 3H), 1.22 (t, 3H); LC/MS (M+H)$^+$ m/z 486.

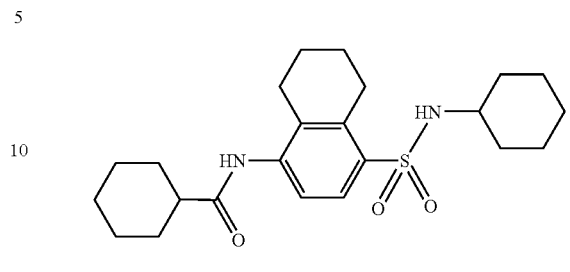

Cyclohexanecarboxylic acid (4-cyclohexylsulfamoyl-5,6,7,8-tetrahydro-naphthalen-1-yl)-amide (E-5)

The title compound was made following general procedure in Scheme 10, substituting cyclohexanecarbonyl chloride for 2-methyl-benzoyl chloride, and cyclohexylamine for 4-amino-piperidine-1-carboxylic acid tert-butyl ester. $^1$H NMR (300 MHz, CDCl$_3$) δ 8.00 (d, 1H), 7.84 (d, 1H), 4.24 (m, 1H), 3.11 (m, 3H), 2.57 (m, 2H), 2.22 (m, 1H), 2.02 (m, 2H), 1.79 (m, 9H), 1.66 (m, 3H), 1.17 (t, 9H); LC/MS (M+H)$^+$ m/z 419.

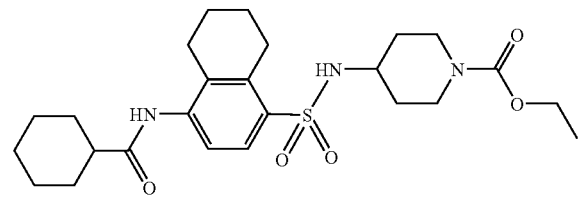

4-(4-(Cyclohexanecarbonyl-amino)-5,6,7,8-tetrahydro-naphthalene-1-sulfonylamino)-piperidine-1-carboxylic acid ethyl ester (E-6)

The title compound was made following general procedure in Scheme 10, substituting cyclohexanecarbonyl chloride for 2-methyl-benzoyl chloride, and ethyl chloroformate for butyryl chloride. $^1$H NMR (300 MHz, MeOD) δ 7.93 (d, 1H), 7.51 (d, 1H), 4.19 (q, 2H), 4.08 (m, 2H), 3.32 (m, 2H), 3.05 (m, 2H), 2.96 (m, 2H), 2.60 (m, 1H), 1.66 (m, 19H), 1.22 (t, 3H); LC/MS (M+H)$^+$ m/z 492.

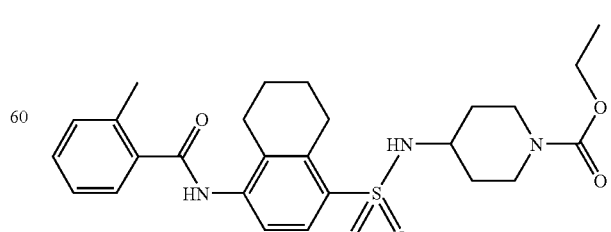

4-[4-(2-Methyl-benzoylamino)-5,6,7,8-tetrahydro-naphthalene-1-sulfonylamino]-piperidine-1-carboxylic acid ethyl ester (E-8)

The title compound was made following general procedure in Scheme 10, substituting ethyl chloroformate for butyryl chloride. $^1$H NMR (300 MHz, MeOD) δ 7.89 (d, 1H), 7.55 (m, 2H), 7.39 (m, 1H), 7.29 (m, 2H), 4.22 (q, 2H), 3.92 (m, 2H), 3.21 (m, 3H), 2.81 (m, 4H), 2.49(s, 3H), 1.81 (m, 4H), 1.70(m, 2H), 1.39 (m, 2H), 1.21 (t, 3H); LC/MS (M+H)$^+$ m/z 500.

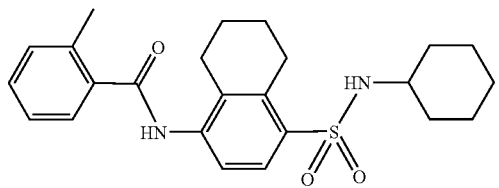

N-(4-Cyclohexylsulfamoyl-5,6,7,8-tetrahydro-naphthalen-1-yl)-2-methyl-benzamide (E-9)

The title compound was made following general procedure in Scheme 10, substituting cyclohexylamine for 4-amino-piperidine-1-carboxylic acid tert-butyl ester. $^1$H NMR (300 MHz, MeOD) δ 7.92 (d, 1H), 7.57 (m, 2H), 7.43 (m, 1H), 7.34 (m, 2H), 3.25 (m, 2H), 3.03 (m, 1H), 2.88 (m, 2H), 2.45 (s, 3H), 1.88 (m, 4H), 1.78 (m, 5H), 1.22 (m, 5H); LC/MS (M+H)$^+$ m/z 427.

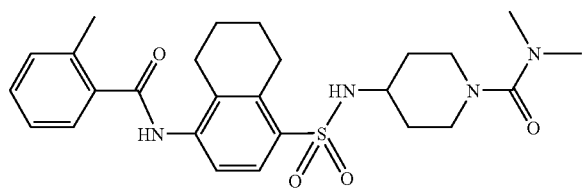

4-[4-(2-Methyl-benzoylamino)-5,6,7,8-tetrahydro-naphthalene-1-sulfonylamino]-piperidine-1-carboxylic acid dimethylamide (E-10)

The title compound was made following general procedure in Scheme 10, substituting dimethylcarbamyl chloride for butyryl chloride. $^1$H NMR (300 MHz, MeOD) δ 7.90 (d, 1H), 7.55 (m, 2H), 7.39 (m, 1H), 7.31 (m, 2H), 3.54 (m, 2H), 3.21 (m, 4H), 2.81 (m, 4H), 2.79 (s, 6H), 2.50 (s, 3H), 1.77(m, 3H), 1.71 (m, 2H), 1.45 (m, 2H)); LC/MS (M+H)$^+$ m/z 499.

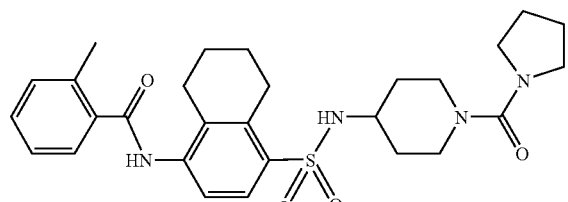

2-Methyl-N-{4-[1-(pyrrolidine-1-carbonyl)-piperidin-4-ylsulfamoyl]-5,6,7,8-tetrahydro-naphthalen-1-yl}-benzamide (E-11)

The title compound was made following general procedure in Scheme 10, substituting pyrrolidine-1-carbonyl chloride for butyryl chloride. $^1$H NMR (300 MHz, MeOD) δ 8.07 (d, 1H), 7.69 (m, 2H), 7.55 (m, 1H), 7.48 (m, 2H), 3.79 (m, 2H), 3.46 (m, 4H), 2.91 (m, 4H), 2.61 (s, 3H), 1.98 (m, 10H), 1.85 (m, 2H), 1.61 (m, 3H) ); LC/MS (M+H)$^+$ m/z 525.

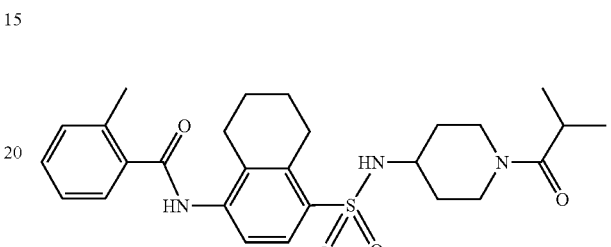

N-[4-(1-Isobutyryl-piperidin-4-ylsulfamoyl)-5,6,7,8-tetrahydro-naphthalen-1-yl]-2-methyl-benzamide (E-12)

The title compound was made following general procedure in Scheme 10, substituting isobutyryl chloride for butyryl chloride. $^1$H NMR (300 MHz, MeOD) δ 7.95 (d, 1H), 7.55 (m, 2H), 7.39 (m, 1H), 7.29 (m, 2H), 4.29 (m, 1H), 3.89 (m, 1H), 3.19 (m, 3H), 2.85 (m, 3H), 2.47 (s, 3H), 1.82 (m, 7H), 1.38 (m, 3H), 1.09 (m, 6H)); LC/MS (M+H)$^+$ m/z 498.

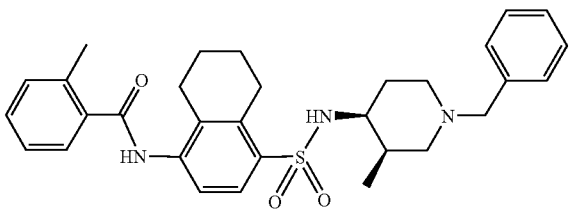

(±)-cis-N-[4-(1-Benzyl-3-methyl-piperidin-4-ylsulfamoyl)-5,6,7,8-tetrahydro-naphthalen-1-yl]-2-methyl-benzamide (E-13)

The title compound was made following general procedure in Scheme 10, substituting 1-benzyl-3-methyl-piperidin-4-ylamine for 4-amino-piperidine-1-carboxylic acid tert-butyl ester. $^1$H NMR (300 MHz, MeOD) δ 7.88 (d, 1H), 7.50 (m, 2H), 7.35 (m, 1H), 7.25 (m, 7H), 3.71 (m, 2H), 3.44 (m, 2H), 3.21 (m, 3H), 2.82 (s, 2H), 2.47 (s, 3H), 2.30 (m, 2H), 1.81 (m, 5H), 1.60 (m, 2H), 0.83 (d, 3H) ); LC/MS (M+H)$^+$ m/z 532.

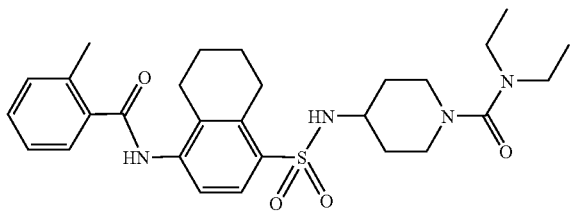

4-[4-(2-Methyl-benzoylamino)-5,6,7,8-tetrahydro-naphthalene-1-sulfonylamino]-piperidine-1-carboxylic acid diethylamide (E-14)

The title compound was made following general procedure in Scheme 10, substituting diethylcarbamyl chloride for butyryl chloride. $^1$H NMR (300 MHz, MeOD) δ 7.90 (d, 1H), 7.51 (m, 2H), 7.39 (m, 1H), 7.31 (m, 2H), 3.50 (m, 2H), 3.20 (m, 4H), 3.18 (q, 4H), 2.80 (m, 4H), 2.50 (s, 3H), 1.85 (m, 3H), 1.73 (m, 2H), 1.49 (m, 2H), 1.11 (t, 6H)); LC/MS (M+H)$^+$ m/z 527.

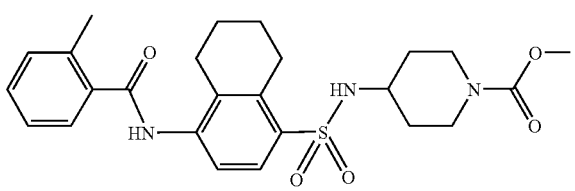

4-[4-(2-Methyl-benzoylamino)-5,6,7,8-tetrahydro-naphthalene-1-sulfonylamino]-piperidine-1-carboxylic acid methyl ester (E-15)

The title compound was made following general procedure in Scheme 10, substituting methyl chlorofomate for butyryl chloride. $^1$H NMR (300 MHz, MeOD) δ 7.90 (d, 1H), 7.55 (m, 2H), 7.39 (m, 1H), 7.31 (m, 2H), 3.92 (m, 2H), 3.63 (s, 3H), 3.20 (m, 4H), 2.85 (m, 4H), 2.50 (s, 3H), 1.85 (m, 3H), 1.72 (m, 2H), 1.41 (m, 2H); LC/MS (M+H)$^+$ m/z 486.

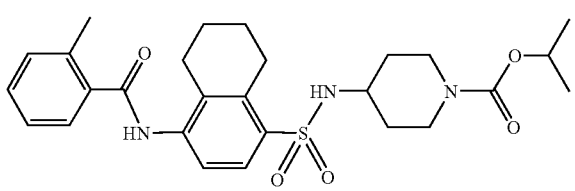

4-[4-(2-Methyl-benzoylamino)-5,6,7,8-tetrahydro-naphthalene-1-sulfonylamino]-piperidine-1-carboxylic acid isopropyl ester (E-16)

The title compound was made following general procedure in Scheme 10, substituting isopropyl chlorofomate chloride for butyryl chloride. $^1$H NMR (300 MHz, MeOD) δ 7.91 (d, 1H), 7.56 (m, 2H), 7.40 (m, 1H), 7.31 (m, 2H), 3.92 (m, 2H), 3.26 (m, 1H), 3.21 (m, 4H), 2.83 (m, 4H), 2.50 (s, 3H), 1.85 (m, 3H), 1.72 (m, 2H), 1.39 (m, 2H), 1.20 (d, 6H) ); LC/MS (M+H)$^+$ m/z 514.

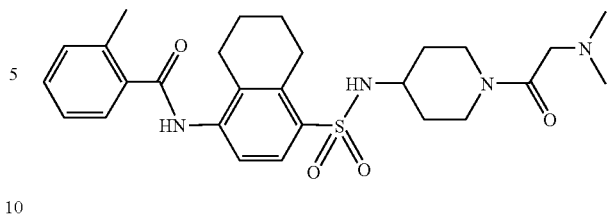

N-{4-[1-(2-Dimethylamino-acetyl)-piperidin-4-yl-sulfamoyl]-5,6,7,8-tetrahydro-naphthalen-1-yl}-2-methyl-benzamide (E-17)

The title compound was made following general procedure in Scheme 10, substituting dimethylamino-acetyl chloride for butyryl chloride. $^1$H NMR (300 MHz, MeOD) δ 7.91 (d, 1H), 7.56 (m, 2H), 7.40 (m, 1H), 7.31 (m, 2H), 4.28 (m, 1H), 3.93 (d, 2H), 3.66 (m, 1H), 3.25 (m, 4H), 2.80 (m, 4H), 2.72 (s, 6H), 2.51 (s, 3H), 1.85 (m, 5H), 1.45 (m, 2H) ); LC/MS (M+H)$^+$ m/z 513.

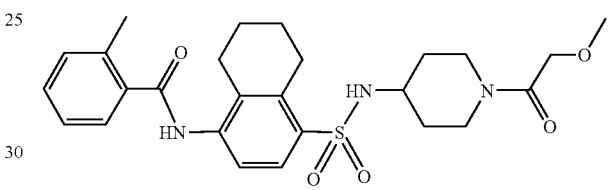

N-{4-[1-(2-Methoxy-acetyl)-piperidin-4-ylsulfamoyl]-5,6,7,8-tetrahydro-naphthalen-1-yl}-2-methyl-benzamide (E-18)

The title compound was made following general procedure in Scheme 10, substituting methoxy-acetyl chloride for butyryl chloride. $^1$H NMR (300 MHz, MeOD) δ 7.92 (d, 1H), 7.56 (m, 2H), 7.41 (m, 1H), 7.35 (m, 2H), 4.25 (m, 1H), 4.12 (d, 2H), 3.73 (m, 1H), 3.36 (s, 3H), 3.26 (m, 4H), 3.02 (m, 1H), 2.80 (m, 3H), 2.49 (s, 3H), 1.84 (m, 5H), 1.40 (m, 2H)); LC/MS (M+H)$^+$ m/z 500.

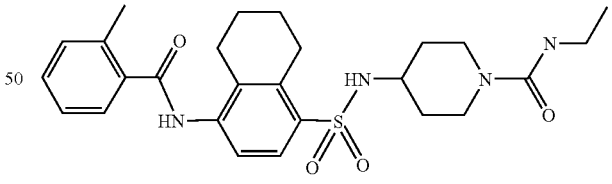

4-[4-(2-Methyl-benzoylamino)-5,6,7,8-tetrahydro-naphthalene-1-sulfonylamino]-piperidine-1-carboxylic acid ethylamide (E-19)

The title compound was made following general procedure in Scheme 10, substituting isocyanato-ethane for butyryl chloride. $^1$H NMR (300 MHz, MeOD) δ 7.90 (d, 1H), 7.55 (m, 2H), 7.41 (m, 1H), 7.31 (m, 2H), 3.83 (m, 2H), 3.24 (m, 4H), 3.14 (q, 2H), 2.79 (m, 4H), 2.50 (s, 3H), 1.84 (m, 3H), 1.70 (m, 2H), 1.38 (m, 2H), 1.07 (t, 3H)); LC/MS (M+H)$^+$ m/z 499.

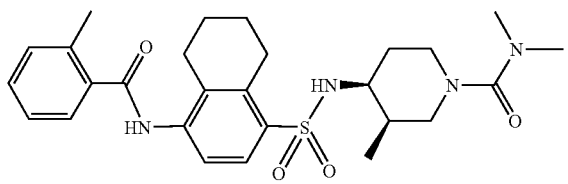

(±)-cis-3-Methyl-4-[4-(2-methyl-benzoylamino)-5,6,
7,8-tetrahydro-naphthalene-1-sulfonylamino]-piperidine-1-carboxylic acid dimethylamide (E-20)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. $^1$H NMR (300 MHz, MeOD) δ 7.91 (d, 1H), 7.55 (m, 2H), 7.39 (m, 1H), 7.31 (m, 2H), 3.36 (m, 2H), 3.22 (m, 2H), 3.10 (m, 3H), 2.82 (m, 2H), 2.80 (s, 6H), 2.49 (s, 3H), 1.85 (m, 5H), 1.65 (m, 1H), 1.51 (m, 1H), 0.82 (d, 3H) ); LC/MS (M+H)$^+$ m/z 513.

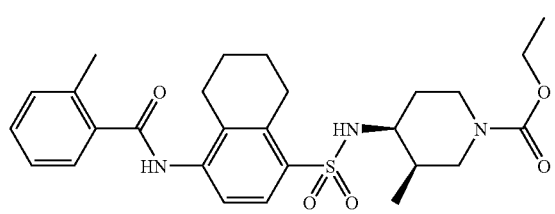

(±)-cis-3-Methyl-4-[4-(2-methyl-benzoylamino)-5,6,
7,8-tetrahydro-naphthalene-1-sulfonylamino]-piperidine-1-carboxylic acid ethyl ester (E-21)

The title compound was made following general procedure in Scheme 10, substituting 1-benzyl-3-methyl-piperidin-4-ylamine for 4-amino-piperidine-1-carboxylic acid tert-butyl ester, and ethyl chlorofomate for butyryl chloride. $^1$H NMR (300 MHz, MeOD) δ 7.92 (d, 1H), 7.58 (m, 2H), 7.41 (m, 1H), 7.35 (m, 2H), 4.12 (q, 2H), 3.71 (m, 1H), 3.29 (m, 6H), 2.88 (m, 2H), 2.52 (s, 3H), 1.88 (m, 5H), 1.62 (m, 1H), 1.51 (m, 1H), 1.25 (t, 3H), 0.89 (d, 3H) ); LC/MS (M+H)$^+$ m/z 514.

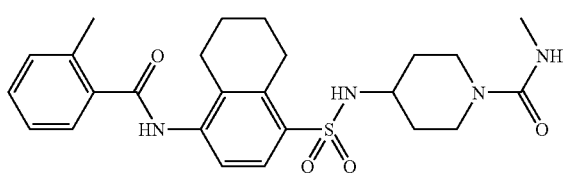

4-[4-(2-Methyl-benzoylamino)-5,6,7,8-tetrahydro-naphthalene-1-sulfonylamino]-piperidine-1-carboxylic acid methylamide (E-22)

The title compound was made following general procedure in Scheme 10, substituting isocyanato-methane for butyryl chloride. $^1$H NMR (300 MHz, MeOD) δ 7.93 (d, 1H), 7.59 (m, 2H), 7.43 (m, 1H), 7.36 (m, 2H), 3.88 (m, 2H), 3.29 (m, 4H), 2.83 (m, 4H), 2.71 (s, 3H), 2.54 (s, 3H), 1.88 (m, 3H), 1.73 (m, 2H), 1.41 (m, 2H)); LC/MS (M+H)$^+$ m/z 486.

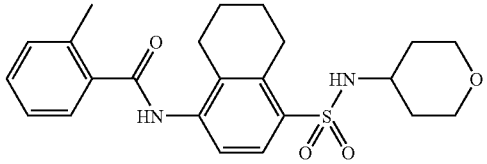

2-Methyl-N-[4-(tetrahydro-pyran-4-ylsulfamoyl)-5,6,7,8-tetrahydro-naphthalen-1-yl]-benzamide (E-23)

The title compound was made following general procedure in Scheme 10, substituting tetrahydro-pyran-4-ylamine for 4-amino-piperidine-1-carboxylic acid tert-butyl ester. $^1$H NMR (300 MHz, MeOD) δ 7.91 (d, 1H), 7.54 (m, 2H), 7.39 (m, 1H), 7.32 (m, 2H), 3.84 (m, 2H), 3.29 (m, 6H), 2.83 (m, 2H), 2.51 (s, 3H), 1.88 (m, 3H), 1.69 (m, 2H), 1.54 (m, 2H)); LC/MS (M+H)$^+$ m/z 429.

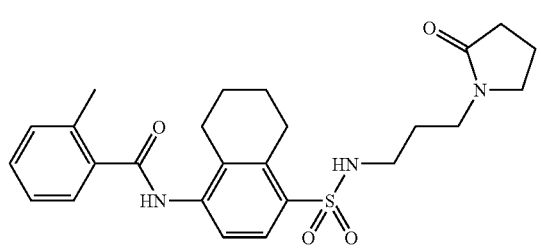

2-Methyl-N-{4-[3-(2-oxo-pyrrolidin-1-yl)-propylsulfamoyl]-5,6,7,8-tetrahydro-naphthalen-1-yl}-benzamide (E-24)

The title compound was made following general procedure in Scheme 10, substituting 1-(3-amino-propyl)-pyrrolidin-2-one for 4-amino-piperidine-1-carboxylic acid tert-butyl ester. $^1$H NMR (300 MHz, MeOD) δ 7.80 (d, 1H), 7.50 (t, 2H), 7.37 (m, 1H), 7.29 (m, 2H), 3.34(t, 2H), 3.21 (t, 2H), 3.17 (m, 2H), 2.86 (t, 2H), 2.79 (m, 2H), 2.46 (s, 3H), 2.31 (t, 2H), 1.98 (m, 2H), 1.82 (m, 4H), 1.65 (m, 2H) ); LC/MS (M+H)$^+$ m/z 470.

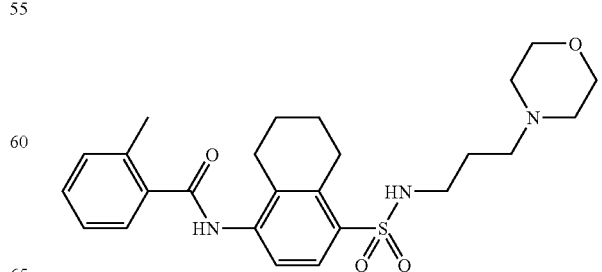

2-Methyl-N-[4-(3-morpholin-4-yl-propylsulfamoyl)-5,6,7,8-tetrahydro-naphthalen-1-yl]-benzamide (E-25)

The title compound was made following general procedure in Scheme 10, substituting 3-morpholin-4-yl-propylamine for 4-amino-piperidine-1-carboxylic acid tert-butyl ester. $^1$H NMR (300 MHz, MeOD) δ 7.83 (d, 1H), 7.54 (t, 2H), 7.41 (m, 1H), 7.31 (m, 2H), 3.74(m, 4H), 3.19 (m, 2H), 2.98 (t, 2H), 2.75 (m, 8H), 2.49 (s, 3H), 1.81 (m, 6H)); LC/MS (M+H)$^+$ m/z 472.

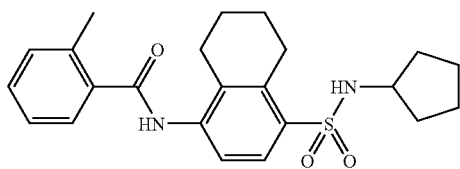

N-(4-Cyclopentylsulfamoyl-5,6,7,8-tetrahydro-naphthalen-1-yl)-2-methyl-benzamide (E-26)

The title compound was made following general procedure in Scheme 10, substituting cyclopentylamine for 4-amino-piperidine-1-carboxylic acid tert-butyl ester. $^1$H NMR (300 MHz, MeOD) δ 7.88 (d, 1H), 7.54 (m, 2H), 7.39 (m, 1H), 7.31 (m, 2H), 3.49 (m, 1H), 3.21 (m, 2H), 2.72 (m, 2H), 2.50 (s, 3H), 1.83 (m, 4H), 1.69 (m, 4H), 1.48 (m, 4H); LC/MS (M+H)$^+$ m/z 413.

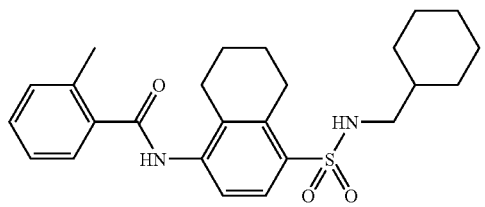

N-[4-(Cyclohexylmethyl-sulfamoyl)-5,6,7,8-tetrahydro-naphthalen-1-yl]-2-methyl-benzamide (E-27)

The title compound was made following general procedure in Scheme 10, substituting C-cyclohexyl-methylamine for 4-amino-piperidine-1-carboxylic acid tert-butyl ester. $^1$H NMR (300 MHz, MeOD) δ 7.82 (d, 1H), 7.54 (m, 2H), 7.39 (m, 1H), 7.31 (m, 2H), 3.21 (m, 2H), 2.83 (m, 2H), 2.69 (d, 2H), 2.49 (s, 3H), 1.83 (m, 3H), 1.69 (m, 6H), 1.39 (m, 1H), 1.19 (m, 3H), 0.85 (m, 2H)); LC/MS (M+H)$^+$ m/z 441.

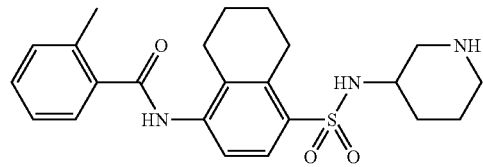

(±)-2-Methyl-N-[4-(piperidin-3-ylsulfamoyl)-5,6,7,8-tetrahydro-naphthalen-1-yl]-benzamide (E-28)

The title compound was made following general procedure in Scheme 10, substituting (R, S)-3-amino-piperidine-1-carboxylic acid tert-butyl ester for 4-amino-piperidine-1-carboxylic acid tert-butyl ester. $^1$H NMR (300 MHz, MeOD) δ 7.91 (d, 1H), 7.57 (m, 2H), 7.41 (m, 1H), 7.33 (m, 2H), 3.23 (m, 4H), 3.11 (m, 1H), 2.85 (m, 2H), 2.70(m, 2H), 2.50 (s, 3H), 1.73 (m, 6H), 1.54 (m, 2H) ); LC/MS (M+H)$^+$ m/z 428.

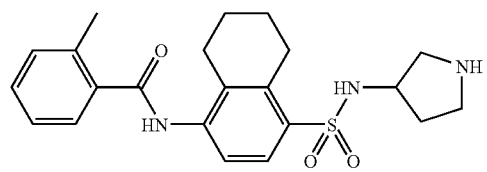

(±)-2-Methyl-N-[4-(pyrrolidin-3-ylsulfamoyl)-5,6,7,8-tetrahydro-naphthalen-1-yl]-benzamide (E-29)

The title compound was made following general procedure in Scheme 10, substituting (R, S)-3-amino-pyrrolidine-1-carboxylic acid tert-butyl ester for 4-amino-piperidine-1-carboxylic acid tert-butyl ester. $^1$H NMR (300 MHz, MeOD) δ 7.89 (d, 1H), 7.57 (m, 2H), 7.41 (m, 1H), 7.33 (m, 2H), 3.81 (m, 1H), 3.22 (m, 7H), 2.84 (m, 2H), 2.50 (s, 3H), 2.09 (m, 1H), 1.83 (m, 4H)); LC/MS (M+H)$^+$ m/z 414.

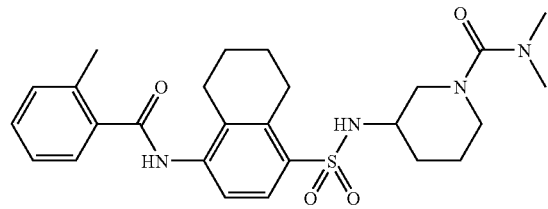

(±)-3-[4-(2-Methyl-benzoylamino)-5,6,7,8-tetrahydro-naphthalene-1-sulfonylamino]-piperidine-1-carboxylic acid dimethylamide (E-30)

The title compound was made following general procedure in Scheme 10, substituting (R, S)-3-amino-piperidine-1-carboxylic acid tert-butyl ester for 4-amino-piperidine-1-carboxylic acid tert-butyl ester, and dimethylcarbamyl chloride for butyryl chloride. $^1$H NMR (300 MHz, MeOD) δ 7.90 (d, 1H), 7.56 (m, 2H), 7.39 (m, 1H), 7.31 (m, 2H), 3.40 (m, 3H), 3.15 (m, 3H), 2.85 (m, 2H), 2.74 (s, 6H), 2.69(m, 2H), 2.50 (s, 3H), 1.73 (m, 4H), 1.69 (m, 1H), 1.44 (m, 2H) ); LC/MS (M+H)$^+$ m/z 499.

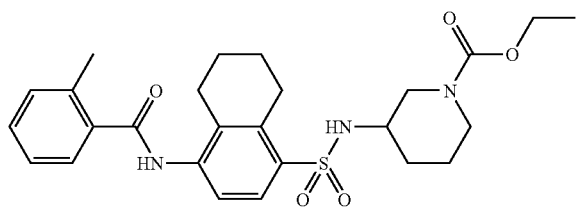

(±)-3-[4-(2-Methyl-benzoylamino)-5,6,7,8-tetrahydro-naphthalene-1-sulfonylamino]-piperidine-1-carboxylic acid ethyl ester (E-31)

The title compound was made following general procedure in Scheme 10, substituting (R, S)-3-amino-piperidine-1-carboxylic acid tert-butyl ester for 4-amino-piperidine-1-carboxylic acid tert-butyl ester, and ethyl chlorofomate for butyryl chloride. $^1$H NMR (300 MHz, MeOD) δ 7.92 (d, 1H), 7.59 (m, 2H), 7.42 (m, 1H), 7.34 (m, 2H), 4.09 (q, 2H), 3.91 (m, 1H), 3.79 (m, 1H), 3.24 (m, 2H), 3.09 (m, 2H), 2.85 (m, 4H), 2.51 (s, 3H), 1.86 (m, 4H), 1.71 (m, 1H), 1.42 (m, 2H), 1.23 (t, 3H) ); LC/MS (M+H)$^+$ m/z 500.

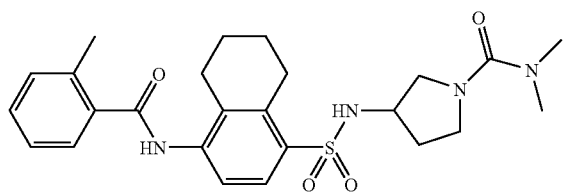

(±)-3-[4-(2-Methyl-benzoylamino)-5,6,7,8-tetrahydro-naphthalene-1-sulfonylamino]-pyrrolidine-1-carboxylic acid dimethylamide (E-32)

The title compound was made following general procedure in Scheme 10, substituting (R,S)-3-amino-pyrrolidine-1-carboxylic acid tert-butyl ester for 4-amino-piperidine-1-carboxylic acid tert-butyl ester, and dimethylcarbamyl chloride for butyryl chloride. $^1$H NMR (300 MHz, MeOD) δ 7.90 (d, 1H), 7.57 (m, 2H), 7.41 (m, 1H), 7.32 (m, 2H), 3.78 (m, 1H), 3.48 (m, 1H), 3.28 (m, 2H), 3.18 (m, 3H), 2.84 (m, 3H), 2.78 (s, 6H), 2.50 (s, 3H), 1.96 (m, 1H), 1.82 (m, 4H) ); LC/MS (M+H)$^+$ m/z 485.

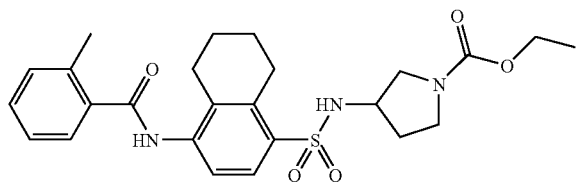

(±)-3-[4-(2-Methyl-benzoylamino)-5,6,7,8-tetrahydro-naphthalene-1-sulfonylamino]-pyrrolidine-1-carboxylic acid ethyl ester (E-33)

The title compound was made following general procedure in Scheme 10, substituting (R, S)-3-amino-pyrrolidine-1-carboxylic acid tert-butyl ester for 4-amino-piperidine-1-carboxylic acid tert-butyl ester, and ethyl chlorofomate for butyryl chloride. $^1$H NMR (300 MHz, MeOD) δ 7.89 (d, 1H), 7.55 (m, 2H), 7.39 (m, 1H), 7.30 (m, 2H), 4.09 (m, 2H), 3.79 (m, 1H), 3.41 (m, 3H), 3.18 (m, 4H), 2.82 (m, 2H), 2.50 (s, 3H), 1.99 (m, 1H), 1.89 (m, 4H), 1.22 (m, 3H) ); LC/MS (M+H)$^+$ m/z 486.

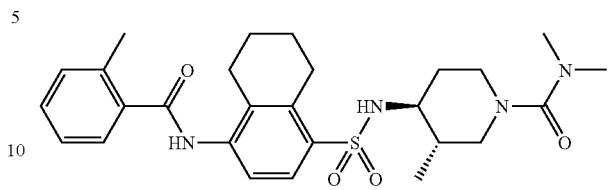

(±)-trans-3-Methyl-4-[4-(2-methyl-benzoylamino)-5,6,7,8-tetrahydro-naphthalene-1-sulfonylamino]-piperidine-1-carboxylic acid dimethylamide (E-34)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. LC/MS (M+H)$^+$ m/z 513.

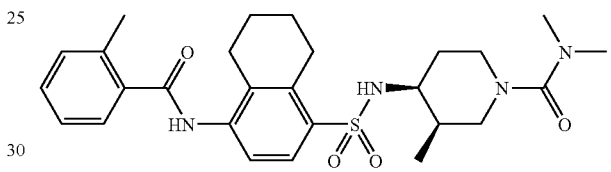

(3R, 4S)-3-Methyl-4-[4-(2-methyl-benzoylamino)-5,6,7,8-tetrahydro-naphthalene-1-sulfonylamino]-piperidine-1-carboxylic acid dimethylamide (E-35)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. Compound E-20 was prepared as described previously, and the enantiomers were separated via chiral HPLC chromatography of E-35; the title compound eluted as peak 1. $^1$H NMR (300 MHz, MeOD) δ 7.90 (d, 1H), 7.55 (m, 2H), 7.39 (m, 1H), 7.31 (m, 2H), 3.36 (m, 2H), 3.22 (m, 2H), 3.10 (m, 3H), 2.82 (m, 2H), 2.80 (s, 6H), 2.49 (s, 3H), 1.85 (m, 4H), 1.65 (m, 1H), 1.49 (m, 1H), 0.83 (d, 3H) ); LC/MS (M+H)$^+$ m/z 537.

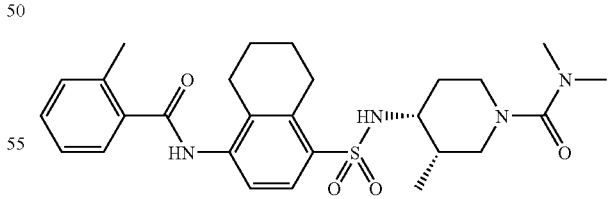

(3S, 4R)-3-Methyl-4-[4-(2-methyl-benzoylamino)-5,6,7,8-tetrahydro-naphthalene-1-sulfonylamino]-piperidine-1-carboxylic acid dimethylamide (E-36)

The title compound was made following general procedure in Scheme 10, substituting 1-benzyl-3-methyl-piperidin-4-ylamine for 4-amino-piperidine-1-carboxylic acid tert-butyl ester, and dimethylcarbamyl chloride for butyryl chloride. Compound E-20 was prepared as described previously, and the enantiomers were separated via chiral HPLC chromatography of E-35; the title compound eluted as peak 2. $^1$H NMR (300 MHz, MeOD) δ 7.90 (d, 1H), 7.55 (m, 2H), 7.39 (m, 1H), 7.31 (m, 2H), 3.36 (m, 2H), 3.22 (m, 2H), 3.10 (m, 3H), 2.82 (m, 2H), 2.80 (s, 6H), 2.49 (s, 3H), 1.85 (m, 4H), 1.65 (m, 1H), 1.49 (m, 1H), 0.83 (d, 3H) ); LC/MS (M+H)$^+$ m/z 513.

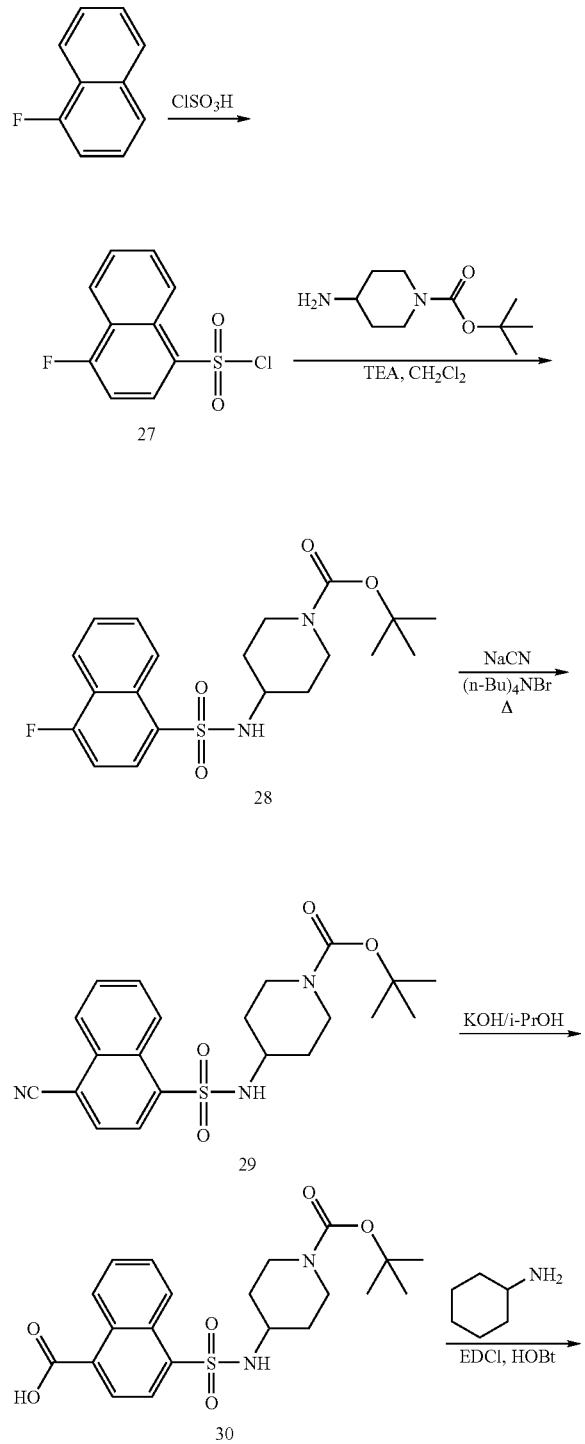

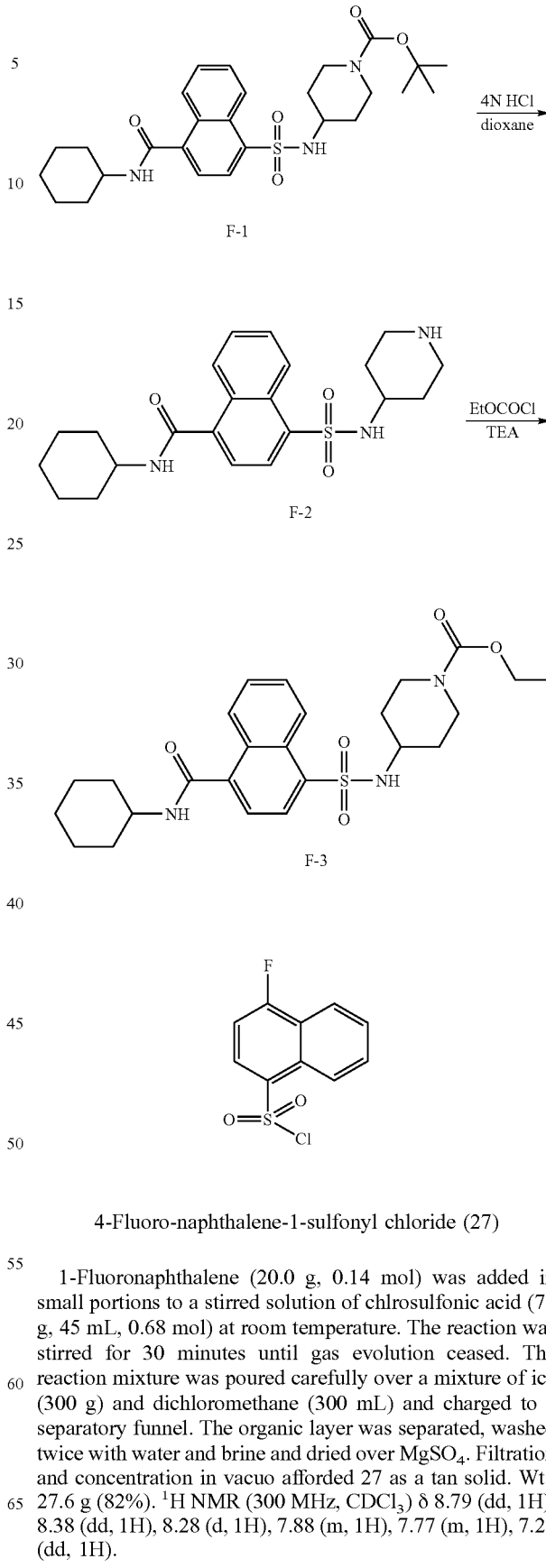

4-Fluoro-naphthalene-1-sulfonyl chloride (27)

1-Fluoronaphthalene (20.0 g, 0.14 mol) was added in small portions to a stirred solution of chlrosulfonic acid (79 g, 45 mL, 0.68 mol) at room temperature. The reaction was stirred for 30 minutes until gas evolution ceased. The reaction mixture was poured carefully over a mixture of ice (300 g) and dichloromethane (300 mL) and charged to a separatory funnel. The organic layer was separated, washed twice with water and brine and dried over MgSO$_4$. Filtration and concentration in vacuo afforded 27 as a tan solid. Wt.: 27.6 g (82%). $^1$H NMR (300 MHz, CDCl$_3$) δ 8.79 (dd, 1H), 8.38 (dd, 1H), 8.28 (d, 1H), 7.88 (m, 1H), 7.77 (m, 1H), 7.26 (dd, 1H).

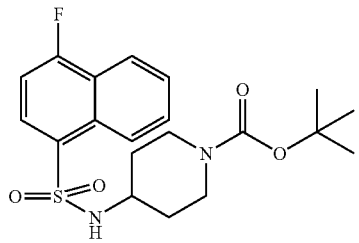

4-(4-Fluoro-naphthalene-1-sulfonylamino)-piperidine-1-carboxylic acid tert-butyl ester (28)

4-Fluoro-naphthalene-1-sulfonyl chloride 27 (10.0 g, 40.9 mmol) was dissolved in THF (100 mL) and stirred at room temperature. 4-Amino-piperidine-1-carboxylic acid tert-butyl ester (8.19 g, 40.9 mmol) and triethylamine (4.14 g, 5.75 mL, 40.9 mmol) were added and the reaction was stirred overnight at room temperature. The solvent was removed in vacuo. Dichloromethane (250 mL) was added and the solution was charged to a separatory funnel. The organic layer was washed twice with water and brine and dried over MgSO$_4$. Filtration and concentration in vacuo afforded 28 as a yellow foam. Wt.: 15.1 g (90%). $^1$H NMR (300 MHz, CDCl$_3$) δ 8.62 (d, 1H), 8.26 (m, 2H), 7.69 (m, 2H), 7.20 (m, 1H), 4.92 (d, 1H), 3.82 (m, 2H), 3.26 (m, 1H), 2.70 (m, 2H), 1.61 (m, 2H), 1.40 (s, 9H), 1.24 (m, 2H); LC/MS m/z 409 (M+H)$^+$.

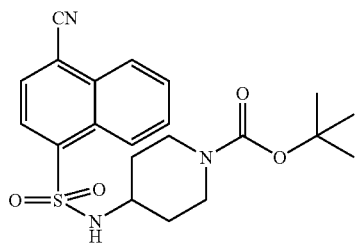

4-(4-Cyano-naphthalene-1-sulfonylamino)-piperidine-1-carboxylic acid tert-butyl ester (29)

4-(4-Fluoro-naphthalene-1-sulfonylamino)-piperidine-1-carboxylic acid tert-butyl ester 28 (2.00 g, 4.9 mmol) was dissolved in DMF (20 mL). Sodium cyanide (1.2 g, 24.5 mmol) and tetra-n-butylammonium bromide (7.9 g, 24.5 mmol) were added and the reaction was heated to 100° C. overnight. The reaction was diluted with dichloromethane (100 mL) and charged to a separatory funnel. The organic layer was washed three times with water, brine and dried over MgSO$_4$. Filtration and concentration in vacuo afforded a dark colored oil. Flash column chromatography (98:2 dichloromethane:methanol) afforded an oil that was rechromatographed (99:1 dichloromethane:methanol) to afford 29 as an orange solid. Wt.: 640 mg (31%). $^1$H NMR (300 MHz, CDCl$_3$) δ 8.71 (m, 1H), 8.40 (m, 1H), 8.34 (d, 1H), 8.00 (d, 1H), 7.83 (m, 2H), 4.80 (d, 1H), 3.87 (m, 2H), 3.32 (m, 1H), 2.61 (m, 2H), 1.63 (m, 2H), 1.38 (s, 9H), 1.27 (m, 2H); LC/MS m/z 414 (M−H)$^−$

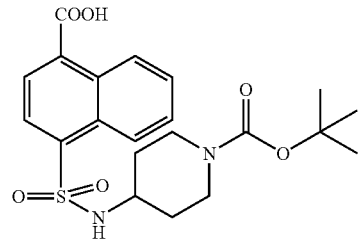

4-(4-Carboxy-naphthalene-1-sulfonylamino)-piperidine-1-carboxylic acid tert-butyl ester (30)

4-(4-Cyano-naphthalene-1-sulfonylamino)-piperidine-1-carboxylic acid tert-butyl ester 29 (0.48 g, 1.15 mmol) was dissolved in a mixture of aqueous potassium hydroxide (20 mL, 1.8N, 36 mmol) and isopropanol (25 mL). The mixture was heated to 75° C. for two days. LC/MS analysis showed a mixture of starting material, carboxylic acid and amide. The isopropanol was removed in vacuo and the aqueous layer was extracted with ethyl acetate and the organic layer discarded. The aqueous layer was acidified to pH 3 and extracted with ethyl acetate. The organic layer washed with water, then brine and dried over MgSO$_4$. Filtration and concentration in vacuo afforded 30 as a tan colored foam. Wt.: 360 mg (72%). $^1$H NMR (300 MHz, CDCl$_3$) δ 9.03 (m, 1H), 8.70 (m, 1H), 8.33 (dd, 2H), 7.74 (m, 2H), 4.78 (d, 1H), 3.85 (m, 2H), 3.31 (m, 1H), 2.71 (m, 2H), 1.62 (m, 2H), 1.40 (s, 9H), 1.27 (m, 2H); LC/MS m/z 433 (M−H)$^−$.

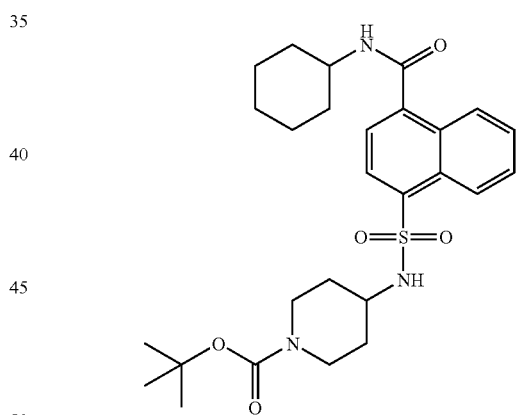

4-(4-Cyclohexylcarbamoyl-naphthalene-1-sulfonylamino)-piperidine-1-carboxylic acid tert-butyl ester (F-1)

4-(4-Carboxy-naphthalene-1-sulfonylamino)-piperidine-1-carboxylic acid tert-butyl ester 5 (400 mg, 0.92 mmol) was dissolved in dichloromethane (5 mL). 1-[3-(Dimethylamino)propyl]-3-ethylcarbodiimide hydrochloride (EDCI) (350 mg, 1.84 mmol), 1-hydroxybenzotriazole (186 mg, 1.38 mmol), triethylamine (280 mg, 0.38 mL, 2.76 mmol) and cyclohexylamine (0.14 g, 0.16 mL, 1.38 mmol) were added and the reaction was stirred overnight at room temperature. The reaction was diluted with dichloromethane (30 mL) and charged to a separatory funnel. The organic layer was washed twice with water and brine and dried over Na₂SO₄. Filtration and concentration in vacuo afforded a foam that was purified via flash column chromatography (98:2 dichloromethane:methanol) to give the title compound. Wt.: 320 mg (68%). ¹H NMR (300 MHz, CDCl₃) δ 8.61 (m, 1H), 8.31 (m, 1H), 8.26 (d, 1H), 7.68 (m, 2H), 7.59 (d, 1H), 5.91 (d, 1H), 4.64 (d, 1H), 4.12 (m, 1H), 3.82 (m, 2H), 3.22 (m, 1H), 2.68 (m, 2H), 2.13 (m, 2H), 1.79 (m, 2H), 1.57 (m, 6H), 1.38 (s, 9H), 1.27 (m, 4H); LC/MS m/z 516 (M+H)⁺.

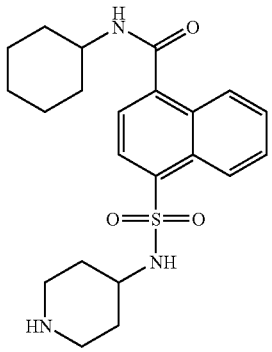

4-(Piperidin-4-ylsulfamoyl)-naphthalene-1-carboxylic acid cyclohexylamide (F-2)

4-(4-Cyclohexylcarbamoyl-naphthalene-1-sulfonylamino)-piperidine-1-carboxylic acid tert-butyl ester F-1 (320 mg, 0.62 mmol) was dissolved in 4N HCl/dioxane (10 mL). The reaction was stirred for 2 hours at room temperature and concentrated in vacuo to afford the title compound as its hydrochloride salt. Wt.: 271 mg (97%) ¹H NMR (300 MHz, d⁶-DMSO) δ 8.68 (d, 1H), 8.59 (d, 1H), 8.40 (d, 1H), 8.15 (m, 2H), 7.72 (m, 2H), 7.60 (d, 1H), 3.75 (m, 1H), 3.67 (m, 1H), 3.08 (m, 2H), 2.80 (m, 2H), 2.54 (m, 1H), 1.92 (m, 2H), 1.74 (m, 2H), 1.62 (m, 4H), 1.48 (m, 1H), 1.32 (m, 4H), 1.25 (m, 1H); LC/MS m/z 416 (M+H)⁺.

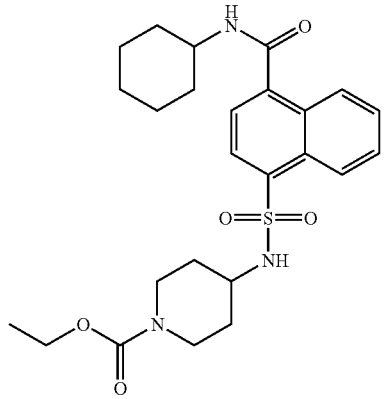

4-(4-Cyclohexylcarbamoyl-naphthalene-1-sulfonylamino)-piperidine-1-carboxylic acid ethyl ester (F-3)

4-(Piperidin-4-ylsulfamoyl)-naphthalene-1-carboxylic acid cyclohexylamide hydrochloride F-2 (87 mg, 0.19 mmol) was dissolved and stirred in dichloromethane (2 mL). Triethylamine (58 mg, 0.08 mL, 0.57 mmol) was added followed by ethyl chloroformate (41 mg, 0.037 mL, 0.39 mmol). The reaction was stirred overnight at room temperature, then charged directly to a flash column. Elution with 99:1 dichloromethane:methanol afforded the titled compound the title compound as a white solid. Wt.: 60 mg (65%). ¹H NMR (300 MHz, CDCl₃) δ 8.59 (m, 1H), 8.28 (m, 1H), 8.19 (d, 1H), 7.64 (m, 2H), 7.54 (d, 1H), 4.10 (m, 1H), 4.03 (q, 2H), 3.80 (m, 2), 3.64 (m, 1H), 3.18 (m, 1H), 2.68 (m, 2H), 2.12 (m, 2H), 1.79 (m, 2H), 1.68 (m, 1H), 1.58 (m, 2H), 1.47 (m, 2H), 1.24 (m, 6H), 1.18 (t, 3H); LC/MS m/z 488 (M+H)⁺.

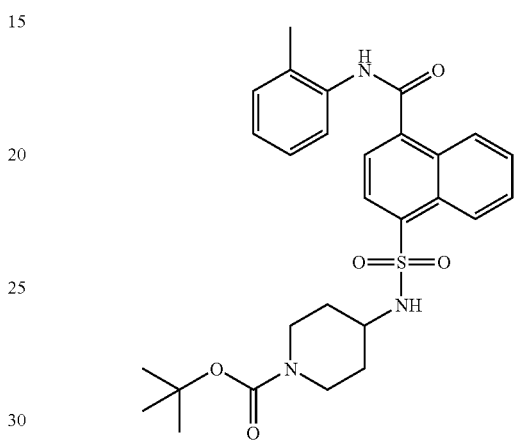

4-(4-o-Tolylcarbamoyl-naphthalene-1-sulfonylamino)-piperidine-1-carboxylic acid tert-butyl ester (F-4)

The titled compound was prepared according to the general procedure in Scheme 11, substituting 2-methylphenylamine for cyclohexylamine. Wt.: 337 mg (70%). ¹H NMR (300 MHz, CDCl₃) δ 8.66 (d, 1H), 8.46 (d, 1H), 8.35 (d, 1H), 8.04 (d, 1H), 7.80 (m, 1H), 7.72 (m, 2H), 7.54 (s, 1H), 7.34 (m, 1H), 7.21 (m, 1H), 4.16 (d, 1H), 3.85 (m, 2H), 3.27 (m, 1H), 2.70 (m, 2H), 2.34 (s, 3H), 2.23 (m, 1H), 1.66 (m, 2H), 1.56 (m, 4H), 1.40 (s, 9H), 1.27 (m, 4H); LC/MS m/z 524 (M+H)⁺.

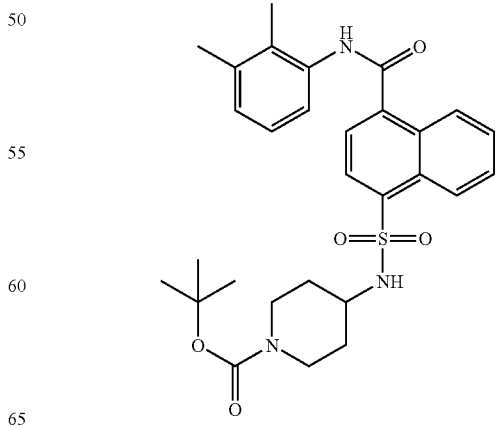

4-[4-(2,3-Dimethyl-phenylcarbamoyl)-naphthalene-1-sulfonylamino]-piperidine-1-carboxylic acid tert-butyl ester (F-13)

The titled compound was prepared according to the general procedure in Scheme 11, substituting 2,3-dimethylphenylamine for cyclohexylamine. Wt.: 353 mg (75%). $^1$H NMR (300 MHz, CDCl$_3$) δ 8.66 (m, 1H), 8.47 (d, 1H), 8.35 (d, 1H), 7.81 (d, 1H), (m, 2H), 7.54 (s, 1H), 7.22 (m, 1H), 7.13 (m, 1H), 4.63 (d, 1H), 3.86 (m, 2H), 3.27 (m, 1H), 2.70 (m, 2H), 2.35 (s, 3H), 2.24 (s, 3H), 1.64 (m, 2H), 1.34 (m, 2H); LC/MS m/z 537 (M−H)$^−$.

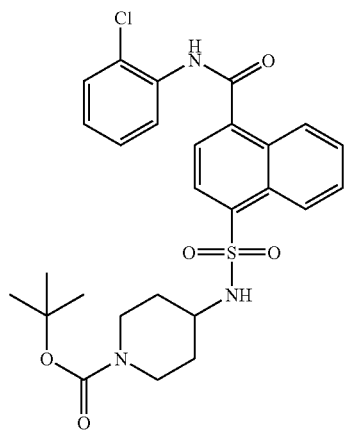

4-[4-(2-Chloro-phenylcarbamoyl)-naphthalene-1-sulfonylamino]-piperidine-1-carboxylic acid tert-butyl ester (F-14)

The titled compound was prepared according to the general procedure in Scheme 11, substituting 2-chlorophenylamine for cyclohexylamine. Wt.: 329 mg (66%). $^1$H NMR (300 MHz, CDCl$_3$) δ 8.68 (m, 1H), 8.62 (m, 1H), 8.46 (d, 1H), 8.37 (m, 1H), 8.20 (s, 1H), 7.83 (d, 1H), 7.73 (m, 2H), 7.46 (m, 1H), 7.40 (m, 1H), 7.17 (m, 1H), 4.68 (d, 1H), 3.87 (m, 2H), 3.30 (m, 1H), 2.62 (m, 2H), 1.68 (m, 2H), 1.40 (s, 9H), 1.26 (m, 2H); LC/MS m/z 543 (M−H)$^−$.

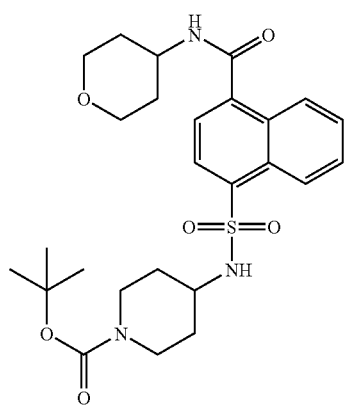

4-[4-(Tetrahydro-pyran-4-ylcarbamoyl)-naphthalene-1-sulfonylamino]-piperidine-1-carboxylic acid tert-butyl ester (F-15)

The title compound was prepared according to the general procedure in Scheme 11, substituting tetrahydro-pyran-4-ylamine for cyclohexylamine. Wt.: 368 mg (77%). $^1$H NMR (300 MHz, CDCl$_3$) δ 8.60 (m, 1H), 8.29 (m, 1H), 8.24 (d, 1H), 7.68 (m, 2H), 7.59 (d, 1H), 6.12 (d, 1H), 4.73 (d, 1H), 4.34 (m, 1H), 4.04 (m, 2H), 3.82 (m, 2H), 3.57 (m, 2H), 3.21 (m, 1H), 2.67 (m, 2H), 2.11 (m, 1H), 1.62 (m, 3H), 1.36 (s, 9H), 1.20 (m, 4H); LC/MS m/z 516 (M−H)$^−$.

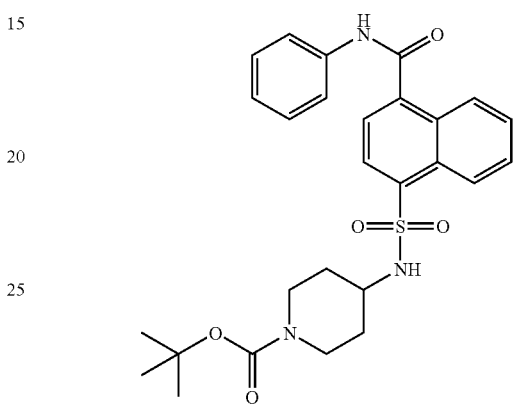

4-(4-Phenylcarbamoyl-naphthalene-1-sulfonylamino)-piperidine-1-carboxylic acid tert-butyl ester The titled compound was prepared according to the general procedure in Scheme 11, substituting phenylamine for cyclohexylamine. Wt.: 66 mg (55%). $^1$H NMR (300 MHz, CDCl$_3$) δ 8.62 (d, 1H), 8.37 (m, 2H), 8.26 (d, 1H), 7.93 (s, 1H), 7.70 (m, 4H), 7.43 (m, 3H), 4.76 (d, 1H), 3.80 (m, 2H), 3.24 (m, 1H), 2.67 (m, 2H), 1.60 (m, 2H), 1.39 (s, 9H), 1.22 (m, 2H); LC/MS m/z 510 (M+H)$^+$.

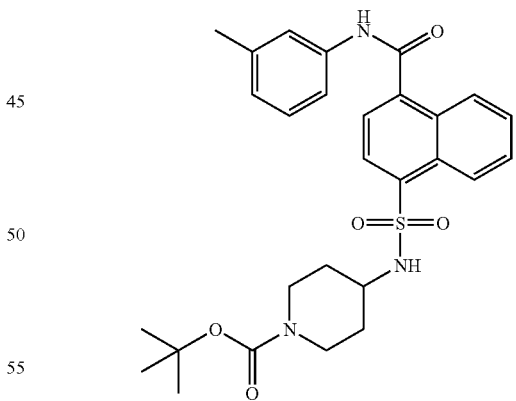

4-(4-m-Tolylcarbamoyl-naphthalene-1-sulfonylamino)-piperidine-1-carboxylic acid tert-butyl ester The title compound was prepared according to the general procedure in Scheme 11, substituting m-tolylamine for cyclohexylamine. Wt.: 61 mg (51%). $^1$H NMR (300 MHz, CDCl$_3$) δ 8.62 (d, 1H), 8.35 (m, 2H), 8.18 (d, 1H), 7.65 (m, 4H), 7.28 (m, 2H), 7.03 (d, 1H), 5.13 (d, 1H), 3.73 (m, 2H), 3.18 (m, 1H), 2.62 (m, 2H), 2.40 (s, 3H), 1.55 (m, 2H), 1.38 (s, 9H), 1.12 (m, 2H); LC/MS m/z 524 (M+H)$^+$.

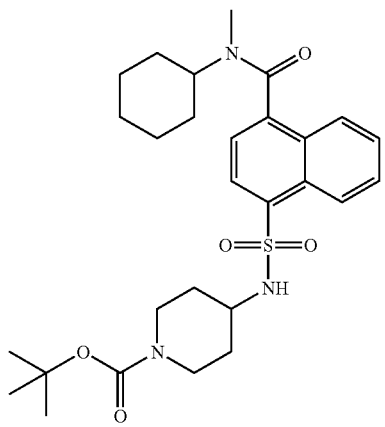

4-[4-(Cyclohexyl-methyl-carbamoyl)-naphthalene-1-sulfonylamino]-piperidine-1-carboxylic acid tert-butyl ester The title compound was prepared according to the general procedure in Scheme 11, substituting cyclohexyl-methylamine for cyclohexylamine, and O-(7-azabenzotriazol-1-yl)-N,N,N',N'-tetramethyluronium hexafluorophosphate for EDCI. Wt.: 440 mg (100%). ¹HNMR (300 MHz, CDCl₃) δ 8.63 (d, 1H), 8.31 (d, 1H), 7.89 (m, 1H), 7.67 (m, 2H), 7.42 (m, 1H), 4.77 (s, 1H), 3.87 (m, 2H), 3.22 (m, 1H), 2.79 (s, 3H), 2.60 (m, 2H), 1.88 (m, 4H), 1.55 (m, 8H), 1.38 (s, 9H), 1.15 (m, 2H); LC/MS m/z 530 (M+H)⁺.

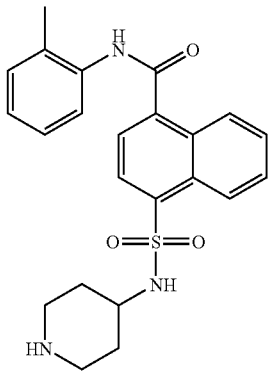

4-(Piperidin-4-ylsulfamoyl)-naphthalene-1-carboxylic acid o-tolylamide (F-5)

The title compound was prepared according to the general procedure in Scheme 11, substituting 4-(4-o-tolylcarbamoyl-naphthalene-1-sulfonylamino)-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 275 mg (97%). ¹H NMR (300 MHz, d⁶-DMSO) δ 10.22 (s, 1H), 8.73 (m, 1H), 8.44 (m, 2H), 8.30 (m, 1H), 8.24 (m, 1H), 7.88 (d, 1H), 7.77 (m, 2H), 7.52 (d, 1H), 7.28 (m, 1H), 7.22 (m, 1H), 3.11 (m, 2H), 2.83 (m, 2H), 2.53 (m, 1H), 2.32 (s, 3H), 1.67 (m, 2H), 1.51 (m, 2H); LC/MS m/z 424 (M+H)⁺.

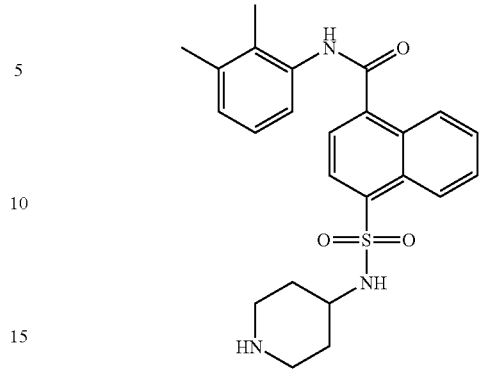

4-(Piperidin-4-ylsulfamoyl)-naphthalene-1-carboxylic acid (2,3-dimethyl-phenyl)-amide (F-16)

The title compound was prepared according to the general procedure in Scheme 11, substituting 4-[4-(2,3-dimethyl-phenylcarbamoyl)-naphthalene-1-sulfonylamino]-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 312 mg (99%). ¹H NMR (300 MHz, d⁶-DMSO) δ 10.27 (s, 1H), 8.72 (d, 1H), 8.47 (d, 1H), 8.30 (m, 1H), 8.23 (d, 1H), 7.90 (d, 1H), 7.75 (m, 2H), 7.31 (d, 1H), 7.12 (m, 2H), 3.68 (m, 1H), 3.10 (m, 2H), 2.80 (m, 2H), 2.30 (s, 3H), 2.20 (s, 3H), 2.02 (m, 1H), 1.67 (m, 2H), 1.53 (m, 2H); LC/MS m/z 436 (M–H)⁻.

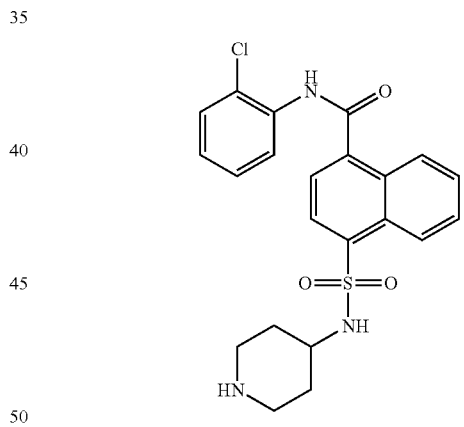

4-(Piperidin-4-ylsulfamoyl)-naphthalene-1-carboxylic acid (2-chloro-phenyl)-amide (F-17)

The title compound was prepared according to the general procedure in Scheme 11, substituting 4-[4-(2-chloro-phenylcarbamoyl)-naphthalene-1-sulfonylamino]-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 219 mg (98%). ¹H NMR (300 MHz, d⁶-DMSO) δ 10.51 (s, 1H), 8.72 (d, 1H), 8.52 (m, 1H), 8.47 (d, 1H), 8.35 (m, 1H), 8.24 (d, 1H), 7.90 (d, 1H), 7.75 (m, 2H), 7.59 (d, 1H), 7.43 (m, 1H), 7.32 (m, 1H), 3.67 (m, 1H), 3.08 (m, 2H), 2.82 (m, 2H), 1.65 (m, 2H), 1.50 (m, 2H); LC/MS m/z 442 (M–H)⁻.

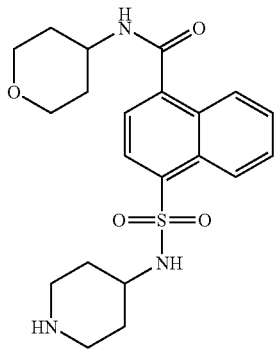

4-(Piperidin-4-ylsulfamoyl)-naphthalene-1-carboxylic acid (tetrahydro-pyran-4-yl)-amide (F-18)

The title compound was prepared according to the general procedure in Scheme 11, substituting 4-[4-(tetrahydro-pyran-4-ylcarbamoyl)-naphthalene-1-sulfonylamino]-piperidine-1-carboxylic acid tert-butyl ester for 4-(4-cyclohexyl-carbamoyl-naphthalene-1-sulfonylamino)-piperidine-1-carboxylic acid tert-butyl ester. Wt.: 321 mg (100%). $^1$H NMR (300 MHz, d$^6$-DMSO) δ 8.69 (m, 2H), 8.42 (m, 2H), 8.15 (m, 1H), 7.72 (m, 2H), 7.63 (d, 1H), 4.08 (m, 1H), 3.87 (m, 2H), 3.42 (m, 2H), 3.08 (m, 2H), 2.80 (m, 2H), 1.86 (m, 2H), 1.64 (m 4H), 1.51 (m, 4H); LC/MS m/z 416 (M−H)$^−$.

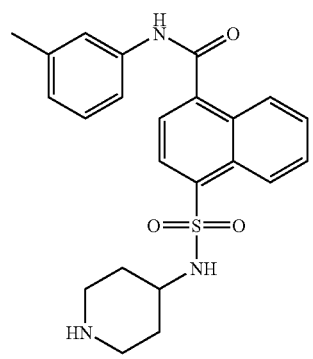

4-(Piperidin-4-ylsulfamoyl)-naphthalene-1-carboxylic acid m-tolylamide

The title compound was prepared according to the general procedure in Scheme 11, substituting 4-(4-m-tolylcarbamoyl-naphthalene-1-sulfonylamino)-piperidine-1-carboxylic acid tert-butyl ester for 4-(4-cyclohexylcarbamoyl-naphthalene-1-sulfonylamino)-piperidine-1-carboxylic acid tert-butyl ester. Wt. 39 mg (75%). LC/MS m/z 424 (M+H)$^+$.

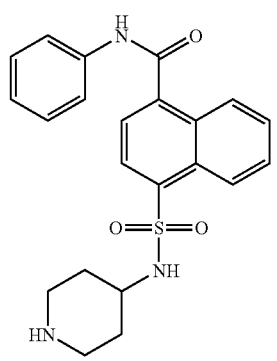

4-(Piperidin-4-ylsulfamoyl)-naphthalene-1-carboxylic acid phenylamide

The title compound was prepared according to the general procedure in Scheme 11, substituting 4-(4-phenylcarbamoyl-naphthalene-1-sulfonylamino)-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 38 mg (67%). LC/MS m/z 410 (M+H)$^+$.

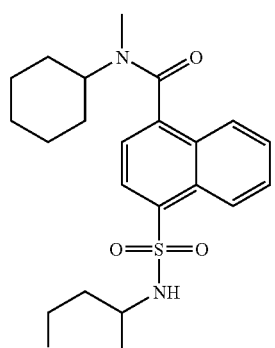

4-(Piperidin-4-ylsulfamoyl)-naphthalene-1-carboxylic acid cyclohexyl-methyl-amide The title compound was prepared according to the general procedure in Scheme 11, substituting 4-[4-(cyclohexyl-methyl-carbamoyl)-naphthalene-1-sulfonylamino]-piperidine-1-carboxylic acid tert-butyl ester for 4-(4-cyclohexylcarbamoyl-naphthalene-1-sulfonylamino)-piperidine-1-carboxylic acid tert-butyl ester. Wt.: 440 mg (100%). LC/MS m/z 424 (M+H)$^+$.

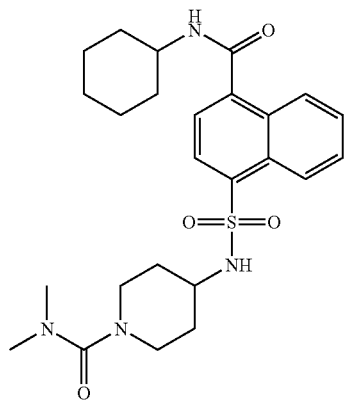

4-(4-Cyclohexylcarbamoyl-naphthalene-1-sulfony-
lamino)-piperidine-1-carboxylic acid dimethylamide
(F-6)

The title compound was prepared according to the general procedure in Scheme 11, substituting dimethylcarbamyl chloride for ethyl chloroformate. Wt.: 56 mg (50%). $^1$H NMR (300 MHz, CDCl$_3$) δ 8.58 (d, 1H), 8.30 (d, 1H), 8.25 (d, 2H), 7.68 (m, 2H), 7.56 (d, 1H), 6.00 (d, 1H), 4.77 (d, 1H), 4.11 (m, 1H), 3.42 (m, 2H), 3.23 (m, 1H), 2.71 (s, 6H), 2.63 (m, 2H), 2.13 (m, 2H), 1.80 (m, 2H), 1.63 (m, 2H), 1.47 (m, 2H), 1.27 (m, 6H); LC/MS m/z 485 (M–H)$^-$.

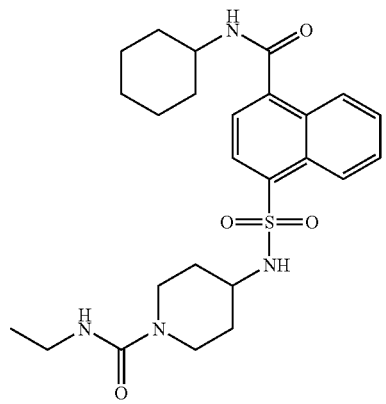

4-(4-Cyclohexylcarbamoyl-naphthalene-1-sulfony-
lamino)-piperidine-1-carboxylic acid ethylamide
(F-8)

The title compound was prepared according to the general procedure in Scheme 11, substituting ethyl isocyanate for ethyl chloroformate. Wt.: 56 mg (49%). $^1$H NMR (300 MHz, CDCl$_3$) δ 8.60 (d, 1H), 8.29 (d, 1H), 8.23 (d, 1H), 7.68 (m, 2H), 7.57 (d, 1H), 6.03 (d, 1H), 4.83 (d, 1H), 4.30 (m, 1H), 4.11 (m, 1H), 3.62 (m, 2H), 3.17 (m, 3H), 2.68 (m, 2H), 2.12 (m, 2H), 1.79 (m, 2H), 1.55 (m, 4H), 1.25 (m, 6H), 1.06 (t, 3H); LC/MS m/z 485 (M–H)$^-$.

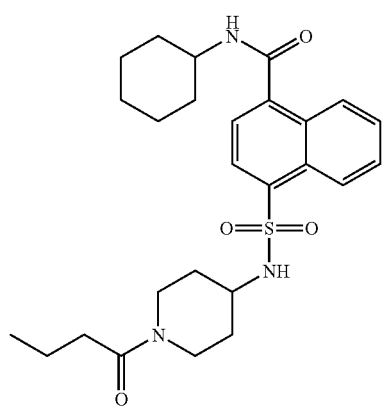

4-(1-Butyryl-piperidin-4-ylsulfamoyl)-naphthalene-
1-carboxylic acid cyclohexylamide (F-7)

The title compound was prepared according to the general procedure in Scheme 11, substituting butyryl chloride for ethyl chloroformate. Wt.: 50 mg (47%). $^1$H NMR (300 MHz, CDCl$_3$) δ 8.60 (d, 1H), 8.32 (d, 1H), 8.27 (d, 1H), 7.72 (m, 2H), 7.57 (d, 1H), 6.00 (d, 1H), 4.78 (d, 1H), 4.24 (m, 1H), 4.11 (m, 1H), 3.64 (m, 1H), 3.27 (m, 1H), 2.91 (m, 1H), 2.56 (m, 1H), 2.15 (m, 4H), 1.62 (m, 8H), 1.25 (m, 4H), 0.95 (m, 2H), 0.88 (t, 3H); LC/MS m/z 484 (M–H)$^-$.

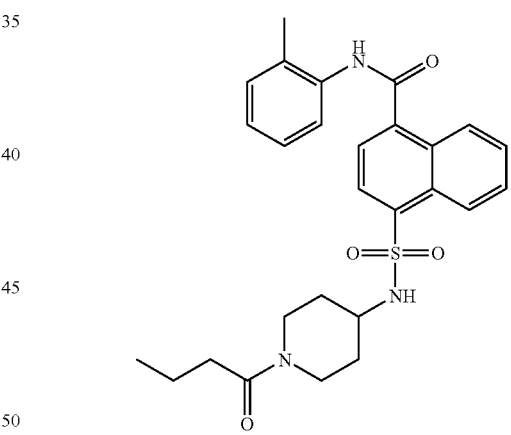

4-(1-Butyryl-piperidin-4-ylsulfamoyl)-naphthalene-
1-carboxylic acid o-tolylamide (F-9)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide, and butyryl chloride for ethyl chloroformate. Wt.: 29 mg (33%). $^1$H NMR (300 MHz, CDCl$_3$) δ 8.66 (d, 1H), 8.45 (d, 1H), 8.34 (d, 1H), 8.04 (d, 1H), 7.78 (d, 1H), 7.71 (m, 2H), 7.60 (s, 1H), 7.30 (m, 2H), 7.20 (m, 2H), 4.75 (d, 1H), 4.29 (d, 1H), 3.66 (d, 1H), 3.31 (m, 1H), 2.95 (m, 1H), 2.60 (m, 1H)2.34 (s, 3H), 2.20 (m, 2H), 1.70 (m, 2H), 1.23 (m, 3H), 0.89 (t, 3H); LC/MS m/z 492 (M–H)$^-$.

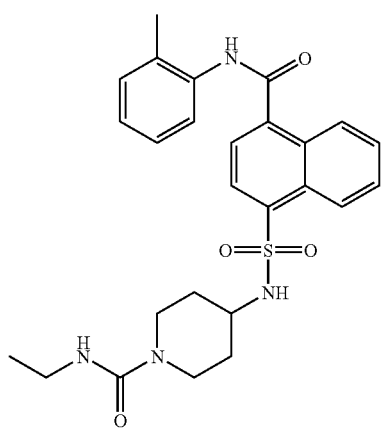

4-(4-o-Tolylcarbamoyl-naphthalene-1-sulfonylamino)-piperidine-1-carboxylic acid ethylamide
(F-10)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide, and ethyl isocyanate for ethyl chloroformate. Wt.: 26 mg (47%). $^1$H NMR (300 MHz, CDCl$_3$) δ 8.65 (d, 1H), 8.46 (d, 1H), 8.32 (d, 1H), 8.03 (d, 1H), 7.77 (d, 1H), 7.70 (m, 2H), 7.64 (s, 1H), 7.30 (m, 2H), 7.20 (m, 2H), 4.81 (d, 1H), 4.28 (m, 1H), 3.66 (m, 2H), 3.27 (m, 1H), 3.17 (m, 2H), 2.71 (m, 2H), 2.32 (s, 3H), 1.65 (m, 1H), 1.25 (m, 2H), 1.07 (t, 3H); LC/MS m/z 493 (M–H)$^-$.

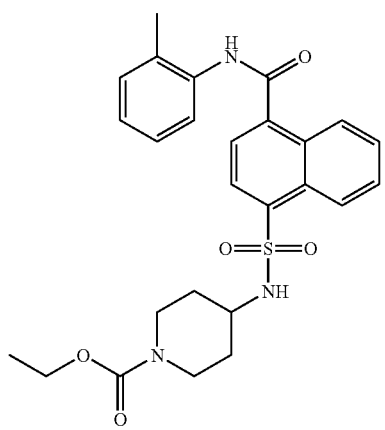

4-(4-o-Tolylcarbamoyl-naphthalene-1-sulfonylamino)-piperidine-1-carboxylic acid ethyl ester
(F-11)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide. Wt.: 60 mg (64%). $^1$H NMR (300 MHz, CDCl$_3$) δ 8.67 (d, 1H), 8.46 (d, 1H), 8.33 (d, 1H), 8.03 (d, 1H), 7.79 (d, 1H), 7.71 (m, 2H), 7.55 (s, 1H), 7.30 (m, 2H), 7.21 (m, 2H), 4.71 (d, 1H), 4.05 (q, 2H), 3.89 (m, 2H), 3.27 (m, 1H), 2.72 (m, 2H), 2.31 (s, 3H), 1.65 (m, 1H), 1.26 (m, 2H), 1.20 (t, 3H); LC/MS m/z 494 (M–H)$^-$.

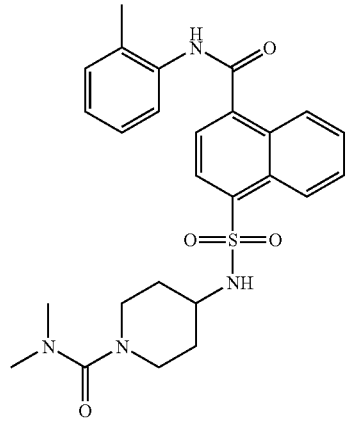

4-(4-o-Tolylcarbamoyl-naphthalene-1-sulfonylamino)-piperidine-1-carboxylic acid dimethylamide
(F-12)

The title compound was prepared according to the general procedure in Scheme 11, substituting 4-(piperidin-4-ylsulfamoyl)-naphthalene-1-carboxylic acid o-tolylamide for 4-(piperidin-4-ylsulfamoyl)-naphthalene-1-carboxylic acid cyclohexylamide, and dimethylcarbamyl chloride for ethyl chloroformate. Wt.: 35 mg (64%). $^1$H NMR (300 MHz, CDCl$_3$) δ 8.63 (d, 1H), 8.45 (d, 1H), 8.33 (d, 1H), 8.05 (d, 1H), 7.80 (d, 1H), 7.71 (m, 2H), 7.54 (s, 1H), 7.30 (m, 2H), 7.20 (m, 2H), 4.68 (d, 1H), 3.43 (m, 2H), 3.30 (m, 1H), 2.71 (s, 6H), 2.68 (m, 2H), 2.34 (s, 3H), 1.62 (m, 1H), 1.31 (m, 2H); LC/MS m/z 493 (M–H)$^-$.

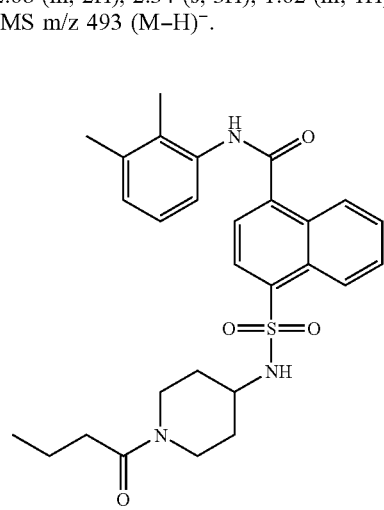

4-(1-Butyryl-piperidin-4-ylsulfamoyl)-naphthalene-1-carboxylic acid (2,3-dimethyl-phenyl)-amide
(F-19)

The title compound was prepared according to the general procedure in Scheme 11, substituting 4-(piperidin-4-ylsulfamoyl)-naphthalene-1-carboxylic acid (2,3-dimethyl-phenyl)-amide for 4-(piperidin-4-ylsulfamoyl)-naphthalene-1- carboxylic acid cyclohexylamide, and butyryl chloride for ethyl chloroformate. Wt.: 64 mg (40%). ¹H NMR (300 MHz, CDCl₃) δ 8.63 (m, 2H), 8.40 (m, 1H), 8.30 (s, 1H), 8.22 (d, 1H), 7.72 (d, 1H), 7.68 (m, 1H), 7.60 (d, 1H), 7.18 (m, 1H), 7.10 (m, 1H), 5.57 (d, 1H), 4.02 (m, 1H), 3.55 (m, 1H), 3.28 (m, 1H), 2.85 (m, 1H), 2.49 (m, 1H), 2.31 (s, 3H), 2.23 (s, 3H), 2.09 (2H), 1.63 (m, 2H), 1.50 (m, 2H), 1.20 (m, 1H), 1.03 (m, 1H), 0.84 (t, 3H); LC/MS m/z 508 (M+H)⁺.

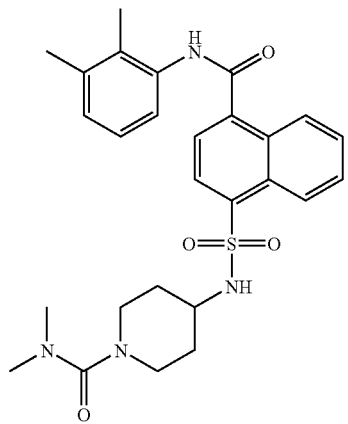

4-[4-(2,3-Dimethyl-phenylcarbamoyl)-naphthalene-1-sulfonylamino]-piperidine-1-carboxylic acid dimethylamide (F-20)

The title compound was prepared according to the general procedure in Scheme 11, substituting 4-(piperidin-4-ylsulfamoyl)-naphthalene-1-carboxylic acid (2,3-dimethyl-phenyl)-amide for 4-(piperidin-4-ylsulfamoyl)-naphthalene-1-carboxylic acid cyclohexylamide, and dimethycarbamyl chloride for ethyl chloroformate. Wt.: 116 mg (72%). ¹H NMR (300 MHz, CDCl₃) δ 8.60 (m, 1H), 8.40 (m, 1H), 8.20 (m, 2H), 7.72 (d, 1H), 7.63 (m, 2H), 7.35 (d, 1H), 7.16 (m, 1H), 7.09 (m, 1H), 5.42 (d, 1H), 3.32 (m, 2H), 3.15 (m, 1H), 2.67 (s, 6H), 2.55 (m, 2H), 2.33 (s, 3H), 2.22 (s, 3H), 1.52 (m, 2), 1.23 (m, 2H); LC/MS m/z 509 (M+H)⁺.

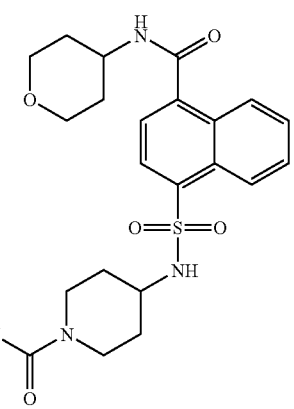

4-[4-(Tetrahydro-pyran-4-ylcarbamoyl)-naphthalene-1-sulfonylamino]-piperidine-1-carboxylic acid dimethylamide (F-21)

The title compound was prepared according to the general procedure in Scheme 11, substituting 4-(piperidin-4-ylsulfamoyl)-naphthalene-1-carboxylic acid (tetrahydro-pyran-4-yl)-amide for 4-(piperidin-4-ylsulfamoyl)-naphthalene-1-carboxylic acid cyclohexylamide, and dimethylcarbamyl chloride for ethyl chloroformate. Wt.: 125 mg (78%). ¹H NMR (300 MHz, CDCl₃) δ 8.8.59 (m, 1H), 8.29 (m, 1H), 8.23 (d, 1H), 7.69 (m, 2H), 7.58 (d, 1H), 6.17 (d, 1H), 4.82 (d, 1H), 4.32 (m, 1H), 4.03 (m, 2H), 3.57 (m, 2H), 3.40 (m, 2H), 3.25 (m, 1H), 2.73 (s, 6H), 2.64 (m, 2H), 2.10 (m, 2H), 1.61 (m, 4H), 1.27 (m, 2H); LC/MS m/z 489 (M+H)⁺.

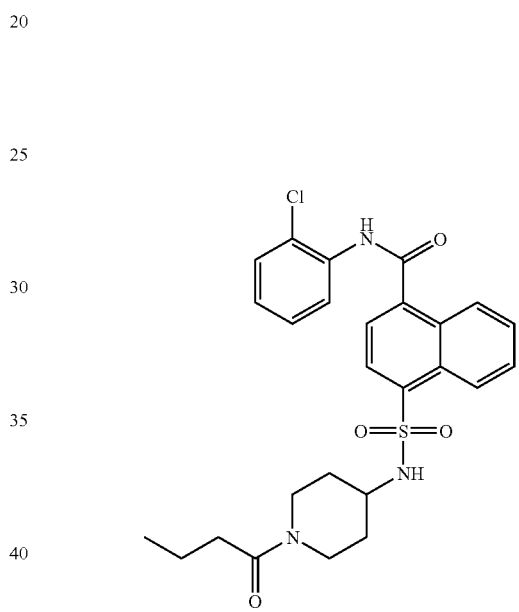

4-(1-Butyryl-piperidin-4-ylsulfamoyl)-naphthalene-1-carboxylic acid (2-chloro-phenyl)-amide (F-22)

The title compound was prepared according to the general procedure in Scheme 11, substituting 4-(piperidin-4-ylsulfamoyl)-naphthalene-1-carboxylic acid (2-chloro-phenyl)-amide for 4-(piperidin-4-ylsulfamoyl)-naphthalene-1-carboxylic acid cyclohexylamide, and butyryl chloride for ethyl chlroformate. Wt.: 21 mg (27%). ¹H NMR (300 MHz, CDCl₃) δ 8.67 (m, 2H), 8.48 (d, 1H), 8.35 (d, 1H), 8.20 (s, 1H), 7.82 (d, 1H), 7.72 (m, 2H), 7.41 (m, 2H), 7.09 (m, 1H), 4.78 (d, 1H), 4.31 (m, 1H), 3.67 (m, 1H), 3.35 (m, 1H), 2.95 (m, 1H), 2.22 (m, 2H), 1.60 (4H), 1.27 (m, 2H), 0.92 (t, 3H); LC/MS m/z 515 (M+H)⁺.

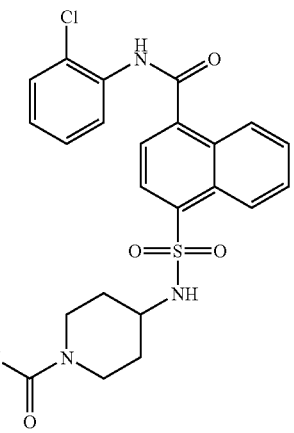

4-[4-(2-Chloro-phenylcarbamoyl)-naphthalene-1-sulfonylamino]-piperidine-1-carboxylic acid dimethylamide (F-23)

The title compound was prepared according to the general procedure in Scheme 11, substituting 4-(piperidin-4-ylsulfamoyl)-naphthalene-1-carboxylic acid (2-chloro-phenyl)-amide for 4-(piperidin-4-ylsulfamoyl)-naphthalene-1-carboxylic acid cyclohexylamide, and dimethylcarbamyl chloride for ethyl chloroformate. Wt.: 28 mg (36%). $^1$H NMR (300 MHz, CDCl$_3$) δ 8.69 (d, 1H), 8.60 (d, 1H), 8.47 (d, 1H), 8.35 (d, 1H), 8.20 (s, 1H), 7.82 (d, 1H), 7.72 (m, 2H), 7.43 (m, 2H), 7.17 (m, 1H), 4.83 (d, 1H), 3.46 (m, 2H), 3.31 (m, 1H), 2.71 (s, 6H), 2.70 (m, 2H), 1.67 (m, 2H), 1.35 (m, 2H); LC/MS m/z 516 (M+H)$^+$.

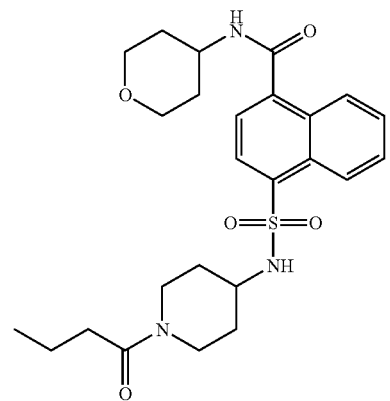

4-(1-Butyryl-piperidin-4-ylsulfamoyl)-naphthalene-1-carboxylic acid (tetrahydro-pyran-4-yl)-amide (F-24)

The title compound was prepared according to the general procedure in Scheme 11, substituting 4-(piperidin-4-ylsulfamoyl)-naphthalene-1-carboxylic acid (tetrahydro-pyran-4-yl)-amide for 4-(piperidin-4-ylsulfamoyl)-naphthalene-1-carboxylic acid cyclohexylamide, and butyryl chloride for ethyl chloroformate. Wt.: 30 mg (19%). $^1$H NMR (300 MHz, CDCl$_3$) δ 8.67 (d, 1H), 8.26 (d, 1H), 8.13 (d, 1H), 7.67 (m, 2H), 7.52 (d, 1H), 6.68 (m, 1H), 5.28 (m, 1H), 4.32 (m, 1H), 4.05 (m, 3H), 3.15 (m, 1H), 2.46 (m, 1H), 2.10 (m, 4H), 1.65 (m, 4H), 1.49 (m, 2H), 1.18 (m, 1H), 9.95 (m, 1H), 0.88 (t, 3H); LC/MS m/z 488 (M+H)$^+$.

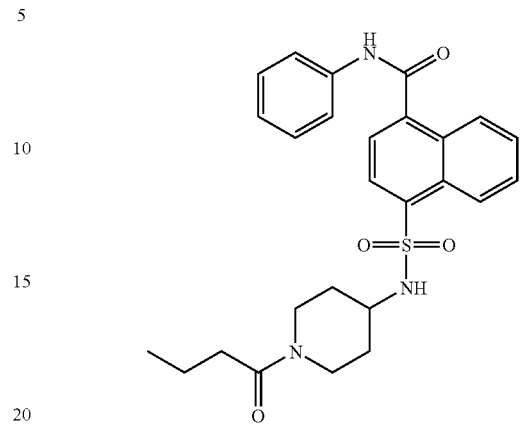

4-(1-Butyryl-piperidin-4-ylsulfamoyl)-naphthalene-1-carboxylic acid phenylamide (F-25)

The title compound was prepared according to the general procedure in Scheme 11, substituting 4-(piperidin-4-ylsulfamoyl)-naphthalene-1-carboxylic acid phenylamide for 4-(piperidin-4-ylsulfamoyl)-naphthalene-1-carboxylic acid cyclohexylamide, and butyryl chloride for ethyl chloroformate. $^1$H NMR (300 MHz, CDCl$_3$) δ 8.87 (s, 1H), 8.67 (m, 1H), 8.36 (m, 2H), 8.25 (d, 1H), 8.08 (m, 2H), 7.87 (d, 1H), 7.78 (d, 1H), 7.70 (m, 1H), 7.63 (m, 1H), 5.50 (d, 1H), 3.95 (m, 1H), 3.55 (m, 1H), 3.26 (m, 1H), 2.88 (m, 1H), 2.48 (m, 1H), 2.13 (m, 2H), 1.66 (m, 2H), 1.48 (m, 3H), 1.19 (m, 1H), 0.88 (t, 3H); LC/MS m/z 480 (M+H)$^+$.

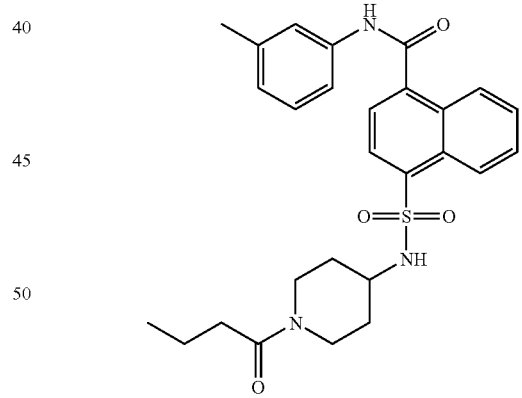

4-(1-Butyryl-piperidin-4-ylsulfamoyl)-naphthalene-1-carboxylic acid m-tolylamide (F-26)

The title compound was prepared according to the general procedure in Scheme 11, substituting 4-(piperidin-4-ylsulfamoyl)-naphthalene-1-carboxylic acid m-tolylamide for 4-(piperidin-4-ylsulfamoyl)-naphthalene-1-carboxylic acid cyclohexylamide, and butyryl chloride for ethyl chloroformate. $^1$H NMR (300 MHz, CDCl$_3$) δ 8.65 (d, 1H), 8.35 (d, 1H), 8.27 (m, 2H), 7.70 (m, 2H), 7.60 (s, 1H), 7.52 (m, 1H), 7.28 (m, 2H), 7.02 (d, 1H), 5.10 (d, 1H), 4.07 (m, 1H), 3.58

(m, 1H), 3.23 (m, 1H), 2.90 (m, 1H), 2.50 (m, 1H), 2.14 (m, 2H), 1.57 (m, 4H), 1.21 (m, 1H), 1.04 (m, 1H), 0.89 (t, 3H); LC/MS m/z 494 (M+H)+.

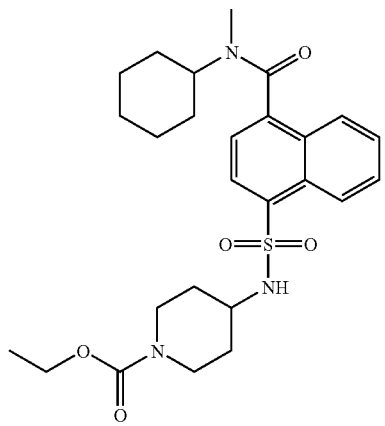

4-[4-(Cyclohexyl-methyl-carbamoyl)-naphthalene-1-sulfonylamino]-piperidine-1-carboxylic acid ethyl ester (F-27)

The title compound was prepared according to the general procedure in Scheme 11, substituting 4-(piperidin-4-ylsulfamoyl)-naphthalene-1-carboxylic acid cyclohexyl-methylamide for 4-(piperidin-4-ylsulfamoyl)-naphthalene-1-carboxylic acid cyclohexylamide. ¹H NMR (300 MHz, CDCl₃) δ 8.61 (d, 1H), 8.29 (d, 1H), 7.88 (m, 1H), 7.65 (m, 2H), 7.42 (m, 1H), 4.83 (m, 1H), 4.72 (m, 1H), 4.05 (q, 2H), 3.88 (m, 2H), 3.25 (m, 1H), 3.05 (m, 1H), 2.80 (s, 3H), 2.74 (m, 1H), 1.90 (m, 4H), 1.54 (m, 8H), 1.20 (t, 3H), 0.85 (m, 2H); LC/MS m/z 502 (M+H)+.

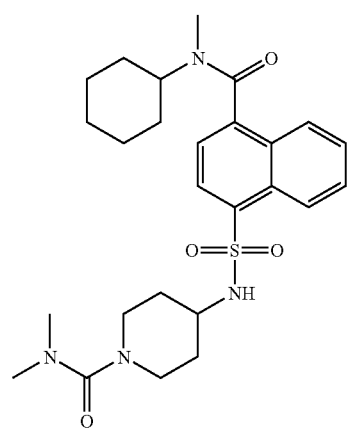

4-[4-(Cyclohexyl-methyl-carbamoyl)-naphthalene-1-sulfonylamino]-piperidine-1-carboxylic acid dimethylamide (F-28)

The title compound was prepared according to the general procedure in Scheme 11, substituting 4-(piperidin-4-ylsulfamoyl)-naphthalene-1-carboxylic acid cyclohexyl-methylamide for 4-(piperidin-4-ylsulfamoyl)-naphthalene-1-carboxylic acid cyclohexylamide, and dimethylcarbamyl chloride for ethyl chloroformate. ¹H NMR (300 MHz, CDCl₃) δ 8.63 (d, 1H), 8.28 (d, 1H), 7.87 (m, 1H), 7.62 (m, 2H), 7.21 (m, 1H), 5.35 (m, 1H), 5.27 (d, 1H), 4.74 (m, 1H), 3.48 (m, 1H), 3.35 (m, 1H), 3.27 (m, 1H), 3.05 (m, 1H), 2.72 (s, 6H), 2.60 (s, 3H), 1.83 (m, 4H), 1.50 (m, 8H), 0.82 (m, 2H); LC/MS m/z 501 (M+H)+.

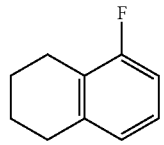

Preparation of
5-fluoro-1,2,3,4-tetrahydro-naphthalene

A modified procedure of Mirsadehgi et al. was used (*J. Org. Chem.* 1989, 54, 3091). Boron trifluoride etherate (30.0 g, 26.8 mL, 0.21 mol) was dissolved and stirred in dimethoxyethane (50 mL) and cooled to 0° C. A solution of tetrahydro-1-naphthylamine (25 g, 0.17 mol) in dimethoxyethane (75 mL) was added dropwise and the solution was allowed to warm slowly to room temperature over the period of 1 hour. The reaction was cooled to 0° C. and a solution of t-butyl nitrite (18.0 g, 20.7 mL, 0.17 mol) in dimethoxyethane (75 mL) was added dropwise. The reaction was stirred for 2 hours at 0° C. upon which a large quantity of material crystallized. The solvent was removed in vacuo and chlorobenzene (200 mL) was charged to the reaction flask. The flask was stirred vigorously and heated to 135° C. (Caution: N₂ evolution) for 1 hour until gas evolution ceased. The flask was cooled to room temperature and the solvent removed in vacuo. Kughelrohr distillation of the residue (1 mm Hg) afforded a yellow liquid. Wt: 14.4 g (56%). ¹H NMR (300 MHz, CDCl₃) δ 7.04 (dd, 1H), 6.83 (m, 2H), 2.75 (m, 4H), 1.80 (m, 4H)

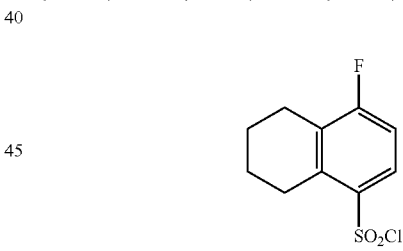

Preparation of
4-fluoro-5,6,7,8-tetrahydro-naphthalene-1-sulfonyl chloride

The compound was prepared according to Scheme 10 in a similar manner to the method for preparing 4-fluoro-naphthalene-1-sulfonyl chloride. Chlorosulfonic acid (2.65 g, 1.5 mL, 22.7 mmol) was stirred in a round-bottom flask cooled by a water bath at room temperature. 5-Fluoro-1,2,3,4-tetrahydro-naphthalene (0.62 g, 4.13 mmol) was added dropwise and the dark mixture was stirred for 30 minutes until gas evolution ceased. The reaction mixture was poured carefully over a mixture of ice (75 g) and dichloromethane (100 mL) and charged to a separatory funnel. The organic layer was separated, washed with brine and dried over MgSO₄. Filtration and concentration in vacuo afforded a tan solid. Wt.: 860 mg (86%). ¹H NMR (300 MHz, CDCl₃) δ 7.97 (dd, 1H), 7.02 (t, 1H), 3.27 (m, 2H), 2.80 (m, 2H), 1.86 (m, 4H).

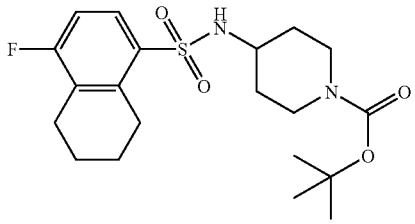

4-(4-Fluoro-5,6,7,8-tetrahydro-naphthalene-1-sulfonylamino)-piperidine-1-carboxylic acid tert-butyl ester 4-Fluoro-5,6,7,8-tetrahydro-naphthalene-1-sulfonyl chloride (860 mg, 3.46 mmol) was dissolved in THF (10 mL). Triethylamine (350 mg, 0.49 mg, 3.46 mmol) was added, followed by 4-amino-piperidine-1-carboxylic acid tert-butyl ester (694 mg, 3.46 mmol). The reaction mixture was stirred overnight at room temperature. The reaction was diluted with dichloromethane (50 mL) and charged to a separatory funnel. The organic layer was washed with water and brine, then dried over MgSO₄. Filtration and concentration in vacuo afforded a yellow foam. Wt.: 1.35 g (95%). ¹H NMR (300 MHz, CDCl₃) δ 7.88 (dd, 1H), 6.95 (t, 1H), 4.47 (d, 1H), 3.93 (m, 2H), 3.27 (m, 1H), 3.11 (m, 2H), 2.76 (m, 4H), 1.81 (m, 6H), 1.44 (s, 9H), 1.32 (m, 2H); LC/MS m/z 411 (M−H)⁻.

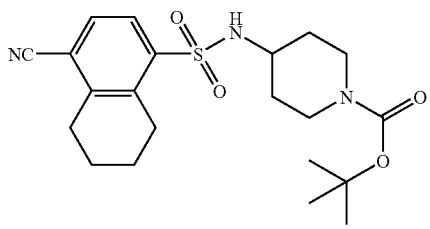

Preparation of 4-(4-Cyano-5,6,7,8-tetrahydro-naphthalene-1-sulfonylamino)-piperidine-1-carboxylic acid tert-butyl ester 4-(4-Fluoro-5,6,7,8-tetrahydro-naphthalene-1-sulfonylamino)-piperidine-1-carboxylic acid tert-butyl ester (970 mg, 2.35 mmol) was dissolved in DMSO (10 mL) and sodium cyanide (577 mg, 11.77 mmol) was added. The mixture was heated overnight at 100° C. An additional 5 equivalents of sodium cyanide (577 mg, 11.77 mmol) were added and the reaction was stirred overnight at 100° C. The reaction was cooled to room temperature and diluted with dichloromethane (100 mL). The mixture was charged to a separatory funnel and extracted three times with water, brine and then dried over MgSO₄. Filtration and concentration in vacuo afforded a brown color foam that was triturated with EtOAc to afford a tan solid. Wt.: 550 mg (56%) ¹H NMR (300 MHz, CDCl₃) δ 7.87 (d, 1H), 7.48 (d, 1H), 4.52 (d, 1H), 3.93 (m, 2H), 3.30 (m, 1H), 3.07 (m, 4H), 2.73 (m, 2H), 1.80 (m, 6H), 1.37 (s, 9H), 1.30 (m, 2H); LC/MS m/z 418 (M−H)⁻.

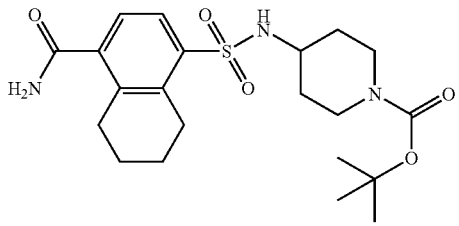

4-(4-Carbamoyl-5,6,7,8-tetrahydro-naphthalene-1-sulfonylamino)-piperidine-1-carboxylic acid tert-butyl ester (F-29) and 4-(4-carboxy-5,6,7,8-tetrahydro-naphthalene-1-sulfonylamino)-piperidine-1-carboxylic acid tert-butyl ester 4-(4-Cyano-5,6,7,8-tetrahydro-naphthalene-1-sulfonylamino)-piperidine-1-carboxylic acid tert-butyl ester (545 mg, 1.30 mmol) was dissolved in a mixture of isopropanol (2 ml) and 2N KOH (4 mL). The reaction was stirred for 5 days at 80° C. The isopropanol was removed in vacuo and the residue was diluted with H₂O (20 mL). The mixture was charged to a separatory funnel and extracted three times with dichloromethane. The combined organic layers were washed with brine, dried over MgSO₄, and concentrated in vacuo to a white solid that was triturated with dichloromethane to afford 4-(4-carbamoyl-5,6,7,8-tetrahydro-naphthalene-1-sulfonylamino)-piperidine-1-carboxylic acid tert-butyl ester F-29 as a white solid. Wt.: 340 mg (60%). ¹H NMR (300 MHz, d⁶-DMSO) δ 7.81 (m, 2H), 7.72 (d, 1H), 7.52 (s, 1H), 7.23 (d, 1H), 3.72 (m, 2H), 3.09 (m, 3H), 2.81 (m, 2H), 2.71 (m, 2H), 1.70 (m, 4H), 1.55 (m, 2H), 1.36 (s, 9H), 1.25 (m, 2H); LC/MS m/z 436 (M−H)⁻.)⁻. The aqueous extract was acidified to pH 2 with 1N HCl and extracted twice with dichloromethane. The combined organic extracts were washed with brine and dried over MgSO₄. Filtration and concentration in vacuo afforded 4-(4-carboxy-5,6,7,8-tetrahydro-naphthalene-1-sulfonylamino)-piperidine-1-carboxylic acid tert-butyl ester as a white solid. Wt.: 76 mg (13%). ¹H NMR (300 MHz, d⁶-DMSO) δ 7.72 (d, 1H), 7.33 (s, 1H), 7.23 (d, 1H), 3.72 (m, 2H), 3.09 (m, 3H), 2.81 (m, 2H), 2.71 (m, 2H), 1.70 (m, 4H), 1.55 (m, 2H), 1.36 (s, 9H), 1.25 (m, 2H); LC/MS m/z 437 (M−H)⁻.

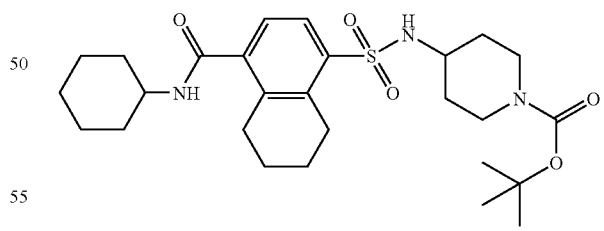

4-[4-(3-Dimethylamino-propylcarbamoyl)-5,6,7,8-tetrahydro-naphthalene-1-sulfonylamino]-piperidine-1-carboxylic acid tert-butyl ester (F-30) and 4-(4-Cyclohexylcarbamoyl-5,6,7,8-tetrahydro-naphthalene-1-sulfonylamino)-piperidine-1-carboxylic acid tert-butyl ester (F-31)

4-(4-Carboxy-5,6,7,8-tetrahydro-naphthalene-1-sulfonylamino)-piperidine-1-carboxylic acid tert-butyl ester (76 mg, 0.17 mmol) was dissolved in dichloromethane (2 mL). 1-[3-(Dimethylamino)propyl]-3-ethylcarbodiimide hydrochloride (32 mg, 0.17 mmol) was added followed by cyclohexylamine (21 mg, 24 ml, 0.21 mmol). The reaction was stirred overnight at room temperature. The reaction was diluted with dichloromethane (15 ml0 and charged to a separatory funnel. The organic layer was washed twice with water, brine and dried over MgSO$_4$. Filtration and concentration in vacuo afforded a clear oil that was subjected to flash column chromatography (96:4 dichloromethane: methanol). Concentration of the more polar fractions afforded 4-[4-(3-dimethylamino-propylcarbamoyl)-5,6,7,8-tetrahydro-naphthalene-1-sulfonylamino]-piperidine-1-carboxylic acid tert-butyl ester (F-30) as a yellow solid. Wt.: 40 mg, (45%). $^1$H NMR (300 MHz, CDCl$_3$) δ 9.05 (s, 1H), 7.98 (d, 1H), 7.31 (d, 1H), 5.02 (d, 1H), 3.96 (m, 3H), 3.37 (m, 2H), 3.20 (m, 2H), 2.83 (m, 4H), 2.70 (s, 6H), 2.14 (m, 2H), 1.97 (m, 2H), 1.83 (m, 4H), 1.42 (s, 9H), 1.32 (m, 4H); LC/MS m/z 523 (M+H)$^+$. Concentration of the less polar fractions afforded 4-(4-cyclohexylcarbamoyl-5,6,7,8-tetrahydro-naphthalene-1-sulfonylamino)-piperidine-1-carboxylic acid tert-butyl ester (F-31) as a clear oil. Wt.: 28 mg (32%) $^1$H NMR (300 MHz, CDCl$_3$) δ 7.87 (d, 1H), 7.20 (d, 1H), 5.73 (d, 1H), 4.38 (d, 1H), 3.91 (m, 3H), 3.22 (m, 1H), 3.12 (m, 2H), 2.89 (m, 2H), 2.73 (m, 2H), 2.03 (m, 2H), 1.78 (m, 8H), 1.74 (m, 2H), 1.43 (s, 9H), 1.27 (m, 6H); LC/MS m/z 518 (M−H)$^{31}$.

4-{4-[(2-Methyl-benzoylamino)-methyl]-naphthalene-1-sulfonylamino}-piperidine-1-carboxylic acid ethyl ester (G-1)

4-(4-cyano-naphthalene-1-sulfonylamino)-piperidine-1-carboxylic acid ethyl ester (31) was prepared according to the procedure in Scheme 11, substituting for 4-(4-fluoro-naphthalene-1-sulfonylamino)-piperidine-1-carboxylic acid ethyl ester for 4-(4-fluoro-naphthalene-1-sulfonylamino)-piperidine-1-carboxylic acid tert-butyl ester. To a 0° C. solution of 4-(4-cyano-naphthalene-1-sulfonylamino)-piperidine-1-carboxylic acid ethyl ester (31) (615 mg, 1.59 mmol) in EtOH (10 mL) was added cobalt chloride (207 mg, 1.59 mmol). After stirring at 0° C. for 5 min under argon, sodium borohydride (181 mg, 4.77 mmol) was added into the reaction mixture. The resultant solution was stirred at 0° C. for 30 minutes, and then warmed up to room temperature. After stirring for another 30 min., the resultant mixture was quenched with water. The aqueous layer was extracted with CH$_2$Cl$_2$. The organic extracts were combined, washed with brine and dried over MgSO$_4$. The solution was filtered and concentrated in vacuo to give the crude product. The crude material was purified by Flash column chromatography (CH$_2$Cl$_2$:MeOH) to provide 268 mg (43.0% yield) of 4-(4-aminomethyl-naphthalene-1-sulfonylamino)-piperidine-1-carboxylic acid ethyl ester (32). LCMS showed m/z: 392 (M+H)$^+$.

To a solution of 4-(4-aminomethyl-naphthalene-1-sulfonylamino)-piperidine-1-carboxylic acid ethyl ester (32) (60 mg, 0.153 mmol) in DCE (5 mL), was added pyridine (62 ul, 0.765 mmol), 2-methyl-benzoyl chloride (22 ul, 0.168 mmol) and dimethyl-pyridin-4-yl-amine (4 mg, 0.031 mmol). After stirring at 70° C. overnight, the resultant solution was concentrated in vacuo to give the crude product. Purification using reverse phase HPLC provided the title compound (G-1). LCMS showed m/z: 510 (M+H)$^+$.

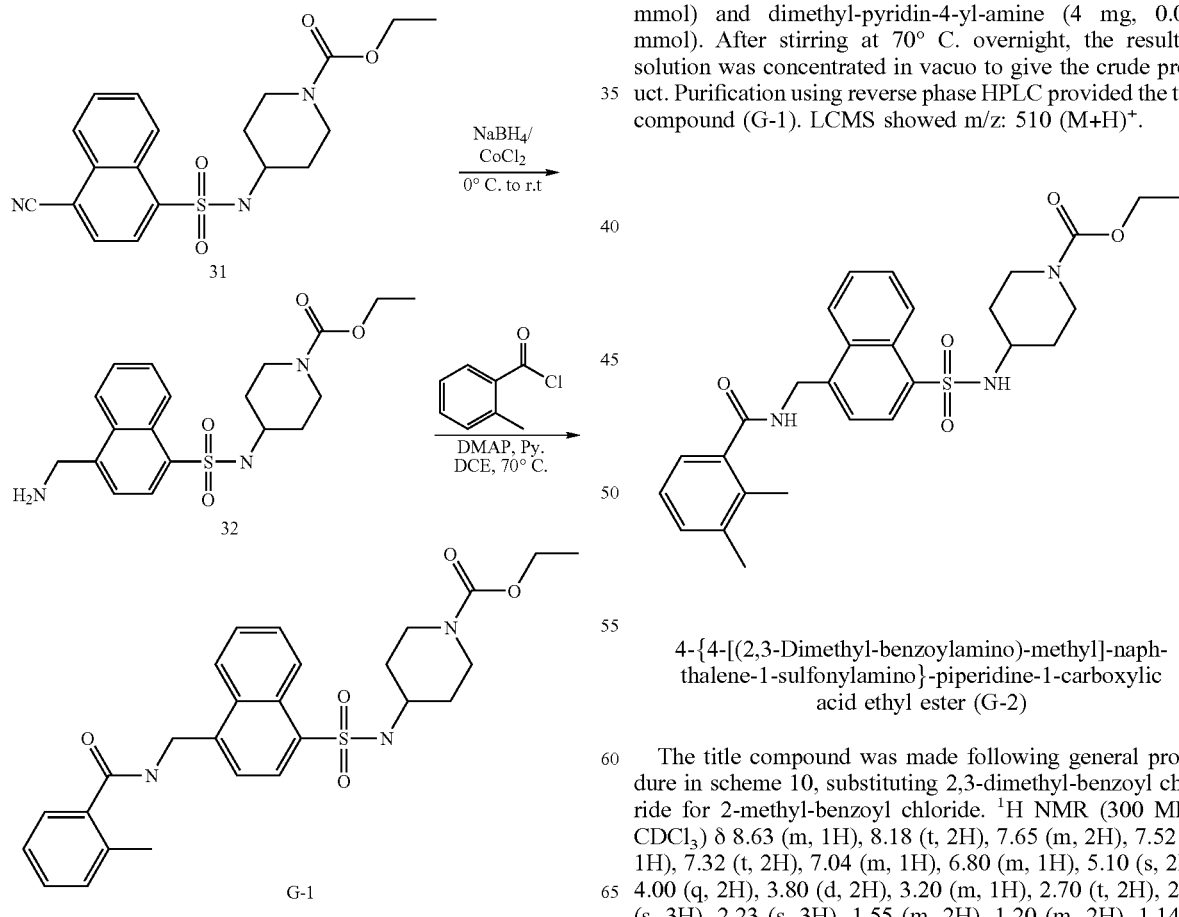

4-{4-[(2,3-Dimethyl-benzoylamino)-methyl]-naphthalene-1-sulfonylamino}-piperidine-1-carboxylic acid ethyl ester (G-2)

The title compound was made following general procedure in scheme 10, substituting 2,3-dimethyl-benzoyl chloride for 2-methyl-benzoyl chloride. $^1$H NMR (300 MHz, CDCl$_3$) δ 8.63 (m, 1H), 8.18 (t, 2H), 7.65 (m, 2H), 7.52 (d, 1H), 7.32 (t, 2H), 7.04 (m, 1H), 6.80 (m, 1H), 5.10 (s, 2H), 4.00 (q, 2H), 3.80 (d, 2H), 3.20 (m, 1H), 2.70 (t, 2H), 2.26 (s, 3H), 2.23 (s, 3H), 1.55 (m, 2H), 1.20 (m, 2H), 1.14 (t, 3H); LC/MS m/z 524 (M+H)$^+$

Scheme 13

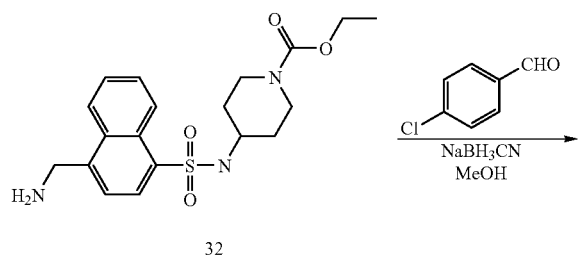

4-{4-[(4-Chloro-benzylamino)-methyl]-naphthalene-1-sulfonylamino}-piperidine-1-carboxylic acid ethyl ester (G-7)

4-(4-Aminomethyl-naphthalene-1-sulfonylamino)-piperidine-1-carboxylic acid ethyl ester (32) was prepared according to the procedure in Scheme 12. To a 25° C. solution of 4-(4-aminomethyl-naphthalene-1-sulfonylamino)-piperidine-1-carboxylic acid ethyl ester (32) (62 mg, 0.159 mmol) in MeOH (4 mL) was added 4-chloro-benzaldehyde (45 mg, 0.318 mmol) and sodium cyanoborohydride (50 mg, 0.795 mmol). After stirring for 2 h at 25° C., the solution was concentrated in vacuo to give a solid. The resultant solid was purified by reverse phase HPLC providing 4-{4-[(4-chloro-benzylamino)-methyl]-naphthalene-1-sulfonylamino}-piperidine-1-carboxylic acid ethyl ester formate salt (G-7). $^1$H NMR (300 MHz, MeOD) δ 8.76 (m, 1H), 8.38 (s, br, 1H), 8.24 (d, 1H), 8.18 (m, 1H), 7.51 (m, 3H), 7.44 (m, 4H), 4.52 (s, 2H), 4.12 (s, 2H), 4.04 (q, 2H), 3.60 (d, 2H), 3.40 (m, 1H), 2.72 (m, 2H), 1.50 (m, 2H), 1.25 (m, 2H), 1.18 (t, 3H); LC/MS m/z 516 (M+H)$^+$.

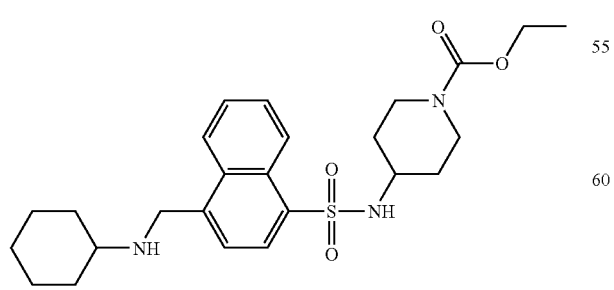

4-(4-Cyclohexylaminomethyl-naphthalene-1-sulfonylamino)-piperidine-1-carboxylic acid ethyl ester (G-8)

The title compound was prepared as its formate salt following the general procedure in Scheme 13, substituting cyclohexanone for 4-chloro-benzaldehyde. $^1$H NMR (300 MHz, CDCl$_3$) δ 8.54 (d, 1H), 8.25 (s, br, 1H), 8.17 (s, 1H), 8.04 (t, 2H), 7.70 (d, 1H), 7.57 (m, 2H), 6.15 (d, 1H), 4.48 (s, 2H), 4.04 (q, 2H), 3.80 (d, 2H), 3.25 (s, br, 1H), 3.00 (t, 1H), 2.70 (s, br, 1H), 2.60 (s, 1H), 2.10 (d, 2H), 1.80 (d, 2H), 1.50 (m, 5H), 1.20 (m, 7H); LC/MS m/z 475 (M+H)$^+$

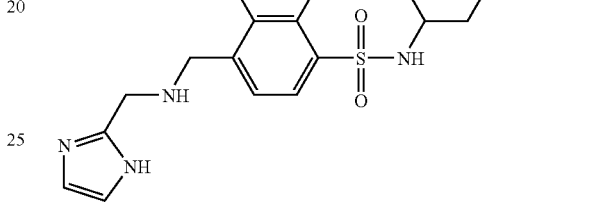

4-(4-{[(1H-Imidazol-2-ylmethyl)-amino]-methyl}-naphthalene-1-sulfonylamino)-piperidine-1-carboxylic acid ethyl ester (G-9)

The title compound was prepared as its formate salt following the general procedure in Scheme 13, substituting 1H-imidazole-2-carbaldehyde for 4-chloro-benzaldehyde. $^1$H NMR (300 MHz, MeOD) δ 8.72 (m, 1H), 8.40 (s, br, 1H), 8.22 (m, 2H), 7.67 (m, 3H), 7.09 (s, 2H), 4.32 (s, 2H), 4.04 (m, 4H), 3.80 (d, 2H), 3.20 (m, 1H), 2.75 (m, 2H), 1.50 (m, 2H), 1.25 (m, 2H), 1.18 (t, 3H); LC/MS m/z 472 (M+H)$^+$

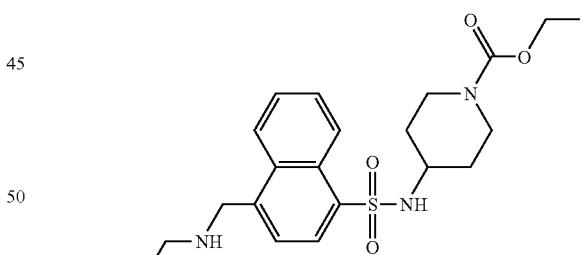

4-{4-[(4-Methoxy-benzylamino)-methyl]-naphthalene-1-sulfonylamino}-piperidine-1-carboxylic acid ethyl ester (G-10)

The title compound was prepared as its formate salt following the general procedure in Scheme 13, substituting 4-methoxy-benzaldehyde for 4-chloro-benzaldehyde. ¹H NMR (300 MHz, MeOD) δ 8.73 (d, 1H), 8.22 (d, 1H), 8.14 (d, 1H), 7.66 (m, 3H), 7.33 (d, 2H), 6.92 (d, 2H), 4.30 (s, 2H), 4.12 (s, 2H), 4.04 (q, 2H), 3.90 (s, 2H), 3.80 (m, 5H), 3.18 (m, 1H), 2.75 (m, 2H), 1.50 (m, 2H), 1.25 (m, 2H), 1.18 (t, 3H); LC/MS m/z 512 (M+H)⁺

NMR (300 MHz, MeOD) δ 8.72 (dd, 1H), 8.57 (s, 1H), 8.44 (d, 1H), 8.22 (m, 2H), 7.90 (d, 1H), 7.64 (m, 3H), 7.42 (dd, 1H), 4.30 (s, 2H), 4.05 (q, 2H), 3.95 (s, 2H), 3.68 (d, 2H), 3.18 (m, 1H), 2.75 (m, 2H), 1.50 (m, 2H), 1.25 (m, 2H), 1.18 (t, 3H); LC/MS m/z 483 (M+H)⁺

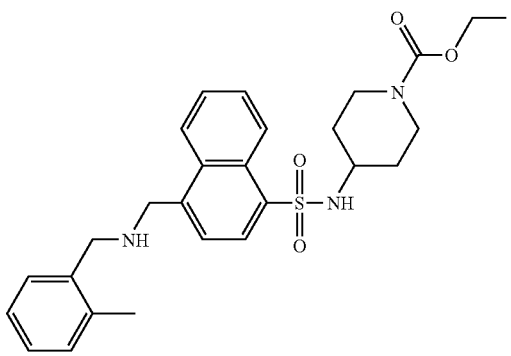

4-{4-[(2-Methyl-benzylamino)-methyl]-naphthalene-1-sulfonylamino}-piperidine-1-carboxylic acid ethyl ester (G-11)

The title compound was prepared as its formate salt following the general procedure in Scheme 13, substituting 2-methyl-benzaldehyde for 4-chloro-benzaldehyde. ¹H NMR (300 MHz, MeOD) δ 8.76 (d, 1H), 8.22 (m, 2H), 7.70 (m, 3H), 7.38 (m, 1H), 7.21 (m, 3H), 4.51 (s, 2H), 4.05 (m, 4H), 3.80 (d, 2H), 3.20 (m, 1H), 2.75 (m, 2H), 2.30 (s, 3H), 1.50 (m, 2H), 1.25 (m, 2H), 1.18 (t, 3H); LC/MS m/z 496 (M+H)⁺

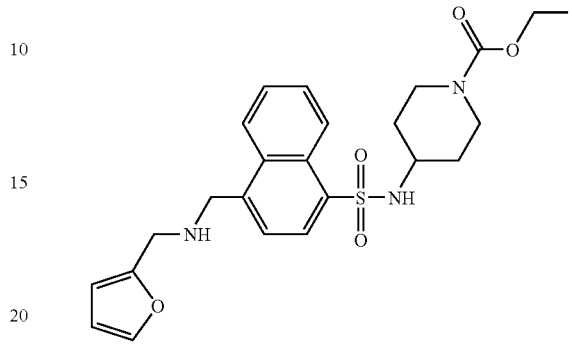

4-(4-{[(Furan-2-ylmethyl)-amino]-methyl}-naphthalene-1-sulfonylamino)-piperidine-1-carboxylic acid ethyl ester (G-13)

The title compound was prepared as its formate salt following the general procedure in Scheme 13, substituting furan-2-carbaldehyde for 4-chloro-benzaldehyde. ¹H NMR (300 MHz, MeOD) δ 8.72 (dd, 1H), 8.18 (m, 2H), 7.65 (m, 3H), 7.49 (m, 1H), 6.39 (m, 1H), 6.34 (m, 1H), 4.28 (s, 2H), 4.05 (q, 2H), 3.92 (s, 2H), 3.80 (d, 2H), 3.18 (m, 1H), 2.75 (m, 2H), 1.50 (m, 2H), 1.25 (m, 2H), 1.18 (t, 3H); LC/MS m/z 472 (M+H)⁺

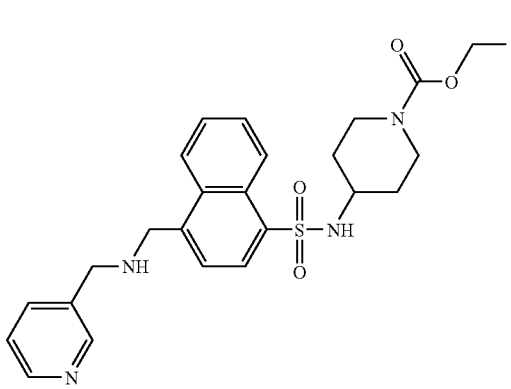

4-(4-{[(Pyridin-3-ylmethyl)-amino]-methyl}-naphthalene-1-sulfonylamino)-piperidine-1-carboxylic acid ethyl ester (G-12)

The title compound was prepared as its formate salt following the general procedure in Scheme 13, substituting pyridine-3-carbaldehyde for 4-chloro-benzaldehyde. ¹H

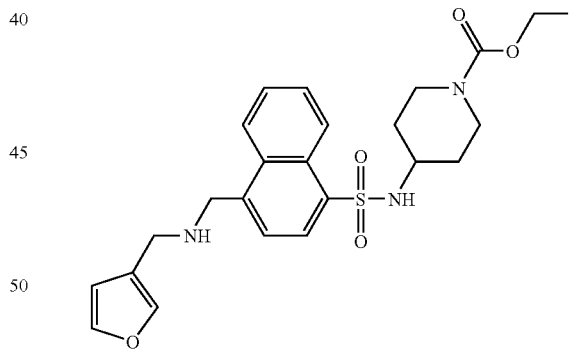

4-(4-{[(Furan-3-ylmethyl)-amino]-methyl}-naphthalene-1-sulfonylamino)-piperidine-1-carboxylic acid ethyl ester (G-14)

The title compound was prepared as its formate salt following the general procedure in Scheme 13, substituting furan-3-carbaldehyde for 4-chloro-benzaldehyde. ¹H NMR (300 MHz, MeOD) δ 8.76 (m, 1H), 8.22 (m, 2H), 7.64 (m, 5H), 6.56 (m, 1H), 4.42 (s, 2H), 4.05 (q, 2H), 3.95 (s, 2H), 3.80 (d, 2H), 3.20 (m, 1H), 2.75 (m, 2H), 1.50 (m, 2H), 1.25 (m, 2H), 1.18 (t, 3H); LC/MS m/z 472 (M+H)⁺

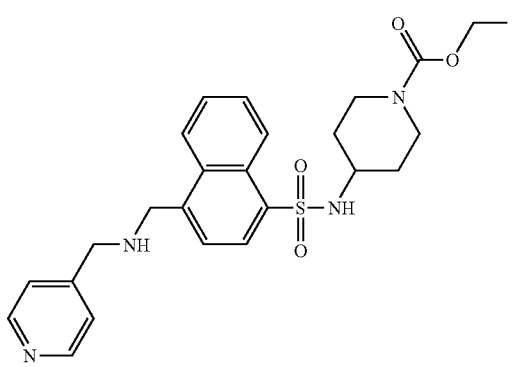

4-(4-{[(Pyridin-4-ylmethyl)-amino]-methyl}-naphthalene-1-sulfonylamino)-piperidine-1-carboxylic acid ethyl ester (G-15)

The title compound was prepared as its formate salt following the general procedure in Scheme 13, substituting pyridine-4-carbaldehyde for 4-chloro-benzaldehyde. $^1$H NMR (300 MHz, MeOD) δ 8.70 (m, 1H), 8.54 (s, 1H), 8.24 (m, 4H), 7.68 (m, 2H), 7.45 (m, 1H), 7.14 (m, 1H), 4.70 (m, 2H), 4.55 (m, 2H), 4.05 (q, 2H), 3.80 (d, 2H), 3.18 (m, 2.75 (m, 2H), 1.50 (m, 2H), 1.25 (m, 2H), 1.18 (t, 3H); LC/MS m/z 483 (M+H)$^+$

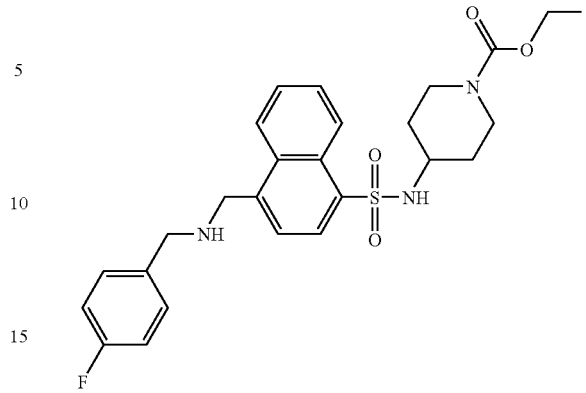

4-{4-[(4-Fluoro-benzylamino)-methyl]-naphthalene-1-sulfonylamino}-piperidine-1-carboxylic acid ethyl ester (G-17)

The title compound was prepared as its formate salt following the general procedure in Scheme 13, substituting 4-fluoro-benzaldehyde for 4-chloro-benzaldehyde. $^1$H NMR (300 MHz, MeOD) δ 8.72 (d, 1H), 8.19 (m, 2H), 7.66 (m, 3H), 7.40 (m, 2H), 7.06 (m, 2H), 4.25 (s, 2H), 4.05 (q, 2H), 3.85 (s, 2H), 3.78 (d, 2H), 3.18 (m, 1H), 2.75 (m, 2H), 1.50 (m, 2H), 1.25 (m, 2H), 1.17 (t, 3H); LC/MS m/z 500 (M+H)$^+$

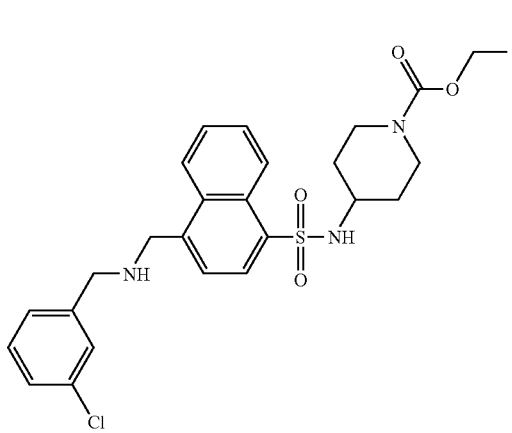

4-{4-[(3-Chloro-benzylamino)-methyl]-naphthalene-1-sulfonylamino}-piperidine-1-carboxylic acid ethyl ester (G-16)

The title compound was prepared as its formate salt following the general procedure in Scheme 13, substituting 3-chloro-benzaldehyde for 4-chloro-benzaldehyde. $^1$H NMR (300 MHz, MeOD) δ 8.72 (d, 1H), 8.20 (m, 2H), 7.66 (m, 3H), 7.45 (s, 1H), 7.30 (m, 3H), 4.25 (s, 2H), 4.05 (q, 2H), 3.90 (s, 2H), 3.78 (d, 2H), 3.20 (m, 1H), 2.75 (m, 2H), 1.50 (m, 2H), 1.25 (m, 2H), 1.17 (t, 3H); LC/MS m/z 516 (M+H)$^+$

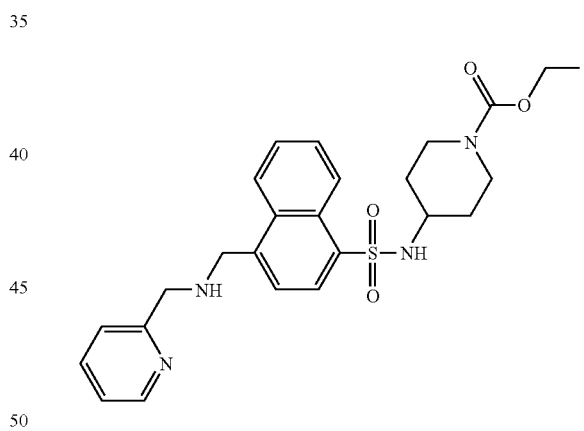

4-(4-{[(Pyridin-2-ylmethyl)-amino]-methyl}-naphthalene-1-sulfonylamino)-piperidine-1-carboxylic acid ethyl ester (G-18)

The title compound was prepared as its formate salt following the general procedure in Scheme 13, substituting pyridine-2-carbaldehyde for 4-chloro-benzaldehyde. $^1$H NMR (300 MHz, MeOD) δ 8.72 (d, 1H), 8.52 (m, 1H), 8.24 (m, 2H), 7.80 (t, 1H), 7.67 (m, 3H), 7.52 (d, 1H), 7.30 (t, 1H), 4.30 (s, 2H), 4.00 (m, 4H), 3.80 (d, 2H), 3.18 (m, 1H), 2.75 (m, 2H), 1.50 (m, 2H), 1.25 (m, 2H), 1.17 (t, 3H); LC/MS m/z 483 (M+H)$^+$

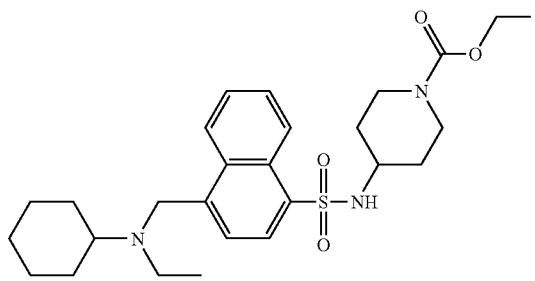

4-{4-[(Cyclohexyl-ethyl-amino)-methyl]-naphthalene-1-sulfonylamino}-piperidine-1-carboxylic acid ethyl ester (G-20)

The title compound was prepared as its formate salt following the general procedure in Scheme 13, substituting acetaldehyde for 4-chloro-benzaldehyde, and substituting 4-(4-cyclohexylaminomethyl-naphthalene-1-sulfonylamino)-piperidine-1-carboxylic acid ethyl ester (G-8) for 4-(4-aminomethyl-naphthalene-1-sulfonylamino)-piperidine-1-carboxylic acid ethyl ester. $^1$H NMR (300 MHz, MeOD) δ 8.79 (m, 1H), 8.36 (m, 2H), 8.27 (dd, 1H), 7.77 (m, 3H), 4.62 (s, 2H), 4.05 (q, 2H), 3.80 (d, 2H), 3.25 (m, 1H), 3.05 (m, 3H), 2.75 (m, 2H), 2.10 (d, 2H), 1.80 (d, 2H), 1.65 (m, 3H), 1.48 (m, 2H), 1.22 (m, 11H); LC/MS m/z 502 (M+H)$^+$

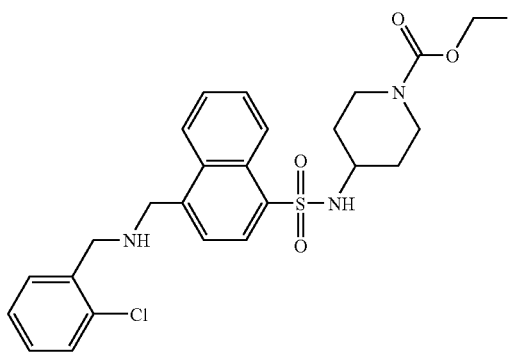

4-{4-[(2-Chloro-benzylamino)-methyl]-naphthalene-1-sulfonylamino}-piperidine-1-carboxylic acid ethyl ester (G-21)

The title compound was prepared as its formate salt following the general procedure in Scheme 13, substituting 2-chloro-benzaldehyde for 4-chloro-benzaldehyde. $^1$H NMR (300 MHz, MeOD) δ 8.72 (d, 1H), 8.15 (d, 2H), 7.66 (m, 3H), 7.52 (m, 1H), 7.38 (m, 1H), 7.28 (m, 2H), 4.30 (s, 2H), 4.00 (m, 4H), 3.78 (d, 2H), 3.18 (m, 1H), 2.72 (m, 2H), 1.50 (m, 2H), 1.25 (m, 2H), 1.17 (t, 3H); LC/MS m/z 516 (M+H)$^+$

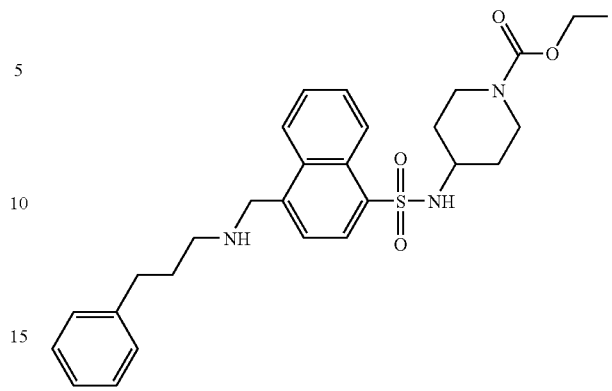

4-{4-[(3-Phenyl-propylamino)-methyl]-naphthalene-1-sulfonylamino}-piperidine-1-carboxylic acid ethyl ester (G-23)

The title compound was prepared as its formate salt following the general procedure in Scheme 13, substituting 3-phenyl-propionaldehyde for 4-chloro-benzaldehyde. $^1$H NMR (300 MHz, MeOD) δ 8.74 (m, 1H), 8.25 (m, 1H), 8.20 (d, 1H), 7.70 (m, 2H), 7.59 (m, 1H), 7.19 (m, 5H), 4.33 (s, 2H), 4.05 (q, 2H), 3.78 (d, 2H), 3.18 (m, 1H), 2.73 (m, 6H), 1.90 (m, 2H), 1.48 (m, 2H), 1.23 (m, 2H), 1.17 (t, 3H); LC/MS m/z 510 (M+H)$^+$

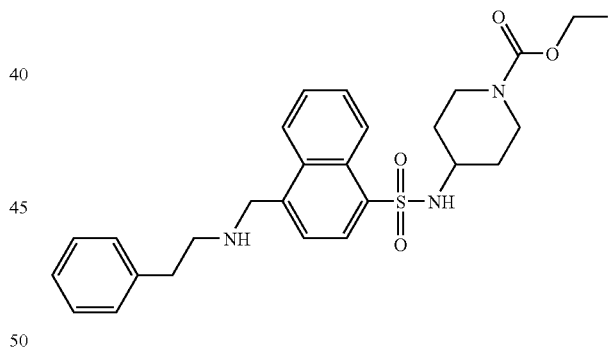

4-[4-(Phenethylamino-methyl)-naphthalene-1-sulfonylamino]-piperidine-1-carboxylic acid ethyl ester (G-24)

The title compound was prepared as its formate salt following the general procedure in Scheme 13, substituting phenyl-acetaldehyde for 4-chloro-benzaldehyde. $^1$H NMR (300 MHz, MeOD) δ 8.74 (m, 1H), 8.19 (m, 2H), 7.67 (m, 2H), 7.59 (m, 1H), 7.22 (m, 5H), 4.35 (s, 2H), 4.05 (q, 2H), 3.78 (d, 2H), 3.18 (m, 1H), 2.92 (m, 4H), 2.62 (m, 2H), 1.90 (m, 2H), 1.48 (m, 2H), 1.25 (m, 2H), 1.17 (t, 3H); LC/MS m/z 496 (M+H)$^+$

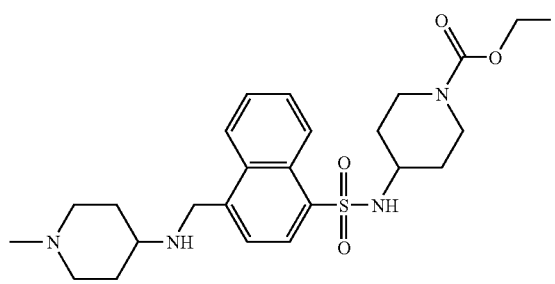

4-{4-[(1-Methyl-piperidin-4-ylamino)-methyl]-naphthalene-1-sulfonylamino}-piperidine-1-carboxylic acid ethyl ester (G-25)

The title compound was prepared as its formate salt following the general procedure in Scheme 13, substituting 1-methyl-piperidin-4-one for 4-chloro-benzaldehyde. $^1$H NMR (300 MHz, CDCl$_3$) δ 8.73 (m, 1H), 8.45 (s, 1H), 8.28 (m, 1H), 8.22 (d, 1H), 7.70 (m, 3H), 4.40 (s, 2H), 4.05 (q, 2H), 3.80 (d, 2H), 3.45 (d, 2H), 3.20 (m, 1H), 3.00 (m, 3H), 2.78 (s, 3H), 2.72 (m, 2H), 2.25 (d, 2H), 1.80 (m, 2H), 1.50 (d, 2H), 1.25 (m, 2H), 1.17 (t, 3H); LC/MS m/z 487 (M+H)$^+$

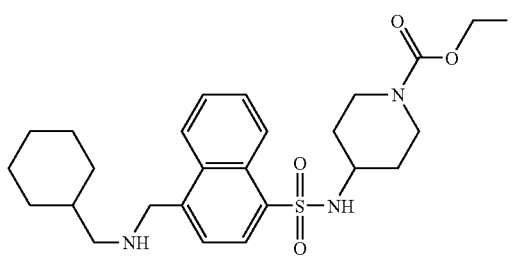

4-{4-[(Cyclohexylmethyl-amino)-methyl]-naphthalene-1-sulfonylamino}-piperidine-1-carboxylic acid ethyl ester (G-27)

The title compound was prepared as its formate salt following the general procedure in Scheme 13, substituting cyclohexanecarbaldehyde for 4-chloro-benzaldehyde. $^1$H NMR (300 MHz, MeOD) δ 8.76 (m, 1H), 8.52 (s, 1H), 8.26 (m, 2H), 7.72 (m, 3H), 4.49 (s, 2H), 4.05 (q, 2H), 3.80 (d, 2H), 3.20 (m, 1H), 2.75 (m, 4H), 1.75 (m, 6H), 1.50 (d, 2H), 1.25 (m, 5H), 1.18 (t, 3H), 1.00 (m, 2H); LC/MS m/z 488 (M+H)$^+$

Scheme 14

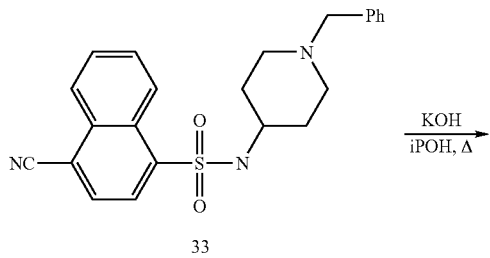

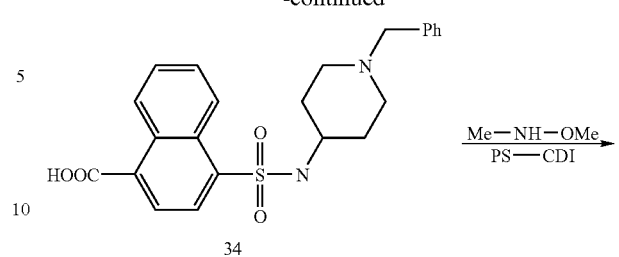

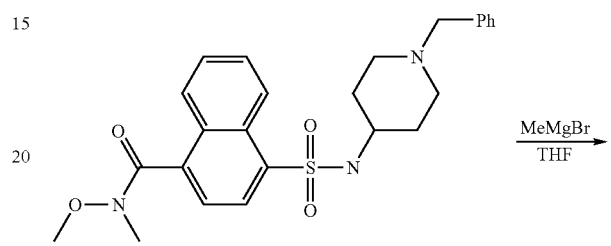

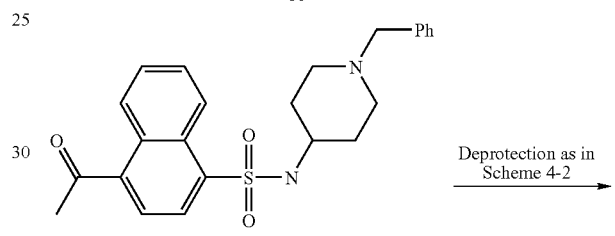

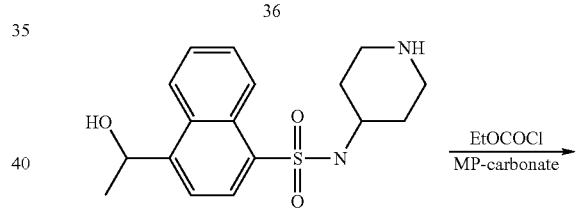

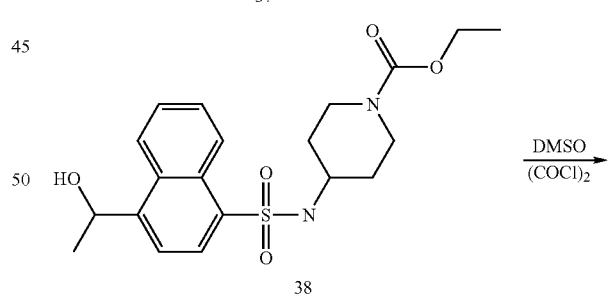

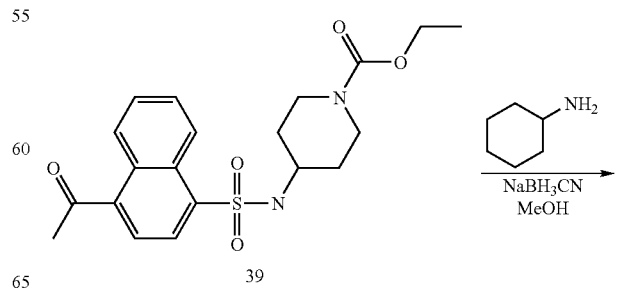

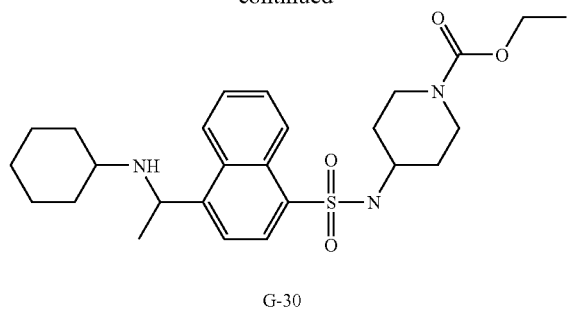

G-30

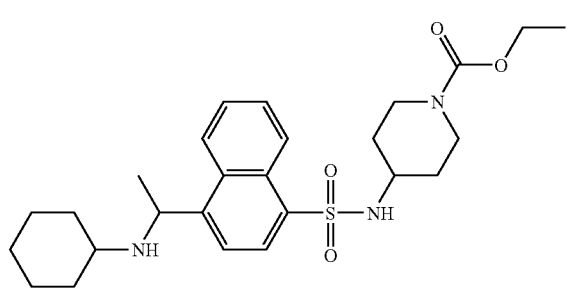

4-[4-(1-Cyclohexylamino-ethyl)-naphthalene-1-sulfonylamino]-piperidine-1-carboxylic acid ethyl ester
(G-30)

4-Cyano-naphthalene-1-sulfonic acid (1-benzyl-piperidin-4-yl)-amide (33) was prepared according to the general procedure in Scheme 11, substituting 1-benzyl-piperidin-4-ylamine piperidin-4-ylamine for 4-amino-piperidine-1-carboxylic acid tert-butyl ester. To a solution of 4-cyano-naphthalene-1-sulfonic acid (1-benzyl-piperidin-4-yl)-amide 33 (3.0 g, 7.43 mmol) in $H_2O$ (70 mL) was added KOH (4.2 g, 75 mmol). After stirring at 100° C. overnight, the resultant mixture became a clear solution. The aqueous layer was washed with $CH_2Cl_2$ twice and acidified to pH 4 by adding hydrochloric acid. After filtration, the resultant solid was dried to give 1.8 g of crude 4-(1-benzyl-piperidin-4-ylsulfamoyl)-naphthalene-1-carboxylic acid 34 in 57% yield. LCMS showed m/z: 425 (M+H)$^+$. This material was used without further purification.

To a solution of 4-(1-benzyl-piperidin-4-ylsulfamoyl)-naphthalene-1-carboxylic acid 34 (212 mg, 0.5 mmol) in DCE (5 mL), was added O,N-dimethyl-hydroxylamine hydrochloride (59 ul, 0.6 mmol), PS-carbodiimide (1.9 g, 2.5 mmol), triethyl amine (140 uL, 1 mmol) and HOAt (102 mg, 0.75 mmol). After stirring at 50° C. overnight, the resultant solution was filtered and concentrated in vacuo to give the crude product 4-(1-benzyl-piperidin-4-ylsulfamoyl)-naphthalene-1-carboxylic acid methoxy-methyl-amide 35. LCMS showed m/z: 468 (M+H)$^+$. This material was used without further purification.

To a 0° C. solution of 4-(1-benzyl-piperidin-4-ylsulfamoyl)-naphthalene-1-carboxylic acid methoxy-methyl-amide 35 (200 mg, 0.43 mmol) in THF (5 mL) was slowly added methylmagnesium bromide (5.71 mL, 17.1 mmol, 1M THF solution). After stirring at 25° C. for 4 h, the resultant mixture was quenched with saturated ammonium chloride solution. The aqueous layer was extracted with $CH_2Cl_2$. The organic extracts were combined, washed with brine and dried over $MgSO_4$. The solution was filtered and concentrated in vacuo to give the crude product. The crude material was purified by Flash column chromatography (hexane/EtOAc) to provide 118 mg of 4-acetyl-naphthalene-1-sulfonic acid (1-benzyl-piperidin-4-yl)-amide 36 in 56% overall yield (for two steps).LCMS showed m/z: 423 (M+H)$^+$.

Following the general procedure in Scheme 4-2, deprotection of 4-acetyl-naphthalene-1-sulfonic acid (1-benzyl-piperidin-4-yl)-amide 36 occurred concomitant with reduction of the ketone group to afford 4-(1-hydroxy-ethyl)-naphthalene-1-sulfonic acid piperidin-4-ylamide acetic acid salt 37 as product. LCMS showed m/z: 334 (M+H)$^+$. This material was used without further purification.

To a solution of 4-(1-hydroxy-ethyl)-naphthalene-1-sulfonic acid piperidin-4-ylamide acetic acid salt 37 (290 mg, 0.74 mmol) in MeOH (10 mL) was added MP-Carbonate (1.45 g, 3.69 mmol, 2.54 mmol/g). After shaking at 25° C. for 1 h, the solution was filtered. To the resultant solution was added ethyl chloroformate (120 mg, 1.11 mmol). After stirred for another 2 h at 25° C., the solution was concentrated in vacuo to give a solid. The crude material was purified by Flash column chromatography ($CH_2Cl_2$:MeOH) to provide 4-[4-(1-hydroxy-ethyl)-naphthalene-1-sulfonylamino]-piperidine-1-carboxylic acid ethyl ester 38. LCMS showed m/z: 407 (M+H)$^+$.

To a −78° C. solution of oxalyl dichloride (85 mg, 0.665 mmol) in $CH_2Cl_2$ (10 mL) was added DMSO (104 mg, 1.33 mmol). After stirred at −78° C. for 10 min, a solution of 4-[4-(1-hydroxy-ethyl)-naphthalene-1-sulfonylamino]-piperidine-1-carboxylic acid ethyl ester 38 (180 mg, 0.443 mmol) in $CH_2Cl_2$ was added into the mixture by dropwise. The resultant mixture was stirred at −78° C. for another 30 min, then was added triethyl amine (224 mg, 2.22 mmol). The reaction mixture was warmed up to room temperature and stirred for 2 h. The resultant mixture was quenched with saturated ammonium chloride solution and the aqueous layer was extracted with $CH_2Cl_2$. The organic extracts were combined, washed with brine and dried over $MgSO_4$. The solution was filtered and concentrated in vacuo to give the crude product. The crude material was purified by Flash column chromatography ($CH_2Cl_2$:MeOH) to provide 45 mg of 4-(4-acetyl-naphthalene-1-sulfonylamino)-piperidine-1-carboxylic acid ethyl ester 39 in 25% yield. LCMS showed m/z: 409 (M+H)$^+$.

To a 25° C. solution of 4-(4-acetyl-naphthalene-1-sulfonylamino)-piperidine-1-carboxylic acid ethyl ester 39 (45 mg, 0.11 mmol) in MeOH (4 mL) was added cyclohexylamine (31 mg, 0.22 mmol) and sodium cyanoborohydride (34 mg, 0.69 mmol). After stirring for 2 h at 25° C., the solution was concentrated in vacuo to give a solid. The resultant solid was purified by reverse phase HPLC providing the title compound (G-30). $^1$H NMR (300 MHz, MeOD) δ 8.84 (m, 1H), 8.42 (s, br, 1H), 8.35 (m, 2H), 7.82 (m, 3H), 5.55 (d, 1H), 4.02 (q, 2H), 3.80 (d, 2H), 3.22(m, 1H), 3.00

(m, 1H), 2.77(s, br, 2H), 2.19 (d, 1H), 2.05 (d, 1H), 1.78 (m, 4H), 1.50 (m, 5H), 1.24 (m, 9H); LC/MS m/z 488 (M+H)⁺.

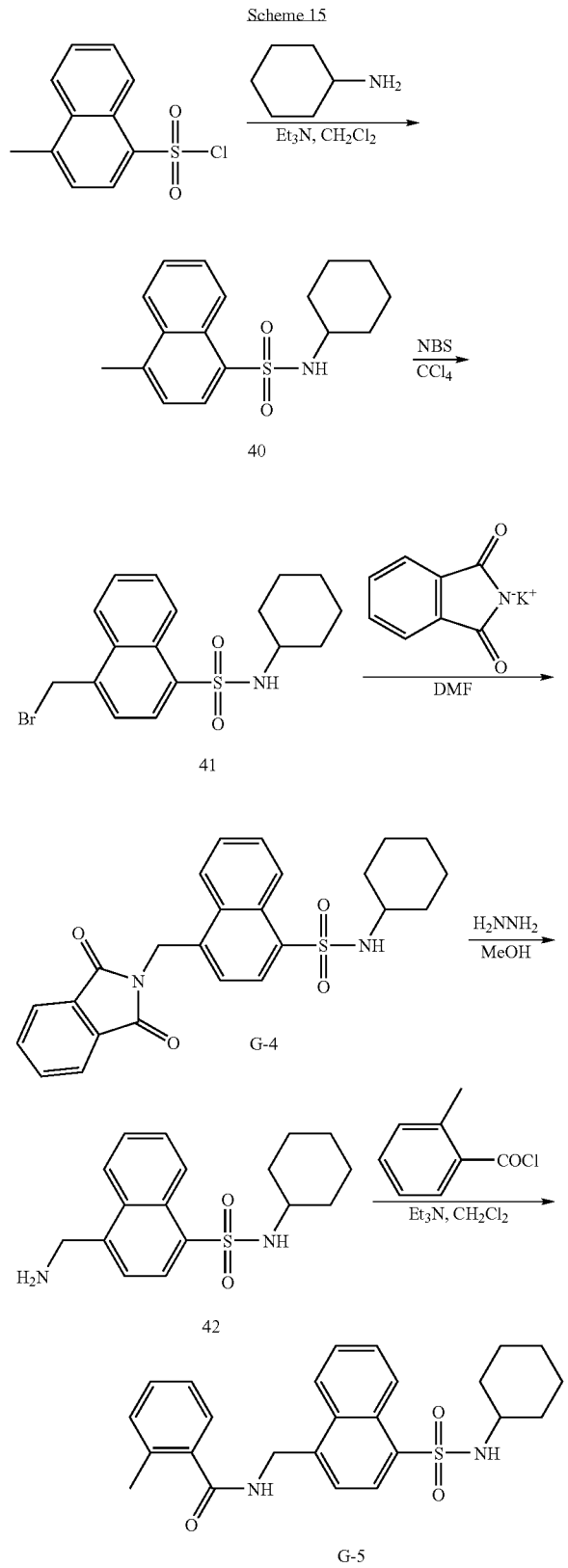

Scheme 15

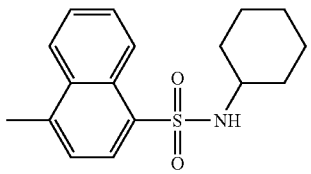

4-Methyl-naphthalene-1-sulfonic acid cyclohexylamide (40)

To a solution of 4-methyl-naphthalene -1-sulfonyl chloride (2.4 g, 10.0 mmol) in CH$_2$Cl$_2$ (30 mL), was added cyclohexylamine (1.4 g, 11.0 mmol) and triethylamine (2.8 mL, 20.0 mmol) and the resultant solution was stirred at room temperature overnight.

The solution was quenched with water and extracted with CH$_2$Cl$_2$ (3×30 mL). The combined organic layers were dried over Na$_2$SO$_4$ and concentrated in vacuo. The resulting residue was purified by Flash column chromatography (hexane/ethyl acetate, gradient elution) to give the title compound 40 (2.0 g) as a yellow solid. ¹H NMR (300 MHz, CDCl3) δ 8.63 (d, 1H), 8.18 (d, 1H), 8.10 (d, 1H), 7.64 (m, 2H), 7.38 (d, 1H), 3.08 (m, 1H), 2.76 (s, 3H), 1.52 (m, 5H), 1.09 (m, 5H); LC/MS m/z 304 (M+H)⁺.

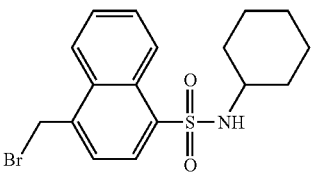

4-Bromomethyl-naphthalene-1-sulfonic acid cyclohexylamide (41)

To a solution of 4-methyl-naphthalene-1-sulfonic acid cyclohexylamide 40 (3.0 g, 10 mmol) in CCl$_4$ (100 mL) was added NBS (2.1 g, 12.0 mmol) and benzoyl peroxide (240 mg, 1.0 mmol), The reaction mixture was heated at reflux overnight. The solid was filtered and the filtrate was concentrated in vacuo. The title compound was a yellow residue (2.5 g, solidified on standing) which was used directly in the next step without further purification. ¹H NMR (300 MHz, CDCl$_3$) δ 8.70 (m, 1H), 8.25 (m, 2H), 7.70 (m, 2H), 7.60 (d, 1H), 4.94 (s, 2H), 4.58 (m, 1H); 3.15 (m, 1H), 1.55 (m, 5H) 1.05 (m, 5H); LC/MS m/z 356 (M+H)⁺ 382.

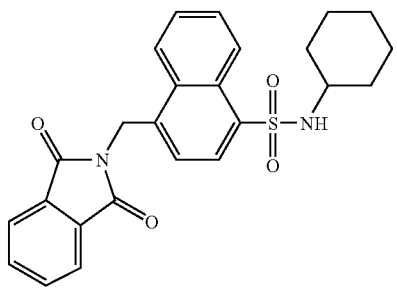

4-(1,3-Dioxo-1,3-dihydro-isoindol-2-ylmethyl)-naphthalene-1-sulfonic acid cyclohexylamide (G-4)

To a solution of 4-bromomethyl-naphthalene-1-sulfonic acid cyclohexylamide 41 (150 mg, 0.39 mmol) in DMF (5 mL) was added potassium phthalimide (109 mg, 0.58 mmol). The resultant solution was stirred at room temperature and then heated to 100° C. for 3 hr. The reaction was quenched with water and extracted with $CH_2Cl_2$. The organic layers were dried and concentrated in vacuo. HPLC purification of the residue gave the title compound (G-4) (63 mg) as white foam. $^1$H NMR (300 MHz, MeOD) δ 8.67 (d, 1H), 8.42 (d, 1H), 8.22 (d, 1H), 7.88 (m, 23H), 7.76 (m, 4H), 5.48 (s, 2H), 4.48 (d, 1H), 3.12 (d, 1H), 1.58 (m, 6H), 1.10 (m, 4H); LC/MS m/z 449 $(M+H)^+$.

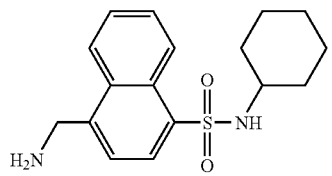

4-Aminomethyl-naphthalene-1-sulfonic acid cyclohexylamide (42)

To a solution of 4-(1,3-dioxo-1,3-dihydro-isoindol-2-ylmethyl)-naphthalene-1-sulfonic acid cyclohexylamide (G-4) (1.6 g, 3.57 mmol) in methanol (30 mL) was added hydrazine (2 mL). The resultant solution was stirred at room temperature overnight. A precipitate was formed and filtered. The solid was further washed with small amount of methanol. The filtrate was collected and solvent was removed in vacuo. Flash chromatography of the residue with Flash column ($MeOH/CH_2Cl_2$: 5-10%) gave the title compound (42) as white solid (0.7 g). $^1$H NMR (300 MHz, DMSO) δ 8.68 (d, 1H), 8.24 (d, 1H), 8.13 (d, 1H), 7.60 (m, 3H), 5.00 (s, 1H), 4.39 (s, 2H), 3.10 (s, 1H), 2.03 (m, 2H), 1.59 (m, 4H), 1.08 (m, 4H); LC/MS m/z 319 $(M+H)^+$.

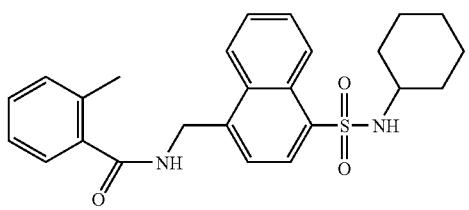

N-(4-Cyclohexylsulfamoyl-naphthalen-1-ylmethyl)-2-methyl-benzamide (G-5)

To a solution of naphthalenyl methylamine 42 (100 mg, 0.32 mmol) in DMF (2 mL) was added o-tolylchloride (49 μL, 0.38 mmol) and triethylamine (88 μL, 0.63 mmol). The resultant solution was stirred at room temperature overnight. The solvent was removed in vacuo and the residue was purified using HPLC to give the title compound (G-5) (30 mg) as pale yellow solid. $^1$H NMR (300 MHz, MeOD) δ 8.78 (d, 1H), 8.34 (d, 1H), 8.20 (d, 1H), 7.72 (m, 2H), 7.63 (d, 1H), 7.35 (d, 1H), 7.30 (d, 1H), 7.20 (d, 1H), 5.07 (s, 2H), 2.95 (s, 1H), 2.34 (s, 3H), 1.55 (m, 5H), 1.05 (m, 5H),; LC/MS m/z 437 $(M+H)^+$.

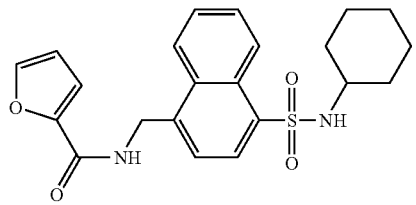

Furan-2-carboxylic acid (4-cyclohexylsulfamoyl-naphthalen-1-ylmethyl)-amide (G-6)

The title compound was made following general procedure in Scheme 15, substituting furan-2-carboxylic chloride for o-tolyl chloride. $^1$H NMR (300 MHz, MeOD) δ 8.76 (d, 1H), 8.26 (d, 1H), 8.18 (d, 1H), 7.67 (d, 1H), 7.50 (d, 1H), 7.16 (d, 1H), 6.58 (m, 1H), 5.08 (s, 2H), 2.87 (s, 1H), 1.52 (m, 5H), 1.11 (m, 5H),; LC/MS m/z 413 $(M+H)^+$.

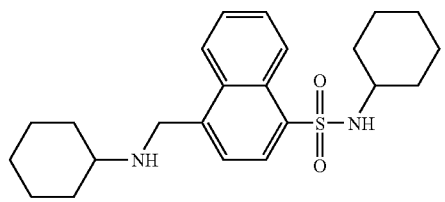

4-Cyclohexylaminomethyl-naphthalene-1-sulfonic acid cyclohexylamide (G-31)

The title compound was prepared according to the general procedure in Scheme 15, substituting cyclohexylamine and potassium carbonate for potassium phthalimide. HPLC purification of the residue gave the title compound (77 mg) as white foam. $^1$H NMR (300 MHz, MeOD) δ 8.80 (m, 1H), 8.37 (s, 1H), 8.26 (d, 2H), 7.78 (m, 3H), 4.79 (s, 2H), 3.36 (m, 1H), 2.96 (m, 1H), 2.30 (m, 2H), 1.90 (m, 2H), 1.72 (m, 1H), 1.48 (m, 10H), 1.10 (m, 2H); LC/MS m/z 401$(M+H)^+$.

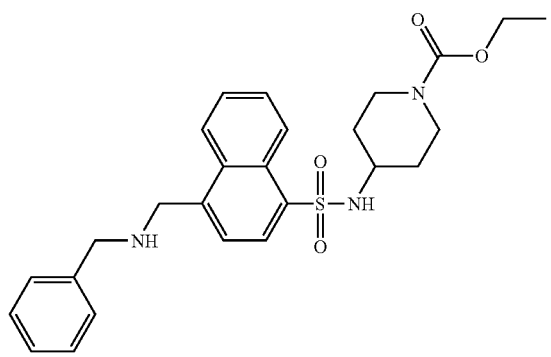

4-[4-(Benzylamino-methyl)-naphthalene-1-sulfonylamino]-piperidine-1-carboxylic acid ethyl ester (G-32)

The intermediate 4-(4-methyl-naphthalene-1-sulfonylamino]-piperidine-1-carboxylic acid tert-butyl ester was prepared according to the general procedure in Scheme 15, substituting 4-amino-piperidine-1-carboxylic acid tert-butyl ester for cyclohexylamine.

The intermediate 4-(4-bromomethyl-naphthalene-1-sulfonylamino)-piperidine-1-carboxylic acid tert-butyl ester was prepared according to the general procedure in Scheme 15 substituting 4-(4-methyl-naphthalene-1-sulfonylamino)-piperidine-1-carboxylic acid tert-butyl ester for 4-methyl-naphthalene-1-sulfonic acid cyclohexylamide (40).

The title compound was prepared according to the general procedure in Scheme 15, substituting phenylamine and potassium carbonate for potassium phthalimide. HPLC purification gave the title compound (15 mg) as a white solid. $^1$H NMR (300 MHz, MeOD) δ 8.73 (d, 1H), 8.29 (s, 1H), 8.22 (m, 1H), 8.04 (m, 1H), 7.68 (m, 3H), 7.20 (m, 2H), 4.59 (s, 2H), 4.23 (s, 2H), 3.97 (AB q, 2H), 3.67 (m, 2H), 3.16 (m, 1H), 2.70 (m, 2H), 1.44 (m, 2H), 1.22 (m, 2H), 1.13 (t, 3H); LC/MS m/z 482 (M+H)$^+$.

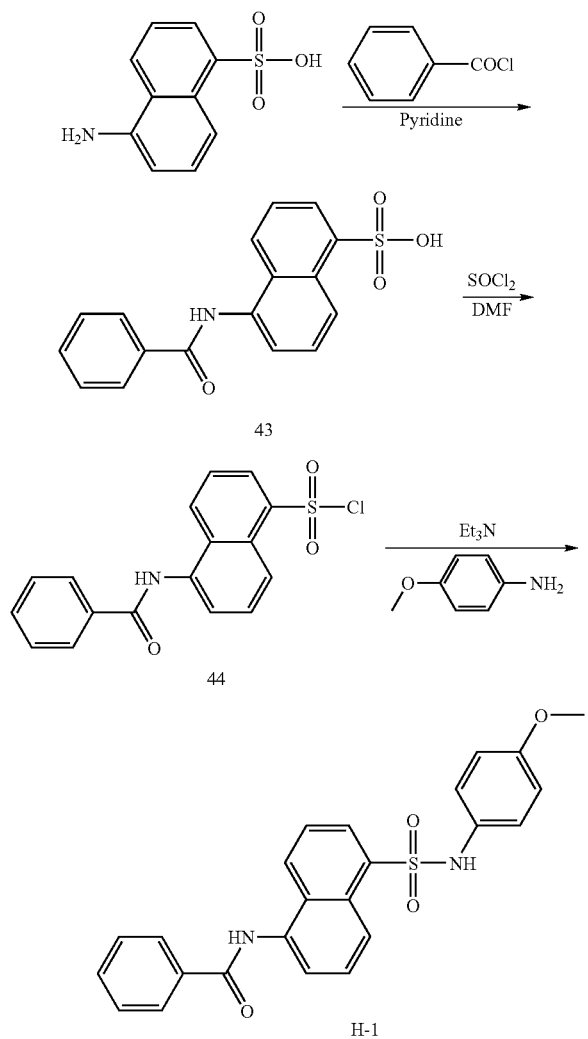

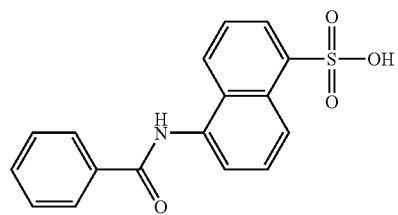

5-Benzoylamino-napthalene-1-sulfonic acid (43)

To an ice cooled solution of 1-naphthylamine-5-sulfonic acid (2 g, 8.9 mmol) in dichloromethane (5 mL), was added triethylamine (1.87 mL, 13.4 mmol). Benzoyl chloride (1.14 ml, 9.85 mmol) was added and the resultant solution was stirred at room temperature overnight. The reaction mixture was quenched by pouring into ice water, and the product was extracted into ethyl acetate. The organic extracts were washed with brine, dried over MgSO$_4$, filtered and concentrated to provide crude intermediate 43 as a white solid that was used without further purification.

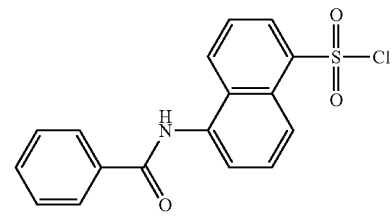

5-Benzoylamio-naphthalene-1-sulfonyl chloride (44)

To an ice-cooled solution of 5-benzoylamino-napthalene-1-sulfonic acid (1.5 g, 3.51 mmol) in dichloromethane (5 ml), was added thionyl chloride (0.359 ml, 4.92 mmol).

The resultant solution was allowed to warm to room temperature and stirred for 3 hours. The reaction mixture was quenched by pouring into ice water and extracting with ethyl acetate. The organic extracts were washed with brine, dried over MgSO$_4$ and concentrated to provide the crude intermediate 44 as a yellow oil that was used without further purification.

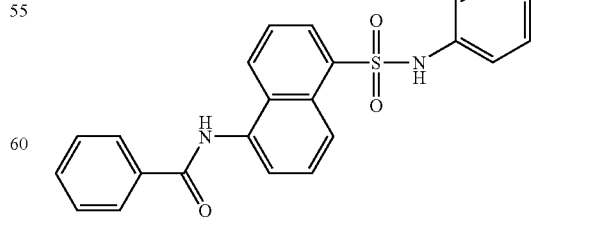

N-[5-(4-Methoxy-phenyl sulfamoyl)-naphthalen-1-yl]-benzamide (H-1)

To a solution of 5-benzoylamino-naphthalene-1-sulfonyl chloride 44 (0.1 g, 0.29 mmol) in dichloromethane (0.5 mL) was added triethylamine (0.06 ml, 0.43 mmol) and p-anisidine (0.05 g, 0.3 mmol). The resultant solution stirred at room temperature for 3 hours. The reaction mixture was quenched with water and the compound extracted into ethyl acetate. The organic extracts were washed with brine, dried over $MgSO_4$, filtered and concentrated to provide the crude product as a yellow oil. $^1$H NMR (300 MHz, DMSO) δ 8.65 (d, 1H), 8.19 (d, 1H), 8.06 (m, 3H), 7.70 (m, 2H), 7.54 (m, 2H), 6.84 (d, 2H), 6.69 (d, 2H), 3.56 (s, 3H); LC/MS $(M+H)^+$ m/z 433.

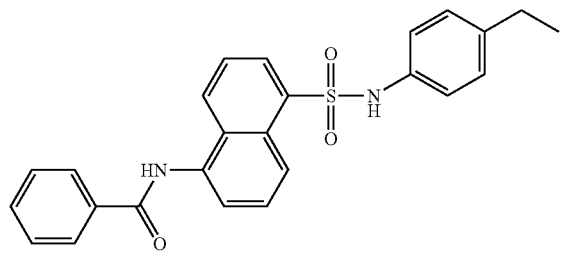

N-[5-(4-Ethyl-phenylsulfamoyl)-naphthalen-1-yl]-benzamide (H-2)

The title compound was made following the general procedure in Scheme 16, substituting p-ethylaniline for p-anisidine. $^1$H NMR (300 MHz, MeOD) δ 8.76 (d, 1H), 8.20 (t, 2H), 8.04 (d, 2H), 7.72 (m, 2H), 7.56 (m, 4H), 6.90 (m, 4H), 2.45 (m, 2H), 1.07 (m, 3H); LC/MS $(M+H)^+$ m/z 431.

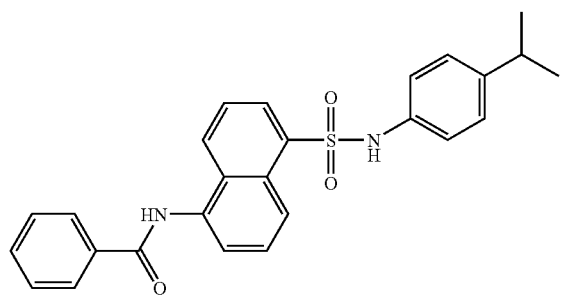

N-[5-(Isopropyl-phenylsulfamoyl)-naphthalen-1-yl]-benzamide (H-3)

The title compound was made following the general procedure in Scheme 16, substituting p-isopropylaniline for p-anisidine. $^1$H NMR (300 MHz, MeOD) δ 8.75 (m, 1H), 8.21 (m, 2H), 8.04 (d, 2H), 7.6 (m, 7H), 6.92 (m, 3H), 2.72 (m, 1H), 1.24 (d, 1H), 1.09 (d, 6H); LC/MS $(M+H)^+$ m/z 445.

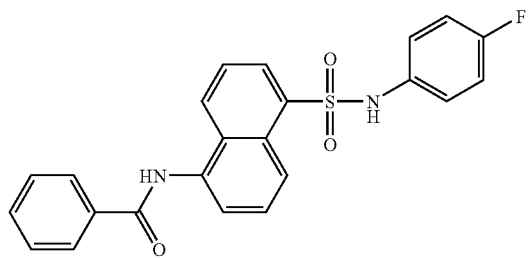

N-[5-(4-Fluoro-phenylsulfamoyl)-naphthalen-1-yl]-benzamide (H-4)

The title compound was made following the general procedure in Scheme 16, substituting p-fluoroaniline for p-anisidine. $^1$H NMR (300 MHz, DMSO) δ 10.62 (s, 1H), 10.50 (s, 1H), 8.61 (d, 1H), 8.23 (d, 1H), 8.14 (d, 1H), 8.04 (s, 1H), 8.02 (s, 1H), 7.72 (m, 2H), 7.55 (m, 4H), 6.98 (s, 2H), 6.95 (s, 2H); LC/MS $(M+H)^+$ m/z 421.

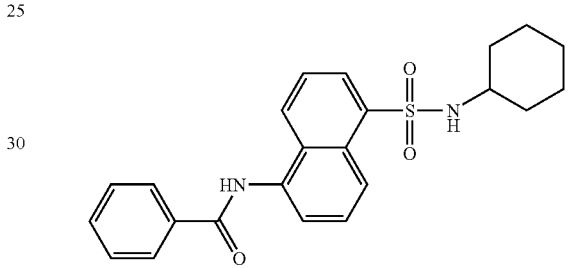

N-(5-Cyclohexylsulfamoyl-naphthalen-1-yl)-benzamide (H-5)

The title compound was made following the general procedure in Scheme 16, substituting cyclohexylamine for p-anisidine. $^1$H NMR (300 MHz, $CDCl_3$) δ 8.50 (d, 1H), 8.13 (t, 2H), 7.96 (d, 2H), 7.66 (d, 1H), 7.52 (t, 1H), 7.40 (m, 4H), 2.80 (m, 4H), 1.20 (m, 7H); LC/MS $(M+H)^+$ m/z 409.

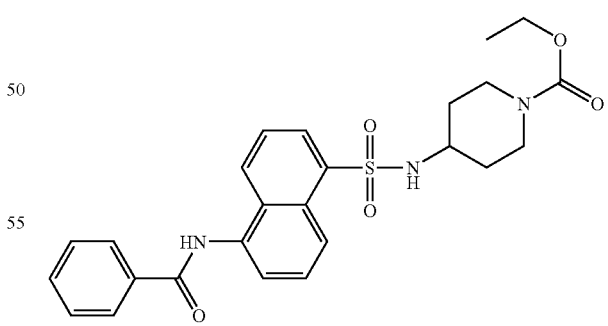

4-(5-Benzoylamino-naphthalene-1-sulfonylamino)-piperidine-1-carboxylic acid ethylester (H-6)

The title compound was made following the general procedure in Scheme 16, substituting 4-amino-piperidine-1-carboxylic acid ethyl ester for p-anisidine. $^1$H NMR (300

MHz, CDCl₃) δ 9.40 (s, 1H, N—H), 8.56 (d, 1H), 8.22 (d, 2H), 8.04 (d, 2H), 7.78 (d, 1H), 7.61 (t, 1H), 7.44 (m, 4H), 6.73 (br s, 1H), 3.98 (q, 2H), 3.80 (m, 2H), 3.13 (m, 1H), 2.68 (m, 2H), 1.56 (m, 2H), 1.24 (m, 2H), 1.12 (t, 3H); LC/MS (M+H)⁺ m/z 482.

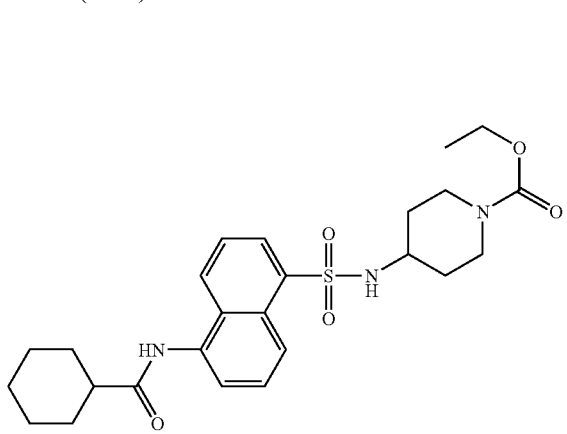

4-[5-(Cyclohexanecarbonyl-amino)-naphthalene-1-sulfonylamino]-piperidine-1-carboxylic acid ethyl ester (H-7)

The title compound was made following the general procedure in Scheme 16, substituting cyclohexane carboxylic acid for benzoyl chloride, and 4-amino-piperidine-1-carboxylic acid ethyl ester for p-anisidine. ¹H NMR (300 MHz, MeOD) δ 8.64 (d, 1H), 8.28 (m, 2H), 7.66 (m, 3H), 4.06 (q, 2H), 3.80 (m, 2H), 3.22 (m, 1H), 2.78 (m, 2H), 2.60 (m, 2H), 2.06 (m, 2H), 2.90 (m, 2H), 1.56 (m, 10H), 1.20 (t, 3H); LC/MS (M+H)⁺ m/z 488.

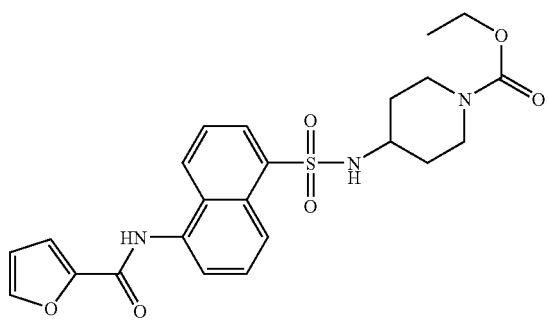

4-{5-[(Furan-2-carbonyl)-amino]-naphthalene-1-sulfonylamino}-piperidine-1-carboxylic acid ethyl ester (H-8)

The title compound was made following the general procedure in Scheme 16, substituting furan-2-carbonyl chloride for benzoyl chloride, and 4-amino-piperidine-1-carboxylic acid ethyl ester for p-anisidine.

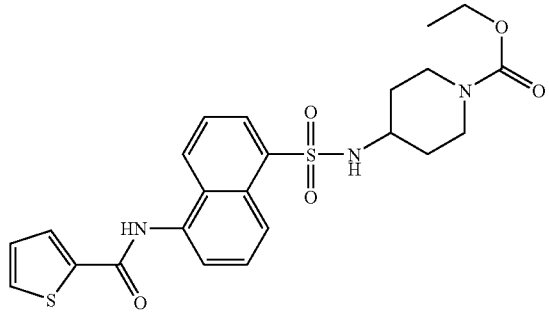

4-{5-[(Thiophene-2-carbonyl)-amino]-naphthalene-1-sulfonylamino}-piperidine-1-carboxylic acid ethyl ester (H-9)

The title compound was made following the general procedure in Scheme 16, substituting thiophene-2-carbonyl chloride for benzoyl chloride, and 4-amino-piperidine-1-carboxylic acid ethyl ester for p-anisidine.

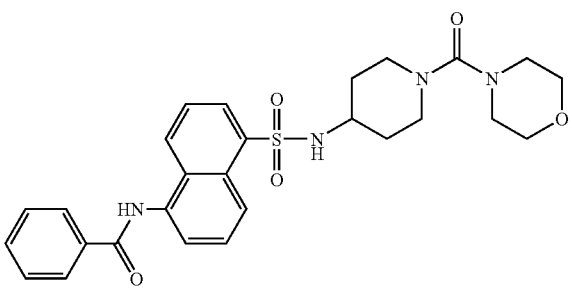

N-{5-[1-(Morpholine-4-carbonyl)-piperidin-4-ylsulfamoyl]-naphthalen-1-yl}-benzamide (H-10)

The title compound was made following the general procedure in Scheme 16, substituting 4-amino-piperidine-1-carboxylic acid tert-butyl ester for p-anisidine to give 4-(5-benzoylamino-naphthalene-1-sulfonylamino)-piperidine-1-carboxylic acid tert-butyl ester. The crude material was dissolved in 4N HCl/dioxane and stirred for 3 hours at room temperature. Concentration in vacuo afforded N-[5-(piperidin-4-ylsulfamoyl)-naphthalen-1-yl]-benzamide as its hydrochloride salt which was directly dissolved in dichloromethane. Triethylamine was added followed by morpholine. The reaction was stirred overnight at room temperature. The crude reaction mixture was charged to HPLC to afford the title compound.

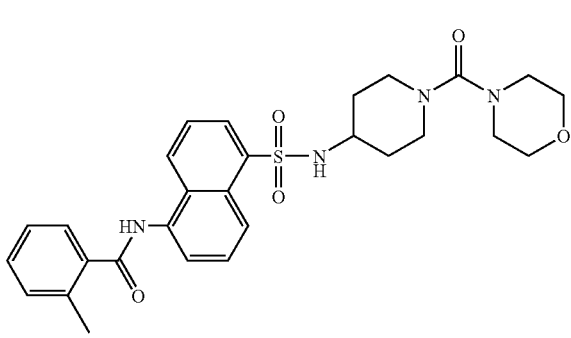

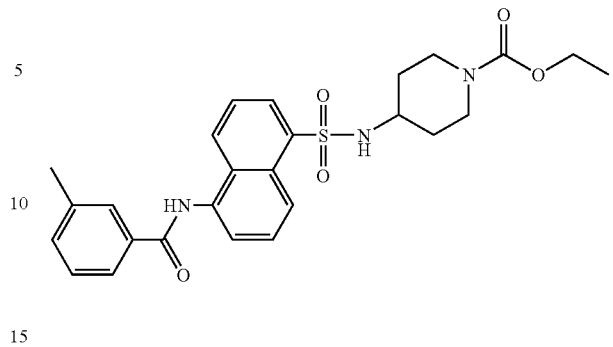

2-Methyl-N-{5-[1-(morpholine-4-carbonyl)-piperidin-4-ylsulfamoyl]-naphthalen-1-yl}-benzamide (H-11)

The title compound was made following the general procedure in Scheme 16, substituting 2-methyl-benzoyl chloride for benzoyl chloride, and 4-amino-piperidine-1-carboxylic acid tert-butyl ester for p-anisidine to give 4-[5-(2-methyl-benzoylamino)-naphthalene-1-sulfonylamino]-piperidine-1-carboxylic acid tert-butyl ester. The crude material was dissolved in 4N HCl/dioxane and stirred for 3 hours at room temperature. Concentration in vacuo afforded 2-methyl-N-[5-(piperidin-4-ylsulfamoyl)-naphthalen-1-yl]-benzamide as its hydrochloride salt which was dissolved in dichloromethane. Triethylamine was added followed by morpholine. The reaction was stirred overnight at room temperature. The crude reaction mixture was charged to HPLC afforded the title compound.

4-[5-(3-Methyl-benzoylamino)-naphthalene-1-sulfonylamino]-piperidine-1-carboxylic acid ethyl ester (H-13)

The title compound was made following the general procedure in Scheme 16, substituting 3-methyl-benzoyl chloride for benzoyl chloride, and 4-amino-piperidine-1-carboxylic acid ethyl ester for p-anisidine.

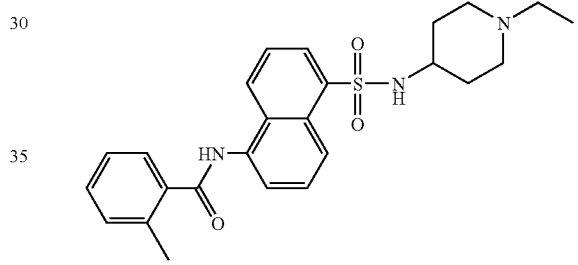

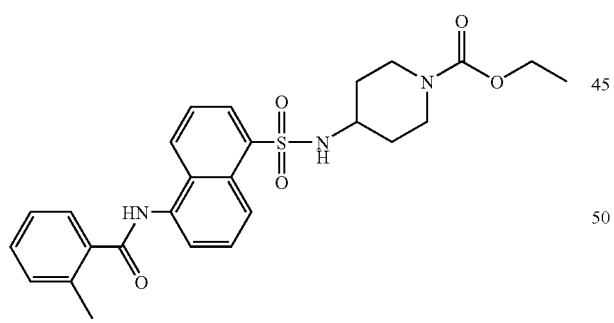

4-[5-(2-Methyl-benzoylamino)-naphthalene-1-sulfonylamino]-piperidine-1-carboxylic acid ethyl ester (H-12)

The title compound was made following the general procedure in Scheme 16, substituting 2-methyl-benzoyl chloride for benzoyl chloride, and 4-amino-piperidine-1-carboxylic acid ethyl ester for p-anisidine.

N-[5-(1-Ethyl-piperidin-4-ylsulfamoyl)-naphthalen-1-yl]-2-methyl-benzamide (H-14)

The title compound was made following the general procedure in Scheme 16, substituting 2-methyl-benzoyl chloride for benzoyl chloride, and 4-amino-piperidine-1-carboxylic acid tert-butyl ester for p-anisidine to give 4-[5-(2-methyl-benzoylamino)-naphthalene-1-sulfonylamino]-piperidine-1-carboxylic acid tert-butyl ester. The crude material was dissolved in 4N HCl/dioxane and stirred for 3 hours at room temperature. Concentration in vacuo afforded 2-methyl-N-[5-(piperidin-4-ylsulfamoyl)-naphthalen-1-yl]-benzamide as its hydrochloride salt which was suitable for use without further purification.

To a 25° C. solution of 2-methyl-N-[5-(piperidin-4-ylsulfamoyl)-naphthalen-1-yl]-benzamide in MeOH was added acetyl aldehyde and sodium cyanoborohydride. After stirring for 2 h at 25° C., the solution was concentrated in vacuo. The crude material was purified by reverse phase HPLC to provide the title compound.

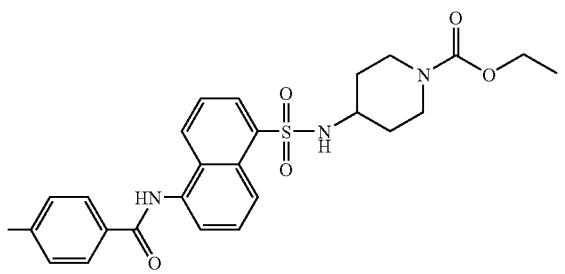

4-[5-(4-Methyl-benzoylamino)-naphthalene-1-sulfonylamino-piperidine-1-carboxylic acid ethyl ester (H-15)

The title compound was made following the general procedure in Scheme 16, substituting 4-methyl-benzoyl chloride for benzoyl chloride, and 4-amino-piperidine-1-carboxylic acid ethyl ester for p-anisidine.

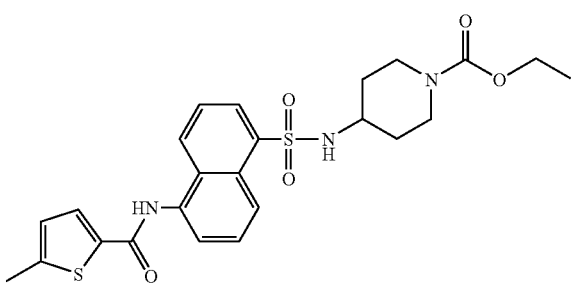

4-{5-[(5-Methyl-thiophene-2-carbonyl)-amino]-naphthalene-1-sulfonylamino}-piperidine-1-carboxylic acid ethyl ester (H-16)

The title compound was made following the general procedure in Scheme 16, substituting 5-methyl-thiophene-2-carbonyl chloride for benzoyl chloride, and 4-amino-piperidine-1-carboxylic acid ethyl ester for p-anisidine.

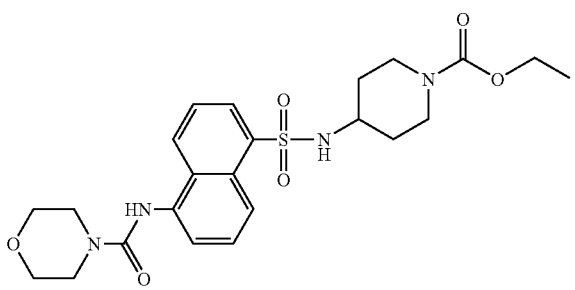

4-{5-[(Morpholine-4-carbonyl)-amino]-naphthalene-1-sulfonylamino}-piperidine-1-carboxylic acid ethyl ester (H-17)

The title compound was made following the general procedure in Scheme 16, substituting morpholine-4-carbonyl chloride for benzoyl chloride, and 4-amino-piperidine-1-carboxylic acid ethyl ester for p-anisidine.

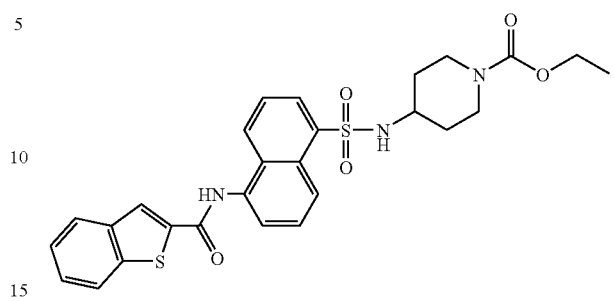

4-{5-[(Benzo[b]thiophene-2-carbonyl)-amino]-naphthalene-1-sulfonylamino}-piperidine-1-carboxylic acid ethyl ester (H-18)

The title compound was made following the general procedure in Scheme 16, substituting benzo[b]thiophene-2-carbonyl chloride for benzoyl chloride, and 4-amino-piperidine-1-carboxylic acid ethyl ester for p-anisidine.

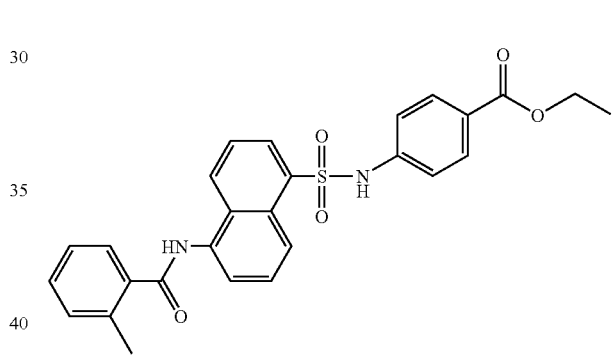

4-[5-(2-Methyl-benzoylamino)-naphthalene-1-sulfonylamino]-benzoic acid ethyl ester (H-19)

The title compound was made following the general procedure in Scheme 16, substituting 2-methyl-benzoyl chloride for benzoyl chloride, and 4-amino-benzoic acid ethyl ester for p-anisidine.

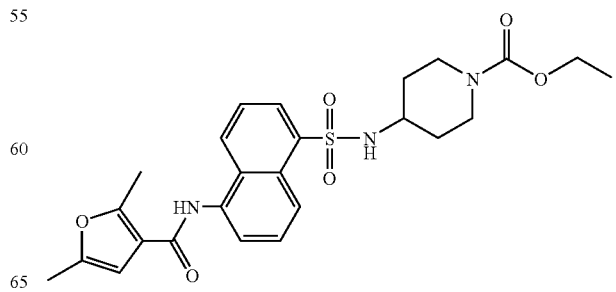

4-{5-[(2,5-Dimethyl-furan-3-carbonyl)-amino]-naphthalene-1-sulfonylamino}-piperidine-1-carboxylic acid ethyl ester (H-20)

The title compound was made following the general procedure in Scheme 16, substituting 2,5-dimethyl-furan-3-carbonyl chloride for benzoyl chloride, and 4-amino-piperidine-1-carboxylic acid ethyl ester for p-anisidine.

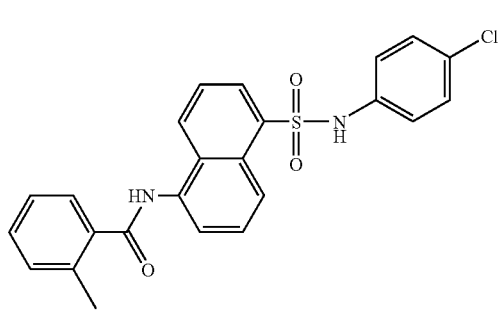

N-[5-(4-Chloro-phenylsulfamoyl)-naphthalen-1-yl]-2-methyl-benzamide (H-21)

The title compound was made following the general procedure in Scheme 16, substituting 2-methyl-benzoyl chloride for benzoyl chloride, and 4-chloro-phenylamine for p-anisidine.

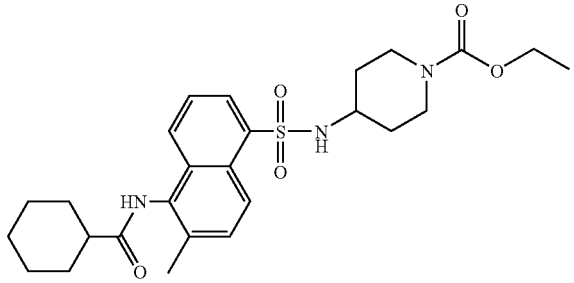

4-[5-(Cyclohexanecarbonyl-amino)-6-methyl-naphthalene-1-sulfonylamino]-piperidine-1-carboxylic acid ethyl ester (H-22)

Compound 5-(cyclohexanecarbonyl-amino)-6-methyl-naphthalene-1-sulfonyl chloride was prepared following general procedure in scheme 10, substituting 2-methyl-naphthalen-1-ylamine for 5,6,7,8-tetrahydro-naphthalen-1-ylamine, and cyclohexanecarbonyl chloride for 2-methyl-benzoyl chloride.

The title compound was made following the general procedure in Scheme 16, substituting 5-(cyclohexanecarbonyl-amino)-6-methyl-naphthalene-1-sulfonyl chloride for 5-Benzoylamio-naphthalene-1-sulfonyl chloride (44), and 4-amino-piperidine-1-carboxylic acid ethyl ester for p-anisidine. $^1$H NMR (300 MHz, MeOD) δ 8.59 (d, 1H), 8.19 (m, 2H), 7.61 (m, 2H), 4.02 (q, 2H), 3.81 (m, 2H), 3.21 (m, 1H), 2.78 (m, 2H), 2.62 (m, 1H), 2.40 (s, 3H), 2.09 (m, 2H), 1.92 (m, 2H), 1.50 (m, 10H), 1.21 (t, 3H), LC/MS (M+H)$^+$ m/z 502.

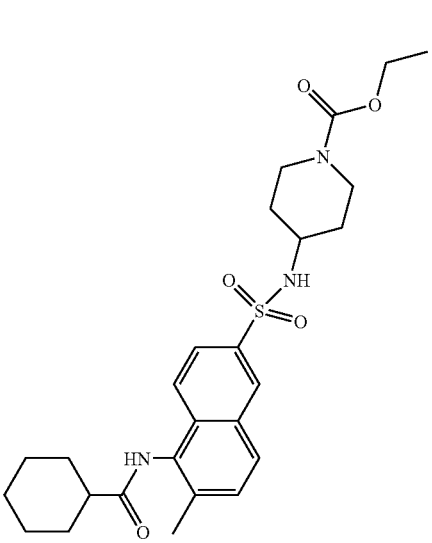

4-[5-(Cyclohexanecarbonyl-amino)-6-methyl-naphthalene-2-sulfonylamino]-piperidine-1-carboxylic acid ethyl ester (H-23)

Compound 5-(Cyclohexanecarbonyl-amino)-6-methyl-naphthalene-2-sulfonyl chloride was prepared following general procedure in scheme 10, substituting 2-methyl-naphthalen-1-ylamine for 5,6,7,8-tetrahydro-naphthalen-1-ylamine, and cyclohexanecarbonyl chloride for 2-methyl-benzoyl chloride.

The title compound was made following the general procedure in Scheme 16, substituting 5-(cyclohexanecarbonyl-amino)-6-methyl-naphthalene-1-sulfonyl chloride for 5-Benzoylamio-naphthalene-1-sulfonyl chloride (44), and 4-amino-piperidine-1-carboxylic acid ethyl ester for p-anisidine. $^1$H NMR (300 MHz, MeOD) δ 8.41 (s, 1H), 7.90 (m, 3H), 7.59 (m, 1H), 4.04 (q, 2H), 3.88 (m, 2H), 3.25 (m, 1H), 2.83 (m, 2H), 2.65 (m, 1H), 2.40 (s, 3H), 2.11 (m, 2H), 1.94 (m, 2H), 1.50 (m, 10H), 1.21 (t, 3H); LC/MS (M+H)$^+$ m/z 502.

Scheme 17

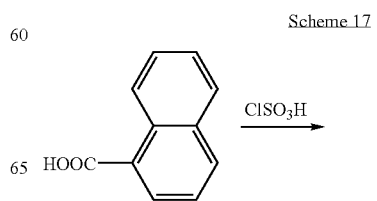

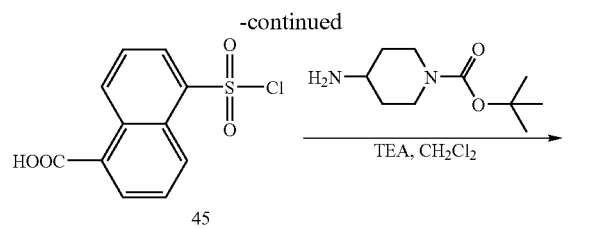

5-Chlorosulfonyl-naphthalene-1-carboxylic acid (45)

The titled compound was prepared using a modified procedure of Reefschlager et al. (see Reefschlager, J., et al., (2000) EP1038868A2). Naphthalene-1-carboxylic acid (6.56 g, 38.1 mmol) was added in small portions to chlorosulfonic acid (22 g, 12.6 mL, 190 mmol) that was cooled in an ice bath. The reaction was stirred overnight at room temperature. The reaction mixture was poured slowly over ice-water (250 mL) and filtered to afford 45 (8.3 g, 80%) as a white solid. $^1$H NMR (300 MHz, d$^6$-DMSO) δ 14.0 (s, 1H), 9.11 (d, 1H), 8.80 (d, 1H), 8.08 (d, 1H), 8.00 (d, 1H), 7.56 (m, 2H).

4-(5-Carboxy-naphthalene-1-sulfonylamino)-piperidine-1-carboxylic acid tert-butyl ester (46)

5-Chlorosulfonyl-naphthalene-1-carboxylic acid 45 (2.00 g, 7.39 mmol) was dissolved in dichloromethane (30 mL). Triethylamine (2.24 g, 3.1 mL, 22.2 mmol) was added followed by 4-amino-piperidine-1-carboxylic acid tert-butyl ester (1.63 g, 8.13 mmol). The reaction was stirred overnight at room temperature. The reaction was diluted with dichloromethane (50 mL) and charged to a separatory funnel. The organic layer was washed twice with water and brine and dried over MgSO$_4$. Filtration and concentration in vacuo afforded 46 (3.0 g, 93%) as a yellow foam. $^1$H NMR (300 MHz, d$^6$-DMSO) δ 9.11 (d, 1H), 8.62 (d, 1H), 8.15 (d, 1H), 7.90 (d, 1H), 7.62 (m, 2H), 3.91 (d, 1H), 3.62 (m, 2H), 3.15 (m, 1H), 2.67 (m, 2H), 1.89 (m, 2H), 1.52 (m, 2H), 1.40 (s, 9H) LC/MS m/z 435 (M+H)$^+$.

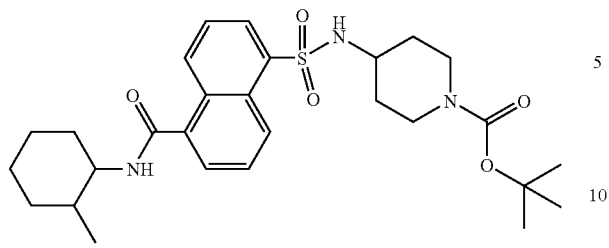

(±)-4-[5-(2-Methyl-cyclohexylcarbamoyl)-naphthalene-1-sulfonylamino]-piperidine-1-carboxylic acid tert-butyl ester (47)

4-(5-Carboxy-naphthalene-1-sulfonylamino)-piperidine-1-carboxylic acid tert-butyl ester 46 (246 mg, 0.57 mmol) was dissolved in dichloromethane (5 mL). O-(7-Azabenzotriazol-1-yl)-N,N,N',N'-tetramethyluronium hexafluorophosphate (HATU) (323 mg, 0.85 mmol) was added followed by diisopropylethyl amine (214 mg, 0.29 mL, 1.66 mmol) and 2-methyl-cyclohexylamine (71 mg, 0.63 mmol). The reaction was stirred overnight at room temperature. The reaction mixture was charged to a flash column. Elution with 99:1 dichloromethane:methanol afforded 47 (380 mg) as a white foam that was contaminated with tetramethylurea, but suitable for use without further purification. $^1$H NMR (300 MHz, CDCl$_3$) (1:1 mixture of diastereomers) δ 8.70 (m, 1H), 8.55 (d, 1H), 8.33 (d. 1H), 7.64 (m, 3H), 5.81 (d, 0.5H), 5.55 (d, 0.5H), 4.66 (d, 1H), 3.82 (m, 2H), 3.00 (m, 2H), 2.70 (m, 2H), 1.80 (m, 2H), 1.40 (s, 9H), 1.23 (m, 5H), 1.11 (d, 1.5H), 0.97 (d, 1.5H); LC/MS m/z 530 (M+H)$^+$.

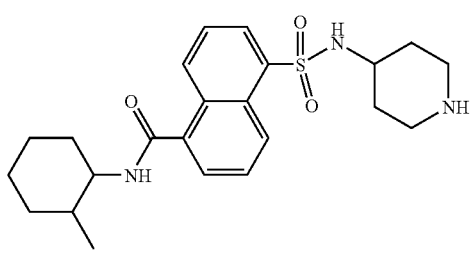

5-(Piperidin-4-ylsulfamoyl)-naphthalene-1-carboxylic acid (2-methyl-cyclohexyl)-amide (48)

4-[5-(2-Methyl-cyclohexylcarbamoyl)-naphthalene-1-sulfonylamino]-piperidine-1-carboxylic acid tert-butyl ester 47 (380 mg) was dissolved in 4N HCl/dioxane (10 mL) and stirred for 3 hours at room temperature. Concentration in vacuo afforded 48 (370 mg) as its hydrochloride salt that was used without further purification. LC/MS m/z 430 (M+H)$^+$.

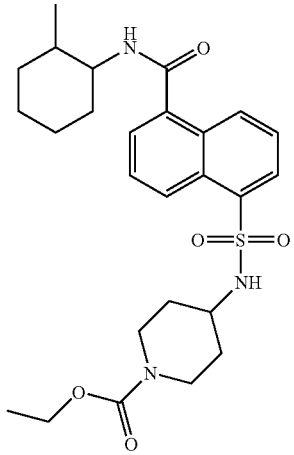

(±)-4-[5-(2-Methyl-cyclohexylcarbamoyl)-naphthalene-1-sulfonylamino]-piperidine-1-carboxylic acid ethyl ester (H-24)

5-(Piperidin-4-ylsulfamoyl)-naphthalene-1-carboxylic acid (2-methyl-cyclohexyl)-amide hydrochloride 48 (190 mg, 0.41 mmol) was dissolved in dichloromethane (1 mL). Triethylamine (0.13 g, 0.18 mL, 1.28 mmol) was added followed by ethyl chloroformate (65 mg, 0.068 mL, 0.60 mmol). The reaction was stirred overnight at room temperature. The crude reaction mixture was charged to a flash column. Elution with 99:1 dichloromethane:methanol afforded H-24 (66 mg, 59%) as a white solid. $^1$H NMR (300 MHz, CDCl$_3$) (1:1 mixture of diastereomers) δ 8.65 (d, 1H), 8.48 (d, 1H), 8.25 (d, 1H), 7.55 (m, 3H), 6.20 (d, 1H), 5.47 (m, 1H), 5.26 (s, 1H), 4.00 (m, 2H), 3.75 (m, 3H), 3.20 (m, 1H), 2.75 (m, 2H), 2.15 (m, 1H), 1.78 (m 3H), 1.57 (m 2H), 1.38 (m, 2H), 1.05 (m, 10H); LC/MS m/z 502 (M+H)$^+$.

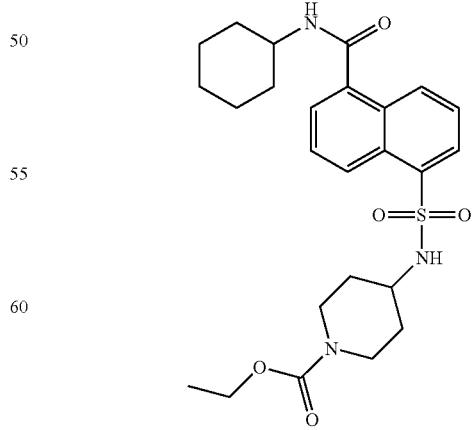

4-(5-Cyclohexylcarbamoyl-naphthalene-1-sulfonylamino)-piperidine-1-carboxylic acid ethyl ester (H-25)

The title compound was prepared according to the general procedure in Scheme 17, substituting cyclohexylamine for 2-methyl-cyclohexylamine. Wt.: 17 mg (36%). $^1$H NMR (300 MHz, d$^6$-DMSO) δ 8.70 (d, 1H), 8.52 (d, 1H), 8.36 (d, 1H), 8.18 (d, 1H), 8.12 (d, 1H), 7.66 (m, 3H), 3.94 (q, 2H), 3.83 (m, 1H), 3.67 (m, 2H), 3.17 (m, 2H), 2.74 (m, 2H), 1.92 (m, 2H), 1.75 (m, 2H), 1.60 (m, 2H), 1.44 (m, 2H), 1.33 (m, 2H), 1.21 (m, 2H), 1.10 (t, 3H); LC/MS m/z 488 (M+H)$^+$.

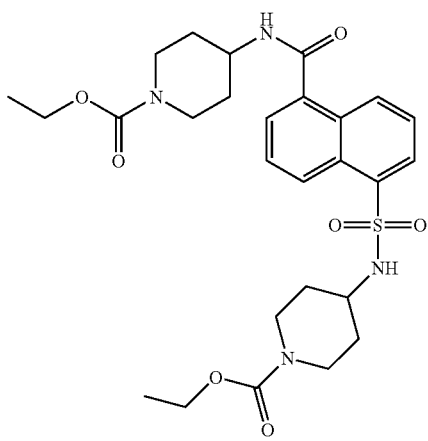

1-(1-Ethoxycarbonyl-piperidin-4-ylsulfamoyl)-naphthalene-5-carboxylic acid-(1-ethoxycarbonyl-piperidin-4-ylcarbamoyl)-amide (H-26)

5-Chlorosulfonyl-naphthalene-1-carboxylic acid 45 (100 mg, 0.37 mmol) was dissolved in dichloromethane (3 mL). Triethylamine (110 mg, 0.15 mL, 1.11 mmol) was added followed by 4-amino-piperidine-1-carboxylic acid ethyl ester (76 mg, 0.44 mmol). The reaction was stirred for 1 hour at room temperature then diluted with dichloromethane (15 mL). The mixture was charged to a separatory funnel and washed with water, brine and dried over Na$_2$SO$_4$. Flash column chromatography (95:5 dichloromethane:methanol) afforded the title compound as a white solid. Wt.: 20 mg (13%)

$^1$H NMR (300 MHz, CDCl$_3$) δ 8.70 (d, 1H), 8.52 (d, 1H), 8.31 (d, 1H), 7.62 (m, 3H) 6.18 (d, 1H), 4.92 (d, 1H), 4.24 (m, 2H), 4.15 (q, 2H), 4.05 (q, 2H), 3.85 (m, 2H), 3.24 (m, 1H), 2.98 (m, 2H), 2.73 (m, 2H), 2.13 (m, 2H), 1.95 (m, 1H), 1.61 (m, 2H), 1.45 (m, 1H), 1.15 (m, 3H); LC/MS m/z 561 (M+H)$^+$.

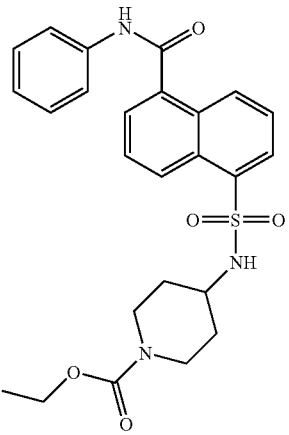

4-(5-Phenylcarbamoyl-naphthalene-1-sulfonylamino)-piperidine-1-carboxylic acid ethyl ester (H-27)

The title compound was prepared according to the general procedure in Scheme 17, substituting phenylamine for 2-methyl-cyclohexylamine. Wt.: 32 mg (47%). $^1$H NMR (300 MHz, CD$_3$OD) δ 8.86 (d, 1H), 8.50 (d, 1H), 8.32 (dd, 1H), 7.87 (dd, 1H), 7.74 (m, 5H), 7.38 (m, 2H), 7.18 (m, 1H), 4.04 (q, 2H), 3.71 (m, 2H), 3.23 (m, 2H), 2.77 (m, 2H), 1.52 (m, 2H), 1.26 (m, 2H), 1.20 (t, 3H); LC/MS m/z 482 (M+H)$^+$.

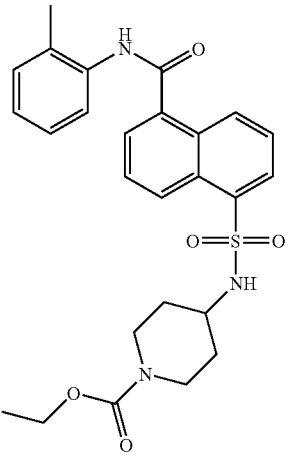

4-(5-o-Tolylcarbamoyl-naphthalene-1-sulfonylamino)-piperidine-1-carboxylic acid ethyl ester (H-28)

The title compound was prepared according to the general procedure in Scheme 17, substituting o-tolylamine for 2-methyl-cyclohexylamine. Wt.: 32 mg (46%). $^1$H NMR (300 MHz, d$^6$-DMSO) δ 10.60 (s, 1H), 8.78 (d, 1H), 8.41 (d, 1H), 8.22 (d, 1H), 8.18 (d, 1H), 7.82 (m, 2H), 7.71 (m, 1H), 7.67 (s, 1H), 7.56 (d, 1H), 7.25 (t, 1H), 6.95 (d, 1H), 3.95 (q, 2H), 3.68 (m, 2H), 3.23 (m, 2H), 2.75 (m, 2H), 2.30 (s, 3H), 1.47 (m, 2H), 1.18 (m, 2H), 1.10 (t, 3H); LC/MS m/z 496 (M+H)$^+$.

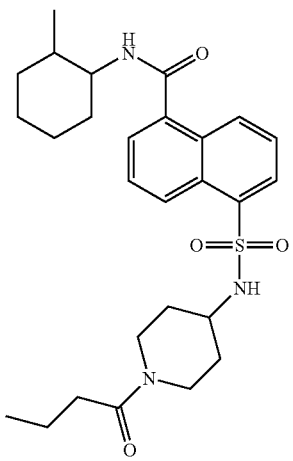

(±)-5-(1-Butyryl-piperidin-4-ylsulfamoyl)-naphthalene-1-carboxylic acid (2-methyl-cyclohexyl)-amide (H-29)

The title compound was prepared according to the general procedure in Scheme 17, substituting butyryl chloride for ethyl chloroformate. Wt.: 63 mg (66%). $^1$H NMR (300 MHz, d$^6$-DMSO) (1:1 mixture of diastereomers) δ 8.72 (d, 1H), 8.47 (d, 1H), 8.33 (m, 1H), 8.15 (m, 2H), 7.68 (m, 3H), 4.00 (m, 1H), 3.56 (m, 1H), 3.26 (m, 1H), 2.87 (m, 1H), 2.52 (m, 1H), 2.13 (m, 2H), 1.90 (m, 1H), 1.68 (m, 2H), 1.39 (m, 6H), 1.28 (m, 2H), 1.13 (m, 2H), 0.95 (m, 4H), 0.75 (m, 5H); LC/MS m/z 500 (M+H)$^+$.

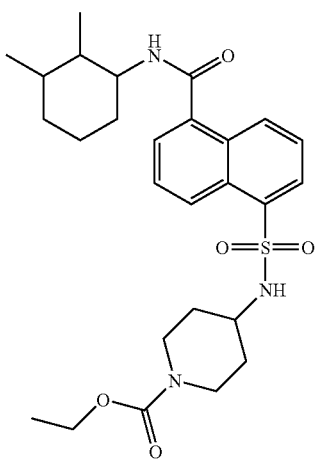

(±)-4-[5-(2,3-Dimethyl-cyclohexylcarbamoyl)-naphthalene-1-sulfonylamino]-piperidine-1-carboxylic acid ethyl ester (H-30)

The title compound was prepared according to the general procedure in Scheme 17, substituting 2,3-dimethyl-cyclohexylamine for 2-methyl-cyclohexylamine. Wt.: 54 mg (24%). $^1$H NMR (300 MHz, CDCl$_3$) (mixture of four diastereomers) δ 8.70 (d, 1H), 8.55 (d, 1H), 8.33 (d, 1H), 7.64 (m, 3H), 5.96 (m, 1H), 4.67 (m, 1H), 4.05 (m, 3H), 3.87 (m, 2H), 3.25 (m, 1H), 2.72 (m, 2H), 2.23 (m, 1H), 2.03 (m, 1H), 1.64 (m, 8H), 1.24 (m, 6H), 1.06 (m, 2H), 0.97 (m, 2H), 0.85 (m, 1H); LC/MS m/z 516 (M+H)$^+$.

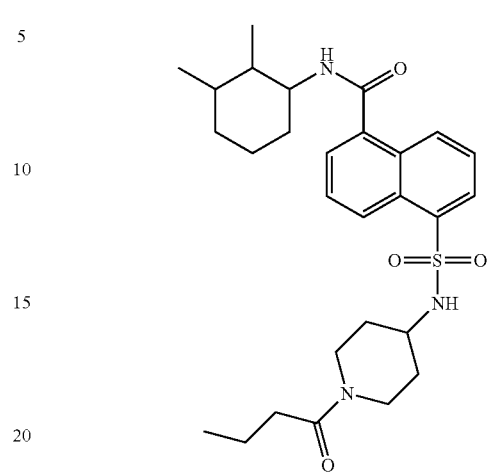

(±)-5-(1-Butyryl-piperidin-4-ylsulfamoyl)-naphthalene-1-carboxylic acid (2,3-dimethyl-cyclohexyl)-amide (H-31)

The title compound was prepared according to the general procedure in Scheme 17, substituting 2,3-dimethyl-cyclohexylamine for 2-methyl-cyclohexylamine, and butyryl chloride for ethyl chloroformate. Wt.: 66 mg (29%) $^1$H NMR (300 MHz, CDCl$_3$) (mixture of four diastereomers) δ 8.70 (d, 1H), 8.55 (d, 1H), 8.33 (d, 1H), 7.66 (m, 3H), 5.96 (m, 1H), 4.73 (m, 1H), 4.27 (m, 1H), 3.63 (m, 1H), 3.27 (m, 2H), 2.94 (m, 1H), 2.58 (m, 1H), 2.18 (m, 2H), 1.60 (m, 12H), 1.15 (m, 4H), 0.93 (m, 7H); LC/MS m/z 514 (M+H)$^+$.

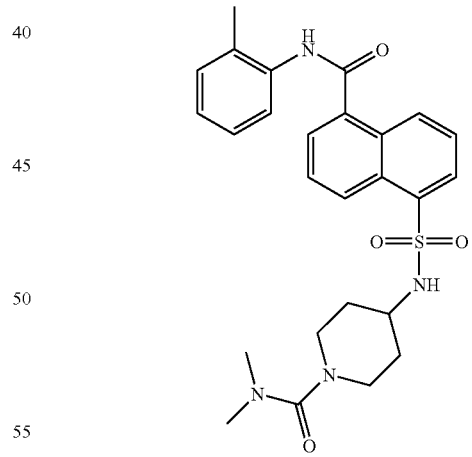

4-(5-o-Tolylcarbamoyl-naphthalene-1-sulfonylamino)-piperidine-1-carboxylic acid dimethylamide (H-32)

The title compound was prepared according to the general procedure in Scheme 17, substituting 2-methyl-phenylamine for 2-methyl-cyclohexylamine, and dimethylcarbamyl chloride for ethyl chloroformate. Wt.: 38 mg (22%). $^1$H NMR (300 MHz, CDCl$_3$) δ 8.77 (d, 1H), 8.67 (d, 1H), 8.35 (d, 1H), 7.97 (d, 1H), 7.85 (d, 1H), 7.68, (m, 3H), 7.25 (m, 3H), 4.95 (d, 1H), 3.46 (m, 2H), 3.29 (m, 1H), 2.69 (m, 2H), 2.54 (s, 3H), 1.62 (m, 2H), 1.33 (m, 2H); LC/MS m/z 495 (M+H)+.

1H), 8.35 (d, 1H), 8.27 (s, 1H), 7.91 (d, 1H), 7.69 (m, 2H), 7.40 (m, 2H), 7.17 (m, 1H), 4.80 (d, 1H), 4.06 (m 2H), 3.90 (m, 2H), 3.31 (m, 1H), 2.74 (m, 2H), 1.80 (m, 2H), 1.22 (m, 2H), 1.20 (t, 3H); LC/MS m/z 517 (M+H)+.

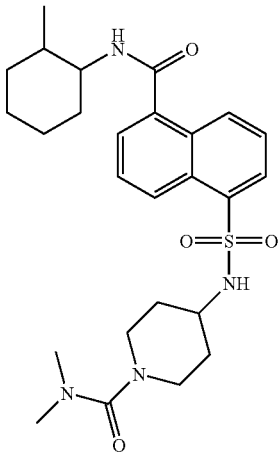

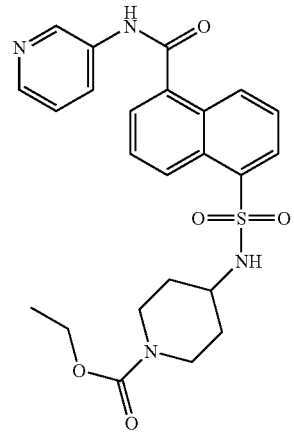

(±)-4-[5-(2-Methyl-cyclohexylcarbamoyl)-naphthalene-1-sulfonylamino]-piperidine-1-carboxylic acid dimethylamide (H-33)

The title compound was prepared according to the general procedure in Scheme 17, substituting dimethylcarbamyl chloride for ethyl chloroformate. Wt.: 20 mg (22%). $^1$H NMR (300 MHz, CDCl$_3$) (1:1 mixture of diastereomers) δ 8.69 (m, 1H), 8.50 (m, 1H), 8.31 (m, 1H), 7.60 (m, 3H), 6.17 (m, 1H), 5.05 (m, 1H), 4.40 (m, 1H), 3.80 (m, 1H), 3.40 (m, 2H), 3.25 (m, 1H), 2.76 (s, 6H), 2.66 (m, 2H), 2.08 (m, 1H), 1.96 (m, 3H), 1.58 (m, 2H), 1.33 (m, 6H), 1.08 (d, 1.5H), 1.02 (d, 1.5H); LC/MS m/z 501 (M+H)+.

4-[5-(Pyridin-3-ylcarbamoyl)-naphthalene-1-sulfonylamino]-piperidine-1-carboxylic acid ethyl ester (H-35)

The title compound was prepared according to the general procedure in Scheme 17, substituting pyridine-3-ylamine for 2-methyl-cyclohexylamine. Wt.: 20 mg (14%). $^1$H NMR (300 MHz, CDCl$_3$) δ 8.81 (s, 2H), 8.70 (d, 1H), 8.65 (m, 1H), 8.60 (d, 1H), 8.40 (d, 1H), 8.27 (d, 1H), 7.81 (m, 1H), 7.61 (m, 2H), 7.40 (m, 2H), 7.22 (m, 1H), 5.40 (d, 1H), 4.04 (q, 2H), 3.80 (m, 2H), 3.24 (m, 1H), 2.70 (m, 2H), 1.80 (m, 2H), 1.60 (m, 2H), 1.22 (m, 2H), 1.20 (t, 3H); LC/MS m/z 483 (M+H)+.

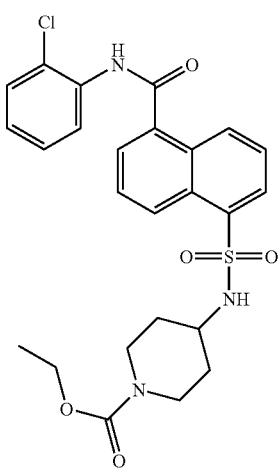

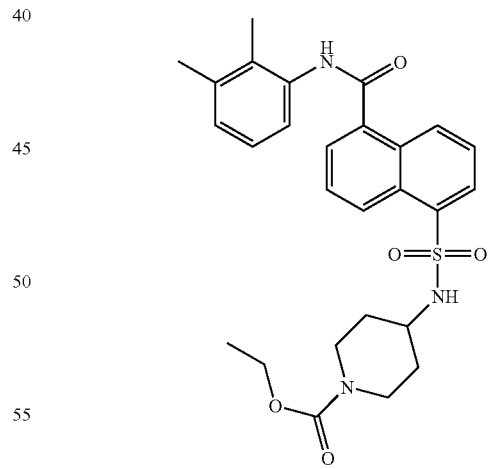

4-[5-(2-chloro-phenylcarbamoyl)-naphthalene-1-sulfonylamino]-piperidine-1-carboxylic acid ethyl ester (H-34)

The title compound was prepared according to the general procedure in Scheme 17, substituting 2-chloro-phenylamine for 2-methyl-cyclohexylamine. Wt.: 36 mg (58%). $^1$H NMR (300 MHz, CDCl$_3$) δ 8.80 (d, 1H), 8.71 (d, 1H), 8.53 (m, 4-[5-(2,3-Dimethyl-phenylcarbamoyl)-naphthalene-1-sulfonylamino]-piperidine-1-carboxylic acid ethyl ester (H-36)

The title compound was prepared according to the general procedure in Scheme 17, substituting 2,3-dimethyl-phenylamine for 2-methyl-cyclohexylamine. Wt.: 86 mg (67%). $^1$H NMR (300 MHz, d$^6$-DMSO) δ 10.18 (s, 1H), 8.77 (d, 1H), 8.51 (d, 1H), 8.23 (d, 1H), 8.17 (d, 1H), 7.93 (d, 1H), 7.82 (d, 1H), 7.72 (m, 1H), 7.30 (d, 1H), 7.12 (m, 2H), 3.94 (q, 2H), 3.68 (m, 2H), 3.20 (m, 1H), 2.76 (m, 2H), 2.32 (s, 3H), 2.20 (s, 3H), 1.45 (m, 2H), 1.18 (m, 2H), 1.04 (t, 3H); LC/MS m/z 510 (M+H)+.

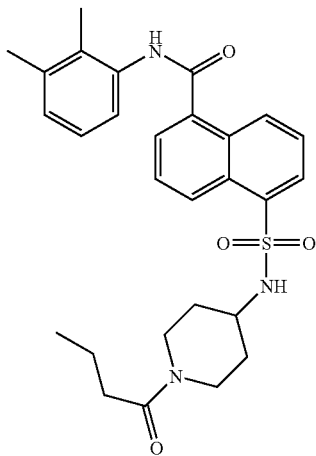

5-(1-Butyryl-piperidin-4-ylsulfamoyl)-naphthalene-1-carboxylic acid (2,3-dimethyl-phenyl)-amide (H-37)

The title compound was prepared according to the general procedure in Scheme 17, substituting 2,3-dimethyl-phenylamine for 2-methyl-cyclohexylamine, and butyryl chloride for ethyl chloroformate. Wt.: 74 mg (58%). $^1$H NMR (300 MHz, d$^6$-DMSO) δ 10.20 (s, 1H), 8.80 (d, 1H), 8.71 (d, 1H), 8.25 (d, 1H), 8.18 (d, 1H), 7.95 (d, 1H), 7.80 (m, 1H), 7.95 (m, 1H), 7.30 (d, 1H), 7.13 (m, 2H), 4.04 (m, 1H), 3.65 (m, 1H), 3.24 (m, 1H), 2.92 (m, 1H), 2.35 (m, 1H), 2.31 (s, 3H) 2.20 (s, 3H), 2.16 (m, 2H), 1.45 (m, 4H), 1.17 (m, 2H), 0.80 (t, 3H); LC/MS m/z 508 (M+H)+.

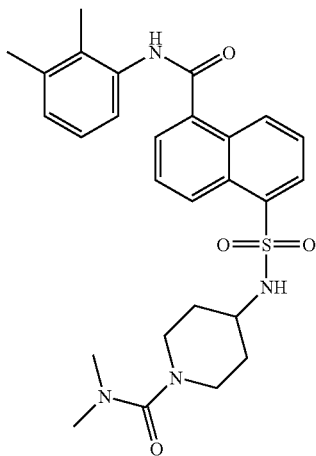

4-[5-(2,3-Dimethyl-phenylcarbamoyl)-naphthalene-1-sulfonylamino]-piperidine-1-carboxylic acid dimethylamide (H-38)

The title compound was prepared according to the general procedure in Scheme 17, substituting 2,3-dimethyl-phenylamine for 2-methyl-cyclohexylamine, and dimethylcarbamyl chloride for ethyl chloroformate. Wt.: 82 mg (64%). $^1$H NMR (300 MHz, d$^6$-DMSO) δ 10.20 (s, 1H), 8.80 (d, 1H), 8.71 (d, 1H), 8.23 (d, 1H), 8.14 (d, 1H), 7.94 (d, 1H), 7.82 (d, 1H), 7.72 (m, 1H), 7.30 (d, 1H), 7.10 (m, 2H), 3.32 (m, 2H), 3.15 (m, 1H), 2.62 (s, 6H), 2.58 (m, 2H), 2.30 (s, 3H), 2.20 (s, 3H), 1.42 (m, 2H), 1.26 (m, 2H); LC/MS m/z 509 (M+H)+.

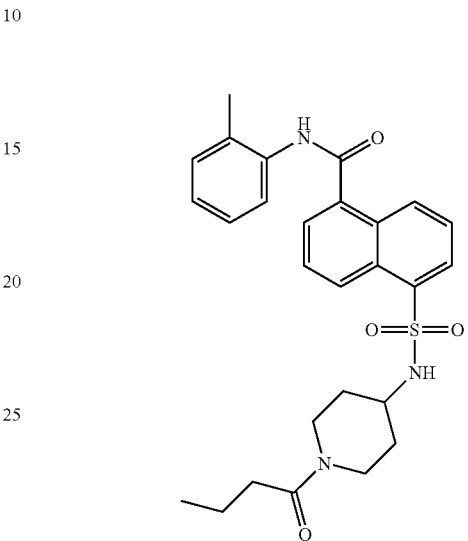

5-(1-Butyryl-piperidin-4-ylsulfamoyl)-naphthalene-1-carboxylic acid o-tolylamide (H-39)

The title compound was prepared according to the general procedure in Scheme 17, substituting 2-methyl-phenylamine for 2-methyl-cyclohexylamine, and butyryl chloride for ethyl chloroformate. Wt.: 38 mg (20%). $^1$H NMR (300 MHz, d$^6$-DMSO) δ 10.15 (s, 1H), 8.80 (d, 1H), 8.72 (d, 1H), 8.22 (d, 1H), 8.15 (m, 1H), 7.95 (m, 2H), 7/77, (m, 2H), 7.52 (d, 1H), 7.23 (m, 3H), 4.03 (m, 1H), 3.63 (m, 1H), 3.25 (m, 1H), 2.96 (m, 1H), 2.55 (m, 1H), 2.31 (s, 3H), 2.14 (m, 2H), 1.43 (m, 4H), 1.16 (m, 2H), 0.80 (t, 3H); LC/MS m/z 494 (M+H)+.

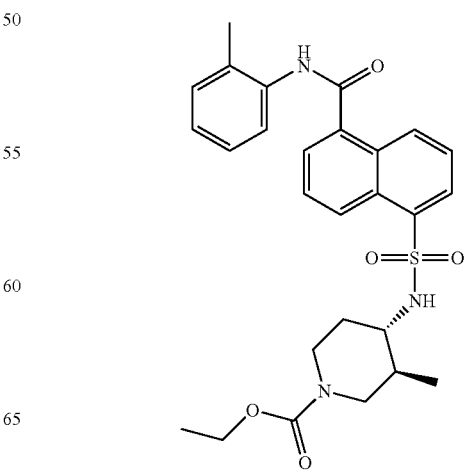

(±)-trans-3-Methyl-4-(5-o-tolylcarbamoyl-naphthalene-1-sulfonylamino)-piperidine-1-carboxylic acid ethyl ester (H-40)

The title compound was prepared according to the general procedure in Scheme 17, substituting (±)-5-(3-methyl-piperidin-4-ylsulfamoyl)-naphthalene-1-carboxylic acid o-tolylamide for 5-(piperidin-4-ylsulfamoyl)-naphthalene-1-carboxylic acid (2-methyl-cyclohexyl)-amide. $^1$H NMR (300 MHz, CDCl$_3$) δ 8.78 (d, 1H), 8.69 (d, 1H), 8.37 (d, 1H), 8.02 (d, 1H), 7.88 (d, 1H), 7.67 (m, 3H), 7.31 (m, 2H), 7.18 (m, 1H), 4.75 (d, 1H), 4.05 (q, 2H), 3.92 (m, 2H), 2.87 (m, 1H), 2.62 (m, 1H), 2.34 (s, 3H), 2.33 (m, 1H), 1.60 (m, 1H), 1.32 (m, 1H), 1.18 (t, 3H), 0.64 (m, 3H); LC/MS m/z 510 (M+H)$^+$.

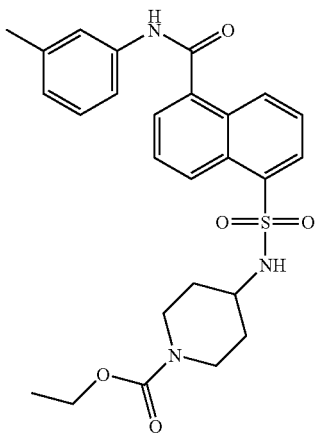

4-(5-m-Tolylcarbamoyl-naphthalene-1-sulfonylamino)-piperidine-1-carboxylic acid ethyl ester (H-41)

The title compound was prepared according to the general procedure in Scheme 17, substituting m-tolylamine for 2-methyl-cyclohexylamine. Wt.: 46 mg (66%). $^1$H NMR (300 MHz, d$^6$-DMSO) δ 10.58 (s, 1H), 8.78 (d, 1H), 8.41 (d, 1H), 8.23 (d, 1H), 8.17 (d, 1H), 7.82 (m, 2H), 7.71 (m, 2H), 7.55 (d, 1H), 7.25 (d, 1H), 6.95 (d, 1H), 3.94 (q, 2H), 3.68 (m, 2H), 3.21 (m, 1H), 2.74 (m, 2H), 2.28 (s, 3H), 1.45 (m, 2H), 1.18 (m, 2H), 1.09 (t, 3H); LC/MS m/z 496 (M+H)$^+$.

Scheme 18

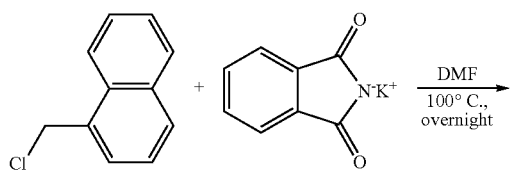

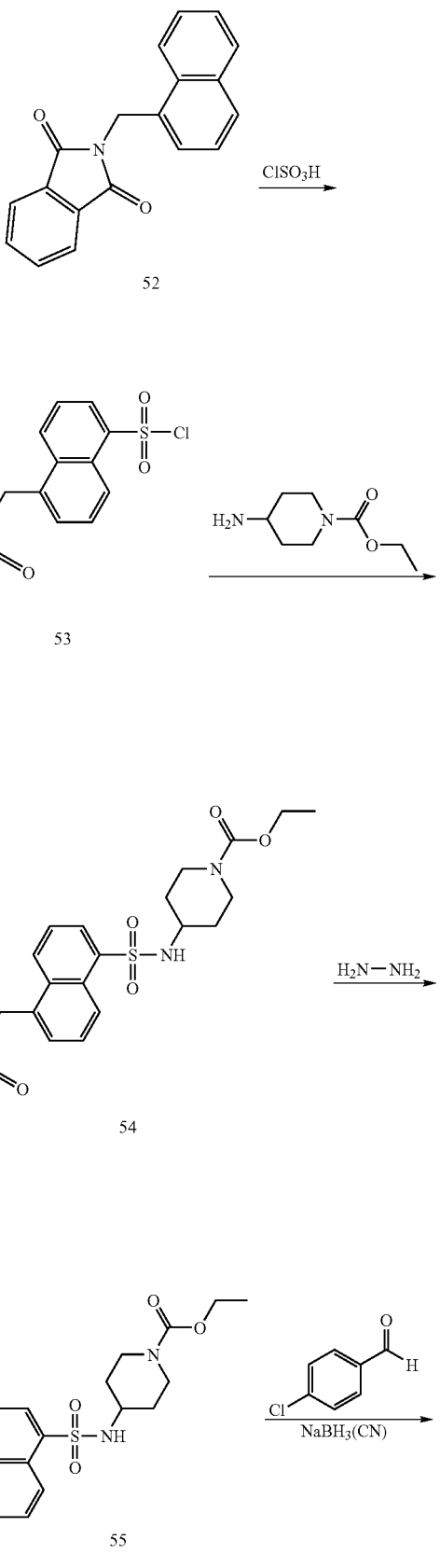

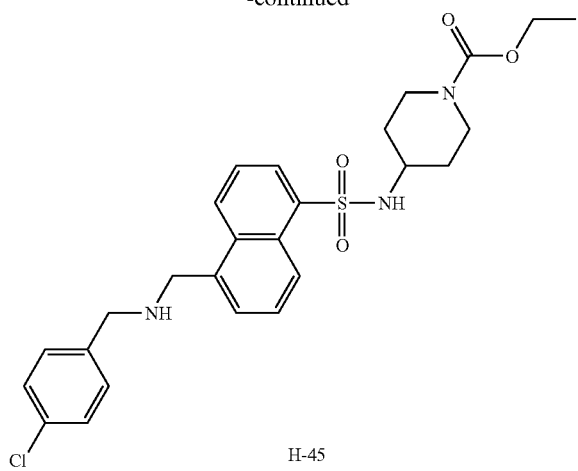

H-45

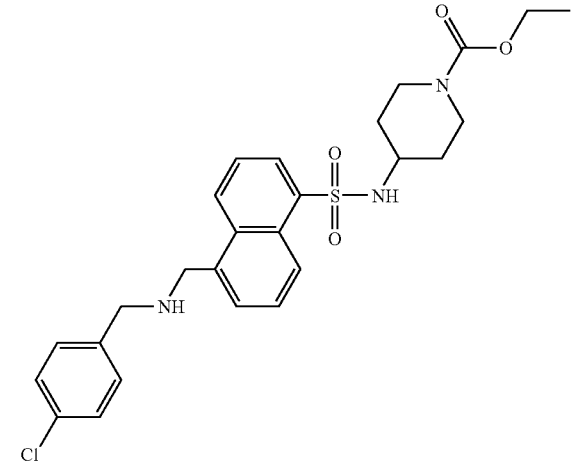

4-{5-1(4-Chloro-benzylamino)-methyl]-naphthalene-1-sulfonylamino}-piperidine-1-carboxylic acid ethyl ester (H-45)

To a solution of 1-chloromethyl-naphthalene (8.83 g, 50 mmol) in DMF (90 mL) was added phthalimide potassium salt (11.1 g, 60 mmol). The resultant solution was stirred at 100° C. overnight. The mixture was poured into ice-cold water and the precipitate was collected, washed with small amount of methanol and dried under vacuo to give 2-naphthalen-1-ylmethyl-isoindole-1,3-dione 52 (14.2 g, 99% yield). This material was used without further purification.

To a 0° C. solution of chlorosulfonic acid (10.8 mL, 160 mmol) was added 2-naphthalen-1-ylmethyl-isoindole-1,3-dione 52 (2.87 g, 10 mmol). The resulting solution was stirred at 25° C. for 2 hr. The mixture was poured into ice; the precipitate was collected and dried in vacuo to give a mixture of 5-(1,3-dioxo-1,3-dihydro-isoindol-2-ylmethyl)-naphthalene-1-sulfonyl chloride 53 and 4-(1,3-dioxo-1,3-dihydro-isoindol-2-ylmethyl)-naphthalene-1-sulfonyl chloride as a byproduct. This material was used without further purification.

To a solution of sulfonyl chlorides 53 (3.86 g, 10 mmol) in dichloromethane (40 mL) was added 4-amino-piperidine-1-carboxylic acid ethyl ester (2.06 g, 12 mmol) and triethyl amine (3.5 mL, 25 mmol). The resulting solution was stirred at 25° C. overnight and quenched with water. The aqueous layer was extracted with $CH_2Cl_2$. The organic extracts were combined, washed with brine and dried over $MgSO_4$. The solution was filtered and concentrated in vacuo to give the crude product. The crude material was purified by flash chromatography (hexane:EtOAc) to provide a mixture of 4-[5-(1,3-dioxo-1,3-dihydro-isoindol-2-ylmethyl)-naphthalene-1-sulfonylamino]-piperidine-1-carboxylic acid ethyl ester 54 and 4-[4-(1,3-dioxo-1,3-dihydro-isoindol-2-ylmethyl)-naphthalene-1-sulfonylamino]-piperidine-1-carboxylic acid ethyl ester as a byproduct.

To a solution of sulfonamide mixtures 54 (3.11 g, 5.97 mmol) in methanol (30 mL) was added hydrazine (3.4 mL). The resulting solution was stirred at 25° C. for 2 hr. The mixture was partitioned between water (20 mL) and $CH_2Cl_2$ (20 mL). The aqueous layer was re-extracted with $CH_2Cl_2$. The organic extracts were combined, washed with brine and dried over $MgSO_4$. The solution was filtered and concentrated in vacuo to give the crude product. The crude material was purified by preparative TLC to provide 4-(5-aminomethyl-naphthalene-1-sulfonylamino)-piperidine-1-carboxylic acid ethyl ester 55 as a white solid.

To a 25° C. solution of 4-(5-aminomethyl-naphthalene-1-sulfonylamino)-piperidine-1-carboxylic acid ethyl ester 55 (62 mg, 0.159 mmol) in MeOH (4 mL) was added 4-chloro-benzaldehyde (45 mg, 0.318 mmol) and sodium cyanoborohydride (50 mg, 0.795 mmol). After stirring for 2 h at 25° C., the solution was concentrated in vacuo and the resultant crude material was purified by reverse phase HPLC to provide the title compound (H-45) as its formate salt. $^1$H NMR (300 MHz, MeOD) δ 8.78 (d, 1H), 8.38 (s, 1H), 8.33 (m, 2H), 7.70 (m, 3H), 7.45 (m, 4H), 4.57 (s, 2H), 4.20 (s, 2H), 4.05 (q, 2H), 3.75 (d, 2H), 3.20 (m, 1H), 2.75 (m, 2H), 1.50 (m, 2H), 1.25 (m, 2H), 1.17 (t, 3H); LC/MS m/z 516 (M+H)$^+$.

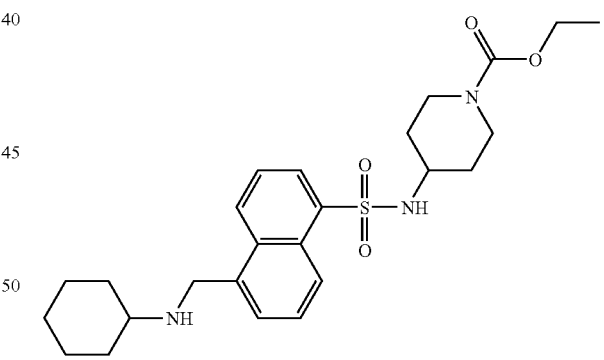

4-(5-Cyclohexylaminomethyl-naphthalene-1-sulfonylamino)-piperidine-1-carboxylic acid ethyl ester (H-46)

The title compound was made following general procedure in Scheme 18, substituting cyclohexanone for 4-chlorobenzaldehyde. $^1$H NMR (300 MHz, MeOD) δ 8.85 (d, 1H), 8.45 (d, 1H), 8.37 (d, 1H), 7.85 (d, 1H), 7.77 (m, 2H), 4.75 (s, 2H), 4.00 (q, 2H), 3.80 (d, 2H), 3.72 (d, 1H), 3.65 (d, 1H), 3.58 (m, 1H), 3.42 (m, 1H), 2.75 (br s, 2H), 2.40 (m, 1H), 1.95 (m, 1H), 1.75 (d, 1H), 1.50 (m, 5H), 1.20 (m, 7H); LC/MS m/z 475 (M+H)$^+$.

Scheme 19

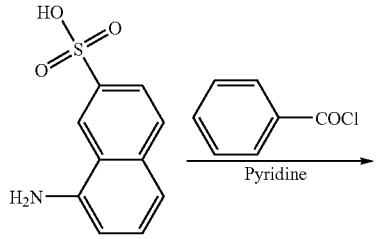

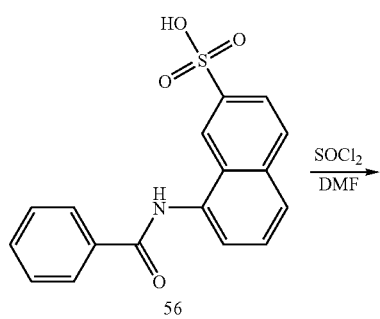

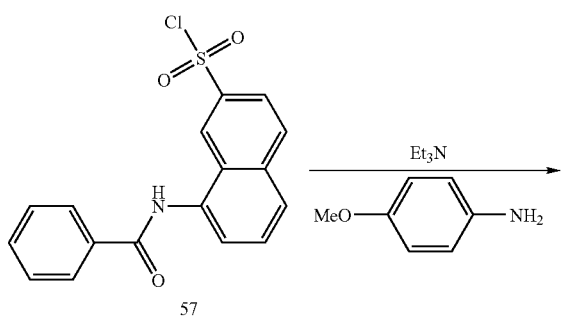

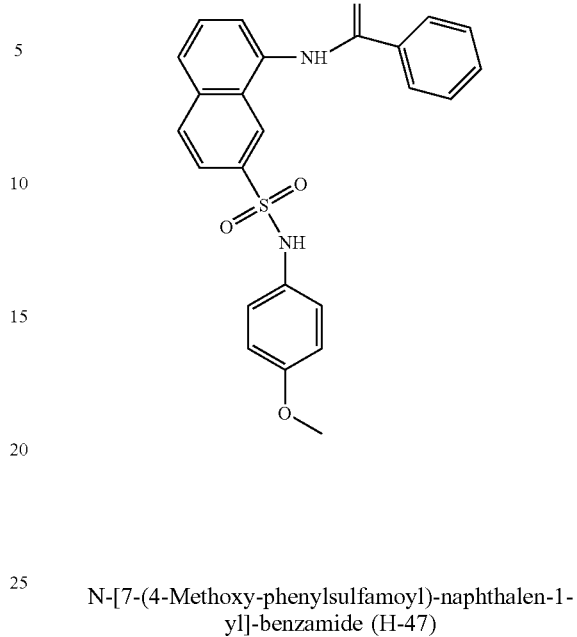

N-[7-(4-Methoxy-phenylsulfamoyl)-naphthalen-1-yl]-benzamide (H-47)

8-Benzoylamino-naphthalene-2-sulfonic acid 56 was prepared following the general procedure in Scheme 16, substituting 8-amino-naphthalene-2-sulfonic acid for 5-amino-naphthalene-1-sulfonic acid.

8-Benzoylamino-naphthalene-2-sulfonyl chloride 57 was prepared following the general procedure in Scheme 16, substituting 8-benzoylamino-naphthalene-2-sulfonic acid for 5-benzoylamino-napthalene-1-sulfonic acid.

The title compound (H-47) was prepared following the general procedure in Scheme 16 substituting 8-benzoylamino-naphthalene-2-sulfonyl chloride for 5-benzoylamino-napthalene-1-sulfonyl chloride. $^1$H NMR (300 MHz, MeOD) δ 8.34 (s, 1H), 8.02 (d, 3H), 7.91 (m, 1H), 7.73 (m, 1H), 7.64 (m, 5H), 6.92 (m, 2H), 6.62 (m, 2H), 3.62 (s, 3H); LC/MS (M+H)$^+$ m/z 433.

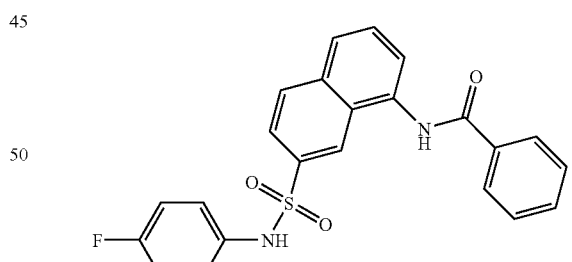

N-[7-(4-Fluoro-phenylsulfamoyl)-naphthalen-1-yl]-benzamide (H-48)

The title compound was made following the general procedure in Scheme 19, substituting p-fluoroaniline for p-anisidine. $^1$H NMR (300 MHz, DMSO) δ 10.60 (s, 1H), 8.37 (s, 1H), 8.08 (m, 3H), 7.93 (d, 1H), 7.68 (m, 6H), 6.96 (m, 4H); LC/MS (M+H)$^+$ m/z 421.

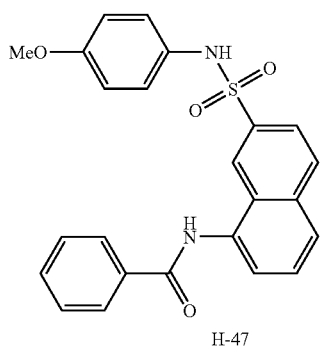

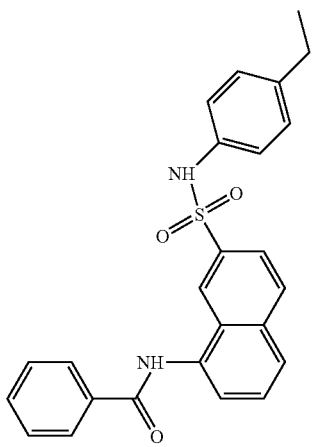

N-[7-(4-Ethyl-phenylsulfamoyl)-naphthalen-1-yl]-benzamide (H-49)

The title compound was made following the general procedure Scheme 19, substituting p-ethylaniline for p-anisidine. ¹H NMR (300 MHz, DMSO) δ 10.61 (s, 1H), 8.42 (s, 1H), 8.09 (m, 3H), 7.94 (d, 1H), 7.69 (m, 7H), 6.96 (s, 3H), 2.40 (m, 2H), 1.03 (t, 3H); LC/MS (M+H)⁺ m/z 431.

N-[7-(4-Isopropyl-phenylsulfamoyl)-naphthalen-1-yl]-benzamide (H-50)

The title compound was made following the general procedure Scheme 19, substituting p-isopropylaniline for p-anisidine. ¹H NMR (300 MHz, DMSO) δ 10.63 (s, 1H), 8.44 (s, 1H), 8.10 (m, 3H), 7.94 (d, 1H), 7.69 (m, 6H), 6.99 (s, 4H), 2.69 (m, 1H), 1.23 (s, 3H), 1.05 (d, 6H); LC/MS (M+H)⁺ m/z 445.

4-(8-Benzoylamino-naphthalene-2-sulfonylamino)-piperidine-1-carboxylic acid ethyl ester (H-51)

The title compound was made following the general procedure Scheme 19, substituting 4-amino-piperidine-1-carboxylic acid ethyl ester for p-anisidine. ¹H NMR (300 MHz, MeOD) δ 8.47 (s, 1H), 8.06 (m, 3H), 7.94 (d, 1H), 7.86 (m, 1H), 7.62 (m, 5H), 4.00 (q, 2H), 3.80 (d, 2H), 3.20 (m, 1H), 2.76 (m, 2H), 1.61 (m, 2H), 1.25 (m, 2H), 1.16 (m, 3H); LC/MS (M+H)⁺ m/z 482.

4-(6-Benzoylamino-naphthalene-2-sulfonylamino)-piperidine-1-carboxylic acid ethyl ester (H-52)

The title compound was made following the general procedure in Scheme 16, substituting 6-amino-naphthalene-2-sulfonic acid for 5-amino-naphthalene-1-sulfonic acid, and 4-amino-piperidine-1-carboxylic acid ethyl ester for p-anisidine.

Scheme 20

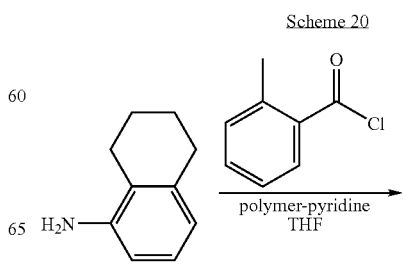

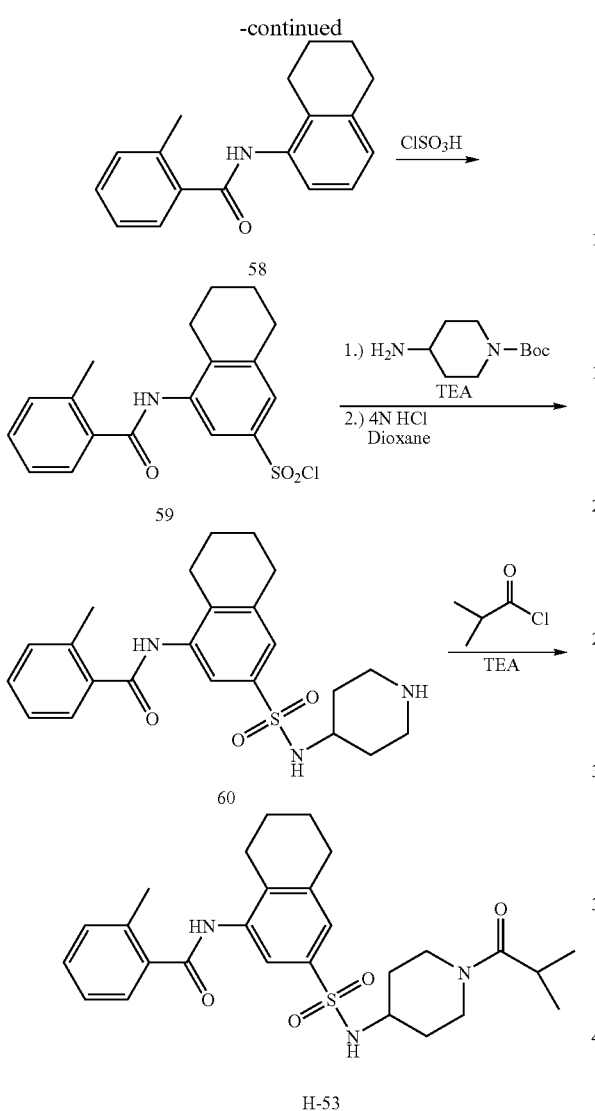

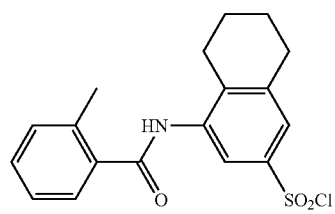

4-(2-Methyl-benzoylamino)-5,6,7,8-tetrahydro-naphthalene-2-sulfonyl chloride (59)

To neat amide (58), at 0° C., was added chlorosulfonic acid (5 eq) dropwise. The temperature was allowed to warm to 25° C. and then heated at 70° C. for 45 minutes. After cooling to 25° C., the reaction mixture was poured into ice water, and the resultant precipitate was collected by filtration to give the title compound as a solid. The product (mixture of regioisomers) was used without further purification.

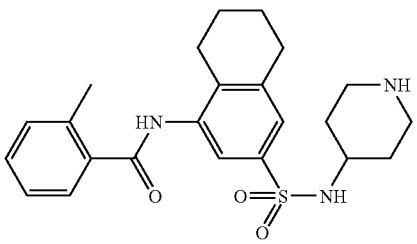

2-Methyl-N-[3-(piperidin-4-ylsulfamoyl)-5,6,7,8-tetrahydro-naphthalen-1-yl]-benzamide (60)

To a 25° C. solution of sulfonyl chloride (59) (1 eq) in anhydrous THF (15 mL per mmol RSO$_2$Cl) was added 4-amino-piperidine-1-carboxylic acid tert-butyl ester (1.1 eq), followed by triethyl amine (1.5 eq). The resultant solution was stirred at 25° C. for 18 hours. The reaction mixture was filtered and the filtrate was concentrated in vacuo. 4 N HCl/Dioxane was added and the reaction was stirred for 2 hours. Filtration afforded a light gray colored solid as the HCl salt of the title compound (in addition to the 1,4 regioisomer). LC/MS (M+H)$^+$ m/z 527.

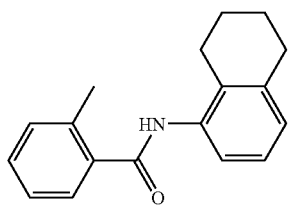

2-Methyl-N-(5,6,7,8-tetrahydro-naphthalen-1-yl)-benzamide (58)

To a 25° C. solution of aniline (1 eq) in anhydrous THF (2 mL per mmol aniline) was added polymer bound pyridine (1.5 eq) followed by 2-methyl-benzoyl chloride (1 eq). The mixture was stirred at 25° C. for 12-24 h. The reaction mixture was filtered and the filtrate concentrated in vacuo. Hexane was added to the residue and the resulting precipitate was collected by filtration, resulting in a white solid (yield 65%). LC/MS (M+H)$^+$ m/z 266. The crude material was used without further purification.

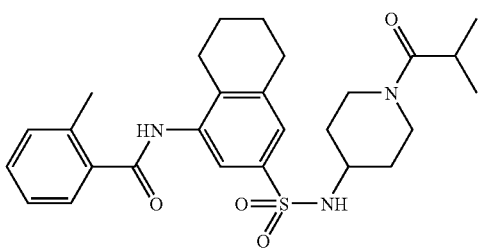

N-[3-(1-Isobutyryl-piperidin-4-ylsulfamoyl)-5,6,7,8-tetrahydro-naphthalen-1-yl]-2-methyl-benzamide (H-53)

To a 25° C. mixture of sulfonamide (60) (185 mg, 0.4 mmol) in THF (10 mL) was added isobutyryl chloride (107 mg, 1 mmol) and triethyl amine (607 mg, 6 mmol). The mixture was stirred for 18 hours, followed by filtration to remove the solid. The filtrate was concentrated in vacuo and purified via chromatography, to afford the title compound as white solid (17 mg). $^1$H NMR (300 MHz, MeOD) δ 7.81 (s, 1H), 7.53 (m, 2H), 7.38 (m, 1H), 7.31 (m, 2H), 4.28 (m, 1H), 3.90 (m, 1H), 3.19 (m, 1H), 3.09 (m, 1H), 2.83 (m, 6H), 2.55 (s, 3H), 1.85 (m, 7H), 1.38 (m, 2H), 1.04 (m, 6H) ); LC/MS (M+H)$^+$ m/z 498.

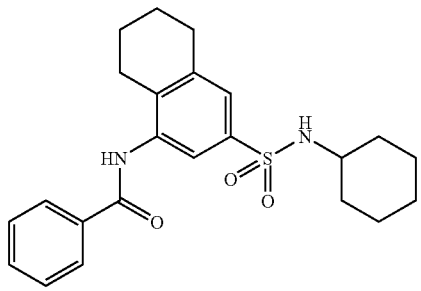

N-(3-Cyclohexylsulfamoyl-5,6,7,8-tetrahydro-naphthalen-1-yl)-benzamide (H-54)

The title compound was made following general procedure in Scheme 20, substituting benzoyl chloride for 2-methyl-benzoyl chloride, and cyclohexylamine for 4-amino-piperidine-1-carboxylic acid tert-butyl ester. $^1$H NMR (300 MHz, CDCl$_3$) δ 8.34 (d, 1H, Ph-H), 7.88 (m, 2H), 7.70 (br s, 1H, N—H), 7.53 (m, 5H), 3.20 (m, 1H), 2.85 (t, 2H), 2.72 (t, 2H), 1.85 (m, 5H,), 1.60 (m, 5H), 1.25 (m, 4H); LC/MS (M+H)$^+$ m/z 4.13.

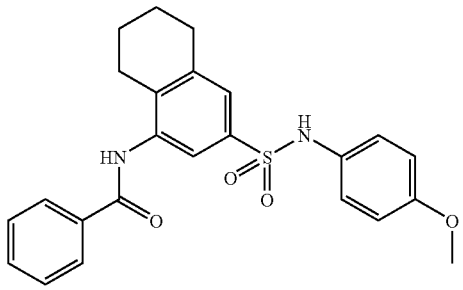

N-[3-(4-Methoxy-phenylsulfamoyl)-5,6,7,8-tetrahydro-naphthalen-1-yl]-benzamide (H-55)

The title compound was made following general procedure in Scheme 20, substituting benzoyl chloride for 2-methyl-benzoyl chloride, and 4-methoxy-phenylamine for 4-amino-piperidine-1-carboxylic acid tert-butyl ester. $^1$H NMR (300 MHz, CDCl$_3$) δ 8.29 (d, 1H), 7.86 (m, 2H), 7.76 (br s, 1H, N—H), 7.55 (m, 3H), 7.20 (d, 1H), 7.06 (dd, 2H), 6.76 (dd, 2H), 6.70 (br s, 1H, N—H), 3.73 (s, 3H), 2.70 (m, 4H), 1.82 (m, 4H); LC/MS (M+H)$^+$ m/z437.

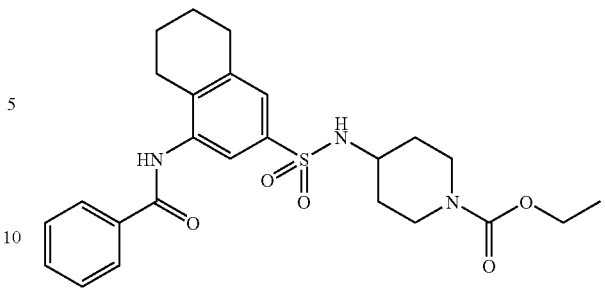

4-(4-Benzoylamino-5,6,7,8-tetrahydro-naphthalene-2-sulfonylamino)-piperidine-1-carboxylic acid ethyl ester (H-56)

The title compound was made following general procedure in Scheme 20, substituting benzoyl chloride for 2-methyl-benzoyl chloride, and 4-amino-piperidine-1-carboxylic acid ethyl ester for 4-amino-piperidine-1-carboxylic acid tert-butyl ester. $^1$H NMR (300 MHz, CDCl$_3$) δ 8.26 (d, 1H), 7.93 (br s, 1H, N—H), 7.86 (m, 2H), 7.50 (m, 4H), 4.08 (q, 2H), 3.92 (m, 2H), 3.32 (m, 1H), 2.82 (m, 6H), 1.90 (m, 6H), 1.36 (m, 2H), 1.24 (t, 3H); LC/MS (M+H)$^+$ m/z 486.

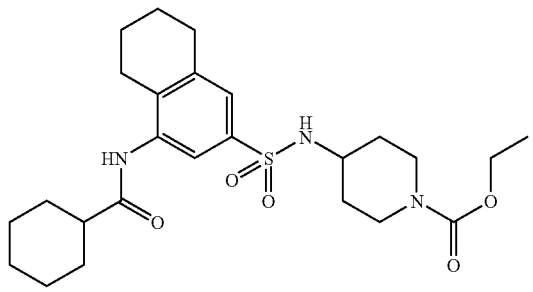

4-[4-(Cyclohexanecarbonyl-amino)-5,6,7,8-tetrahydro-naphthalene-2-sulfonylamino]-piperidine-1-carboxylic acid ethyl ester (H-57)

The title compound was made following general procedure in Scheme 20, substituting cyclohexanecarbonyl chloride for 2-methyl-benzoyl chloride, and 4-amino-piperidine-1-carboxylic acid ethyl ester for 4-amino-piperidine-1-carboxylic acid tert-butyl ester. $^1$H NMR (300 MHz, MeOD) δ 7.74 (s, 1H), 7.53 (s, 1H), 5.65(m, 1H), 4.11 (q, 2H), 3.98 (m, 2H), 3.32 (m, 1H), 2.72 (m, 6H), 1.82 (m, 18H), 1.30 (t, 3H); LC/MS (M+H)$^+$ m/z 492.

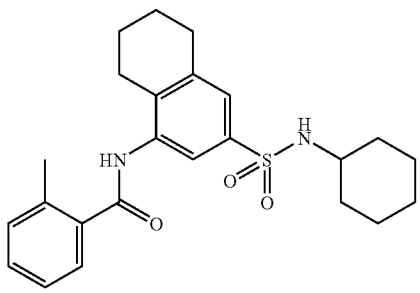

N-(3-Cyclohexylsulfamoyl-5,6,7,8-tetrahydro-naphthalen-1-yl)-2-methyl-benzamide (H-58)

The title compound was made following general procedure in Scheme 20, substituting cyclohexylamine for 4-amino-piperidine-1-carboxylic acid tert-butyl ester. $^1$H NMR (300 MHz, DMSO) δ 9.79 (s, 1H), 7.72 (s, 1H), 7.55(m, 2H), 7.39 (m, 2H), 7.31 (m, 2H), 2.94 (m, 1H), 2.79 (m, 4H), 2.44 (s, 3H), 1.69 (m, 8H), 1.46 (m, 1H), 1.13 (m, 5H); LC/MS (M+H)$^+$ m/z 427.

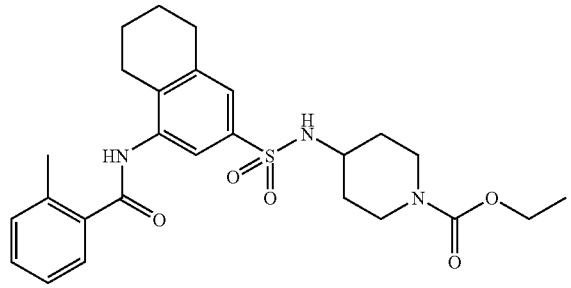

4-[4-(2-Methyl-benzoylamino)-5,6,7,8-tetrahydro-naphthalene-2-sulfonylamino]-piperidine-1-carboxylic acid ethyl ester (H-59)

The title compound was made following general procedure in Scheme 20, substituting 4-amino-piperidine-1-carboxylic acid ethyl ester for 4-amino-piperidine-1-carboxylic acid tert-butyl ester. $^1$H NMR (300 MHz, DMSO) δ 9.82 (s, 1H), 7.77 (m, 2H), 7.53(m, 1H), 7.39 (m, 2H), 7.31 (m, 2H), 3.99 (q, 2H), 3.78 (m, 2H), 3.25 (m, 1H), 2.82 (m, 6H), 2.42 (s, 3H), 1.72 (m, 6H), 1.27 (m, 2H), 1.14 (t, 3H); LC/MS (M+H)$^+$ m/z 500.

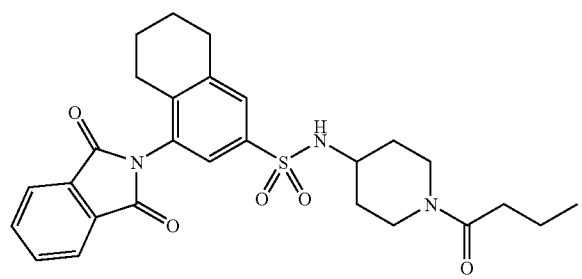

4-(1,3-Dioxo-1,3-dihydro-isoindol-2-yl)-5,6,7,8-tetrahydro-naphthalene-2-sulfonic acid (1-butyryl-piperidin-4-yl)-amide (H-60)

The title compound was prepared following general procedure in Scheme 20, substituting phthaloyl dichloride for 2-methyl-benzoyl chloride and butyryl chloride for isobutyryl chloride. $^1$H NMR (300 MHz, DMSO) δ 7.97 (m, 1H), 7.96 (s, 1H), 7.92 (s, 1H), 7.91 (m, 1H), 7.76 (d, 1H), 7.66 (d, 2H), 4.06 (d, 1H), 3.69 (d, 1H), 3.25 (m, 1H), 3.01 (m, 1H), 2.88 (t, 2H), 2.69 (t, 1H), 2.24 (t, 2H), 1.70 (m, 7H), 1.47 (m, 2H), 1.24 (m, 2H), 0.85 (t, 3H). LC/MS m/z 509 (M–H)$^-$, 511 (M+H)$^+$.

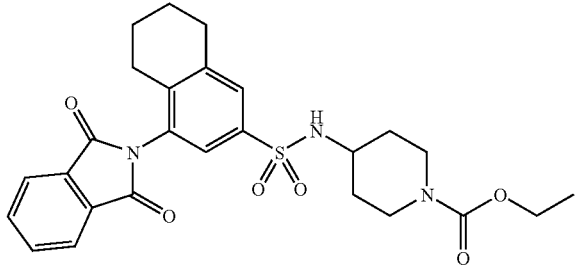

4-[4-(1,3-Dioxo-1,3-dihydro-isoindol-2-yl)-5,6,7,8-tetrahydro-naphthalene-2-sulfonylamino]-piperidine-1-carboxylic acid ethyl ester (H-61)

The title compound was prepared following general procedure in Scheme 20, substituting phthaloyl dichloride for 2-methyl-benzoyl chloride and diethylpyrocarbonate for isobutyryl chloride. $^1$H NMR (300 MHz, DMSO) δ 7.97 (m, 1H), 7.96 (s, 1H), 7.92 (s, 1H), 7.91 (m, 1H), 7.76 (d, 1H), 7.65 (d, 2H), 4.00 (q, 2H), 3.74 (d, 2H), 3.23 (d, 2H), 2.88 (m, 4H), 1.71 (m, 7H), 1.25 (m, 2H), 1.14 (t, 3H). LC/MS m/z 511 (M–H)$^-$, 513 (M+H)$^+$.

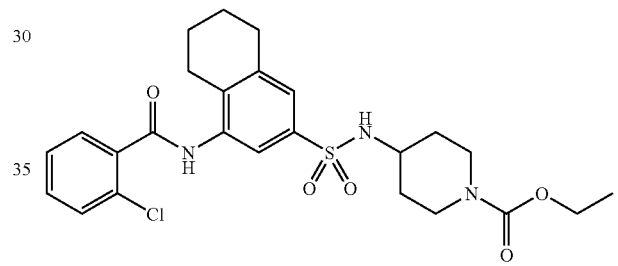

4-[4-(2-Chloro-benzoylamino)-5,6,7,8-tetrahydro-naphthalene-2-sulfonylamino]-piperidine-1-carboxylic acid ethyl ester (H-62)

The title compound was prepared following general procedure in Scheme 20, substituting 2-chloro-benzoyl chloride for 2-methyl-benzoyl chloride and diethylpyrocarbonate for isobutyryl chloride. $^1$H NMR (300 MHz, DMSO) δ 10.04 (s, 1H), 7.81 (s, 1H), 7.77 (s, 1H), 7.63 (dd, 1H), 7.56 (dt, 1H), 7.49 (dt, 2H), 7.43 (s, 1H), 3.97 (q, 2H), 3.72 (d, 2H), 3.19 (m, 1H), 2.82 (m, 4H), 2.76 (m, 2H), 1.75 (d, 4H), 1.73 (m, 2H), 1.27 (m, 2H), 1.14 (t, 3H). LC/MS m/z 519 (M–H)$^-$, 520 (M+H)$^+$.

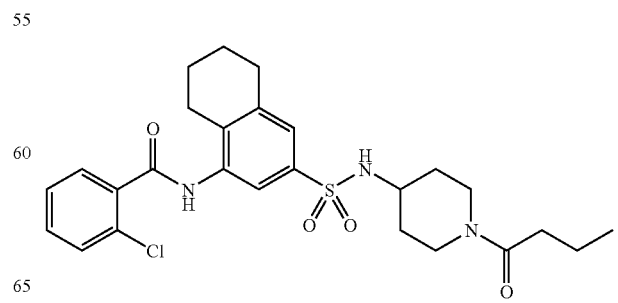

N-[3-(1-Butyryl-piperidin-4-ylsulfamoyl)-5,6,7,8-tetrahydro-naphthalen-1-yl]-2-chloro-benzamide (H-63)

The title compound was prepared following general procedure in Scheme 20, substituting 2-chloro-benzoyl chloride for 2-methyl-benzoyl chloride and butyryl chloride for isobutyryl chloride. $^1$H NMR (300 MHz, DMSO) δ 10.04 (s, 1H), 7.79 (s, 1H), 7.64 (dd, 1H), 7.56 (dt, 1H), 7.49 (dt, 2H), 7.43 (s, 1H), 4.05 (d, 1H), 3.67 (d, 1H), 3.24 (m, 1H), 3.02 (m, 1H), 2.76 (m, 2H), 2.68 (m, 3H), 2.22 (t, 2H), 1.74 (m, 5H), 1.64 (m, 2H), 1.44 (m, 2H), 1.25 (m, 2H), 0.85 (t, 3H). LC/MS m/z 517 (M−H)$^-$, 519 (M+H)$^+$.

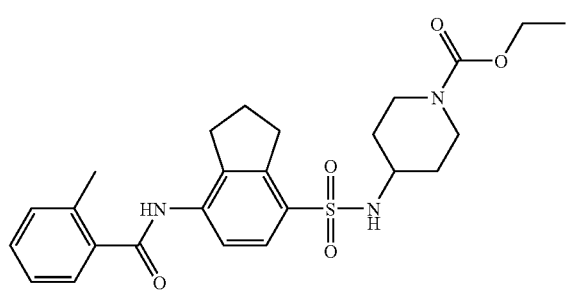

4-[7-(2-Methyl-benzoylamino)-indane-4-sulfonylamino]-piperidine-1-carboxylic acid ethyl ester (H-64)

The title compound was made following general procedure in Scheme 10, substituting indan-4-ylamine for 5,6,7,8-tetrahydro-naphthalen-1-ylamine, and ethyl chloroformate for butyryl chloride. $^1$H NMR (300 MHz, DMSO) δ 7.65 (m, 3H), 7.48 (d, 1H), 7.38 (d, 1H), 7.30 (m, 2H), 3.97 (q, 2H), 3.76 (d, 2H), 3.18 (m, 2H), 2.93 (m, 2H), 2.79 (m, 2H), 2.49 (s, 3H), 2.05 (m, 2H), 1.55 (m, 2H), 1.23 (m, 2H), 1.13 (t, 3H); LC/MS m/z 486 (M+H)$^+$.

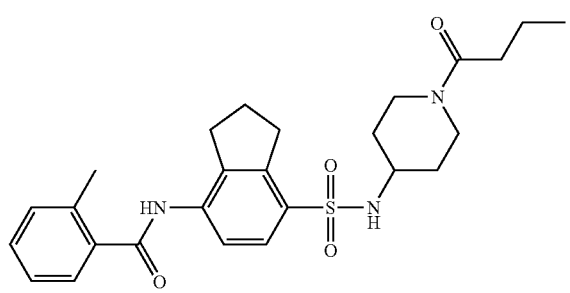

N-[7-(1-Butyryl-piperidin-4-ylsulfamoyl)-indan-4-yl]-2-methyl-benzamide (H-65)

The title compound was made following general procedure in Scheme 10, substituting indan-4-ylamine for 5,6,7,8-tetrahydro-naphthalen-1-ylamine. $^1$H NMR (300 MHz, DMSO) δ 7.66 (m, 3H), 7.44 (d, 1H), 7.40 (m, 1H), 7.29 (m, 2H), 4.10 (d, 1H), 3.68 (d, 1H), 3.17 (m, 3H), 2.92 (m, 3H), 2.60 (t, 2H); 2.41 (s, 3H), 2.16 (m, 2H), 1.55 (m, 1H), 1.47 (m, 2H), 1.23 (m, 2H), 0.84 (t, 6H); LC/MS m/z 482 (M−H)$^-$.

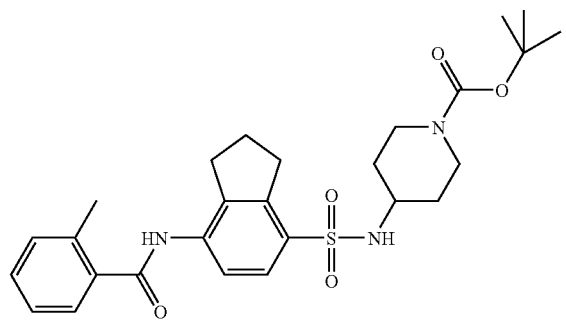

4-[7-(2-Methyl-benzoylamino)-indane-4-sulfonylamino]-piperidine-1-carboxylic acid tert-butyl ester (H-66)

The title compound was made following general procedure in scheme 10, substituting indan-4-ylamine for 5,6,7,8-tetrahydro-naphthalen-1-ylamine. $^1$H NMR (300 MHz, CDCl$_3$) δ 8.24 (d, 1H), 7.79 (d, 1H), 7.50 (d, 1H), 7.38 (m, 2H), 7.27 (m, 2H), 4.59 (d, 1H), 3.90 (d, 2H), 3.28 (m, 3H), 2.80 (m, 3H); 2.53 (s, 3H), 2.20 (m, 2H), 1.75 (d, 2H), 1.42 (s, 9H), 1.35 (m, 2H); LC/MS m/z 514 (M+H)$^+$.

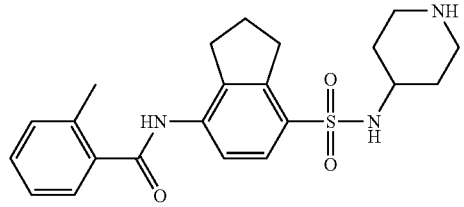

2-Methyl-N-[7-(piperidin-4-ylsulfamoyl)-indan-4-yl]-benzamide (H-67)

The title compound was made following general procedure in Scheme 10, substituting indan-4-ylamine for 5,6,7,8-tetrahydro-naphthalen-1-ylamine. $^1$H NMR (300 MHz, DMSO) δ 8.90 (m, 2H), 7.92 (d, 1H), 7.65 (q, 2H), 7.49 (d, 1H), 7.38 (m, 1H), 7.28 (m, 2H), 3.37 (br s, 1H), 3.18 (m, 5H), 2.93 (m, 4H); 2.40 (s, 3H), 2.08 (m, 2H), 1.67 (m, 4H); LC/MS m/z 414 (M+H)$^+$.

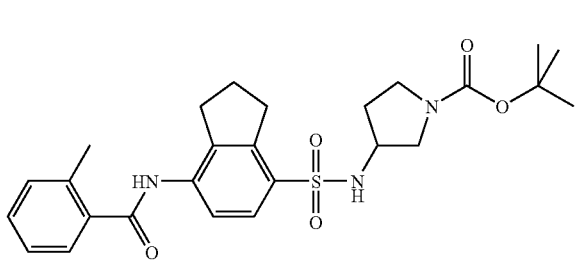

(±)-3-[7-(2-Methyl-benzoylamino)-indane-4-sulfonylamino]-pyrrolidine-1-carboxylic acid tert-butyl ester (H-68)

The title compound was made following general procedure in Scheme 10, substituting indan-4-ylamine for 5,6,7,8-tetrahydro-naphthalen-1-ylamine and 3-amino-pyrrolidine-1-carboxylic acid tert-butyl ester for 4-amino-piperidine-1-carboxylic acid tert-butyl ester. $^1$H NMR (300 MHz, MeOD) δ 7.72 (s, 2H), 7.50 (d, 1H), 7.40 (m, 1H), 7.28 (m, 2H), 3.76 (m, 1H), 3.30 (m, 5H), 3.07 (dd, 1H), 2.97 (t, 2H), 2.48 (s, 3H); 2.16 (m, 2H), 1.98 (m, 1H), 1.78 (m, 1H), 1.40 (s, 9H); LC/MS m/z 500 (M+H)$^+$.

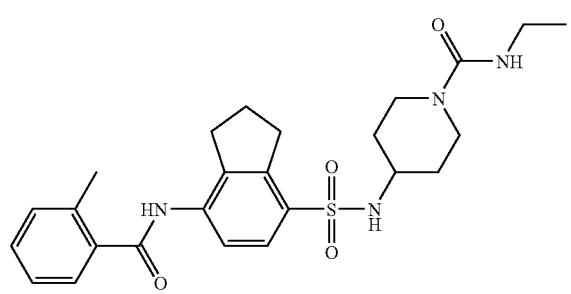

4-[7-(2-Methyl-benzoylamino)-indane-4-sulfonylamino]-piperidine-1-carboxylic acid ethylamide (H-69)

The title compound was made following general procedure in Scheme 10, substituting indan-4-ylamine for 5,6,7,8-tetrahydro-naphthalen-1-ylamine. $^1$H NMR (300 MHz, MeOD) δ 7.73 (m, 2H), 7.51 (d, 1H), 7.30 (m, 3H), 6.41 (m, 1H), 3.83 (d, 2H), 3.19 (m, 2H), 2.96 (t, 2H), 2.77 (t, 2H), 2.48 (s, 3H); 2.16 (m, 2H), 1.64 (m, 2H), 1.33 (m, 2H), 1.06 (t, 3H); LC/MS m/z 485 (M+H)$^+$.

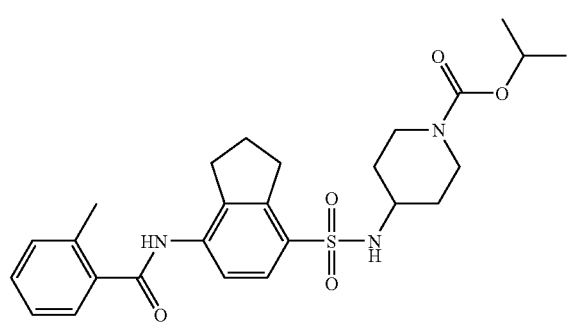

4-[7-(2-Methyl-benzoylamino)-indane-4-sulfonylamino]-piperidine-1-carboxylic acid isopropyl ester (H-70)

The title compound was made following general procedure in Scheme 10, substituting indan-4-ylamine for 5,6,7,8-tetrahydro-naphthalen-1-ylamine and isopropyl chloroformate for butyryl chloride. $^1$H NMR (300 MHz, MeOD) δ 7.68 (m, 2H), 7.51 (d, 1H), 7.38 (m, 3H), 3.91 (d, 2H), 2.98 (m, 2H), 2.82 (m, 2H), 2.48 (s, 3H), 2.17 (m, 2H), 1.68 (d, 2H); 1.33 (m, 2H), 1.20 (d, 6H); LC/MS m/z 500 (M+H)$^+$.

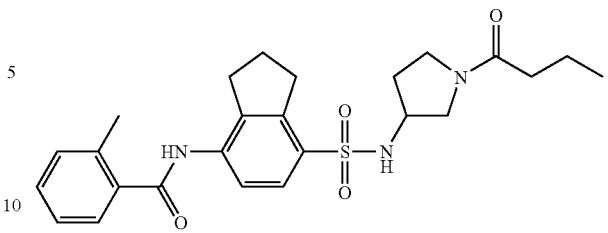

(±)-N-[7-(1-Butyryl-pyrrolidin-3-ylsulfamoyl)-indan-4-yl]-2-methyl-benzamide (H-71)

The title compound was made following general procedure in Scheme 10, substituting indan-4-ylamine for 5,6,7,8-tetrahydro-naphthalen-1-ylamine and 3-amino-pyrrolidine-1-carboxylic acid tert-butyl ester for 4-amino-piperidine-1-carboxylic acid tert-butyl ester. $^1$H NMR (300 MHz, CDCl$_3$) δ 8.22 (m, 1H), 7.76 (dd, 1H), 7.49 (m, 2H), 7.39 (m, 1H), 7.28 (m, 2H), 5.32 (dd, 1H), 3.80 (m, 1H), 3.40 (m, 5H), 2.88 (t, 2H); 2.52 (s, 3H), 2.20 (m, 6H), 1.90 (m, 1H), 1.60 (m, 2H), 0.84 (t, 3H); LC/MS m/z 470 (M+H)$^+$.

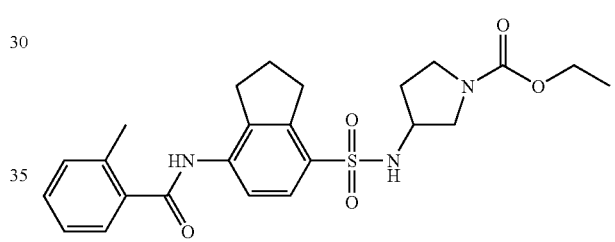

(±)-3-[7-(2-Methyl-benzoylamino)-indane-4-sulfonylamino]-pyrrolidine-1-carboxylic acid ethyl ester (H-72)

The title compound was made following general procedure in Scheme 10, substituting indan-4-ylamine for 5,6,7,8-tetrahydro-naphthalen-1-ylamine, 3-amino-pyrrolidine-1-carboxylic acid tert-butyl ester for 4-amino-piperidine-1-carboxylic acid tert-butyl ester and ethyl chloroformate for butyryl chloride. $^1$H NMR (300 MHz, CDCl$_3$) δ 8.22 (d, 1H), 7.76 (d, 1H), 7.50 (m, 2H), 7.38 (m, 1H), 7.26 (m, 2H), 5.18 (d, 1H), 4.06 (q, 2H), 3.80 (m, 1H), 2.86 (t, 2H); 2.52 (s, 3H), 2.20 (m, 2H), 2.00 (m, 1H), 1.22 (t, 3H), LC/MS m/z 472 (M+H)$^+$.

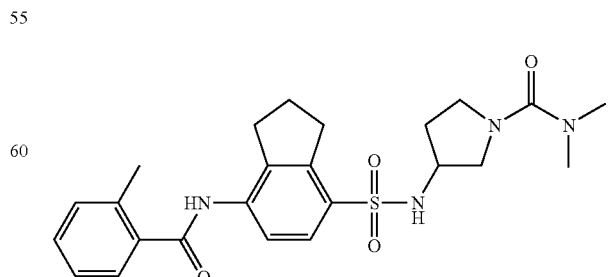

(±)-3-[7-(2-Methyl-benzoylamino)-indane-4-sulfonylamino]-pyrrolidine-1-carboxylic acid dimethylamide (H-73)

The title compound was made following general procedure in Scheme 10, substituting indan-4-ylamine for 5,6,7,8-tetrahydro-naphthalen-1-ylamine, 3-amino-pyrrolidine-1-carboxylic acid tert-butyl ester for 4-amino-piperidine-1-carboxylic acid tert-butyl ester and dimethylcarbamyl chloride for butyryl chloride. $^1$H NMR (300 MHz, CDCl$_3$) δ 8.21 (d, 1H), 7.77 (d, 1H), 7.50 (m, 2H), 7.40 (m, 1H), 7.28 (d, 2H), 5.35 (d, 1H), 3.77 (m, 1H), 3.35 (m, 6H), 2.87 (t, 2H); 2.52 (s, 3H), 2.19 (m, 2H), 1.96 (m, 1H), 1.84 (m, 1H); LC/MS m/z 471 (M+H)$^+$.

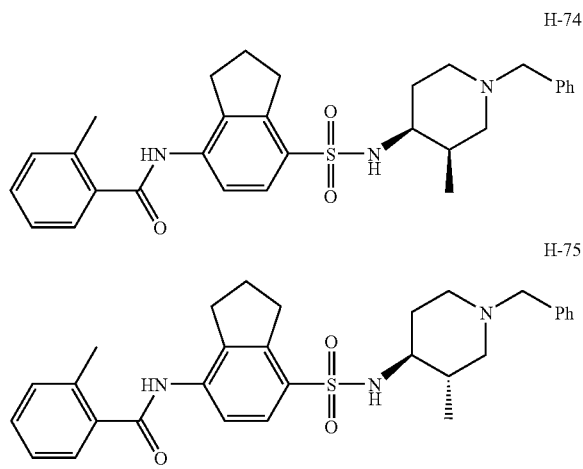

H-74

H-75

(±)-cis-N-[7-(1-Benzyl-3-methyl-piperidin-4-ylsulfamoyl)-indan-4-yl]-2-methyl-benzamide (H-74) and
(±)-trans-N-[7-(1-Benzyl-3-methyl-piperidin-4-ylsulfamoyl)-indan-4-yl]-2-methyl-benzamide (H-75)

The title compounds were made following general procedure in Scheme 10, substituting indan-4-ylamine for 5,6,7,8-tetrahydro-naphthalen-1-ylamine and (±)-4-amino-1-benzyl-3-methyl-piperidine for 4-amino-piperidine-1-carboxylic acid tert-butyl ester. The diastereomers H-74 and H-75 were separated by flash column chromatography. H-74: $^1$H NMR (300 MHz, CDCl$_3$) δ 8.25 (d, 1H), 7.79 (d, 1H), 7.50 (d, 1H), 7.30 (m, 8H), 4.46 (d, 1H), 3.42 (q, 2H), 3.35 (m, 4H), 2.82 (t, 2H), 2.54 (s, 3H), 2.23 (m, 2H), 2.28 (m, 2H), 1.87 (m, 1H), 1.56 (m, 3H), 0.83 (m, 3H); LC/MS m/z 518 (M+H)$^+$. H-75: $^1$H NMR (300 MHz, CDCl$_3$) δ 8.24 (d, 1H), 7.79 (d, 1H), 7.50 (d, 1H), 7.30 (m, 8H), 4.24 (d, 1H), 3.42 (q, 2H), 3.29 (m, 2H), 2.80 (m, 4H), 2.54 (s, 3H), 2.20 (m, 2H), 1.89 (m, 1H), 1.67 (m, 2H), 1.40 (m, 1H), 0.78 (d, 3H); LC/MS m/z 518 (M+H)$^+$.

The Sulfonamides Inhibit CCR8:

This whole cell binding screen evaluates the ability of compounds to inhibit biotinlyated human 1309 binding to the cloned human CCR8 receptor stably expressed in L1.2 cells. Human CCR8 gene was amplified by PCR using PFU polymerase under standard conditions from human genomic DNA purchased from Stratagene. The PCR primers used were:

(SEQ ID NO: 1)
5' CCR8
5'tttggatccatggattatacacttgacctcagtgtg3'

(SEQ ID NO: 2)
3' CCR8
5'tttgcggccgctcacaaaatgtagtctacgctggagg3'

The 5' and 3' primers contained flanking enzyme sites (Bam Hi and Not 1, respectively), which were used to subclone the gene into pcDNA3.1. The vector containing the CCR8 gene was sequenced by manual sequencing and matched to the reported hCCR8 sequence. The CCR8 vector was then transfected into L1.2 cells (murine pre-B cells) by electroporation. Positive clones were selected by functional chemotaxis and binding to the ligand I309.

Compounds were screened using the FMAT™ 8100 HTS System (purchased from Applied Biosystems).

A suspension was prepared of L1.2/ hCCR8 cells at 4.0×10$^5$ cells/mL in a binding buffer (Buffer consisting of Hanks Balanced Salt Solution (without phenol red), 10 mM HEPES, 0.1% Fatty Acid Free BSA, 0.02% Sodium Azide). A solution of 0.375 nM of Human I-309 (Biotinylated at the C-terminus of the ligand after an additional lysine residue using the Applied Biosystems 433 peptide synthesizer) and 0.375 nM of mouse Cy-5 Mab-α-Biotin (Jackson ImmunoResearch Laboratories, Inc., Code Number 200-172-096) was prepared in binding buffer immediately prior to the assay.

Dilution series of 10 mM stock concentrations of the test compounds were prepared in DMSO and further diluted into binding buffer defined above) to three times the final assay concentration.

10 point concentration response curve is constructed for each compound, starting at 10 μM (final assay concentration in Binding Buffer). 25 μl of each concentration of test were transferred into the appropriate wells of a 384 plate. 25 μl of cold 100 nM 1-309 (R and D Systems: Catalog Number 272-I/CF) were then transferred into empty wells to serve as a control for non-specific binding. 25 μl of the 0.375 nM Biotinylated Human I-309/ 0.375nM Cy5-α-Biotin solution were then transferred into each well of the same 384 well plate, followed by addition of 25 μl of the resuspended cell solution into each well. The components were mixed in wells by covering the plate with aluminum foil and rotating for 0.5 hours. The plates was allowed to incubate at room temperature for approximately 1-2 hours and then read on FMAT™ 8100 HTS System (PMT=490/518 or 537/568, Set threshold=1SD MAT). Average fluorescence reported for each concentration was normalized to percent inhibition based on negative (no inhibitor) and positive (100 nM excess unlabeled I309 (R and D Systems)) controls.

TABLE 1

| Ki of compounds to inhibit I-309 binding to CCR8 (uM) | |
|---|---|
| No | Ki, uM |
| A-1 | <0.5 |
| A-2 | <30 |
| A-3 | <0.5 |
| A-7 | <1 |
| A-9 | <30 |
| A-10 | <1 |
| A-11 | <30 |
| A-13 | <30 |
| A-14 | <0.5 |

TABLE 1-continued

Ki of compounds to inhibit I-309 binding to CCR8 (uM)

| | |
|---|---|
| A-16 | <30 |
| A-17 | <0.5 |
| A-18 | <0.5 |
| A-19 | <0.5 |
| A-20 | — |
| A-21 | <1 |
| A-22 | <30 |
| A-23 | <0.5 |
| A-24 | <0.5 |
| A-25 | <0.5 |
| A-26 | <0.5 |
| A-27 | <1 |
| A-28 | <0.5 |
| A-29 | <30 |
| A-30 | <30 |
| A-31 | <0.5 |
| A-32 | <0.5 |
| A-34 | <30 |
| A-35 | <0.5 |
| A-37 | <0.5 |
| A-38 | <0.5 |
| A-40 | <0.5 |
| A-41 | — |
| A-42 | — |
| A-43 | <0.5 |
| A-44 | — |
| A-45 | <30 |
| A-46 | <30 |
| A-47 | <30 |
| A-48 | <30 |
| A-49 | — |
| A-50 | — |
| B-2 | <0.5 |
| B-3 | <30 |
| B-4 | <0.5 |
| B-5 | <1 |
| B-6 | <30 |
| B-7 | <0.5 |
| B-8 | <1 |
| B-9 | <30 |
| B-10 | <30 |
| B-11 | <0.5 |
| B-12 | <0.5 |
| B-13 | <1 |
| B-14 | <0.5 |
| B-15 | <0.5 |
| B-16 | <1 |
| B-17 | <30 |
| B-18 | <30 |
| B-19 | <0.5 |
| B-20 | <1 |
| B-21 | <30 |
| B-22 | <30 |
| B-23 | <30 |
| B-24 | <0.5 |
| B-26 | <0.5 |
| B-27 | <0.5 |
| B-28 | <0.5 |
| B-33 | <30 |
| C-1 | <1 |
| C-2 | <0.5 |
| C-4 | <0.5 |
| C-5 | <0.5 |
| C-7 | <0.5 |
| C-9 | <1 |
| C-10 | <0.5 |
| C-11 | <0.5 |
| C-12 | <0.5 |
| C-13 | <0.5 |
| C-14 | <0.5 |
| C-15 | <0.5 |
| C-16 | <0.5 |
| C-17 | <0.5 |
| C-18 | <0.5 |
| C-19 | <0.5 |
| C-20 | <0.5 |
| C-21 | <0.5 |
| C-22 | <0.5 |
| C-23 | <30 |
| C-24 | <0.5 |
| C-25 | <0.5 |
| C-26 | <0.5 |
| C-27 | <0.5 |
| C-28 | <1 |
| C-29 | <0.5 |
| C-30 | <0.5 |
| C-31 | <0.5 |
| C-32 | <1 |
| C-33 | <1 |
| C-34 | <0.5 |
| C-35 | <0.5 |
| C-36 | <0.5 |
| C-37 | <0.5 |
| C-38 | <0.5 |
| C-39 | <0.5 |
| C-40 | <0.5 |
| C-41 | <0.5 |
| C-42 | <0.5 |
| C-43 | <0.5 |
| C-44 | <1 |
| C-45 | <0.5 |
| C-46 | <0.5 |
| C-47 | <0.5 |
| C-48 | <0.5 |
| C-49 | <0.5 |
| C-50 | <0.5 |
| C-51 | <0.5 |
| C-52 | <0.5 |
| C-53 | <0.5 |
| C-54 | <0.5 |
| C-55 | <0.5 |
| C-56 | <0.5 |
| C-57 | <0.5 |
| C-58 | <0.5 |
| C-59 | <0.5 |
| C-60 | <0.5 |
| C-61 | — |
| C-62 | — |
| C-63 | — |
| C-64 | <0.5 |
| C-65 | <0.5 |
| C-66 | <0.5 |
| C-67 | <0.5 |
| C-68 | <30 |
| C-69 | <1 |
| C-70 | <1 |
| C-71 | <1 |
| C-72 | <1 |
| C-73 | <1 |
| C-74 | <30 |
| C-75 | <0.5 |
| C-76 | <0.5 |
| C-77 | <30 |
| C-78 | <30 |
| C-79 | <30 |
| C-80 | <0.5 |
| C-81 | <0.5 |
| C-82 | <0.5 |
| C-83 | <30 |
| C-84 | — |
| C-85 | — |
| C-86 | — |
| C-87 | — |
| C-88 | — |
| C-89 | — |
| C-90 | — |
| C-91 | — |
| C-92 | — |
| C-93 | — |
| C-94 | — |
| C-95 | — |
| C-96 | — |
| C-97 | — |
| C-98 | <1 |

TABLE 1-continued

Ki of compounds to inhibit I-309 binding to CCR8 (uM)

| | |
|---|---|
| C-99 | <0.5 |
| C-100 | <0.5 |
| C-101 | <0.5 |
| C-102 | <0.5 |
| C-103 | <0.5 |
| C-104 | <0.5 |
| C-105 | <0.5 |
| C-106 | <1 |
| C-107 | <30 |
| C-108 | — |
| C-109 | <1 |
| C-110 | <0.5 |
| C-111 | <0.5 |
| C-112 | <1 |
| C-113 | <0.5 |
| C-114 | <0.5 |
| C-115 | <0.5 |
| C-116 | — |
| C-117 | — |
| C-118 | — |
| C-119 | — |
| C-120 | <0.5 |
| C-121 | <0.5 |
| C-122 | <0.5 |
| C-123 | <0.5 |
| C-124 | <0.5 |
| C-125 | <0.5 |
| C-126 | <0.5 |
| C-127 | — |
| C-128 | — |
| C-129 | — |
| C-130 | — |
| C-131 | — |
| C-132 | — |
| C-133 | — |
| C-134 | — |
| C-135 | — |
| C-136 | <0.5 |
| C-137 | <0.5 |
| C-138 | <1 |
| C-139 | <0.5 |
| C-140 | <0.5 |
| C-141 | <1 |
| C-142 | <0.5 |
| C-143 | <30 |
| C-144 | <30 |
| C-145 | <1 |
| C-146 | — |
| C-147 | <0.5 |
| C-148 | <30 |
| D-1 | <30 |
| D-2 | <30 |
| D-3 | <0.5 |
| D-4 | <0.5 |
| D-5 | <0.5 |
| D-6 | <0.5 |
| D-7 | <0.5 |
| D-8 | <0.5 |
| D-9 | <0.5 |
| D-10 | <0.5 |
| D-11 | <30 |
| D-12 | <30 |
| D-13 | <30 |
| D-14 | <0.5 |
| D-15 | <0.5 |
| D-16 | <0.5 |
| D-17 | <30 |
| D-18 | <0.5 |
| D-19 | <0.5 |
| D-20 | <0.5 |
| D-21 | <30 |
| D-22 | <30 |
| D-23 | <30 |
| D-24 | <30 |
| E-1 | <0.5 |
| E-2 | <0.5 |
| E-3 | <0.5 |
| E-4 | <1 |
| E-5 | <0.5 |
| E-6 | <0.5 |
| E-7 | <30 |
| E-8 | <0.5 |
| E-9 | <0.5 |
| E-10 | <0.5 |
| E-11 | <0.5 |
| E-12 | <0.5 |
| E-13 | <1 |
| E-14 | <1 |
| E-15 | <0.5 |
| E-16 | <0.5 |
| E-17 | <0.5 |
| E-18 | <0.5 |
| E-19 | <0.5 |
| E-20 | <0.5 |
| E-21 | <0.5 |
| E-22 | <0.5 |
| E-23 | <0.5 |
| E-24 | <1 |
| E-25 | <30 |
| E-26 | <1 |
| E-27 | <0.5 |
| E-28 | <0.5 |
| E-29 | <0.5 |
| E-30 | <0.5 |
| E-31 | <0.5 |
| E-32 | <0.5 |
| E-33 | <0.5 |
| E-34 | — |
| E-35 | — |
| E-36 | — |
| F-1 | <1 |
| F-2 | <30 |
| F-3 | <0.5 |
| F-4 | <0.5 |
| F-5 | <30 |
| F-6 | <0.5 |
| F-7 | <0.5 |
| F-8 | <0.5 |
| F-9 | <0.5 |
| F-10 | <0.5 |
| F-11 | <0.5 |
| F-12 | <0.5 |
| F-13 | <0.5 |
| F-14 | <1 |
| F-15 | <30 |
| F-16 | <30 |
| F-17 | <30 |
| F-18 | <30 |
| F-19 | <0.5 |
| F-20 | <0.5 |
| F-21 | <0.5 |
| F-22 | <0.5 |
| F-23 | <0.5 |
| F-24 | <1 |
| F-25 | <0.5 |
| F-26 | <0.5 |
| F-27 | <0.5 |
| F-28 | <0.5 |
| F-29 | — |
| F-30 | — |
| F-31 | — |
| G-1 | <0.5 |
| G-2 | <0.5 |
| G-4 | <30 |
| G-5 | <1 |
| G-6 | <1 |
| G-7 | <0.5 |
| G-8 | <0.5 |
| G-11 | <0.5 |
| G-9 | <30 |
| G-10 | <0.5 |
| G-12 | <0.5 |
| G-13 | <0.5 |
| G-14 | <0.5 |

TABLE 1-continued

Ki of compounds to inhibit I-309 binding to CCR8 (uM)

| | |
|---|---|
| G-15 | <1 |
| G-16 | — |
| G-17 | — |
| G-18 | — |
| G-20 | <0.5 |
| G-21 | <0.5 |
| G-24 | <0.5 |
| G-25 | <30 |
| G-27 | <0.5 |
| G-30 | — |
| G-31 | <0.5 |
| G-32 | <0.5 |
| H-1 | <0.5 |
| H-2 | <30 |
| H-3 | <0.5 |
| H-4 | <30 |
| H-5 | <0.5 |
| H-6 | <0.5 |
| H-7 | <0.5 |
| H-8 | <0.5 |
| H-9 | <1 |
| H-10 | <0.5 |
| H-11 | <0.5 |
| H-12 | <1 |
| H-13 | <30 |
| H-14 | <0.5 |
| H-15 | <1 |
| H-16 | <0.5 |
| H-17 | <1 |
| H-18 | <0.5 |
| H-19 | <30 |
| H-20 | <1 |

| No | Result Value |
|---|---|
| H-21 | <1 |
| H-22 | <1 |
| H-23 | — |
| H-24 | <0.5 |
| H-25 | <1 |
| H-26 | — |
| H-27 | <1 |
| H-28 | <0.5 |
| H-29 | <0.5 |
| H-30 | <0.5 |
| H-31 | <0.5 |
| H-32 | <0.5 |
| H-33 | <0.5 |
| H-34 | <0.5 |

TABLE 1-continued

Ki of compounds to inhibit I-309 binding to CCR8 (uM)

| | |
|---|---|
| H-35 | <1 |
| H-36 | <0.5 |
| H-37 | <0.5 |
| H-38 | <0.5 |
| H-39 | <0.5 |
| H-40 | <0.5 |
| H-41 | <30 |
| H-45 | <0.5 |
| H-46 | <0.5 |
| H-47 | <0.5 |
| H-48 | <30 |
| H-49 | <30 |
| H-50 | <30 |
| H-51 | <30 |
| H-52 | — |
| H-53 | <30 |
| H-54 | <0.5 |
| H-55 | <30 |
| H-56 | <0.5 |
| H-57 | <1 |
| H-58 | <1 |
| H-59 | <1 |
| H-60 | <30 |
| H-61 | — |
| H-62 | — |
| H-63 | <30 |
| H-64 | <0.5 |
| H-65 | <0.5 |
| H-66 | <1 |
| H-67 | <1 |
| H-68 | <0.5 |
| H-69 | <0.5 |
| H-70 | <0.5 |
| H-71 | <0.5 |
| H-72 | <0.5 |
| H-73 | <1 |
| H-74 | <1 |
| H-75 | <1 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

$$\begin{array}{c} R^4 \\ | \\ S(O)_2-NR^3 \\ \end{array}$$

[Structure: naphthalene with rings A and B; ring B bears $S(O)_2$—$NR^3R^4$ substituent; ring A bears NH—C(O)—(CH$_2$)$_m$—R$^1$ substituent]

wherein Rings A and B are unsubstituted;

R$^1$ is a substituted or unsubstituted cycloalkyl group or an aromatic group optionally substituted with one or more groups R$^{10}$;

R$^3$ is —H;

R$^4$ is a substituted or unsubstituted N-piperidinyl, piperidinyl, N-pyrrolidinyl or pyrrolidinyl group;

m is 0 or 1;

wherein R$^{10}$ is halogen, —R$^0$, —OH, —OR$^0$, —O(haloalkyl), —SH, —SR$^0$, 1,2-methylene-dioxy, 1,2-ethylenedioxy, phenyl (Ph), substituted Ph, —O(Ph), substituted —O (Ph), —CH$_2$(Ph), substituted —CH$_2$(Ph), —CH$_2$CH$_2$(Ph), substituted —CH$_2$CH$_2$(Ph), —NO$_2$ —CN, —N(R')$_2$, —NR'CO$_2$R$^0$, —NR'C(O)R$^0$, —NR'NR'C(O)R$^0$, —N(R')C(O)N(R')$_2$, —NR'NR'C(O)N(R')$_2$, —NR'NR'CO$_2$R$^0$, —C(O)C(O)R$^0$, —C(O)CH$_2$C(O)R$^0$, —CO$_2$R$^0$, —C(O)R$^0$, —C(O)N(R$^0$)$_2$, —OC(O)R$^0$, —OC(O)N(R$^0$)$_2$, —S(O)$_2$R$^0$, —SO$_2$N(R')$_2$, —S(O)R$^0$, —NR'SO$_2$N(R')$_2$, —NR'SO$_2$R$^0$, —C(=S)N(R')$_2$, —C(=NH)—N(R')$_2$, haloalkyl, —V—R$^0$, —V—OH, —V—OR$^0$, —V—SH, —V—SR$^0$, —V—NO$_2$, —V—CN, —V—N(R')$_2$, —V—NR'CO$_2$R$^0$, —V—NR'C(O)R$^0$, —V—NR'NR'C(O)R$^0$, —V—N(R')C(O)N(R')$_2$, —V—N R'NR'C(O)N(R')$_2$, —V—NR'NR'CO$_2$R$^0$, —V—C(O)C(O)R$^0$, —V—C(O)CH$_2$C(O)R$^0$, —V—CO$_2$R$^0$, —V—C(O)R$^0$, —V—C(O)N(R$^0$)$_2$, —V—OC(O)R$^0$, —V—OC(O)N(R$^0$)$_2$, —V—S(O)$_2$R$^0$, —V—SO$_2$N(R')$_2$, —V—S(O)R$^0$, —V—NR'SO$_2$N(R')$_2$, —V—NR'SO$_2$R$^0$, —V—C(=S)N(R')$_2$, or —V—C(=NH)—N(R')$_2$;

each substitutable carbon atom of: i) the non-aromatic ring represented by R$^1$ or R$^4$ is optionally and independently substituted with —R$^0$, —OH, —OR$^0$, —O(haloalkyl), —SH, —SR$^0$, 1,2-methylene-dioxy, 1,2-ethylenedioxy, phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —CN, —NO$_2$, —N(R')$_2$, —C(O)N(R$^0$)$_2$, —NR'C(O)R$^0$, —NR'C(O)R$^0$, —V—(O)C(O)R$^0$, —C(O)CH$_2$C(O)R$^0$, —CO$_2$R$^0$, —C(O)R$^0$, —OC(O)R$^0$, —OC(O)N(R$^0$)$_2$, —S(O)$_2$R$^0$, —SO$_2$N(R')$_2$, —S(O) R$^0$, —NR'SO$_2$N(R')$_2$, —NR'SO$_2$R$^0$, —C(=S)N(R')$_2$, —C(=NH)—N(R')$_2$, haloalkyl, —V—R$^0$, —V—OH, —V—OR$^0$, —V—SH, —V—SR$^0$, —NR'C(O)R$^0$, —V—NO$_2$, —V—CN, —V—N(R')$_2$, —V—NR'CO$_2$R$^0$, —V—NR'C(O)R$^0$, —V—NR'NR'C(O)R$^0$, —V—N(R')C(O)N(R')$_2$, —V—NR'NR'C(O)N(R')$_2$, —V—NR'NR'CO$_2$R$^0$, —V—C(O)C(O)R$^0$, —V—C(O)CH$_2$C(O)R$^0$, —V—CO$_2$R$^0$, —V—C(O)R$^0$, —V—C(O)N(R$^0$)$_2$, —V—OC(O)R$^0$, —V—OC(O)N(R$^0$)$_2$, —V—S(O)$_2$R$^0$, —V—SO$_2$N (R')$_2$, —V—S(O)R$^0$, —V—NR'SO$_2$N(R')$_2$, —V—NR'SO$_2$R$^0$, —V—C(=S)N(R')$_2$, —V—C(=NH)—N(R')$_2$, =O, =S, =N NHR*, =NN(R*)$_2$, =NNHC(O)R*, =NNHCO$_2$(alkyl), =NNHSO$_2$(alkyl), or =NR*;

each R$^0$ is independently hydrogen or substituted or unsubstituted aliphatic group, a substituted or unsubstituted cycloaliphatic, a substituted or unsubstituted non-aromatic heterocyclic group or a substituted or unsubstituted aromatic group selected from phenyl, naphthyl, 2-furanyl, 3-furanyl, N-imidazolyl, 2-imidazolyl, 4-imidazolyl, 5-imidazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl or benzoisazolyl;

each R' is independently R$^0$, —CO$_2$R$^0$, —SO$_2$R$^0$ or —C(O)R$^0$;

each R* is independently hydrogen, an unsubstituted aliphatic group or a substituted aliphatic group;

V is a C1-C6 alkylene group; and each substitutable carbon atom of: i) the aliphatic, cycloaliphatic, non-aromatic heterocyclic group and aromatic group represented by R$^0$; and ii) the aliphatic group represented by R* is optionally and independently substituted with amino, alkylamino, dialkylamino, aminocarbonyl, halogen, alkyl, aminoalkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl;

each substitutable nitrogen atom of: i) the non-aromatic ring represented by R$^1$ or R$^4$; and ii) the non-aromatic heterocyclic group represented by R$^0$ is optionally and independently substituted with R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, —NR$^+$SO$_2$R$^+$, —C(O)—NHR$^+$, —C(O)—N(R$^+$)$_2$, —C(O)—CH[N(R$^+$)$_2$]R$^+$ or —C(O)—CH[OR$^+$]R$^+$;

each R$^+$ is independently hydrogen, an unsubstituted heteroaryl or an aliphatic, cycloaliphatic, non-aromatic heterocyclic group, phenyl or benzyl group, wherein each substitutable carbon atom of the aliphatic, cycloaliphatic, non-aromatic heterocyclic ring, phenyl or benzyl group represented by R⁺ is optionally substituted with amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl or N(R⁺)₂ is a non-aromatic heterocyclic group; and each substitutable nitrogen atom of the non-aromatic heterocyclic group represented by R⁺ is optionally substituted with alkyl, alkoxycarbonyl, alkylcarbonyl, alkylaminocarbonyl or dialkylaminocarbonyl.

2. A compound represented by the following structural formula:

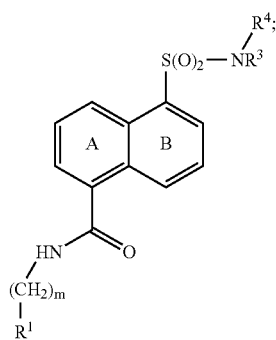

wherein:
R¹ is a substituted or unsubstituted cycloalkyl group or an aromatic group substituted at zero, one or more substitutable carbon atoms by R¹⁰;
R³ is —H and R⁴ is a substituted or unsubstituted N-piperidinyl, piperidinyl, N-pyrrolidinyl or pyrrolidinyl group;
m is 0 or 1;
Rings A and B are unsubstituted;
wherein R¹⁰ is halogen, —R⁰, —OH, —OR⁰, —O(haloalkyl), —SH, —SR⁰, 1,2-methylene-dioxy, 1,2-ethylenedioxy, phenyl (Ph), substituted Ph, —O(Ph), substituted —O(Ph), —CH₂(Ph), substituted —CH₂(Ph), —CH₂CH₂(Ph), substituted —CH₂CH₂(Ph), —NO₂, —CN, —N (R')₂, —NR'CO₂R⁰, —NR'C(O)R⁰, —NR'NR'C(O)R⁰, —N(R')C(O)N(R')₂, —N R'NR'C(O)N(R')₂, —NR'NR'CO₂R⁰, —C(O)C(O)R⁰, —C(O)CH₂C(O)R⁰, —C O₂R⁰, —C(O)R⁰, —C(O)N(R⁰)₂, —OC(O)R⁰, —OC(O)N(R⁰)₂, —S (O)₂R⁰, —SO₂N(R')₂, —S(O)R⁰, —NR'SO₂N (R')₂, —NR'S O₂R⁰, —C(=S)N(R')₂, —C(=NH)—N(R')₂, haloalkyl, —V—R⁰, —V—O H, —V—OR⁰, —V—SH, —V—SR⁰, —V—NO₂, —V—CN, —V—N(R')₂, —V—N R'CO₂R⁰, —V—NR'C(O)R⁰, —V—NR'NR'C(O)R⁰, —V—N(R')C(O)N (R')₂, —V—NR'NR'C(O)N(R')₂, —V—NR'NR'CO₂R⁰, —V—C(O) C(O)R⁰, —V—C(O)CH₂C(O)R⁰, —V—CO₂R⁰, —V—C(O)R⁰, —V—C (O)N(R⁰)₂, —V —OC(O)R⁰, —V—OC(O)N(R⁰)₂, —V—S(O)₂R⁰, —V—S O₂N(R')₂, —V—S(O)R⁰, —VNR'SO₂N (R')₂, —V—NR'SO₂R⁰, —V—C (=S)N(R')₂, or —V—C(=NH)—N(R')₂;

each substitutable carbon atom of: i) the non-aromatic ring represented by R¹ or R⁴ is optionally and independently substituted with —R⁰, —OH, —OR⁰, —O(haloalkyl), —S H, —SR⁰, 1,2-methylene-dioxy, 1,2-ethylenedioxy, phenyl (Ph, substituted Ph, —O(Ph), substituted —O(Ph), —CH₂(Ph), substituted —CH₂ (Ph), —CH₂CH₂(Ph), substituted —CH₂CH₂(Ph), —CN, —NO₂, —N(R')₂, —C(O)N(R⁰)₂, —NR'C(O)R⁰, —NR'C(O)R⁰, —V—N(R')₂, —V—NR'C(O)R⁰, —V—C(O)N (R⁰)₂, —NR'CO₂R⁰, —NR'NR'C(O)R⁰, —N(R')C(O)N(R')₂, —NR'NR'C (O)N(R')₂, —NR'NR'CO₂R⁰, —C(O)C(O)R⁰, —C (O)CH₂C(O)R⁰, —CO₂R⁰, —C(O)R⁰, —OC (O)R⁰, —OC(O)N(R⁰)₂, —S(O)₂R⁰, —SO₂N(R')₂, —S(O) R⁰, —NR'SO₂N(R')₂, —NR'SO₂R⁰, —C(=S)N(R')₂, —C(=NH)—N(R')₂, haloalkyl, —V—R⁰, —V—O H, —V—OR⁰, —V—SH, —V—SR⁰, —NR'C(O)R⁰, —V—NO₂, —V—C N, —V—N(R')₂, —V—NR'CO₂R⁰, —V—NR'C(O)R⁰, —V—NR'N R'C(O)R⁰, —V—N(R')C(O)N(R')₂, —V—NR'NR'C(O) N (R')₂, —V—NR'NR'CO₂R⁰, —V—C(O)C(O) R⁰, —V—C(O)CH₂C (O)R⁰, —V—CO₂R⁰, —V—C (O)R⁰, —V—C(O)N(R⁰)₂, —V—OC(O)R⁰, —V—OC(O)N(R⁰)₂, —V—S (O)₂R⁰, —V—SO₂N (R')₂, —V—S (O)R⁰, —V—NR'SO₂N(R')₂, —V—NR'SO₂R⁰, —V—C (=S)N(R')₂, —V——V—C(=NH)—N(R')₂, =O, =S, =NNHR*, =NN (R*)₂, =NNHC(O)R*, =NNHCO₂(alkyl), =NNHSO₂ (alkyl), or =NR*;

each R⁰ is independently hydrogen or substituted or unsubstituted aliphatic group, a substituted or unsubstituted cycloaliphatic, a substituted or unsubstituted non-aromatic heterocyclic group or a substituted or unsubstituted aromatic group selected from phenyl, naphthyl, 2-furanyl, 3-furanyl, N-imidazolyl, 2-imidazolyl, 4-imidazolyl, 5-imidazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl or benzoisazolyl;

each R' is independently R⁰, —CO₂R⁰, —SO₂R⁰ or —C(O)R⁰;

each R* is independently hydrogen, an unsubstituted aliphatic group or a substituted aliphatic group;

V is a C1-C6 alkylene group;

each substitutable carbon atom of: i) the aliphatic, cycloaliphatic, non-aromatic heterocyclic group and aromatic group represented by R⁰: and ii) the aliphatic group represented by R* is optionally and independently substituted with amino, alkylamino, dialkylamino, aminocarbonyl, halogen, alkyl, aminoalkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl;

each substitutable nitrogen atom of: i) the non-aromatic ring represented by R¹ or R⁴; and ii) the non-aromatic heterocyclic group represented by R⁰ is optionally and independently substituted with R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, —NR⁺SO₂R⁺, —C(O)—NHR⁺, —C(O)—N(R⁺)₂, —C(O)—CH[N(R⁺)₂]R⁺ or —C(O)—CH[OR⁺]R⁺;

each R⁺ is independently hydrogen, an unsubstituted heteroaryl or an aliphatic, cycloaliphatic, non-aromatic heterocyclic group, phenyl or benzyl group, wherein each substitutable carbon atom of the aliphatic, cycloaliphatic, non-aromatic heterocyclic ring, phenyl or benzyl group represented by R+ is optionally substituted with amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl or N(R+)2 is a non-aromatic heterocyclic group; and each substitutable nitrogen atom of the non-aromatic heterocyclic group represented by R+ is optionally substituted with alkyl, alkoxycarbonyl, alkylcarbonyl, alkylaminocarbonyl or dialkylaminocarbonyl.

3. The compound of claim 1 wherein R⁴ is a piperidinyl group or an N-substituted piperidinyl group.

4. The compound of claim 3 wherein the compound is represented by the following structural formula:

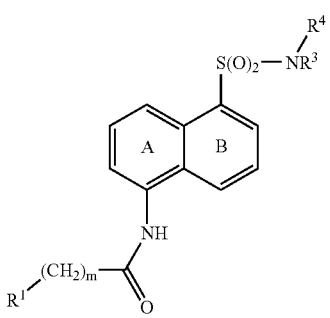

R⁴ is a piperidinyl group N-substituted with R¹⁵, —C(O)R¹⁵, —C(O)OR¹⁵, —C(O)—NHR¹⁵, —C(O)—N(R¹⁵)₂, or —C(O)CH[N(R¹⁶)₂]R¹⁷;

each substitutable carbon of the piperidinyl group represented by R⁴ is optionally and independently substituted with an aliphatic group or substituted aliphatic group;

R¹⁵ is —H, a substituted or unsubstituted non-aromatic ring, or a substituted or unsubstituted aliphatic group or a substituted or unsubstituted C7-C9 aralkyl group, provided that —COOR¹⁵ is not —COOH, or N(R¹⁵)₂ taken together is a substituted or unsubstituted five or six membered non-aromatic nitrogen-containing heterocyclic group;

R¹⁶ is —H or an alkyl group; and

R¹⁷ is —H; a C1-C6 alkyl group optionally substituted with —OH or —NH₂; indolyl; imidazolyl; or phenyl or benzyl optionally substituted with —OH.

5. A compound of represented by a structural formula selected from:

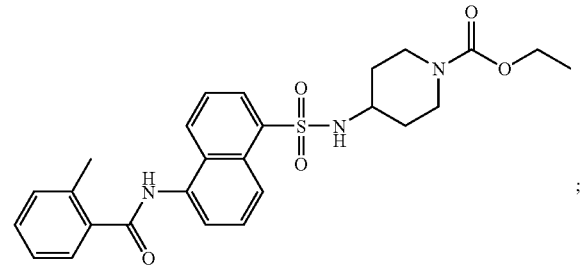

-continued

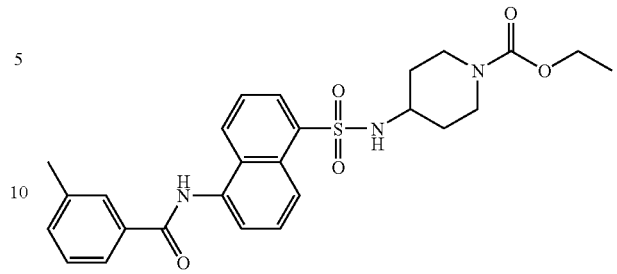

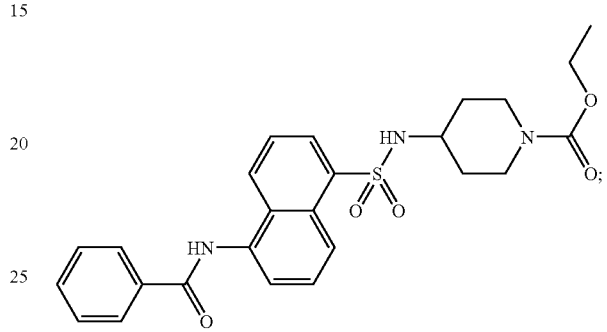

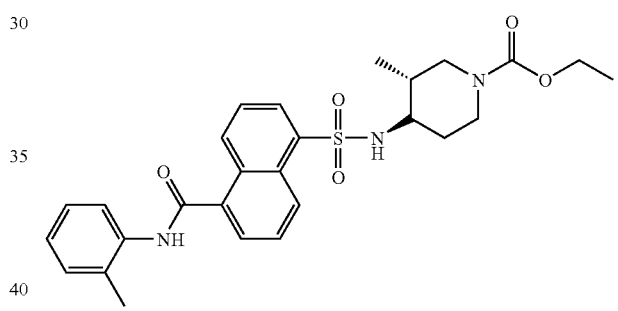

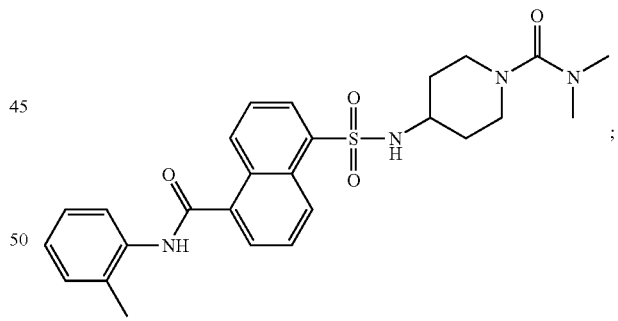

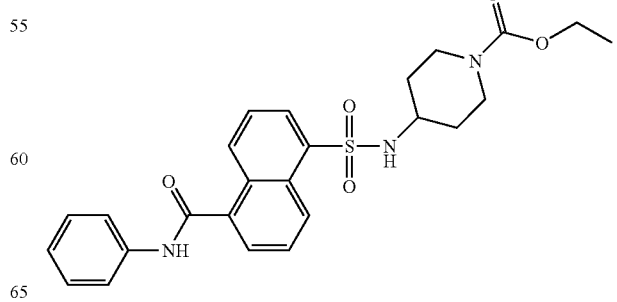

-continued

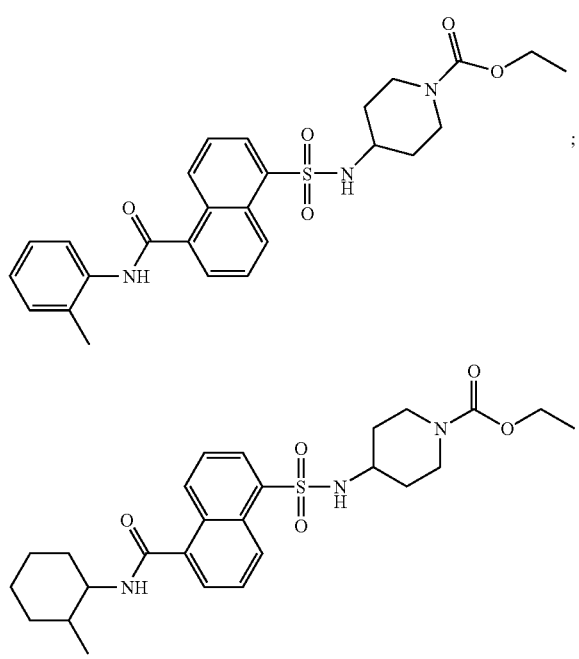

or a pharmaceutically acceptable salt thereof.

6. A compound represented by the following structural formula:

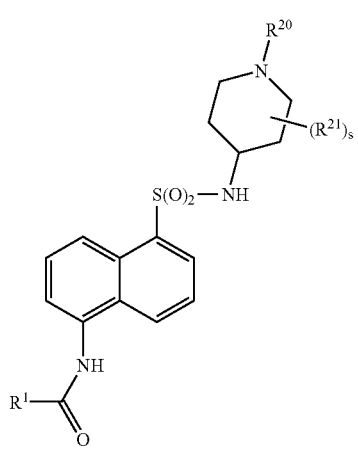

or a pharmaceutically acceptable salt thereof, wherein:

R$^1$ is cyclohexyl or phenyl, furanyl, thienyl or pyridyl optionally substituted with C1-C4 alkyl, C1-C4 alkoxy, C1-C4 haloalkyl, C1-C4 haloalkoxy, methylenedioxy, ethylenedioxy, halogen, cyano or nitro;

R$^{20}$ is —C(O)R$^{22}$, , ,

-continued

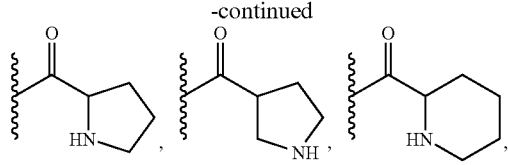

—C(O)OR$^{22}$, —C(O)—NHR$^{22}$, —C(O)—N(R$^{22}$)$_2$ or —C(O)CH[N(R$^{23}$)$_2$]R$^{24}$;

R$^{21}$ is methyl, ethyl, 2-hydroxyethyl or iso-propyl;

R$^{22}$ is —H or C1-C4 alkyl or —N(R$^{22}$)$_2$ taken together is N-pyrollidinyl or N-piperidinyl, provided that R$^{22}$ is not —H when R$^{20}$ is —COOR$^{22}$;

R$^{23}$ is —H, methyl or ethyl;

R$^{24}$ is —H, methyl, ethyl, phenyl, benzyl, 4-hydroxyphenyl or 4-hydroxybenzyl; and s is 0, 1, 2, 3 or 4.

7. A composition comprising a pharmaceutically acceptable carrier or diluent and the compound of claim 1 or 2.

8. The compound of claim 2 wherein R$^4$ is a piperidinyl group or an N-substituted piperidinyl group.

9. The compound of claim 8 wherein the compound is represented by the following structural formula:

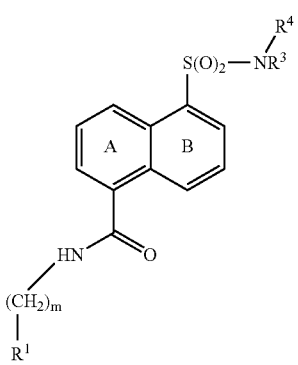

or a pharmaceutically acceptable salt thereof, wherein:

R$^4$ is a piperidinyl group N-substituted with R$^{15}$, —C(O) R$^{15}$, —C(O)OR$^{15}$, —C(O)—NHR$^{15}$, —C(O)—N (R$^{15}$)$_2$, or —C(O)CH[N(R$^{16}$)$_2$]R$^{17}$;

each substitutable carbon of the piperidinyl group represented by R$^4$ is optionally and independently substituted with an aliphatic group or substituted aliphatic group;

R$^{15}$ is —H, a substituted or unsubstituted non-aromatic ring, or a substituted or unsubstituted aliphatic group or a substituted or unsubstituted C7-C9 aralkyl group, provided that —COOR$^{15}$ is not —COOH, or N(R$^{15}$)$_2$ taken together is a substituted or unsubstituted five or six membered non-aromatic nitrogen-containing heterocyclic group;

R$^{16}$ is —H or an alkyl group; and

R$^{17}$ is —H; a C1-C6 alkyl group optionally substituted with —OH or —NH$_2$; indolyl; imidazolyl; or phenyl or benzyl optionally substituted with —OH.

* * * * *